United States Patent
Klein et al.

[11] Patent Number: 6,140,504
[45] Date of Patent: Oct. 31, 2000

[54] SUBSTITUTED INTERMEDIATE COMPOUNDS FOR THE PREPARATION OF N-[(AMINOIMINOMETHYL OR AMINOMETHYL)PHENYL]PROPYL AMIDES

[75] Inventors: Scott I. Klein, Norristown, Pa.; Kevin R. Guertin, Verona, N.J.; Alfred P. Spada, Lansdale, Pa.

[73] Assignee: Aventis Pharmaceuticals Products Inc., Bridgewater, N.J.

[21] Appl. No.: 09/499,335

[22] Filed: Feb. 4, 2000

Related U.S. Application Data

[63] Continuation of application No. 08/884,405, filed as application No. PCT/US96/20770, Dec. 23, 1996.
[60] Provisional application No. 60/009,485, Jan. 2, 1996.

[51] Int. Cl.⁷ ........................ C07D 213/57; C07C 255/58
[52] U.S. Cl. ............................ 546/330; 558/414
[58] Field of Search ............................ 546/330; 558/414

[56] References Cited

U.S. PATENT DOCUMENTS 5,424,334  6/1995  Abood et al. .

*Primary Examiner*—Robert Gerstl
*Attorney, Agent, or Firm*—Irving Newman; Peter Butch

[57] ABSTRACT

Compounds of the formula:

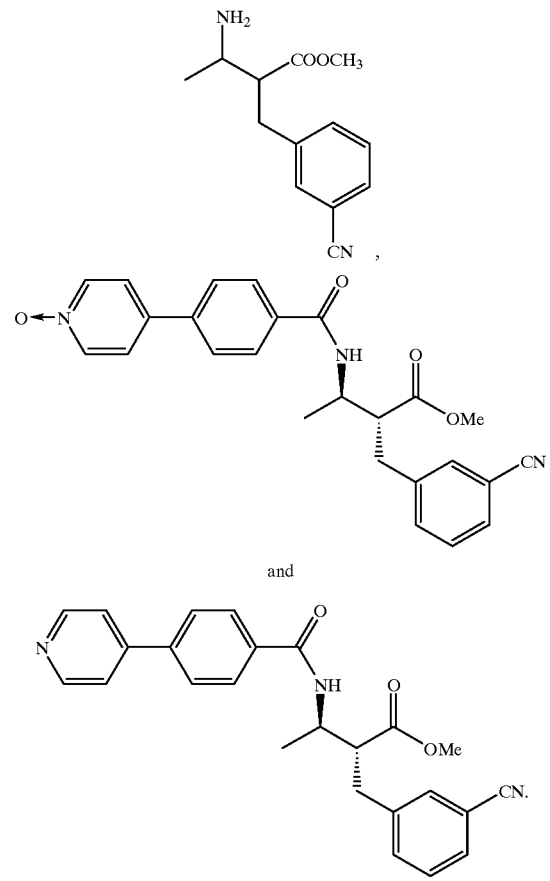

2 Claims, No Drawings

SUBSTITUTED INTERMEDIATE COMPOUNDS FOR THE PREPARATION OF N-[(AMINOIMINOMETHYL OR AMINOMETHYL)PHENYL]PROPYL AMIDES

CROSS REFERENCE TO RELATED APPLICATIONS

This application is a Continuation Application of U.S. patent application Ser. No. 08/884,405 filed Jun. 27, 1997, which claims priority benefit under 35 U.S.C. §371 of International Application Serial No. PCT/US96/20770 (designating the United States) filed Dec. 23, 1996, which, in turn, claims priority benefit of U.S. Provisional Patent Application Serial No. 60/009,485 filed Jan. 2, 1996. The disclosures of all three applications are incorporated herein by reference.

FIELD OF THE INVENTION

The compounds of formula I exhibit useful pharmacological activity and accordingly are incorporated into pharmaceutical compositions and used in the treatment of patients suffering from certain medical disorders. More especially, they are Factor Xa inhibitors. The present invention is directed to compounds of formula I, compositions containing compounds of formula I, and their use, which are for treating a patient suffering from, or subject to, conditions which can be ameliorated by the administration of an inhibitor of Factor Xa.

Factor Xa is the penultimate enzyme in the coagulation cascade. Both free factor Xa and factor Xa assembled in the prothrombinase complex (Factor Xa, Factor Va, calcium and phospholipid) are inhibited by compounds of formula I. Factor Xa inhibition is obtained by direct complex formation between the inhibitor and the enzyme and is therefore independent of the plasma co-factor antithrombin III. Effective factor Xa inhibition is achieved by administering the compounds either by oral administration, continuous intravenous infusion, bolus intravenous administration or any other parenteral route such that it achieves the desired effect of preventing the factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening clots throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

SUMMARY OF THE INVENTION

This invention is directed to the pharmaceutical use of a compound of formula I below to inhibit the production or physiological effects of Factor Xa in the treatment of a patient suffering from a disease state associated with a physiologically detrimental excess of Factor Xa, where formula I is as follows:

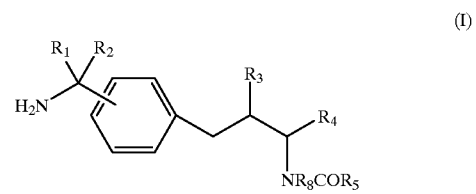

(I)

$R_1$ and $R_2$ are hydrogen or taken together are $=NR_9$;
$R_3$ is hydrogen, $-CO_2R_6$, $-C(O)R_6$, $-CONR_6R_6$, $-CH_2OR_7$ or $-CH_2SR_7$;
$R_4$ is hydrogen, alkyl, Q-alkyl, thiocycloalkyl, or cycloalkylalkyl, or a group of formula

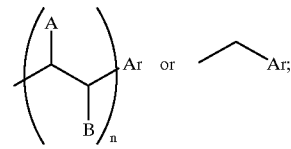

$R_5$ is alkyl, alkenyl, alkynyl, optionally substituted cycloalkyl, optionally substituted heterocyclyl, optionally substituted aryl, optionally substituted heteroaryl, optionally substituted aralkyl, optionally substituted heteroaralkyl, optionally substituted aralkenyl, optionally substituted heteroaralkenyl, optionally substituted aralkynyl, optionally substituted heteroaralkynyl;
$R_6$ is hydrogen or lower alkyl;
$R_7$ is hydrogen, lower alkyl, Ar(lower alkyl), lower acyl, aroyl or heteroaroyl;
$R_8$ is hydrogen or lower alkyl;
$R_9$ is hydrogen, $R_{10}O_2C-$, $R_{10}O-$, $HO-$, cyano, $R_{10}CO-$, $HCO-$, lower alkyl, nitro, or $Y^{1a}Y^{2a}N-$;
$R_{10}$ is optionally substituted alkyl, optionally substituted aralkyl, or optionally substituted heteroaralkyl;
$Y^{1a}$ and $Y^{2a}$ are independently hydrogen or alkyl;
A and B are hydrogen or taken together are a bond;
Q is $R_7O-$ or $R_7S-$ or $Y^1Y^2N-$;
Ar is optionally substituted aryl or optionally substituted heteroaryl; and
n is 0, 1 or 2; or
a pharmaceutically acceptable salt thereof, an N-oxide thereof, a hydrate thereof, a solvate thereof, or prodrug thereof.

DETAILED DESCRIPTION OF THE INVENTION

As used above, and throughout the description of the invention, the following terms, unless otherwise indicated, shall be understood to have the following meanings:

Definitions

"Patient" includes both human and other mammals.

"Alkyl" means an aliphatic hydrocarbon group which may be straight or branched having about 1 to about 15 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 6 carbon atoms in the chain which may be straight or branched. The alkyl group may be substituted by one or more halo, cycloalkyl or cycloalkenyl. Exemplary alkyl groups include methyl, fluoromethyl, difluoromethyl, trifluoromethyl, cyclopropylmethyl, cyclopentylmethyl, ethyl, n-propyl, i-propyl, n-butyl, t-butyl, n-pentyl, 3-pentyl, heptyl, octyl, nonyl, decyl and dodecyl.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 6 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group may be substituted by one or more halo. Exemplary alkenyl groups include ethenyl, propenyl, n-butenyl, i-butenyl, 3-methylbut-2-enyl, n-pentenyl, heptenyl, octenyl and decenyl.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Branched means that one or more lower alkyl groups such as methyl, ethyl or propyl are attached to a linear alkynyl chain. "Lower alkynyl" means about 2 to about 4 carbon atoms in the chain which may be straight or branched. Exemplary alkynyl groups include ethynyl, propynyl, n-butynyl, 2-butynyl, 3-methylbutynyl, n-pentynyl, heptynyl, octynyl and decynyl.

"Cycloalkyl" means a non-aromatic mono- or multicyclic ring system of about 3 to about 10 carbon atoms. Exemplary monocyclic cycloalkyl rings include cyclopentyl, fluorocyclopentyl, cyclohexyl and cycloheptyl. The cycloalkyl group may be substituted by one or more halo, methylene ($H_2C=$), alkyl, cycloalkyl, heterocyclyl, aralkyl, heteroaralkyl, aryl or heteroaryl. Exemplary multicyclic cycloalkyl rings include 1-decalin, adamant-(1- or 2-)yl and norbornyl.

"Cycloalkenyl" means a non-aromatic monocyclic or multicyclic ring system containing a carbon-carbon double bond and having about 3 to about 10 carbon atoms. Exemplary monocyclic cycloalkenyl rings include cyclopentenyl, cyclohexenyl or cycloheptenyl. An exemplary multicyclic cycloalkenyl ring is norbornylenyl. The cycloalkenyl group may be substituted by one or more halo, methylene ($H_2C=$), alkyl, cycloalkyl, heterocyclyl, aralkyl, heteroaralkyl, aryl or heteroaryl.

"Heterocylyl" means a non-aromatic monocyclic or multicyclic ring system of about 3 to about 10 ring atoms. Preferred rings include about 5 to about 6 ring atoms wherein one of the ring atoms is oxygen, nitrogen or sulfur. The heterocyclyl may be optionally substituted by one or more halo, methylene ($H_2C=$), alkyl, cycloalkyl, heterocyclyl, aralkyl, heteroaralkyl, aryl or heteroaryl. Preferred monocyclic heterocyclyl rings include pyrrolidine, tetrahydrothiophenyl and tetrahydrothiopyranyl. The thio or nitrogen moiety of the heterocyclyl may also be optionally oxidized to the corresponding N-oxide, S-oxide or S,S-dioxide.

"Aryl" means aromatic carbocyclic radical containing about 6 to about 12 carbon atoms. Exemplary aryl include phenyl (Ph) or naphthyl optionally substituted with one or more aryl group substituents which may be the same or different, where "aryl group substituent" includes hydrogen, alkyl, cycloalkyl, heterocyclyl, optionally substituted aryl, optionally substituted heteroaryl, aralkyl, aralkenyl, aralkynyl, heteroaralkyl, heteroaralkenyl, heteroaralkynyl, hydroxy, hydroxyalkyl, alkoxy, aryloxy, aralkoxy, carboxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, alkylsulfinyl, arylsulfinyl, alkylthio, arylthio, aralkylthio, —O-($C_{1-3}$alkylenyl)-O—, $Y^1Y^2N$—, $Y^1Y^2$N-alkyl-, $Y^1Y^2$NCO— or $Y^1Y^2NSO_2$—, wherein $Y^1$ and $Y^2$ are independently hydrogen, alkyl, aryl, and aralkyl, or two adjacent $Y^1Y^2$NCO— substituents taken together with the carbon atoms to which the $Y^1Y^2$NCO— substituents are attached form an imide (—$CONY^1CO$—), or where the substituent is $Y^1Y^2N$— or $Y^1Y^2$N-alkyl- then one of $Y^1$ and $Y^2$ is acyl or aroyl and the other of $Y^1$ and $Y^2$ is hydrogen, alkyl, aryl, and aralkyl. Preferred aryl group substituents include hydrogen, alkyl, optionally substituted aryl, optionally substituted heteroaryl, hydroxy, acyl, aroyl, halo, nitro, cyano, alkoxycarbonyl, acylamino, alkylthio, $Y^1Y^2$N-(lower alkyl)-, $Y^1Y^2N$—, $Y^1Y^2$NCO—, or $Y^1Y^2NSO^2$—, wherein $Y^1$ and $Y^2$ are independently hydrogen and alkyl.

"Heteroaryl" means about a 5- to about a 12- membered aromatic mono-cyclic or multicyclic hydrocarbon ring system in which one or more of the carbon atoms in the ring system is/are element(s) other than carbon, for example nitrogen, oxygen or sulfur. The "heteroaryl" may also be substituted by one or more aryl group substituents. Exemplary heteroaryl groups include pyrrolyl, imidazolyl, pyrazolyl, triazolyl, furanyl, thienyl, 1,2,4-thiadiazolyl, pyridyl, pyrimidinyl, pyrazinyl, pyridazinyl, oxazolyl, isoxazolyl, thiazolyl, quinolinyl, isoquinolinyl, indolyl, quinazolinyl, quinoxalinyl, phthalazinyl, imidazo[1,2-a] pyridine, benzoazaindole.

"Aralkyl" means an aryl-alkyl- group in which the aryl and alkyl are as previously described. Preferred aralkyls contain a lower alkyl moiety. Exemplary aralkyl groups include benzyl, 2-phenethyl and naphthlenemethyl.

"Aralkenyl" means an aryl-alkenyl group in which the aryl and alkenyl are as previously described. Preferred aralkenyls contain a lower alkenyl moiety. Exemplary aralkenyl groups include 2-phenethenyl and 2-naphthylethenyl.

"Aralkynyl" means an aryl-alkynyl- group in which the aryl and alkynyl are as previously described. Preferred aralkynyls contain a lower alkynyl moiety. Exemplary aralkynyl groups include phenacetylenyl and naphthylacetylenyl.

"Heteroaralkyl" means an heteroaryl-alkyl- group in which the heteroaryl and alkyl are as previously described. Preferred hetararalkyls contain a lower alkyl moiety. Exemplary aralkyl groups include pyridylmethyl, 2-(furan-3-yl) ethyl and quinolin-3-ylmethyl.

"Heteroaralkenyl" means an heteroaryl-alkenyl group in which the heteroaryl and alkenyl are as previously described. Preferred heteroaralkenyls contain a lower alkenyl moiety. Exemplary heteroaralkenyl groups include 2-(pyrid-3-yl) ethenyl and 2-(quinolin-3-yl)ethenyl.

"Heteroaralkynyl" means an heteroaryl-alkynyl group in which the heteroaryl and alkynyl are as previously described. Preferred heteroaralkynyls contain a lower alkynyl moiety. Exemplary heteroaralkynyl groups include pyrid-3-ylacetylenyl and quinolin-3-ylacetylenyl.

"Hydroxyalkyl" means a HO-alkyl- group in which alkyl is as previously defined. Preferred hydroxyalkyls contain lower alkyl. Exemplary hydroxyalkyl groups include hydroxymethyl and 2-hydroxyethyl.

"Acyl" means an H—CO— or alkyl-CO— group in which the alkyl group is as previously described. Preferred acyls contain a lower alkyl. Exemplary acyl groups include formyl, acetyl, propanoyl, 2-methylpropanoyl, butanoyl and palmitoyl.

"Aroyl" means an aryl-CO— group in which the aryl group is as previously described. Exemplary groups include benzoyl and 1- and 2-naphthoyl.

"Heteroaroyl" means a heteroaryl-CO— group in which the heteroaryl group is as previously described. Exemplary groups include nicotinoyl and pyrrol-2-ylcarbonyl and 1- and 2-naphthoyl.

"Alkoxy" means an alkyl-O— group in which the alkyl group is as previously described. Exemplary alkoxy groups include methoxy, ethoxy, n-propoxy, i-propoxy, n-butoxy and heptoxy.

"Aryloxy" means an aryl-O— group in which the aryl group is as previously described. Exemplary aryloxy groups include phenoxy and naphthoxy.

"Aralkyloxy" means an aralkyl-O— group in which the aralkyl groups is as previously described. Exemplary aralkyloxy groups include benzyloxy and 1- or 2-naphthalenemethoxy.

"Alkylthio" means an alkyl-S— group in which the alkyl group is as previously described. Exemplary alkylthio groups include methylthio, ethylthio, i-propylthio and heptylthio.

"Arylthio" means an aryl-S— group in which the aryl group is as previously described. Exemplary arylthio groups include phenylthio and naphthylthio.

"Aralkylthio" means an aralkyl-S— group in which the aralkyl group is as previously described. An exemplary aralkylthio group is benzylthio.

"$Y^1Y^2N$—" means a substituted or unsubstituted amino group, wherein $Y^1$ and $Y^2$ are as previously described. Exemplary groups include amino ($H_2N$—), methylamino, ethylmethylamino, dimethylamino and diethylamino.

"Alkoxycarbonyl" means an alkyl-O—CO — group. Exemplary alkoxycarbonyl groups include methoxy- and ethoxycarbonyl.

"Aryloxycarbonyl" means an aryl-O—CO — group. Exemplary aryloxycarbonyl groups include phenoxy- and naphthoxycarbonyl.

"Aralkoxycarbonyl" means an aralkyl-O—CO — group. An exemplary aralkoxycarbonyl group is benzyloxycarbonyl.

"$Y^1Y^2NCO$—" means a substituted or unsubstituted carbamoyl group, wherein $Y^1$ and $Y^2$ are as previously described. Exemplary groups are carbamoyl ($H_2NCO$—) and dimethylaminocarbamoyl ($Me_2NCO$—).

"$Y^1Y^2NSO_2$—" means a substituted or unsubstituted sulfamoyl group, wherein $y^1$ and $Y^2$ are as previously described. Exemplary groups are aminosulfamoyl ($H_2NSO_2$—) and dimethylaminosulfamoyl ($Me_2NSO_2$—).

"Acylamino" is an acyl-NH— group wherein acyl is as defined herein.

"Aroylamino" is an aroyl-NH— group wherein aroyl is as defined herein.

"Alkylsulfonyl" means an alkyl-$SO_2$— group. Preferred groups are those in which the alkyl group is lower alkyl.

"Alkylsulfinyl" means an alkyl-SO— group. Preferred groups are those in which the alkyl group is lower alkyl.

"Arylsulfonyl" means an aryl-$SO_2$— group.

"Arylsulfinyl" means an aryl-SO— group.

"Halo" means fluoro, chloro, bromo, or iodo. Preferred are fluoro, chloro or bromo, and more preferred are fluoro or chloro.

"Prodrug" means a form of the compound of formula which may or may not itself be biologically active but which may be converted, for example by metabolic, solvolytic, or other physiological means, to a biologically active chemical entity, and is suitable for administration to a patient without undue toxicity, irritation, allergic response, and the like, and effective for their intended use, including ketal, ester and zwitterionic forms. A prodrug is transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A. C. S. Symposium Series, and in Edward B. Roche, ed., *Bioreversible Carriers in Drug Design*, American Pharmaceutical Association and Pergamon Press, 1987, both of which are incorporated herein by reference.

Preferred Embodiments

A preferred embodiment of the invention is a method for treating a disease state capable of being modulated by inhibiting production of Factor Xa to a patient suffering from said disease state an effective amount of the compound of formula I.

A preferred compound aspect of the invention is the compound of formula I wherein $R_1$ and $R_2$ taken together are =$NR_9$;

$R_3$ is hydrogen, —$CO_2R_6$, —$C(O)R_6$, —$CH_2OR_7$ or —$CH_2SR_7$;

$R_4$ is hydrogen, alkyl or Q-alkyl, or a group of formula

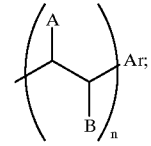

$R_5$ is optionally substituted cycloalkyl, optionally substituted heterocyclyl, optionally substituted aryl, optionally substituted heteroaryl, optionally substituted aralkyl or optionally substituted aralkynyl;

$R_7$ is hydrogen or lower alkyl;

A, B, $R_8$ and $R_9$ are hydrogen;

Q is $R_7O$—;

n is 1; or a pharmaceutically acceptable salt thereof, an N-oxide thereof or prodrug thereof.

Another preferred compound aspect of the invention is the compound of formula I wherein $R_1$ and $R_2$ taken together are =NH.

Another preferred compound aspect of the invention is the compound of formula I wherein $R_3$ is hydrogen, —$CO_2R_6$, —$CH_2OR_7$ or —$CH_2SR_7$; more preferred $R_3$ is hydrogen, —$CO_2R_6$ or —$CH_2OR_7$.

Another preferred compound aspect of the invention is the compound of formula I wherein $R_3$ is —$CO_2R_6$ and $R_6$ is lower alkyl.

Another preferred compound aspect of the invention is the compound of formula I wherein $R_3$ is —$CH_2OR_7$ or —$CH_2SR_7$ and $R_7$ is hydrogen or lower alkyl.

Another preferred compound aspect of the invention is the compound of formula I wherein $R_4$ is lower alkyl, $R_7O$(lower alkyl)-, or a group of formula

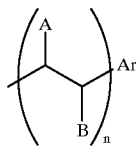

where A and B are hydrogen and n is 1.

Another preferred compound aspect of the invention is the compound of formula I wherein $R_5$ is optionally substituted cycloalkyl, optionally substituted heterocyclyl, optionally substituted aryl, optionally substituted heteroaryl, optionally substituted aralkyl or optionally substituted aralkynyl.

Another preferred compound aspect of the invention is the compound of formula I wherein $R_5$ is optionally substituted phenyl, optionally substituted optionally substituted naphthyl, or optionally substituted heteroaryl.

Another preferred compound aspect of the invention is the compound of formula I wherein $R_5$ as optionally substituted phenyl or optionally substituted heteroaryl is optionally substituted (phenyl substituted phenyl), optionally substituted (heteroaryl substituted phenyl), optionally substituted (phenyl substituted heteroaryl) or optionally substituted (heteroaryl substituted heteroaryl).

Another preferred compound aspect of the invention is the compound of formula I wherein $R_6$ is lower alkyl.

Another preferred compound aspect of the invention is the compound of formula I wherein $R_7$ is hydrogen or lower alkyl.

Another preferred compound aspect of the invention is the compound of formula I wherein $R_8$ is hydrogen.

Another preferred compound aspect of the invention is the compound of formula I wherein $R_9$ is hydrogen.

Another preferred compound aspect of the invention is the compound of formula I wherein $R_{10}$ is lower alkyl.

Another preferred compound aspect of the invention is the compound of formula I wherein n is 1.

Another preferred compound aspect of the invention is the compound of formula I wherein the

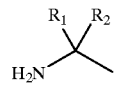

moiety is in the meta position to the position of attachment of the phenyl moiety to the

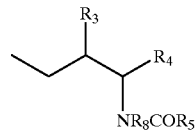

moiety.

Another preferred compound aspect of the invention is the compound of formula I wherein Ar is optionally substituted aryl.

Another preferred compound aspect of the invention is the compound of formula I wherein Ar is phenyl.

Included within the scope of formula I are compounds wherein $R_1$ and $R_2$ taken together are $=NR_9$, wherein $R_9$ is $R_{10}O_2C-$, $R_{10}O-$, cyano, $R_{10}CO-$, optionally substituted lower alkyl, nitro, or $Y^1Y^2N-$. Such derivatives may themselves comprise the biologically active compound useful for treating a disease state capable of being modulated by inhibiting production of Factor Xa to a patient suffering from said disease state, or may act as pro-drugs to such biologically active compounds which are formed therefrom under physiological conditions.

Species according to the invention are selected from the following:

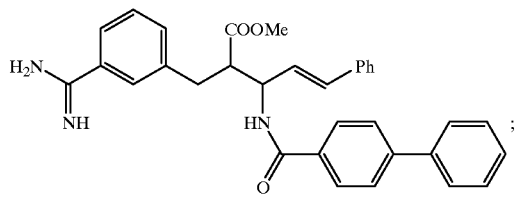

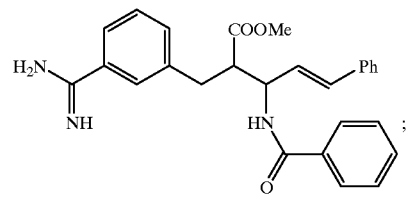

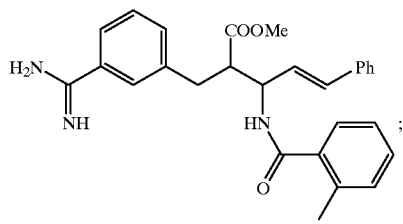

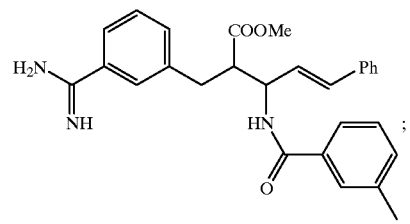

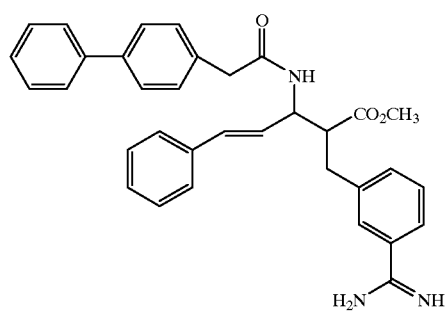
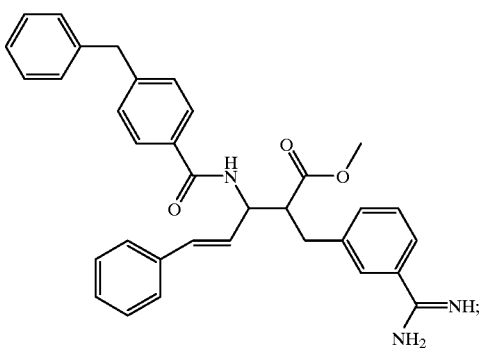
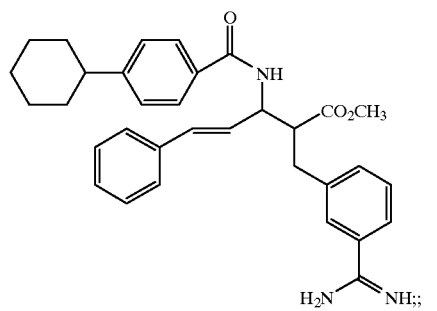
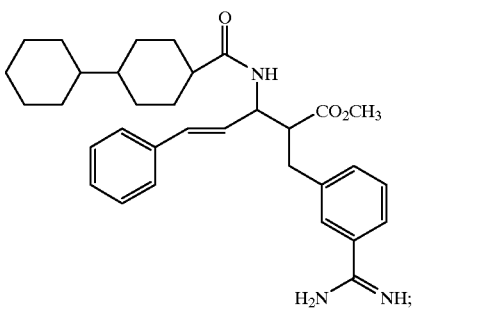
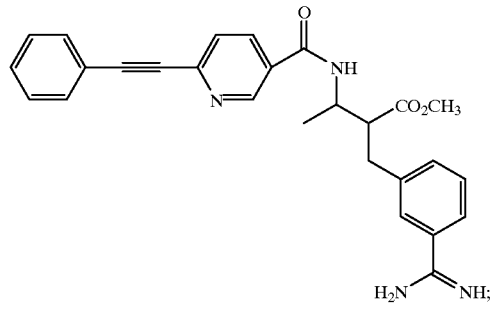
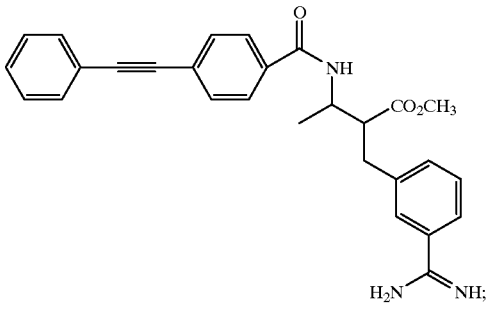
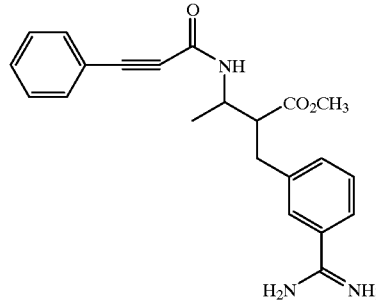
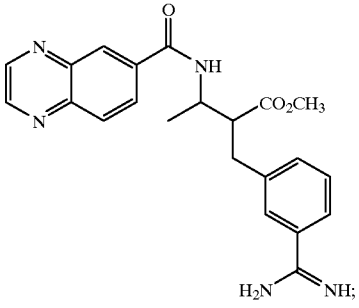
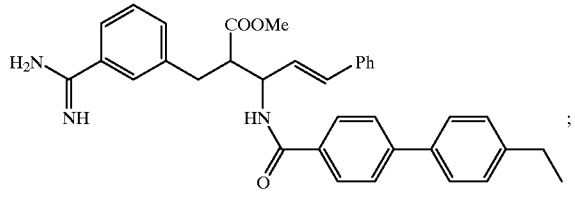
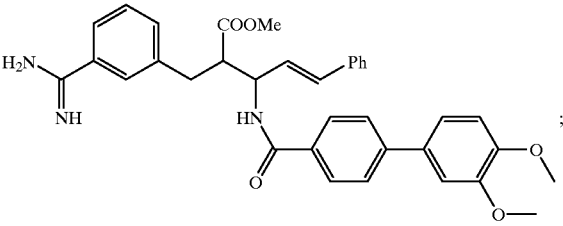
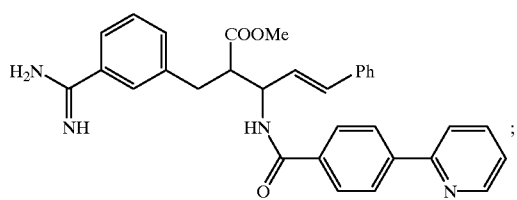
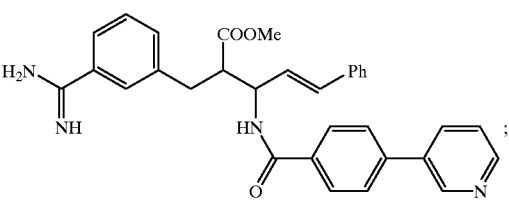

-continued
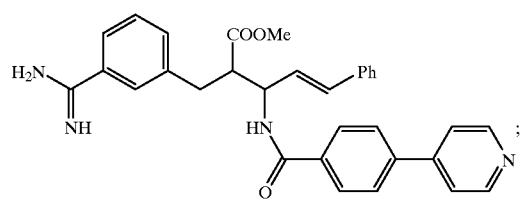
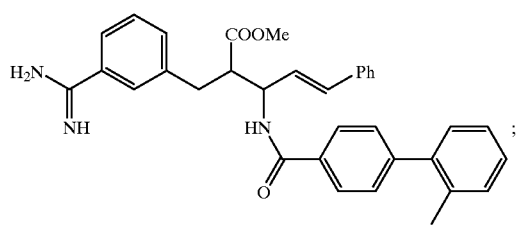
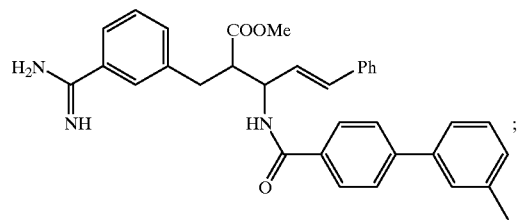
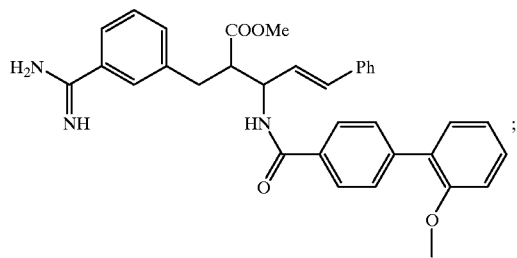
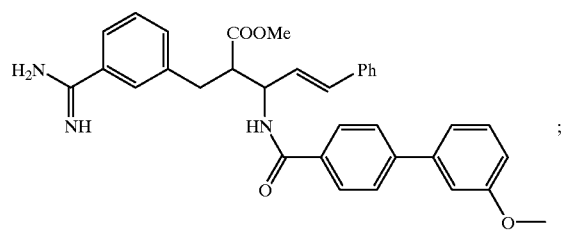
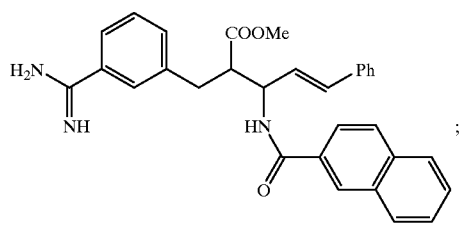
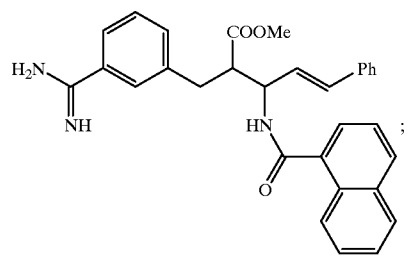
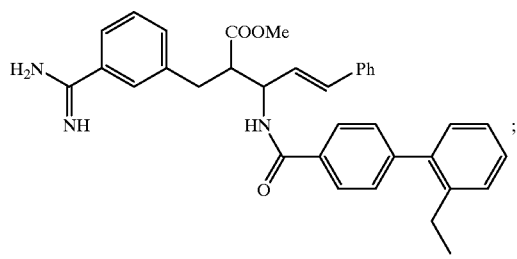
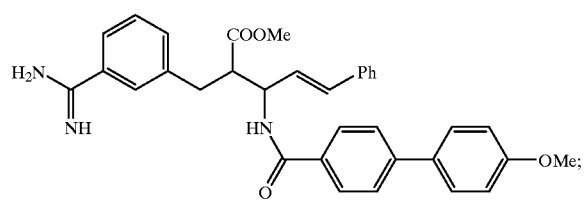
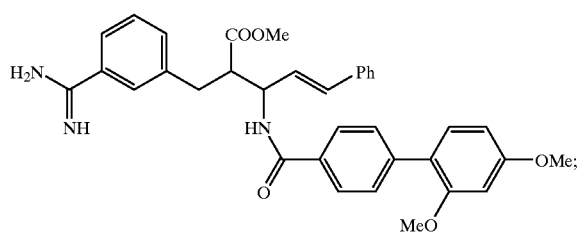
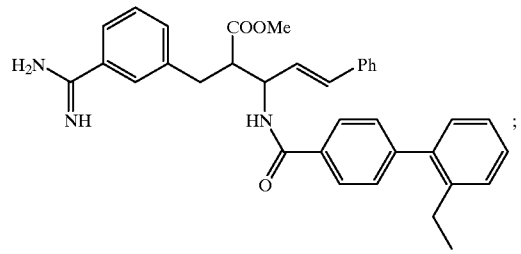
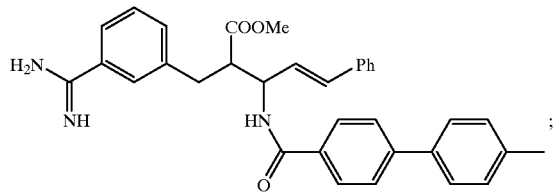

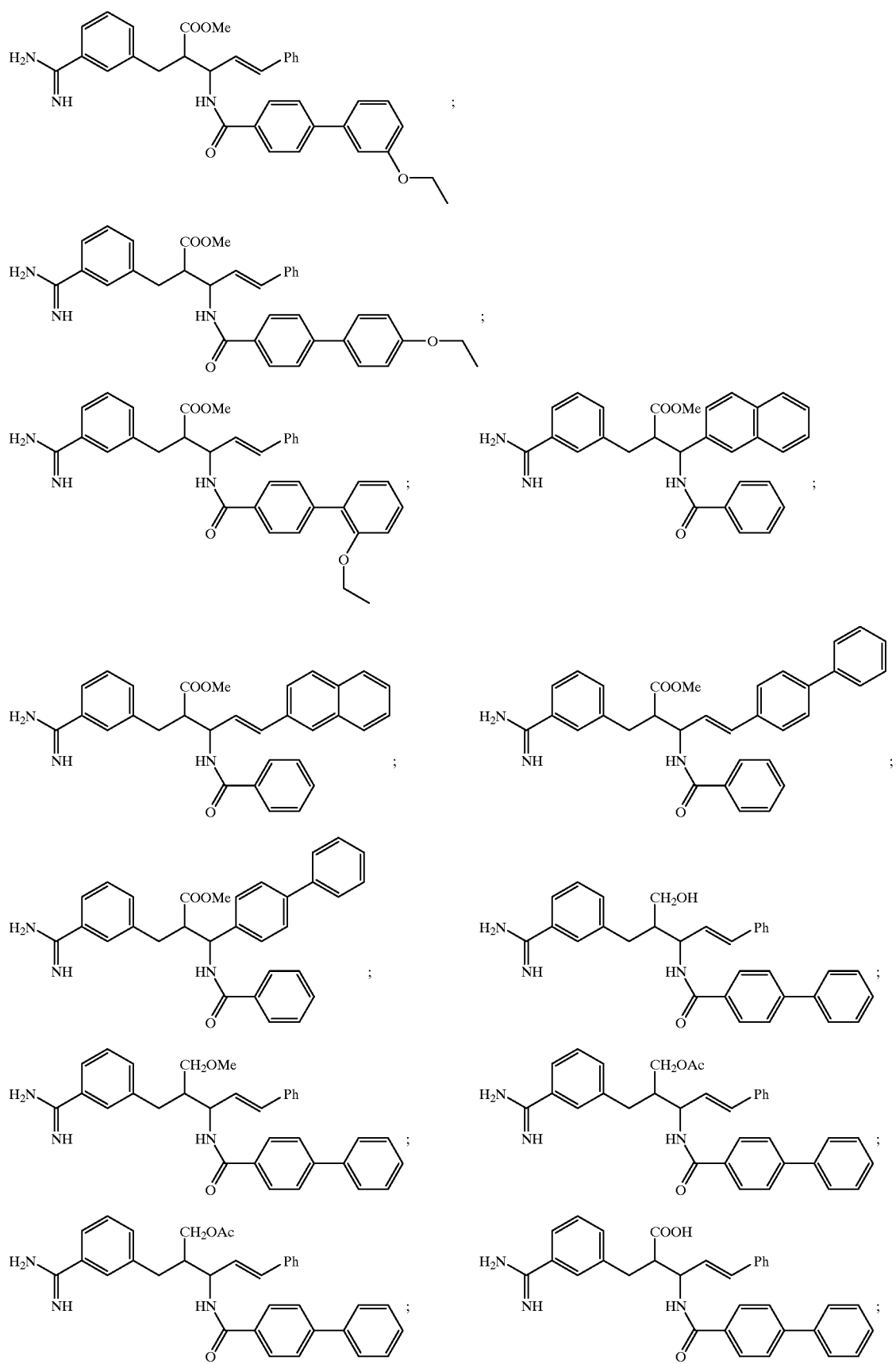

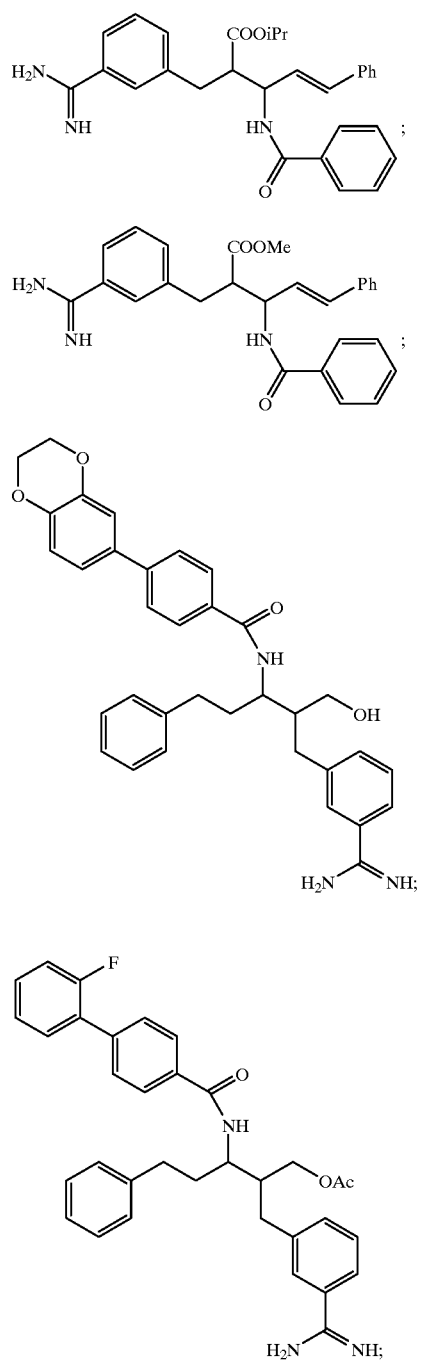
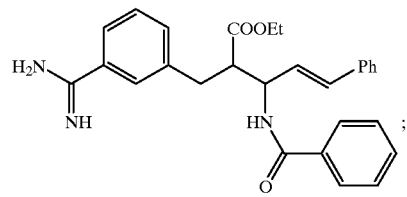
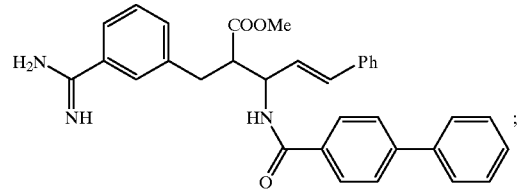
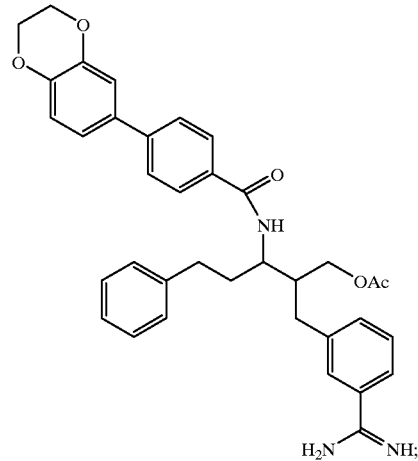
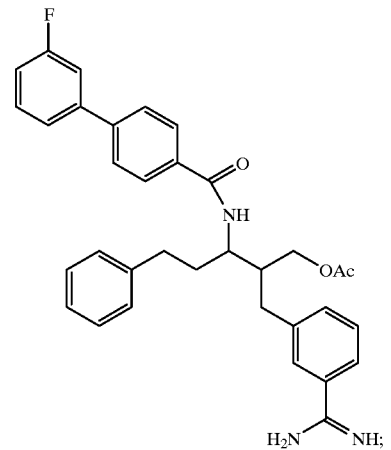

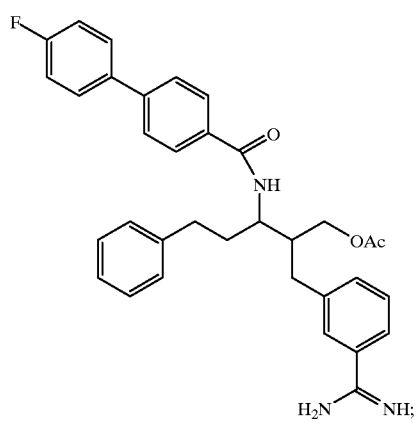
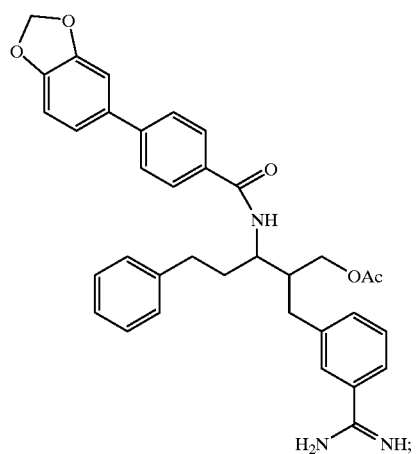
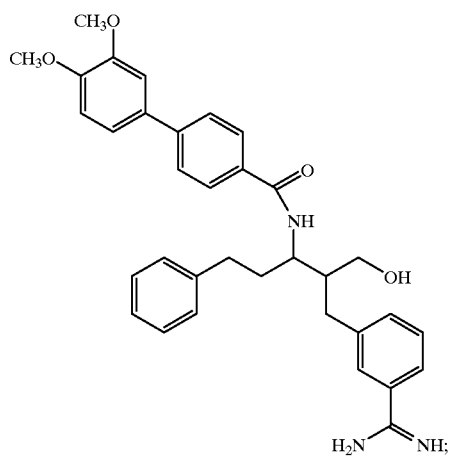
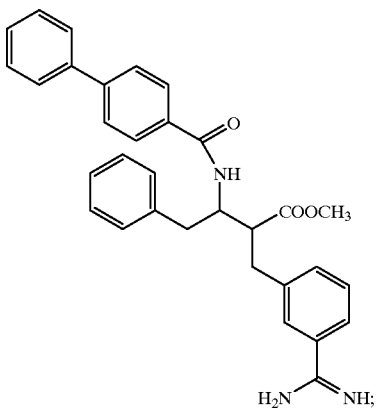
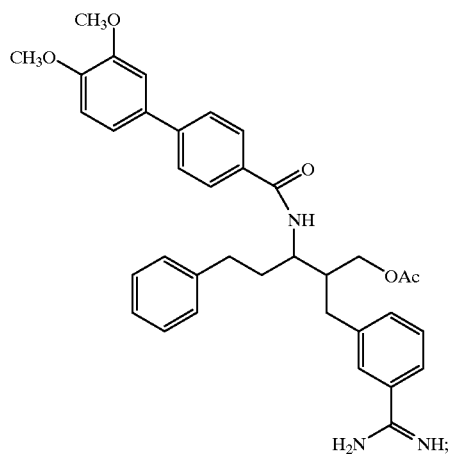
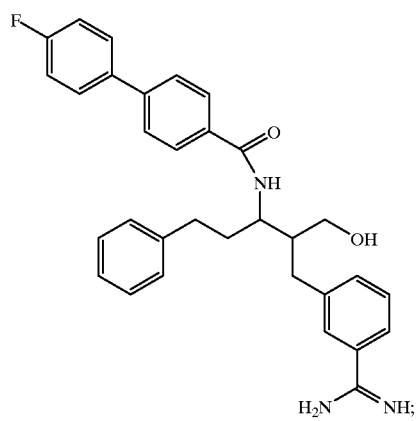

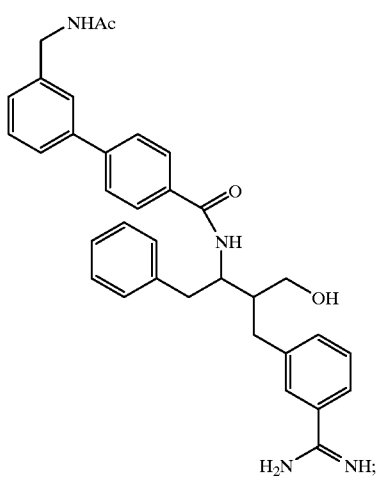
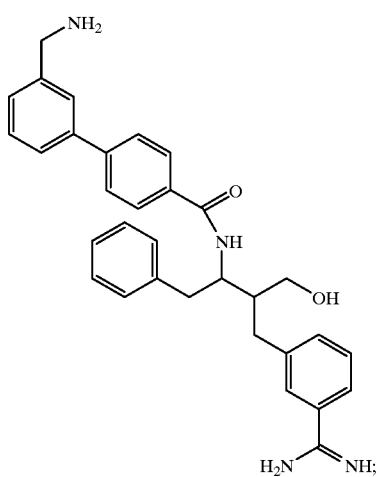
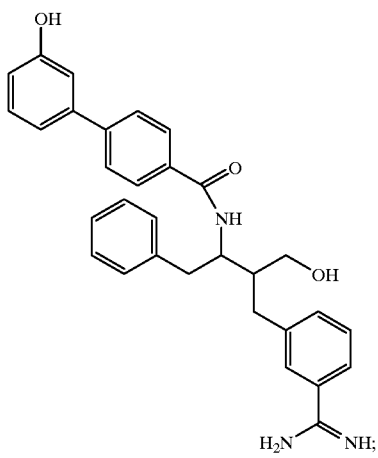
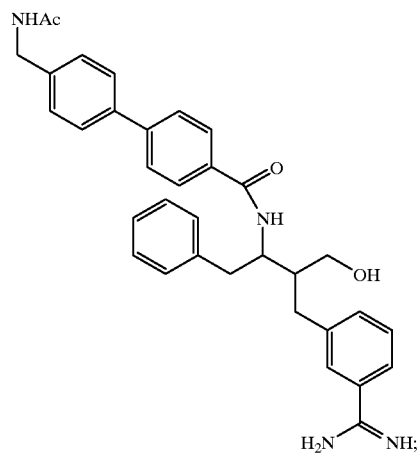
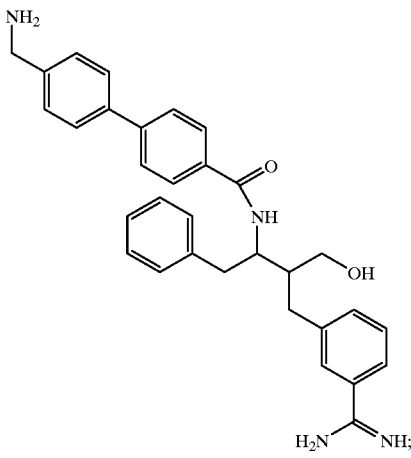
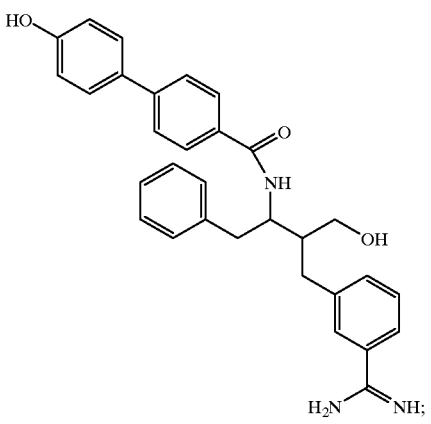

21
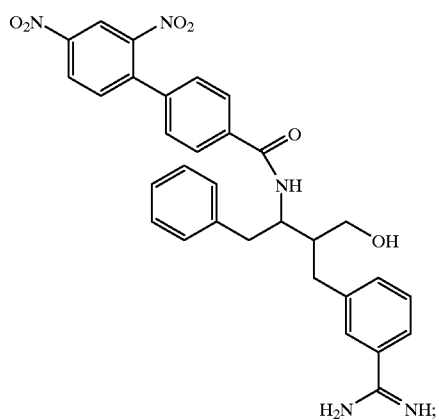
22
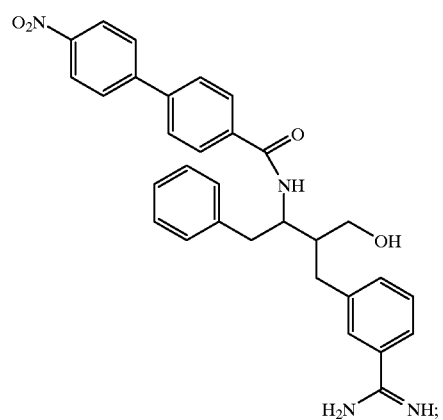
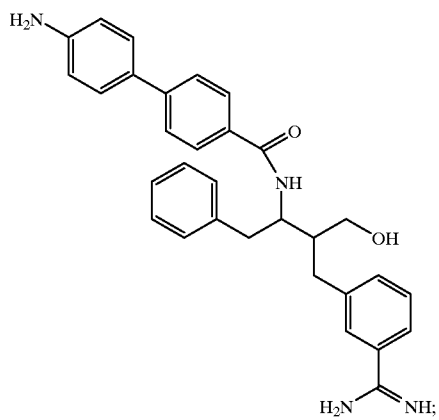
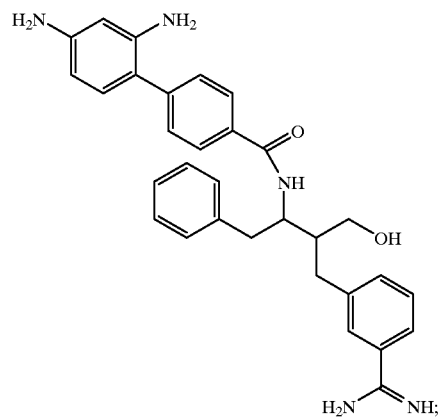
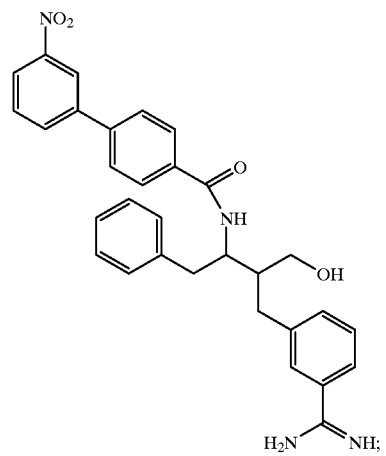
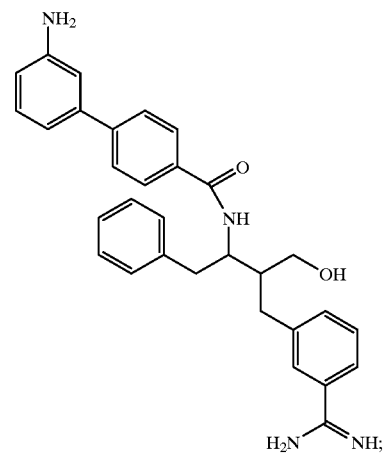

-continued
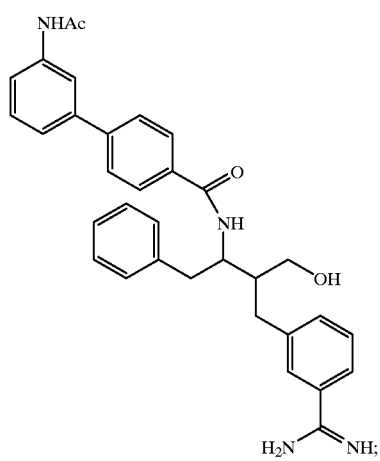
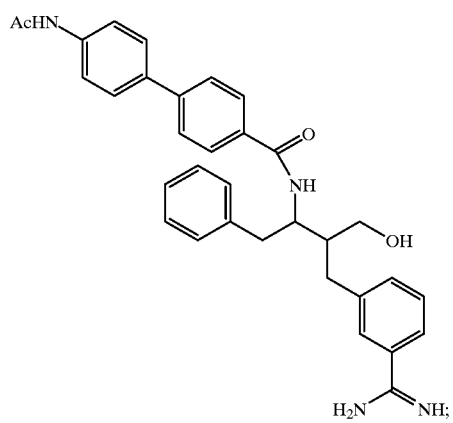
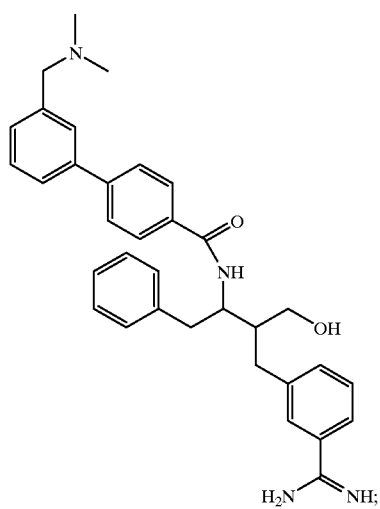
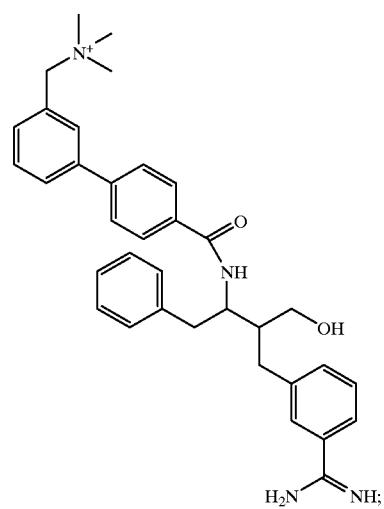
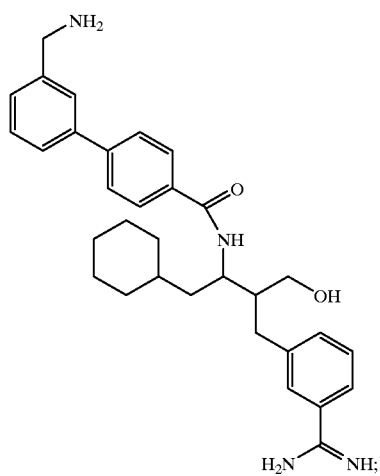
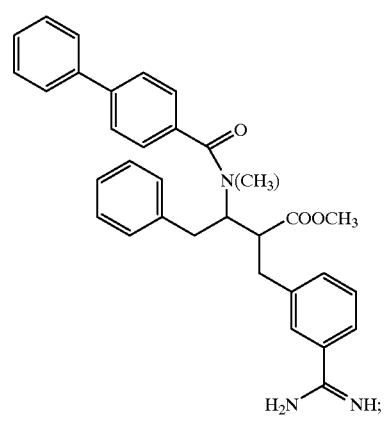

25 26
-continued
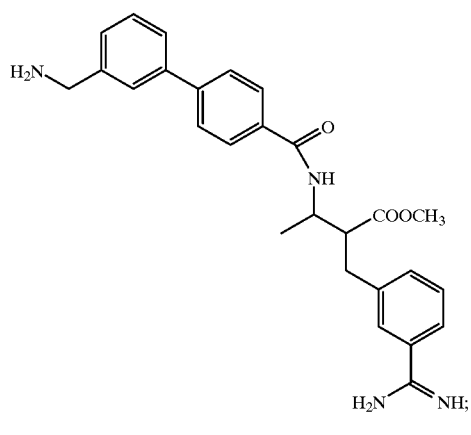
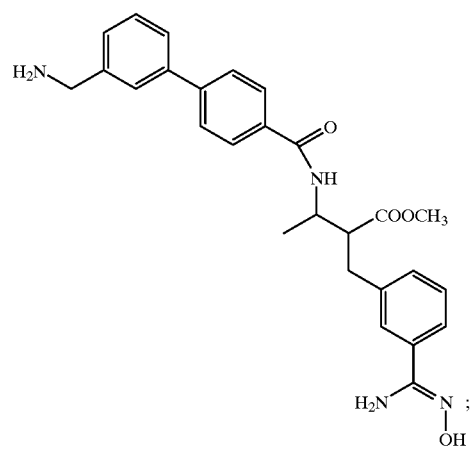
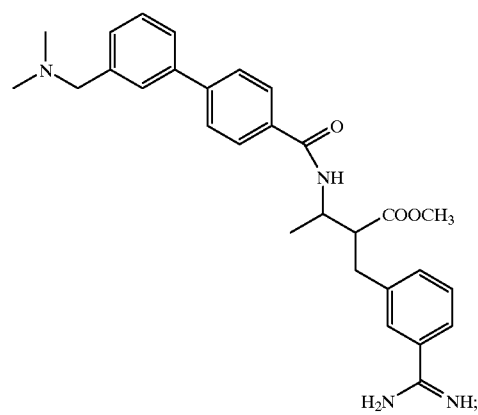
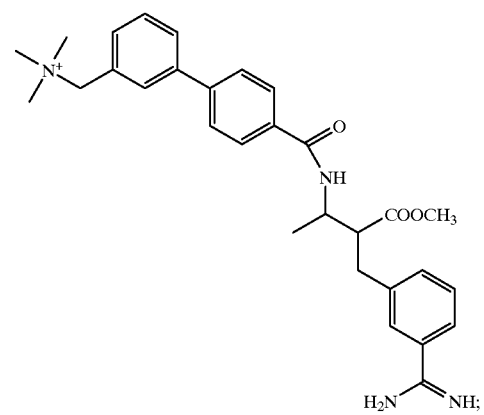
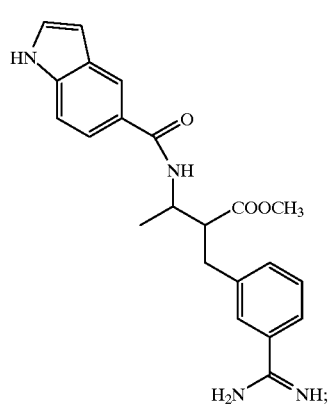
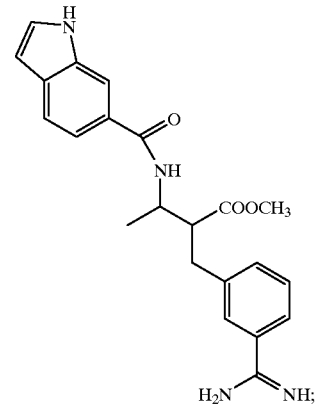

-continued
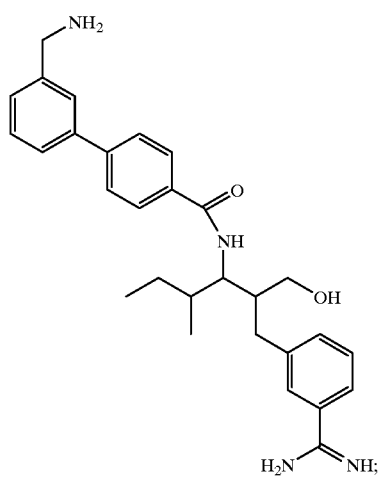
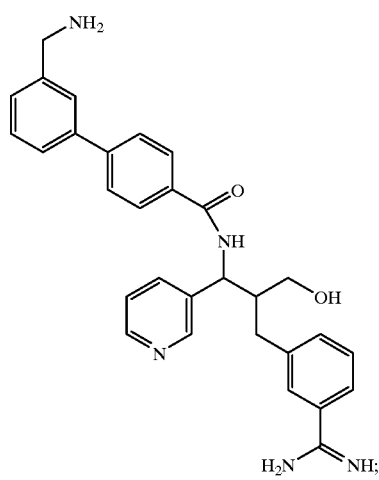
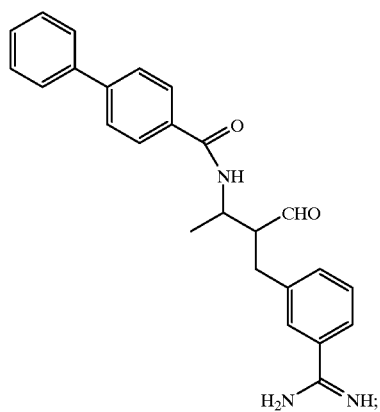
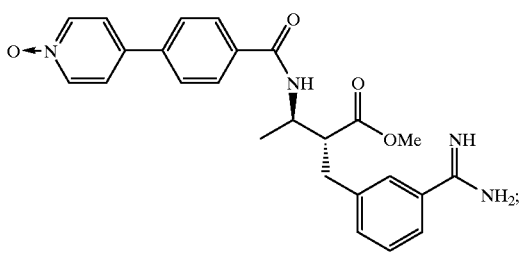
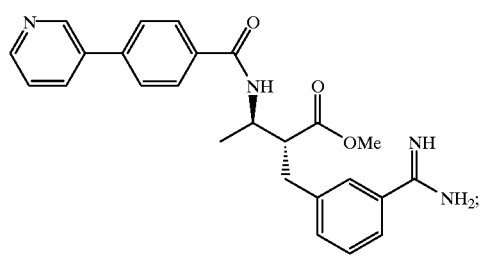
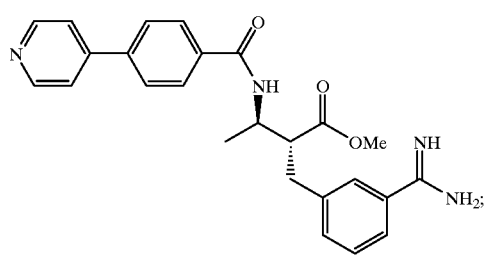
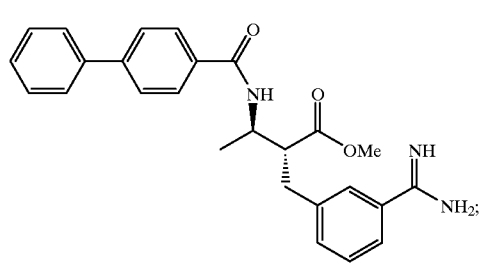
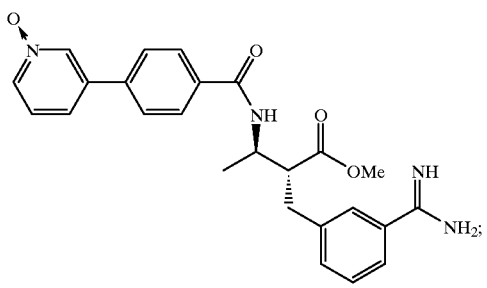

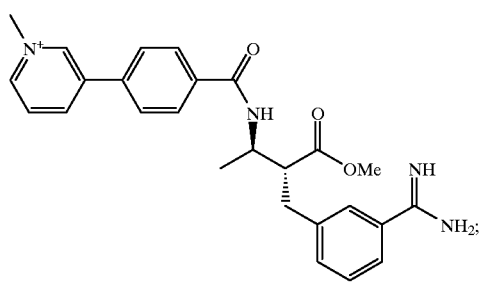
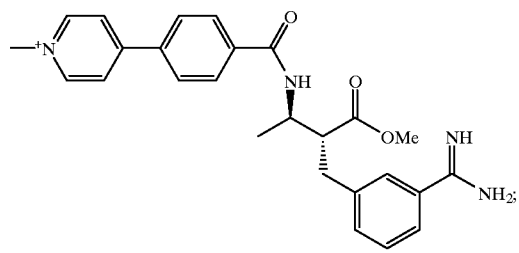
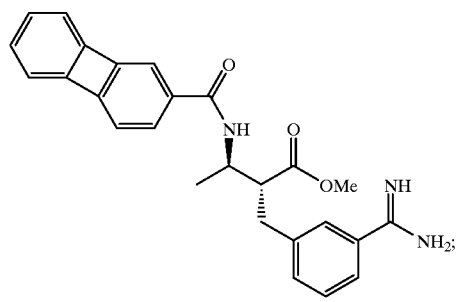
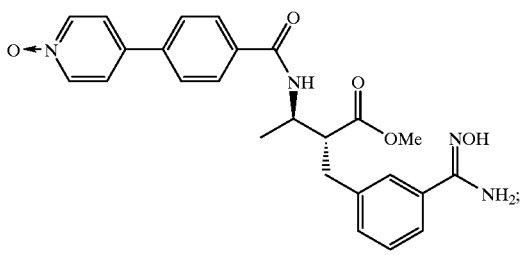
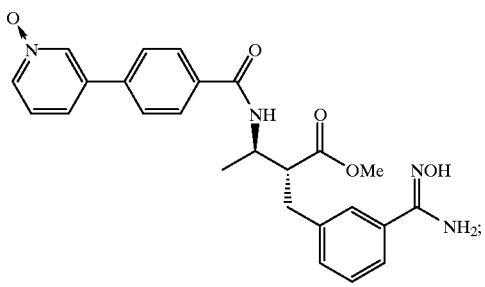
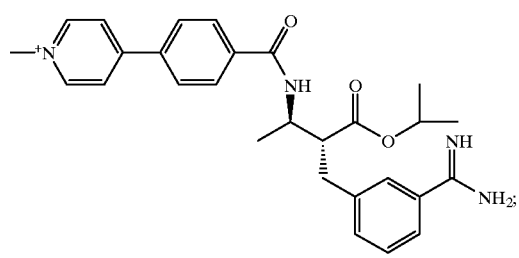
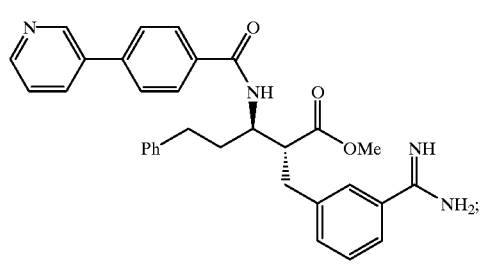
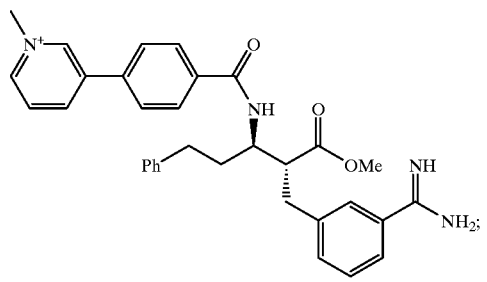
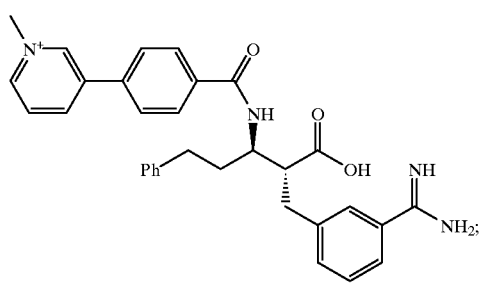
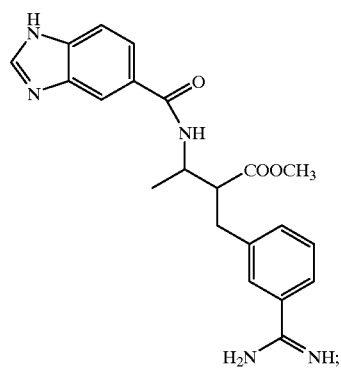

31
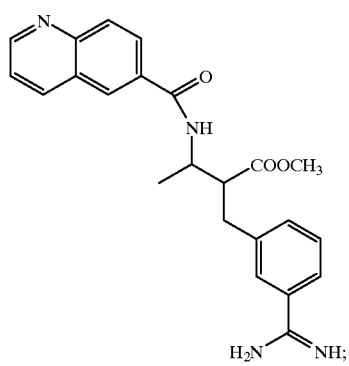
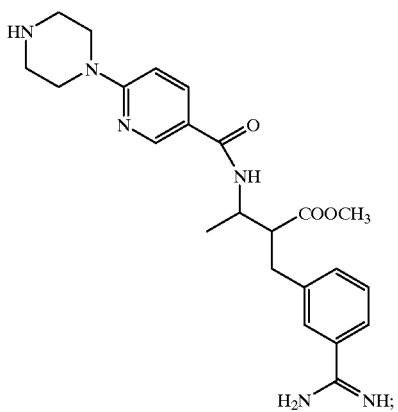
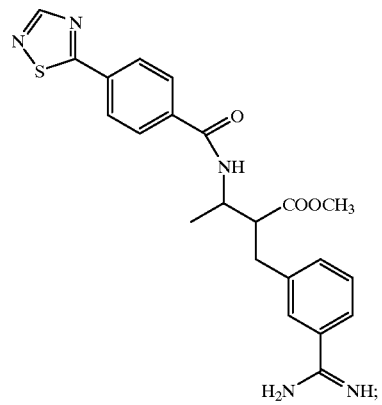
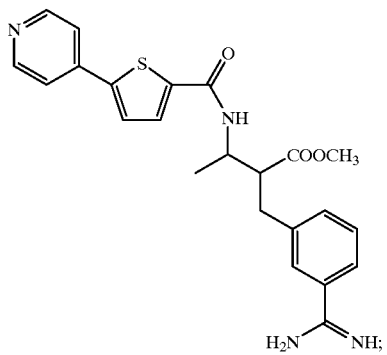
32
-continued
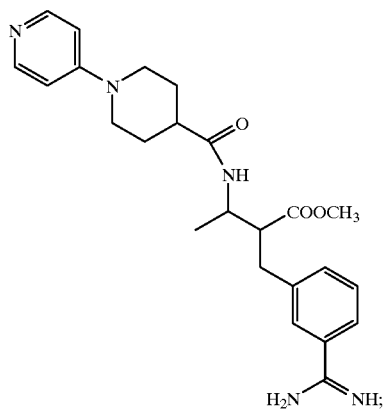
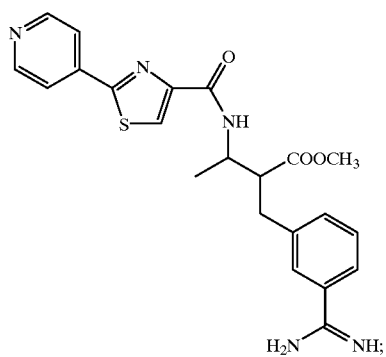
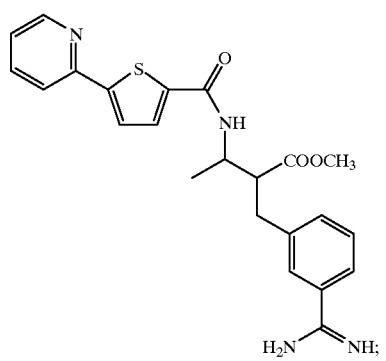
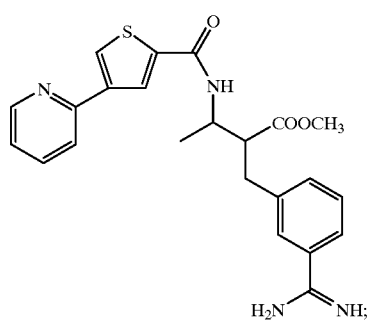

33
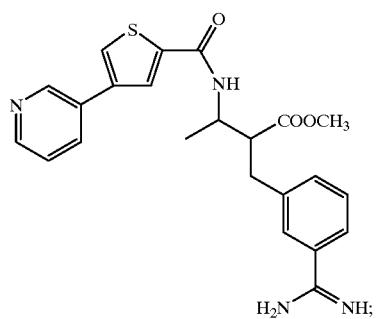
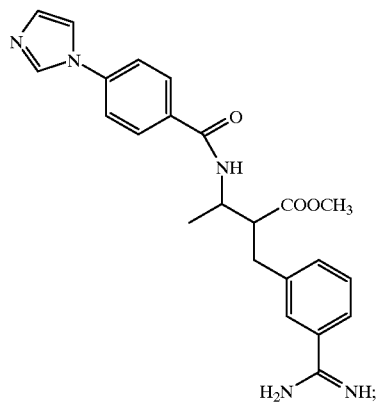
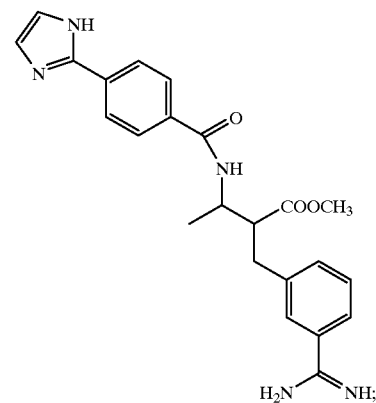
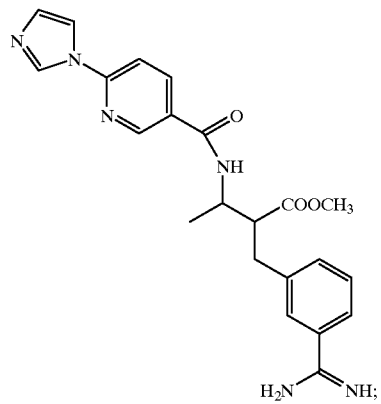
34
-continued
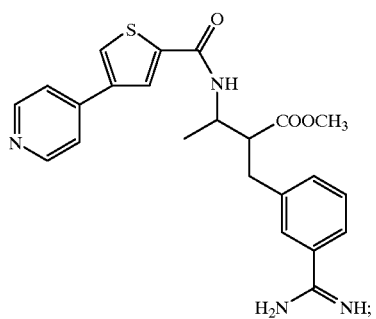
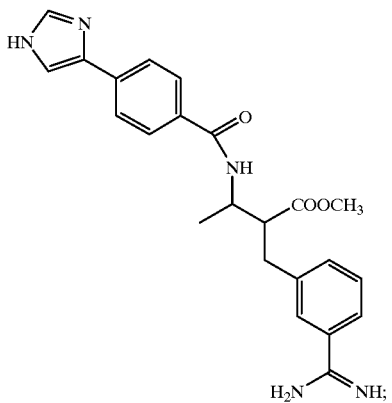
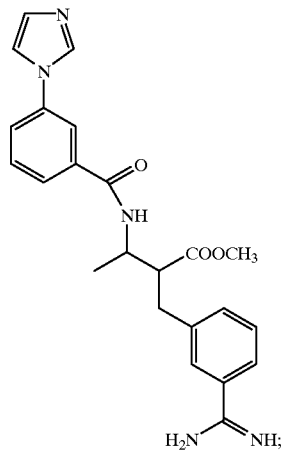
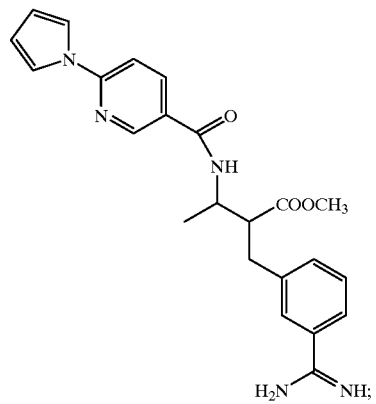

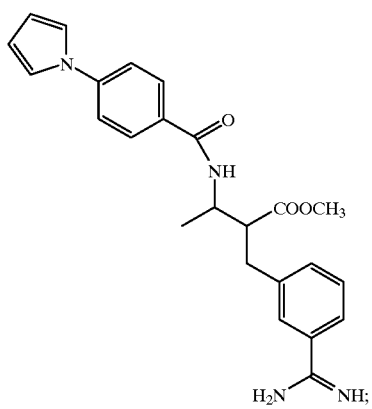
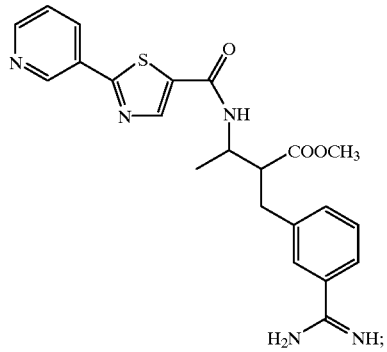
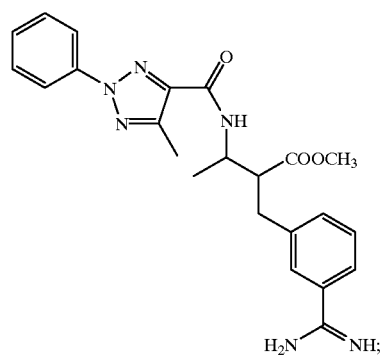
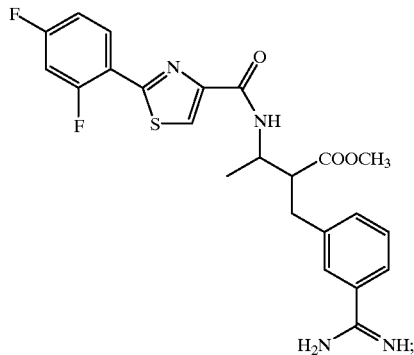
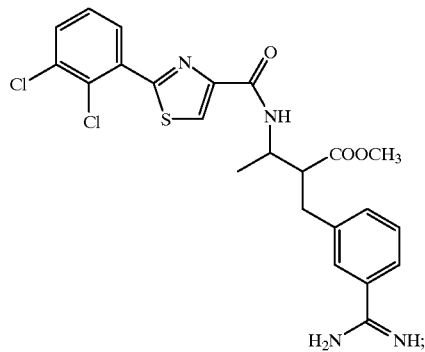
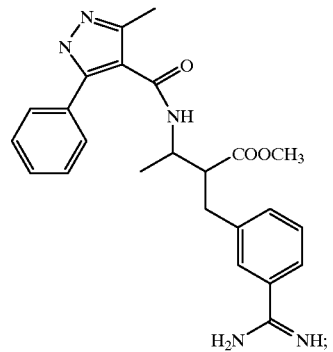
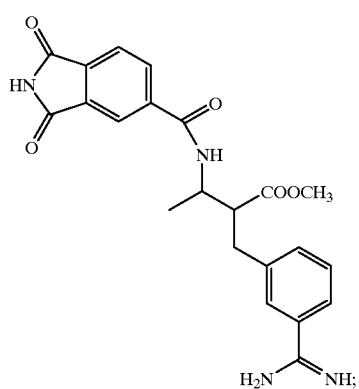
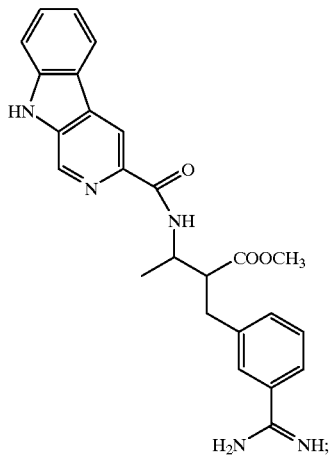

-continued
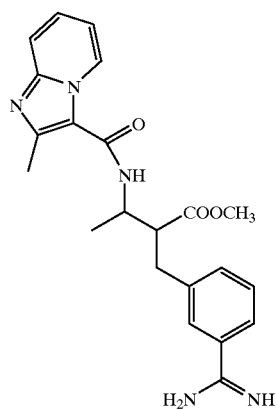
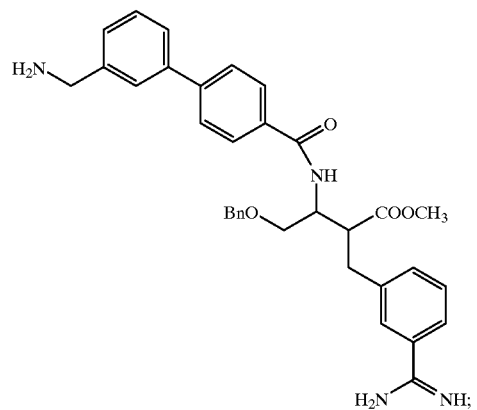
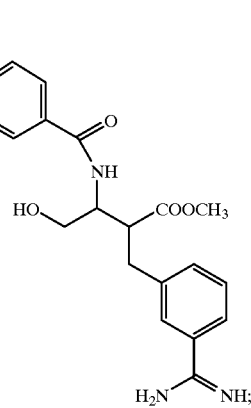
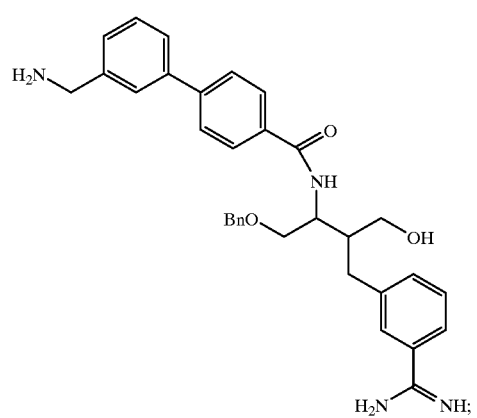
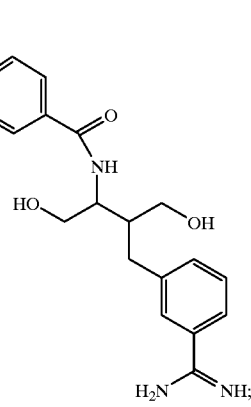
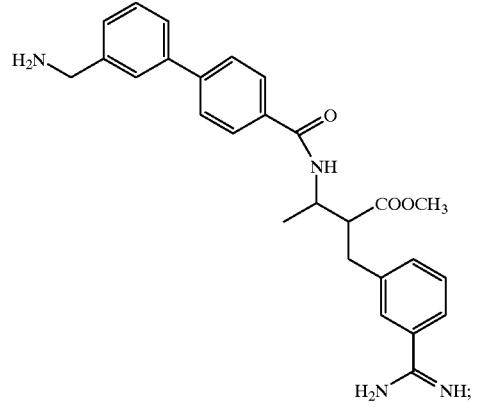
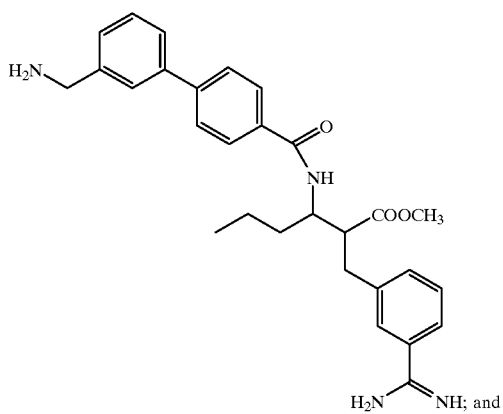
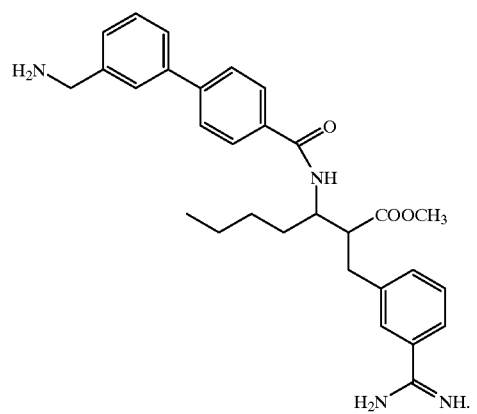

More preferred species according to the invention are compounds 188, 209–211, 213, 217, 231, 276–277, 280–281, 297 and 300–301.

Compounds of Formula I may be prepared by the application or adaptation of known methods, by which is meant methods used heretofore or described in the literature, or by methods according to this invention herein.

Scheme A exemplifies a general method for preparing intermediates for use in preparing compounds of formula I according to the invention.

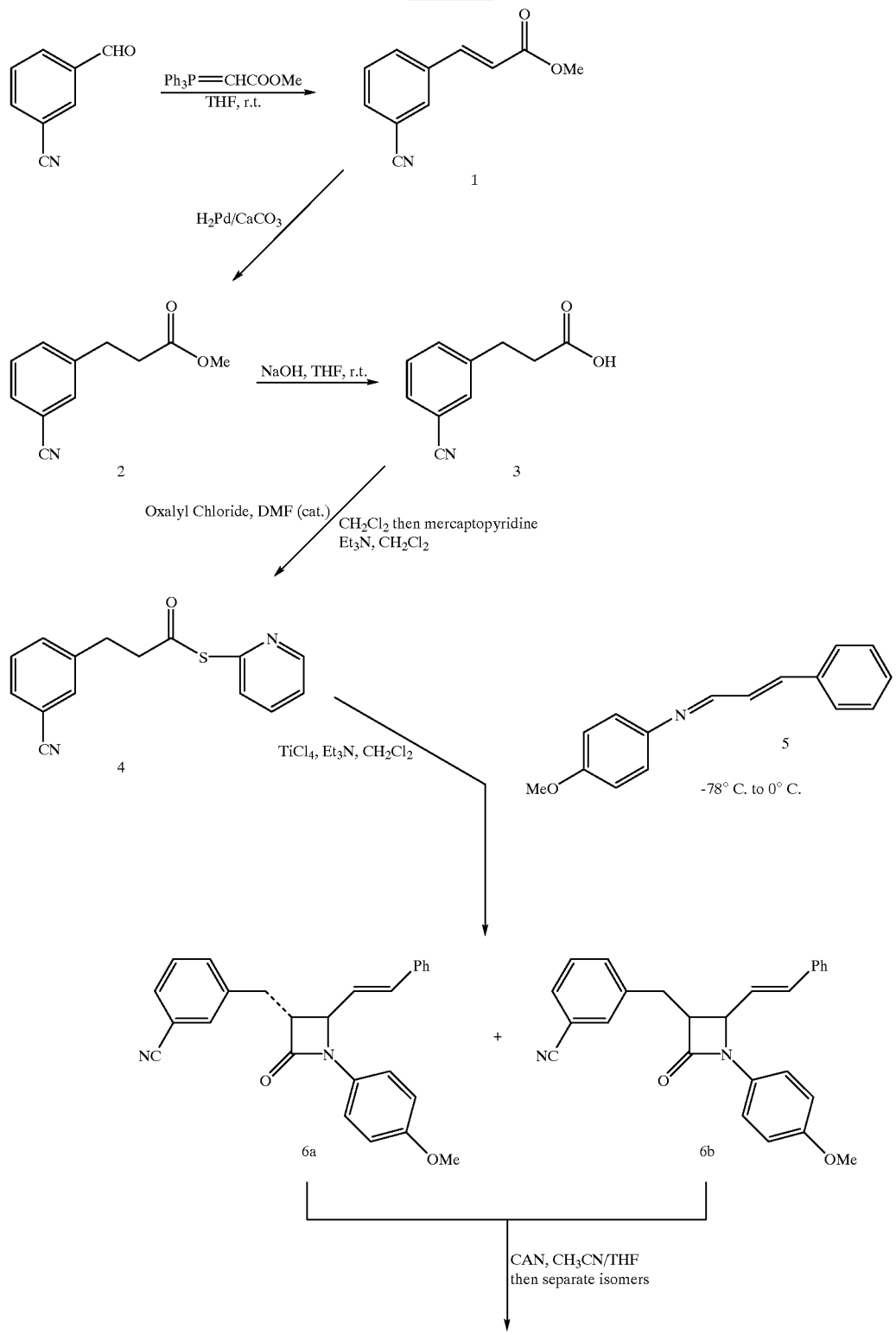

-continued
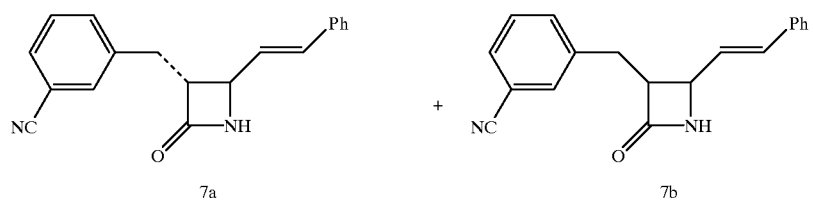
Scheme B exemplifies a general method for converting the intermediates prepared according to Scheme A to compounds of formula I according to the invention.
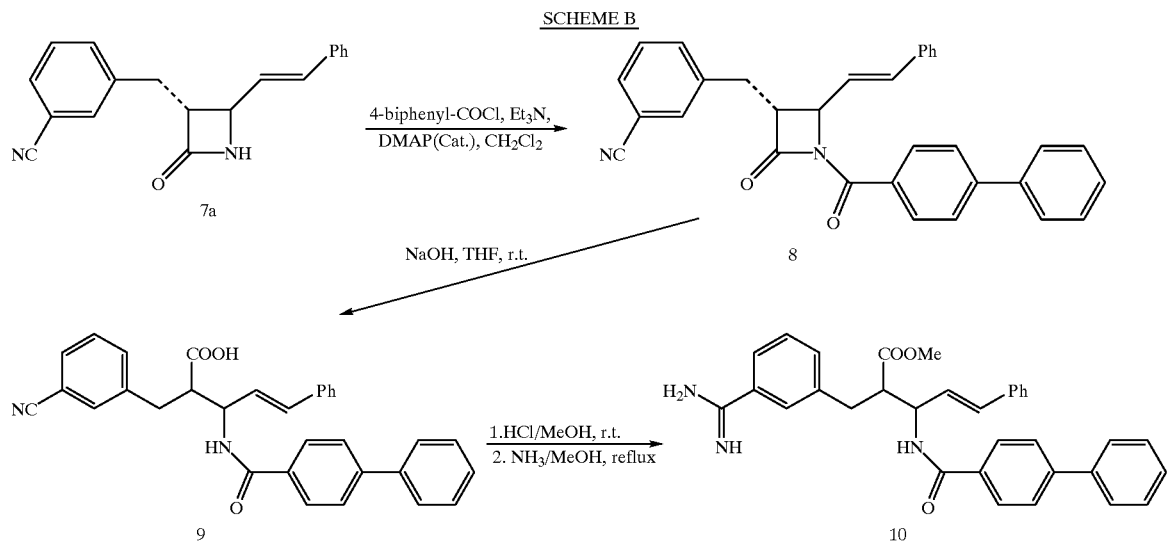
Scheme C exemplifies a general method for effecting interconversions between compounds of formula I according to the invention.

SCHEME C

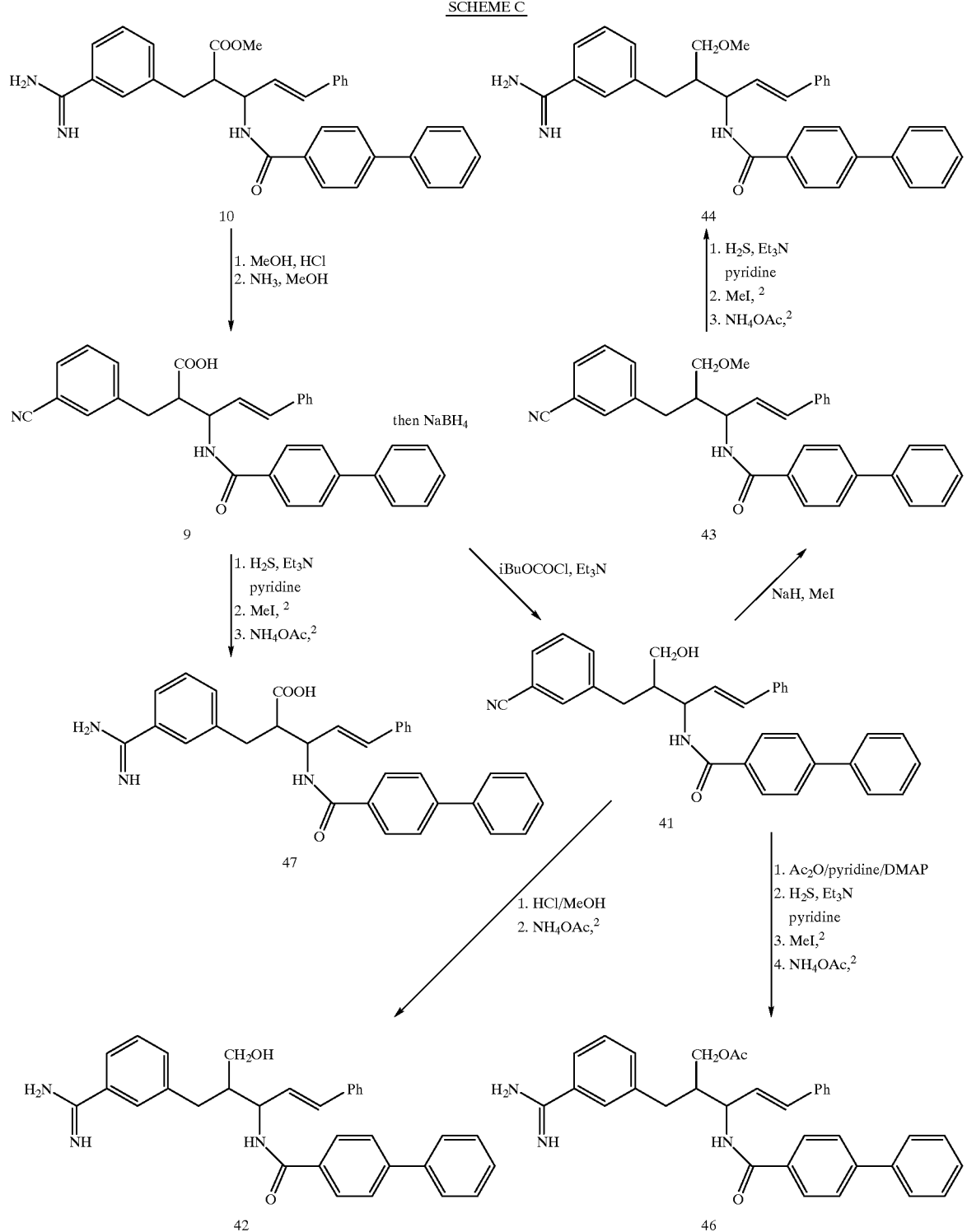

In addition, the compounds of formula 1 wherein $R_3$ is hydroxymethyl may be converted to the corresponding thiolmethyl compounds by treating the alcohol with an alkyl or aryl sulfonyl halide and displacing the alkyl or aryl sulfonate with NaSH. the thiolmethyl compounds may then be alkylated or acylated to give other compounds within the scope of the invention.

Scheme D exemplifies a general method for converting a nitrile intermediate to a compound of formula I and additional general methods for effecting interconversions between compounds of formula I according to the invention.

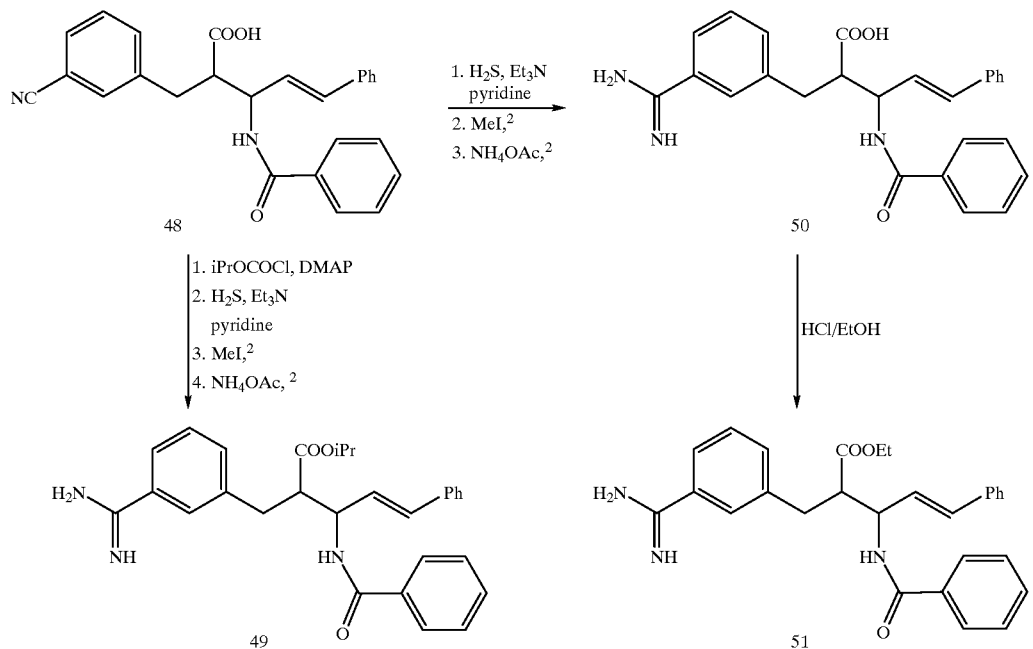
Scheme E exemplifies an additional general method for effecting interconversions between compounds of formula I according to the invention.
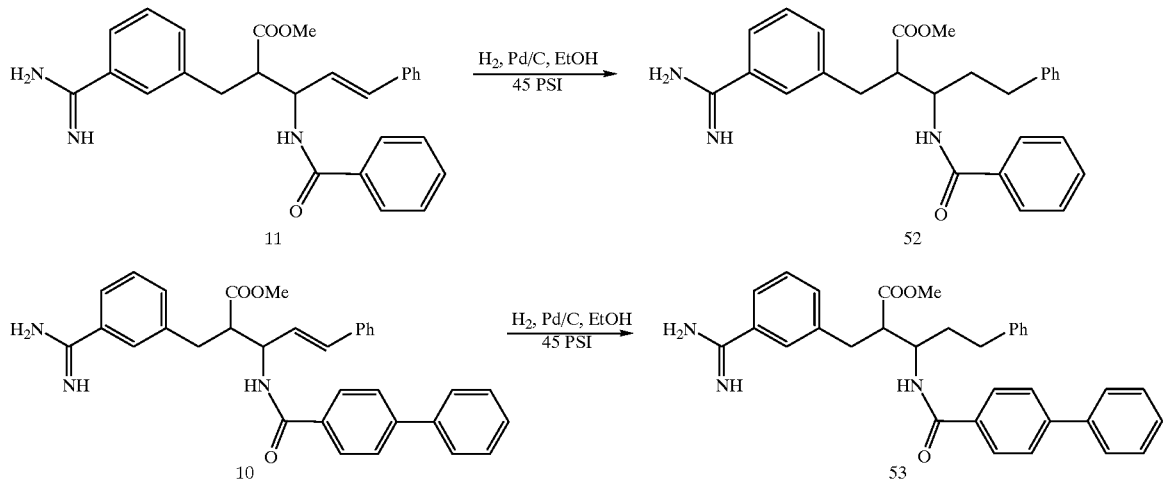

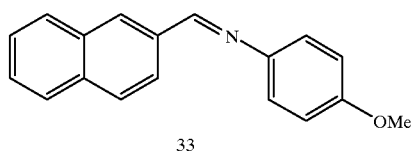
33
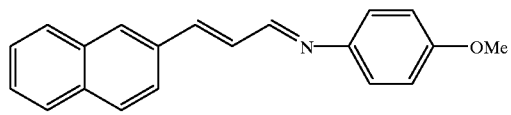
34
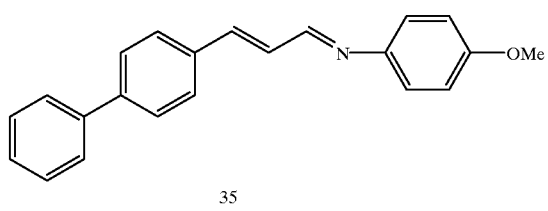
35
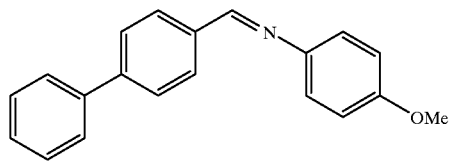
36
Scheme F exemplifies a general method for preparing compounds according to the present invention wherein $R_4$ of formula I is optionally substituted phenethyl.
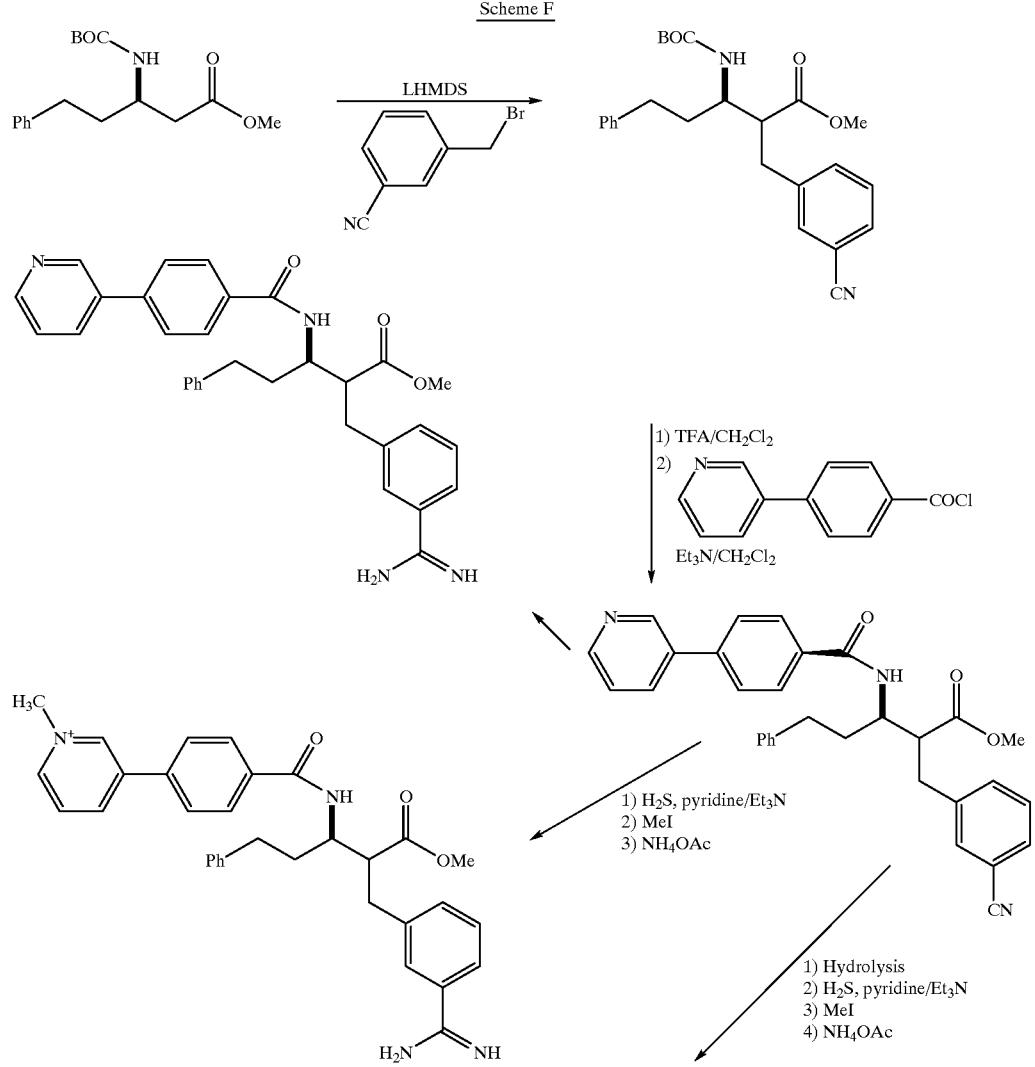

-continued
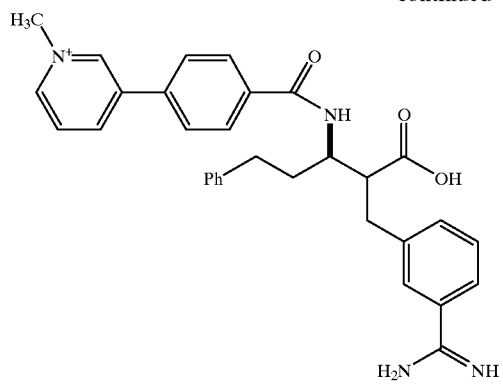
Scheme G exemplifies a general method for preparing compounds according to the present invention wherein $R_4$ of formula I is methyl.
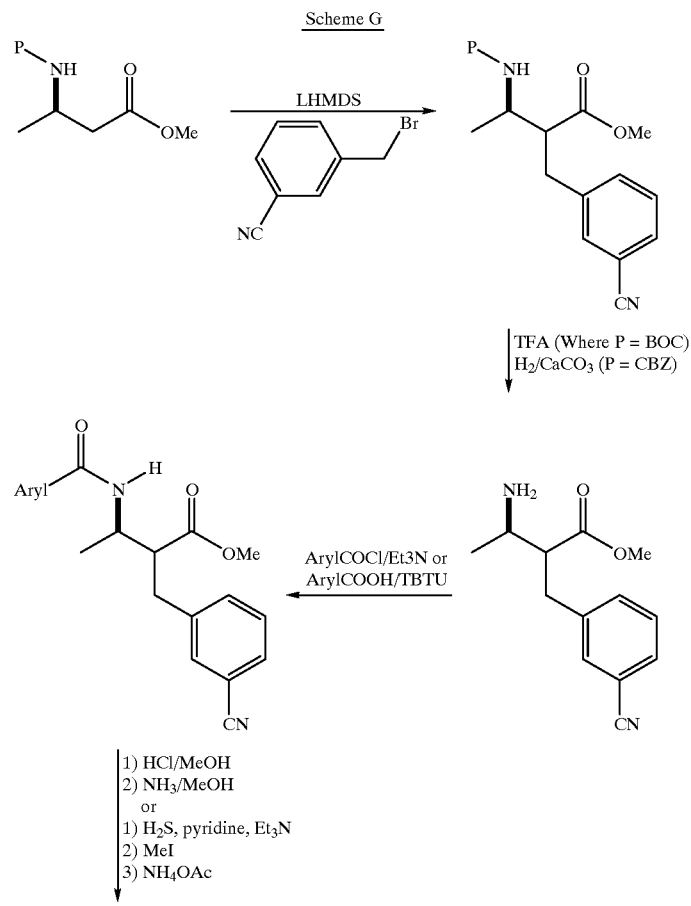

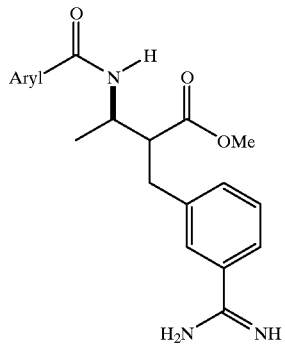

It will be apparent to those skilled in the art that certain compounds of formula I can exhibit isomerism, for example geometrical isomerism, e.g., E or Z isomerism, and optical isomerism, e.g., R or S configurations. Geometrical isomers include the cis and trans forms of compounds of the invention having alkenyl moieties. Individual geometrical isomers and stereoisomers within formula I, and their mixtures, are within the scope of the invention.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on Factor Xa inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-B-hydroxynaphthoates, gentisates, mesylates, isethionates and di-p-toluoyltartratesmethanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on Factor Xa inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)-aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g. hydrochloric acid.

Pharmaceutically accetable salts also include quaternary lower alkyl ammonium salts. The quaternary salts are prepared by the exhaustive alkylation of basic nitrogen atoms in compounds, including nonaromatic and aromatic basic nitrogen atoms, according to the invention, i.e., alkylating the non-bonded pair of electrons of the nitrogen moieties with an alkylating agent such as methylhalide, particularly methyl iodide, or dimethyl sulfate. Quaternarization results in the nitrogen moiety becoming positively charged and having a negative counter ion associated therewith.

As will be self-evident to those skilled in the art, some of the compounds of this invention do not form stable salts. However, acid addition salts are most likely to be formed by compounds of this invention having a nitrogen-containing heteroaryl group and/or wherein the compounds contain an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

The starting materials and intermediates are prepared by the application or adaptation of known methods, for example methods as described in the Reference Examples or their obvious chemical equivalents, or by methods according to this invention.

The present invention is further exemplified but not limited by the following illustrative examples which illustrate the preparation of the compounds according to the invention.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad.

EXAMPLE 1

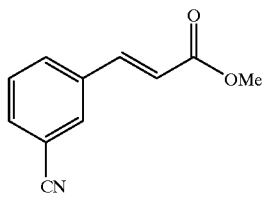

Compound 1

To a stirred solution of 3-cyanobenzaldehyde (20 g; 153 mmol) in 100 mL of dry THF under $N_2$ at room temperature is added methyl (triphenylphosphoranylidene) acetate (61.2 g; 183 mmol). The mixture is allowed to stir overnight at room temperature and then concentrated in vacuo. The crude residue is chromatographed (40% EtOAc:Hexane) to give 27.3 g (96%) of the acrylate 1.

$^1$H NMR (CDCl$_3$, d): 7.43–7.8 (m, 5H), 6.47 (d, J=12 Hz, 1H), 3.8 (s, 3H).

EXAMPLE 2

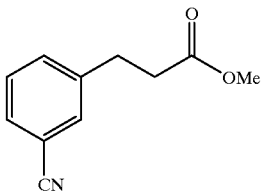

Compound 2

To a stirred solution of compound 1 (27.33 g) in 150 mL of EtOH is added 2 g of 10% Pd/CaCO$_3$. The resulting mixture is hydrogenated under 45 PSI H$_2$ on a Parr shaker for 8 hours at room temperature. The mixture is then filtered through a plug of celite and the filtrate concentrated in vacuo to give 26.93 g (98%) of 2 as a clear oil.

$^1$H NMR (CDCl$_3$, d): 7.33–7.72 (m, 4H), 3.66 (s, 3H), 2.97 (t, J=7.8 Hz, 2H) 2.62 (t, J=7.8 Hz, 2H).

EXAMPLE 3

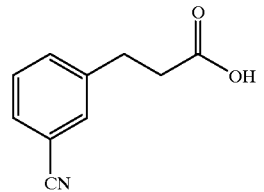

Compound 3

To a stirred solution of compound 2 (16.8 g; 89 mmol) in 200 mL of THF:MeOH (2:1) at room temperature is added 9 mL of 10 N NaOH solution dropwise. After 2 h, most of the solvent is removed in vacuo and 30 mL of 5N HCl is added. The resulting mixture is extracted several times with EtOAc. The combined extracts are dried (MgSO$_4$), filtered and concentrated to give 9.8 g (63%) of pure acid 3 as a white solid.

$^1$H NMR (CDCl$_3$, d): 7.35–7.55 (m, 4H), 2.98 (t, J=7.9 Hz, 2H), 2.7 (t, J=7.9 Hz, 2H).

EXAMPLE 4

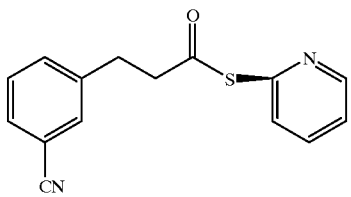
Compound 4

To a stirred solution of the carboxylic acid 3 (8.2 g; 47 mmol) and DMF (0.5 mL) in dry $CH_2Cl_2$ under $N_2$ at room temperature is added oxalyl chloride (6.1 mL; 70 mmol) dropwise. After 1 hour, gas evolution ceased and the solvent and excess oxalyl chloride is removed in vacuo. The residue is redissolved in 100 mL of dry $CH_2Cl_2$ and cooled to 0° C. Mercaptopyridine (5.6 g; 50 mmol) is added followed by triethylamine (7.9 mL; 56 mmol). The mixture is allowed to warm to r.t. and stirred for 1 hour. The mixture is diluted with $CH_2Cl_2$ and washed with 1 N NaOH. The organic layer is dried (MgSO4), filtered and concentrated. The residue is chromatographed (eluent=50% EtOAc:Hexane) to give 5.12 g (84%) of the thioester 4 as a yellow oil.

$^1$H NMR ($CDCl_3$, d): 8.63 (d, J=9 Hz,1H), 7.7–7.8 (m,1H), 7.27–7.62 (m, 6H), 3.05 (s, 4H).

EXAMPLE 5

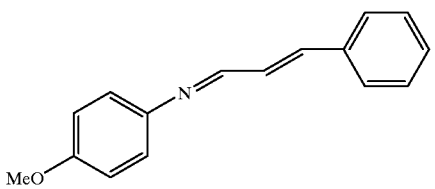
Compound 5

Added $MgSO_4$ (19.55 g; 162 mmol) to a stirred solution of cinnamaldehyde (10.2 mL; 81 mmol) and p-anisidine (10 g; 81 mmol) in 200 mL of $CH_2Cl_2$ under $N_2$ at 0° C. After 4 hours, the mixture is filtered and the filtrate concentrated to give 18.87 g (98%) of the imine compound 5 as a gold: brown solid.

$^1$H NMR ($CDCl_3$, d): 8.28 (m, 1H), 7.52 (m, 2H), 7.38 (m, 3H), 7.2 (m, 2H), 7.12 (m, 2H), 6.93 (m, 2H), 3.82 (s, 3H).

EXAMPLE 6

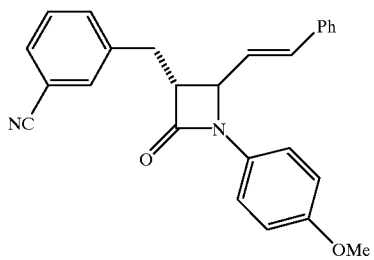
Compound 6

To a stirred solution of the thioester 5 (7 g; 26 mmol) in dry $CH_2Cl_2$ (120 mL) under $N_2$ at −78° C. is added $TiCl_4$ solution (26.1 mL of 1 M solution in $CH_2Cl_2$). After 15 minutes, triethylamine (3.6 mL; 26 mmol) is added dropwise. The resulting mixture is allowed to stir for ½ h at −78° C. and then a solution of imine 1 (4.42 g; 19 mmol in 20 mL $CH_2Cl_2$) is added dropwise. The mixture is then warmed to 0° C. After 1.5 hours at this temperature, the mixture is quenched with saturated $NaHCO_3$ solution and partitioned with water. The organic layer is washed with 1 N NaOH, dried ($MgSO_4$) and concentrated in vacuo. The crude product is chromatographed (eluent=40% EtOAc:hexane) to give 2.42 g (32%) of a 5:1 mixture of trans-/cis-b-lactam 6a and 6b as a gum.

Major trans-Isomer 6a $^1$H NMR ($CDCl_3$, d): 7.2–7.6 (m, 11H), 6.8 (d, J=11 Hz, 2H), 6.65 (d, J=15.8 Hz, 1H), 6.2 (dd, J=15.8, 7.9 Hz, 1H), 4.32 (m, 1H), 3.72 (s, 3H), 3–3.42 (m, 3H).

EXAMPLE 7

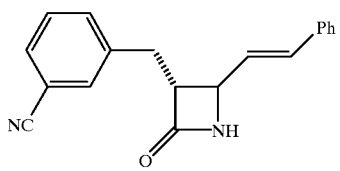
Compound 7

To a stirred solution of 6a, 6b (1.5 g; 3.8 mmol) in 60 mL of THF/$CH_3CN$ (1/3) at −20° C. is added a solution of ceric ammonium nitrate (CAN, 3.13 g; 5.7 mmol in 10 mL water). After 15 minutes, another 1.5 g of CAN in 5 mL of water is added. After a further 30 minutes, the mixture is quenched with saturated $NaHCO_3$ solution and allowed to come to room temperature. The resulting suspension is filtered through a bed of celite, washing the celite pad several times with $CH_2Cl_2$ (total ca. 200 mL). The filtrate layers are separated and the organic layer dried ($MgSO_4$), filtered and concentrated in vacuo. The crude product is chromatographed (eluent=60% EtOAc:hexane) to give 476 mg (43%) of pure trans-isomer 7a together with 85 mg of a mixture of cis-7b and trans-7a isomers.

Major trans-isomer 7a $^1$H NMR ($CDCl_3$, d): 7.17–7.65 (m, 9H), 6.52 (d, J=15.8 Hz, 1H), 6.25 (s, 1H), 6.14 (dd, J=15.8, 7.9 Hz, 1H), 3.97 (m, 1H), 3–3.33 (m, 3H).

Minor cis-isomer 7b $^1$H NMR ($CDCl_3$, d): 7.21–7.52 (m, 9H), 6.62 (d, J=15.8 Hz, 1H), 6.45 (s, 1H), 6.1 (dd, J=15.8, 7.9 Hz, 1H), 4.46 (m, 1H), 3.7 (m, 1H), 3.02–3.17 (m, 1 H), 2.8–2.93 (m,1H).

EXAMPLE 8

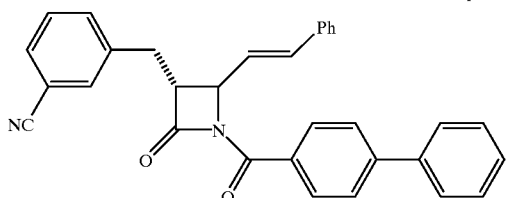
Compound 8

To a stirred solution of the trans-β-lactam 7a in dry $CH_2Cl_2$ under $N_2$ at r.t. is added triethylamine (4.04 mL; 29 mmol) dropwise. Biphenylcarbonyl chloride (5.05 g; 23.2 mmol) is then added followed by DMAP (50 mg). After 30 minutes the mixture is diluted with $CH_2Cl_2$ and washed with 1 N HCl. The organic layer is then dried ($Na_2SO_4$), filtered and concentrated. The crude product is chromatographed (eluent 30% EtOAc:Hexane) gave 2.19 g (81%) of the product 8 as a solid.

$^1$H NMR (CDCl$_3$, d): 8.06 (m, 2H), 7.2–7.75 (m, 16H), 6.67 (d, J=15.8, Hz, 1H), 6.23 (dd, J=15.8, 7.9 Hz, 1H), 4.63 (m, 1H), 3.46 (m, 1H), 3.1–3.3 (m, 2H).

EXAMPLE 9

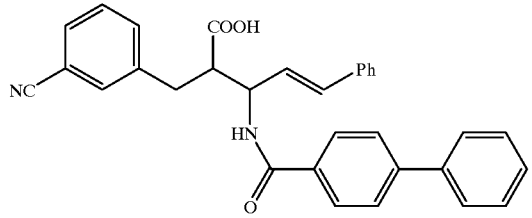

Compound 9

To a stirred solution of the β-lactam 8 (2.19 g; 4.7 mmol) in 50 mL of THF at r.t. is added 1 N NaOH solution (13.6 mL) dropwise. After 2 hours, most of the THF is removed in vacuo and 20 mL of 1 N HCl is added. The resulting mixture is extracted with EtOAc. The extract is dried (Na$_2$SO$_4$), filtered and concentrated in vacuo. The crude product is purified by RPHPLC (CH$_3$CN: water, 0.1% TFA, 40–100 gradient) and the fractions containing product are lyophilized to give 1.1 g (50%) of carboxylic acid 9 as a white solid.

$^1$H NMR (CDCl$_3$, d): 7.18–7.97 (m, 18H), 6.61 (d, J=15.8 Hz, 1H), 6.2 (dd, J=15.8, 7.9 Hz, 1H), 5.14 (m, 1H), 3–3.22 (m, 3H).

EXAMPLE 10

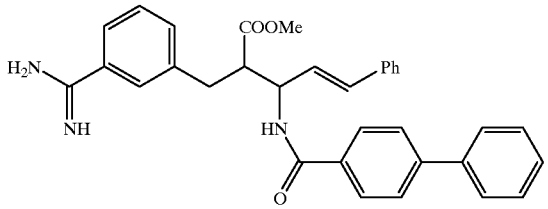

Compound 10

To a stirred solution of the carboxylic acid 9 (105 mg; 0.22 mmol) in 3 mL of dry MeOH at r.t. is added molecular sieves (ca. 50 mg). Gaseous HCl is then bubbled in for ca. 2 minutes. The mixture is then allowed to stir over night at room temperature and then concentrated under a stream of N$_2$. A solution of NH$_3$ in MeOH (3 mL of 7 N solution) is then added to the residue and the mixture refluxed for 1.5 hours, allowed to cool and the solvent removed in vacuo. The residue is purified by RPHPLC (CH$_3$CN: water: 0.1% TFA, 40–100 gradient) and the fractions containing product are lyophilized to give 73 mg (53%) of the product 10 as a white solid.

$^1$H NMR (DMSO-d$_6$, d): 8.7 (d, J=8.6Hz, 1H), 7.92 (d, J=9 Hz, 2H), 7.78 (d, J=9 Hz, 2H), 7.75–7.21 (m, 14H), 6.67 (d, J=16.1 Hz, 1H), 6.4 (dd, J=16.1, 7.8 Hz, 1H), 4.98 (dd, J=16.1, 7.8 Hz, 1H), 3.46 (s, 3H), 3.25–3.18 (m, 1H), 3.05–2.88 (m, 2H).

EXAMPLE 11

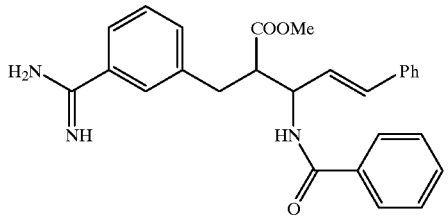

Compound 11

This compound is prepared in a manner similar to compound 10 above starting from imine 5 and thioester 4. Benzoyl chloride is substituted for 4-biphenylcarbonyl chloride in the β-lactam acylation step. The final product 11 is purified by reverse phase HPLC (CH$_3$CN:H$_2$O, 0.1% TFA) and lyophilized.

$^1$H NMR (MeOH-d$_4$, d): 8.61 (d, J=11.3 Hz, 1H), 7.83 (d, J=7.5 Hz, 2H), 7.15–7.67 (m, 14H), 6.67 (d, J=15.8 Hz, 1H), 6.3 (dd, J=15.8, 7.9 Hz, 1H), 4.98 (m, 1H), 3.55 (s, 3H), 3.27 (m, 1H), 3.1 (m, 2H).

EXAMPLE 12

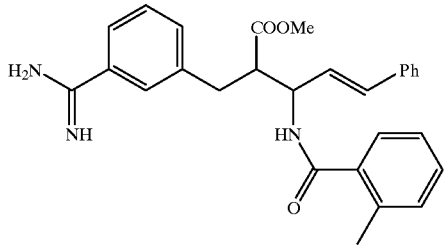

Compound 12

This compound is prepared in a manner similar to compound 10 above starting from imine 5 and thioester 4. o-Toluoyl chloride is substituted for 4-biphenylcarbonyl chloride in the β-lactam acylation step. The final product 12 is purified by reverse phase HPLC (CH$_3$CN:H$_2$O, 0.1% TFA) and lyophilized.

$^1$H NMR (DMSO-d$_6$, d): 9.3 (s, 1H), 9.15 (s, 1H), 8.7 (d, J=7.6 Hz, 1H), 7.7 (d, J=8 Hz, 2H), 7.6 (d, J=9 Hz, 2H), 7.2–7.6 (m, 12H), 6.9 (d, J=8 Hz, 1 H), 6.6 (d, J=15 Hz, 1H), 6.35 (dd, J=15, 6 Hz, 1H), 4.9 (dd, J=15, 6 Hz, 1H), 3.55 (s, 3H), 3.2–3.3 (m, 1H), 2.8–3 (m, 1H), 2.3 (s, 3H).

EXAMPLE 13

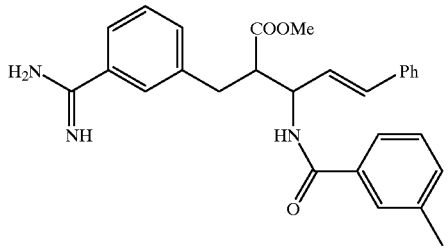

Compound 13

This compound is prepared in a manner similar to compound 10 above starting from imine 5 and thioester 4. m-Toluoyl chloride is substituted for 4-biphenylcarbonyl chloride in the β-lactam acylation step. The final product 13 is purified by reverse phase HPLC (CH$_3$CN:H$_2$O, 0.1% TFA) and lyophilized.

$^1$H NMR (DMSO-d$_6$, d): 9.3 (s, 1H), 9.2 (s, 1H), 8.7 (d, J=7.6 Hz, 1H), 7.7 (d, J=8 Hz, 2H), 7.6 (d, J=9 Hz, 2H), 7.2–7.6 (m, 12H), 6.9 (d, J=8 Hz, 6.6 (d, J=15 Hz, 1H), 6.35 (dd, J=15, 6 Hz, 1H), 4.9 (dd, J=16, 6 Hz, 1H), 3.6 (s, 3H), 3.2–3.3 (m, 1H), 2.8–3 (m, 1H), 2.35 (s, 3H).
Other compounds prepared in a manner similar, using the appropriate starting material, include the following:
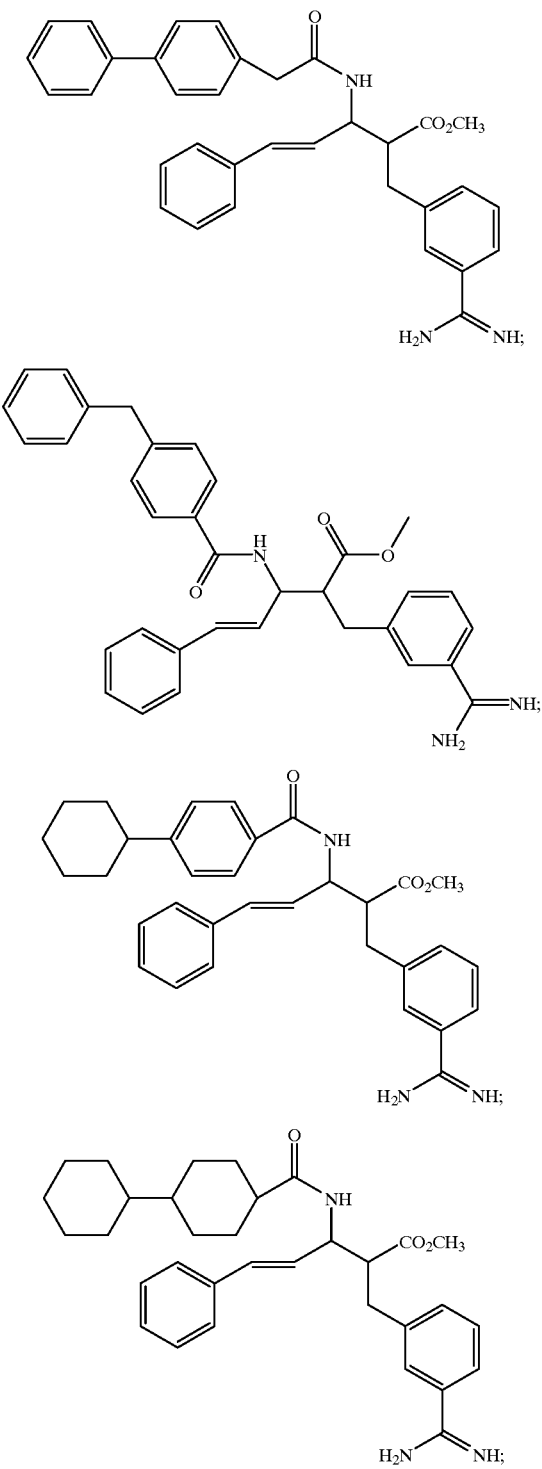
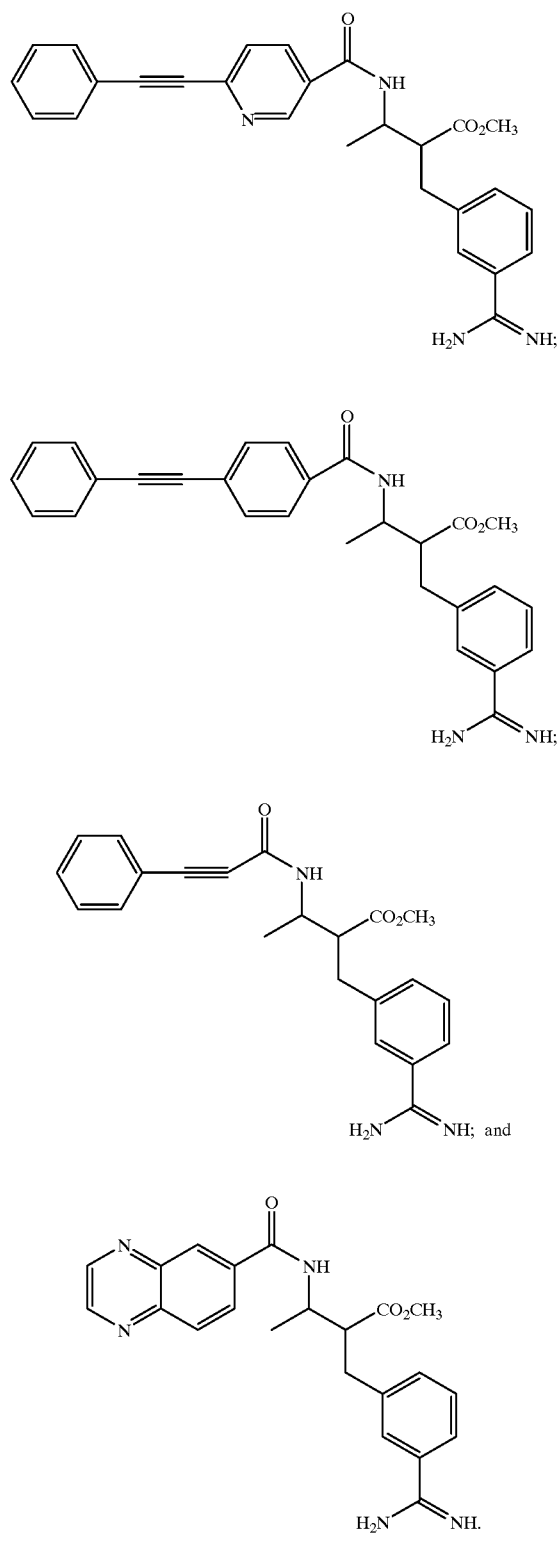

EXAMPLE 14

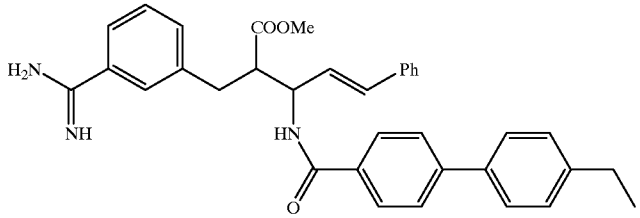

Compound 14

This compound is prepared in a manner similar to compound 10 above starting from imine 5 and thioester 4. 4'-Ethyl-4-biphenylcarbonyl chloride is substituted for 4-biphenylcarbonyl chloride in the β-lactam acylation step. The final product 14 is purified by reverse phase HPLC (CH$_3$CN:H$_2$O, 0.1% TFA) and lyophilized.

$^1$H NMR (DMSO-d$_6$, d): 9.3 (s, 1H), 9.15 (s, 1H), 8.9 (d, J=7.6 Hz, 1H), 8.2 (d, J=8 Hz, 2H), 8 (d, J=9 Hz, 2H), 7.4–7.9 (m, 12H), 7.2 (d, J=8 Hz, 1H), 6.9 (d, J=15 Hz, 1H), 6.6 (dd, J=15, 6 Hz, 1H), 5.2 (dd, J=16, 6 Hz, 1H), 3.7 (s, 3H), 3.4–3.5 (m, 1H), 3.1–3.2 (m, 1H), 2.85 (q, 2H), 1.4 (t, 3H).

EXAMPLE 15

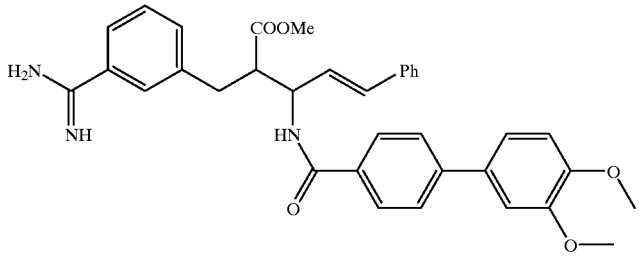

Compound 15

This compound is prepared in a manner similar to compound 10 above starting from imine 5 and thioester 4. 3',4'-Dimethoxy-4-biphenylcarbonyl chloride is substituted for 4-biphenylcarbonyl chloride in the β-lactam acylation step. The final product 15 is purified by reverse phase HPLC (CH$_3$CN:H$_2$O, 0.1% TFA) and lyophilized.

$^1$H NMR (DMSO-d$_6$, d): 9.5 (s, 1H), 9.3 (s, 1H), 8.9 (d, J=7.6 Hz, 1H), 8.1 (d, J=8 Hz, 2H), 7.9 (d, J=9 Hz, 2H), 7.8 (s, 2H), 7.4–7.7 (m, 11H), 7.25 (d, J=8 Hz, 1H), 6.6 (d, J=15 Hz, 1H), 6.4 (dd, J=15, 6 Hz, 1H), 4 (s, 3H), 3.9 (s, 3H), 3.7 (s, 3H), 3.4–3.5 (m, 1H), 3.2–3.4 (m, 1H).

EXAMPLE 16

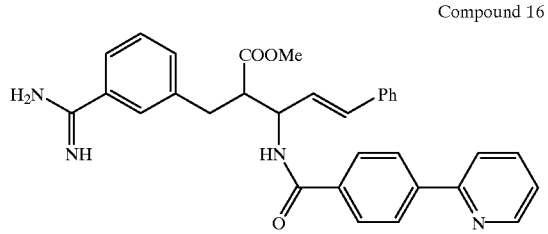

Compound 16

This compound is prepared in a manner similar to compound 10 above starting from imine 5 and thioester 4. 4-(2'-pyridyl) benzoyl chloride is substituted for 4-biphenylcarbonyl chloride in the β-lactam acylation step. The final product 16 is purified by reverse phase HPLC (CH$_3$CN:H$_2$O, 0.1% TFA) and lyophilized.

$^1$H NMR (DMSO-d$_6$, d): 9.5 (s, 1H), 9.3 (s, 1H), 8.9 (d, J=7.6 Hz, 1H), 8.8 (s, 1H), 8.4 (d, J=8 Hz, 2H), 8.3 (d, J=9 Hz, 1H), 8.1 (d, J=8 Hz, 2H), 7.9 (s, 2H), 7.4–7.8 (m, 10H), 7.4 (d, J=8 Hz, 1H), 6.9 (d, J=15 Hz, 1H), 6.6 (dd, J=15, 6 Hz, 1H), 5.2 (dd, J=16, 6 Hz, 1H), 3.7 (s, 3H), 3.4–3.5 (m, 1H), 3.2–3.4 (m, 1H).

EXAMPLE 17

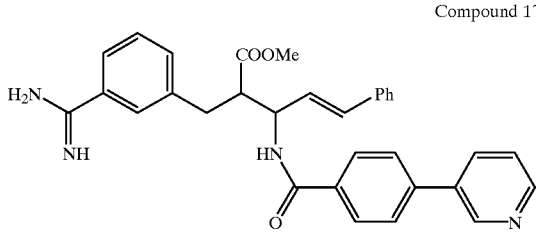

Compound 17

This compound is prepared in a manner similar to compound 10 above starting from imine 5 and thioester 4. 4-(3'-Pyridyl)benzoyl chloride is substituted for 4-biphenylcarbonyl chloride in the β-lactam acylation step. The final product 17 is purified by reverse phase HPLC ($CH_3CN:H_2O$, 0.1% TFA) and lyophilized.

$^1$H NMR (DMSO-$d_6$, d): 9.5 (s, 1H), 9.3 (s, 1H), 8.9 (d, J=7.6 Hz, 1H), 8.5 (s, 1H), 8.2 (d, J=8 Hz, 2H), 8.1 (d, J=9 Hz, 2H), 8 (d, J=8 Hz, 1H), 7.9 (s, 2H), 7.4–7.8 (m, 9H), 7.4 (d, J=8 Hz, 1H), 6.9 (d, J=15 Hz, 1H), 6.6 (dd, J=15, 6 Hz, 1H), 5.2 (dd, J=16, 6 Hz, 1H), 3.7 (s, 3H), 3.4–3.5 (m, 1H), 3.2–3.4 (m, 1H).

EXAMPLE 18

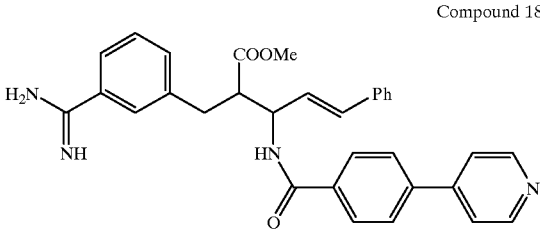

Compound 18

This compound is prepared in a manner similar to compound 10 above starting from imine 5 and thioester 4. 4-(4'-Pyridyl)benzoyl chloride is substituted for 4-biphenylcarbonyl chloride in the β-lactam acylation step. The final product 18 is purified by reverse phase HPLC ($CH_3CN:H_2O$, 0.1% TFA) and lyophilized.

$^1$H NMR (DMSO-$d_6$, d): 9.5 (s, 1H), 9.3 (s, 1H), 9 (d, J=7.6 Hz, 1H), 8.2 (s, 4H), 7.8 (s, 2H), 7.5–7.8 (m, 11H), 7.4 (d, J=8 Hz, 1H), 6.9 (d, J=15 Hz, 1H), 6.6 (dd, J=15, 6 Hz, 1H), 5.2 (dd, J=16, 6 Hz, 1H), 3.7 (s, 3H), 3.4–3.5 (m, 1H), 3.2–3.4 (m, 1H).

EXAMPLE 19

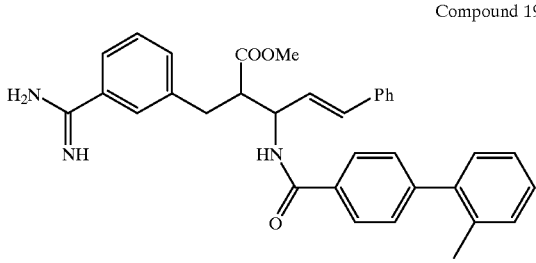

Compound 19

This compound is prepared in a manner similar to compound 10 above starting from imine 5 and thioester 4. 2'-Methyl4-biphenylcarbonyl chloride is substituted for 4-biphenylcarbonyl chloride in the β-lactam acylation step. The final product 19 is purified by reverse phase HPLC ($CH_3CN:H_2O$, 0.1% TFA) and lyophilized.

$^1$H NMR (DMSO-$d_6$, d): 9.25 (s, 1H), 9.03 (s, 1H), 8.71 (d, J=8.7 Hz, 1H), 7.86 (d, J=8 Hz, 2H), 7.61 (d, J=8 Hz, 2H), 7.6–7.12 (m, 13H), 6.67 (d, J=15.9 Hz, 1H), 6.42 (dd, J=15.9, 7.8 Hz, 1H), 5.0 (dd, J=16, 7.9 Hz, 1H), 3.32 (s, 3H), 3.3–3.15 (m, 1H), 3.11–2.9 (m, 2H), 2.21 (s, 3H).

EXAMPLE 20

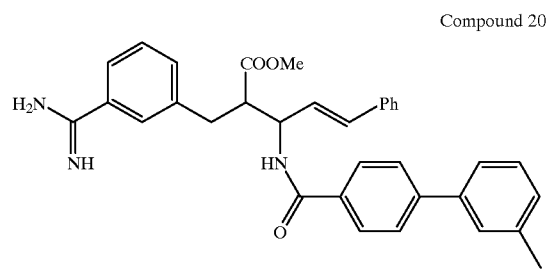

Compound 20

This compound is prepared in a manner similar to compound 10 above starting from imine 5 and thioester 4. 3'-Methyl-4-biphenylcarbonyl chloride is substituted for 4-biphenylcarbonyl chloride in the β-lactam acylation step. The final product 20 is purified by reverse phase HPLC ($CH_3CN:H_2O$, 0.1% TFA) and lyophilized.

$^1$H NMR (DMSO-$d_6$, d): 9.25 (s, 1H), 8.99 (s, 1H), 8.68 (d, J=8.7 Hz, 1H), 7.9 (d, J=9 Hz, 1H), 7.75 (d, J=9 Hz, 1H), 7.68–7.15 (m, 13H), 6.68 (d, J=15.9 Hz, 1H), 6.4 (dd, J=15.9, 7.8 Hz, 1H), 5.0 (dd, J=16, 7.9 Hz, 1H), 3.46 (s, 3H) 3.28–3.18 (m, 1H), 3.1–2.9 (m, 2H), 2.36 (s, 3H).

EXAMPLE 21

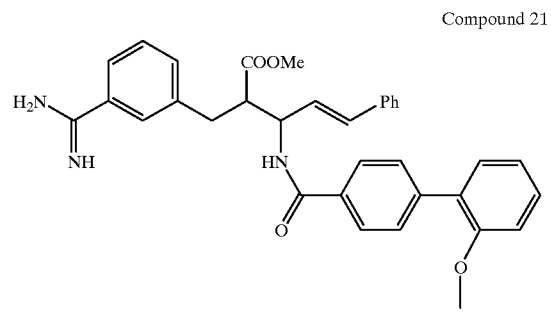

Compound 21

This compound is prepared in a manner similar to compound 10 above starting from imine 5 and thioester 4. 2'-Methoxy-4-biphenylcarbonyl chloride is substituted for 4-biphenylcarbonyl chloride in the β-lactam acylation step. The final product 21 is purified by reverse phase HPLC ($CH_3CN:H_2O$, 0.1% TFA) and lyophilized.

$^1$H NMR (DMSO-$d_6$, d): 9.25 (s, 1H), 9.03 (s, 1H), 8.76 (d, J=8.7 Hz, 1H), 7.83 (d, J=9.5 Hz, 2H), 7.65–6.95 (m, 15H), 6.64 (d, J=15.9 Hz, 1H), 6.4 (dd, J=15.9, 7.8 Hz, 1H), 4.99 (dd, J=16, 7.9 Hz, 1H), 3.75 (s, 3H), 3.46 (s, 3H), 3.3–3.17 (m, 1H), 3.1–2.9 (m, 2H).

EXAMPLE 22

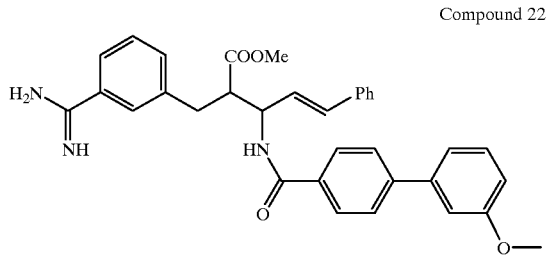

Compound 22

This compound is prepared in a manner similar to compound 10 above starting from imine 5 and thioester 4. 3'-Methoxy-4-biphenylcarbonyl chloride is substituted for 4-biphenylcarbonyl chloride in the β-lactam acylation step. The final product 22 is purified by reverse phase HPLC (CH$_3$CN:H$_2$O, 0.1% TFA) and lyophilized.

$^1$H NMR (DMSO-d$_6$, d): 9.23 (s, 1H), 8.96 (s, 1H), 8.69 (d, J=8.7 Hz, 1H), 7.9 (d, J=9.6 Hz, 2H), 7.68–7.18 (m, 12H), 6.96 (dd, J=9.6, 2 Hz, 1H), 6.64 (d, J=15.9 Hz, 1H), 6.39 (dd, J=15.9, 7.8 Hz, 1H), 4.98 (dd, J=16, 7.9 Hz, 1H), 3.81 (s, 3H), 3.47 (s, 3H), 3.28–3.17 (m, 1H), 3.08–2.86 (m, 2H).

EXAMPLE 23

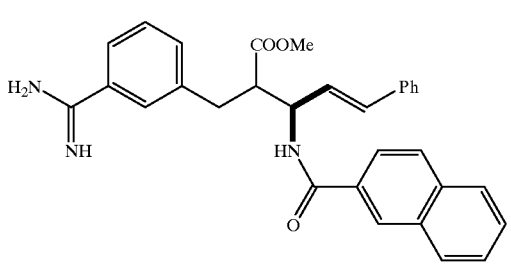

Compound 23

This compound is prepared in a manner similar to compound 10 above starting from imine 5 and thioester 4. 2-Naphthylcarbonyl chloride is substituted for 4-biphenylcarbonyl chloride in the β-lactam acylation step. The final product 23 is purified by reverse phase HPLC (CH$_3$CN:H$_2$O, 0.1% TFA) and lyophilized.

$^1$H NMR (DMSO-d$_6$, d): 9.24 (s, 1H), 9.02 (s, 1H), 8.83 (d, J=8.6 Hz, 1H), 8.4 (s, 1H), 8.08–7.85 (m, 4H), 7.68–7.2 (m, 12H), 6.68 (d, J=15.8 Hz, 1H), 6.34 (dd, J=15.8, 7.8 Hz, 1H), 5.03 (dd, J=15.8, 7.8 Hz, 1H), 3.46 (s, 3H), 3.28–3.2 (m, 1H), 3.13–2.95 (m, 2H).

EXAMPLE 24

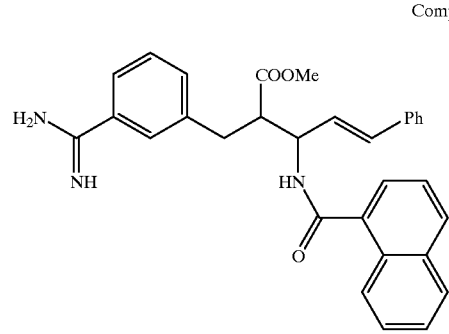

Compound 24

This compound is prepared in a manner similar to compound 10 above starting from imine 5 and thioester 4. 1-Naphthylcarbonyl chloride is substituted for 4-biphenylcarbonyl chloride in the β-lactam acylation step. The final product 24 is purified by reverse phase HPLC (CH$_3$CN:H$_2$O, 0.1% TFA) and lyophilized.

$^1$H NMR (DMSO-d$_6$, d): 9.27 (s, 1H), 9.11 (s, 1H), 8.88 (d, J=8.67 Hz, 1H), 8.18–8.07 (m, 1H), 8.05–7.9 (m, 2H), 7.7–7.2 (m, 13H), 6.73 (d, J=15.9 Hz, 1H), 6.4 (dd, J=15.9, 7.8 Hz, 1H), 5.07 (dd, J=16, 7.9 Hz, 1H), 3.52 (s, 3H), 3.28–3.17 (m, 1H), 3.12–2.95 (m, 2H).

EXAMPLE 25

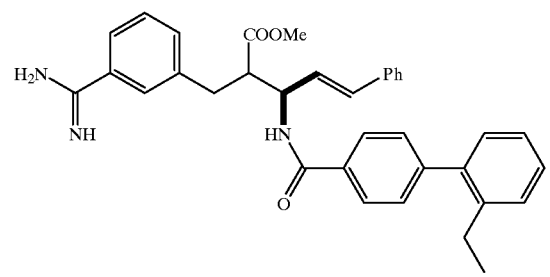

Compound 25

This compound is prepared in a manner similar to compound 10 above starting from imine 5 and thioester 4. 3'-Ethyl-4-biphenylcarbonyl chloride is substituted for 4-biphenylcarbonyl chloride in the β-lactam acylation step. The final product 25 is purified by reverse phase HPLC (CH$_3$CN:H$_2$O, 0.1% TFA) and lyophilized.

$^1$H NMR (DMSO-d$_6$, d): 9.25 (s, 1H), 9.05 (s, 1H), 8.68 (d, J=8.6 Hz, 1H), 7.88 (d, J=9 Hz, 2H), 7.76 (d, J=9 Hz, 2H), 7.62 (m, 2H), 7.55–7.15 (m, 11H), 6.66 (d, J=16 Hz, 1H), 6.4 (dd, J=16, 7.8 Hz, 1H), 4.96 (dd, J=16, 7.8 Hz, 1H), 3.47 (s, 3H), 3.3–3.18 (m, 1H), 3.1–2.88 (m, 2H), 2.67 (q, J=8.5 Hz, 2H), 1.22 (t, J=8.5 Hz, 3H).

EXAMPLE 26

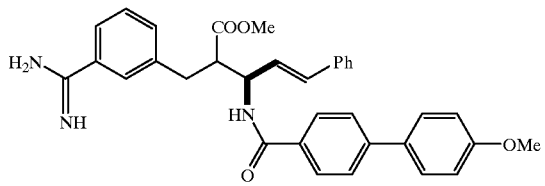

Compound 26

This compound is prepared in a manner similar to compound 10 above starting from imine 5 and thioester 4. 4'-Methoxy-4-biphenylcarbonyl chloride is substituted for 4-biphenylcarbonyl chloride in the β-lactam acylation step. The final product 26 is purified by reverse phase HPLC (CH$_3$CN:H$_2$O, 0.1% TFA) and lyophilized.

$^1$H NMR (DMSO-d$_6$, d): 9.23 (s, 1H), 8.96 (s, 1H), 8.66 (d, J=8.7 Hz, 1H), 7.88 (d, J=9.1 Hz, 2H), 7.72–7.22 (m, 11H), 7.03 (d, J=8.7 Hz, 2H), 6.64 (d, J=16.1 Hz, 1H), 6.4 (dd, J=16.1, 7.9 Hz, 1H), 4.97 (dd, J=16.1, 7.9 Hz, 1H), 3.77 (s, 3H), 3.46 (s, 3H), 3.28–3.15 (m, 1H), 3.08–2.88 (m, 2H).

EXAMPLE 27

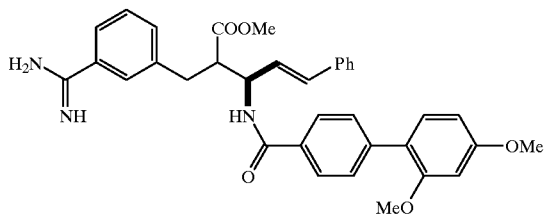

Compound 27

This compound is prepared in a manner similar to compound 10 above starting from imine 5 and thioester 4. 2',4'-Dimethoxy-4-biphenylcarbonyl chloride is substituted for 4-biphenylcarbonyl chloride in the β-lactam acylation step. The final product 27 is purified by reverse phase HPLC (CH$_3$CN:H$_2$O, 0.1% TFA) and lyophilized.

$^1$H NMR (DMSO-d$_6$, d): 9.23 (s, 1H), 9.07 (s, 1H), 8.63 (d, J=9 Hz, 1H), 7.81 (d, J=8.9 Hz, 2H), 7.68–7.15 (m, 14H), 6.72–6.52 (m, 1H), 6.45–6.3 (m, 1H), 5.04–4.9 (m, 1H), 3.78 (s, 3H), 3.75 (s, 3H), 3.51 (s, 3H), 3.21–3.15 (m, 1H), 3.08–2.85 (m, 2H).

EXAMPLE 28

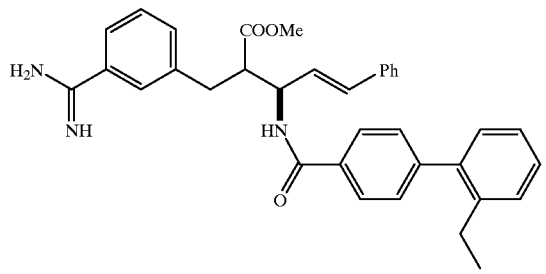

Compound 28

This compound is prepared in a manner similar to compound 10 above starting from imine 5 and thioester 4. 2'-Ethyl-4-biphenylcarbonyl chloride is substituted for 4-biphenylcarbonyl chloride in the β-lactam acylation step. The final product 28 is purified by reverse phase HPLC (CH$_3$CN:H$_2$O, 0.1% TFA) and lyophilized.

$^1$H NMR (DMSO-d$_6$, d): 9.25 (s, 1H), 8.92 (s, 1H), 8.69 (d, J=8.7 Hz, 1H), 7.78 (d, J=9 Hz, 2H), 7.68 –7.08 (m, 15H), 6.65 (d, J=15.9 Hz, 1H), 6.38 (dd, J=15.9, 7.8 Hz, 1H), 5.0 (dd, J=16, 7.9 Hz, 1H), 3.46 (s, 3H), 3.28 –3.18 (m 1H), 2.52 (q, J=9.6 Hz, 2H), 0.98 (t, J=9.6 Hz, 3H).

EXAMPLE 29

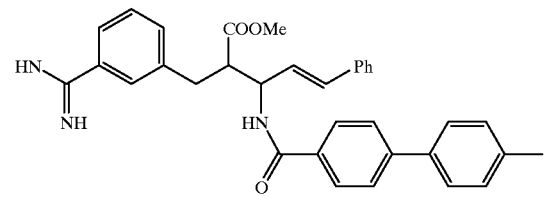

Compound 29

This compound is prepared in a manner similar to compound 10 above starting from imine 5 and thioester 4. 4'-Methyl-4-biphenylcarbonyl chloride is substituted for 4-biphenylcarbonyl chloride in the β-lactam acylation step. The final product 29 is purified by reverse phase HPLC (CH$_3$CN:H$_2$O, 0.1% TFA) and lyophilized.

$^1$H NMR (DMSO-d$_6$, d): 9.22 (s, 1H), 8.91 (s, 1H), 8.68 (d, J=8.7 Hz, 1H), 7.85 (d, J=9 Hz, 2H), 7.75 (d, J=9 Hz, 2H), 7.65–7.2 (m, 13H), 6.65 (d, J=15.9 Hz, 1H), 6.39 (dd, J=15.9, 7.8 Hz, 1H), 4.99 (dd, J=16, 7.9 Hz, 1H), 3.46 (s, 3H), 3.28–3.18 (m, 1H), 3.08–2.88 (m, 2H), 2.35 (s, 3H).

EXAMPLE 30

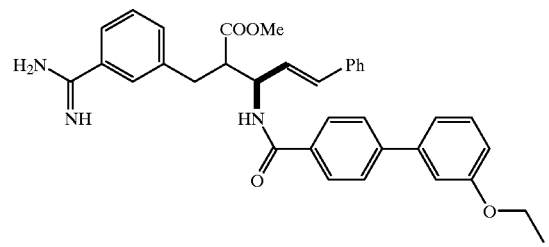

Compound 30

This compound is prepared in a manner similar to compound 10 above starting from imine 5 and thioester 4. 3'-Ethoxy-4-biphenylcarbonyl chloride is substituted for 4-biphenylcarbonyl chloride in the β-lactam acylation step. The final product 30 is purified by reverse phase HPLC (CH$_3$CN:H$_2$O, 0.1% TFA) and lyophilized.

$^1$H NMR (DMSO-d$_6$, d): 9.22 (s, 1H), 9.05 (s, 1H), 8.7 (d, J=8.7 Hz, 1H), 7.88 (d, J=9 Hz, 2H), 7.76 (d, J=9 Hz, 2H), 7.68–7.12 (m, 12H), 6.98–6.85 (m, 1H), 6.67 (d, J=16 Hz, 1H), 6.4 (dd, J=16, 7.8 Hz, 1H), 5.01 (dd, J=16, 7.8 Hz, 1H), 4.08 (q, J=7.5 Hz, 2H), 3.45 (s, 3H), 3.25–3.15 (m, 1H), 3.08–2.89 (m, 2H), 1.32 (t, J=7.5 Hz, 2H).

EXAMPLE 31

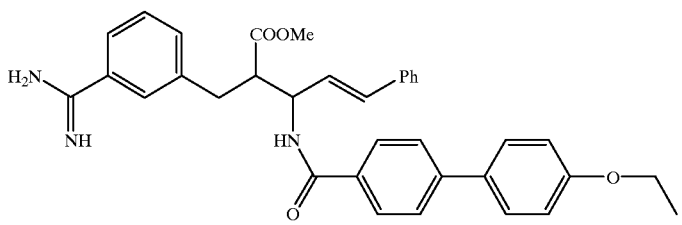

Compound 31

This compound is prepared in a manner similar to compound 10 above starting from imine 5 and thioester 4. 4'-Ethoxy-4-biphenylcarbonyl chloride is substituted for 4-biphenylcarbonyl chloride in the β-lactam acylation step. The final product 31 is purified by reverse phase HPLC (CH$_3$CN:H$_2$O, 0.1% TFA) and lyophilized.

$^1$H NMR (DMSO-d$_6$, d): 9.26 (s, 1H), 9.02 (s, 1H), 8.64 (d, J=8.7 Hz, 1H), 7.86 (d, J=9 Hz, 2H), 7.72 (d, J=9 Hz, 2H), 7.7–7.22 (m, 11H), 7.01 (d, J=10.4 Hz, 2H), 6.64 (d, J=15.9 Hz, 1H), 6.38 (dd, J=15.9, 7.8 Hz, 1H), 4.98 (dd, J=16, 7.8 Hz, 1H), 4.06 (q, J=8.2 Hz, 2H), 3.45 (s, 3H), 3.3–3.18 (m, 1H), 3.08–2.85 (m, 2H), 1.32 (t, J=8.2 Hz, 3H).

EXAMPLE 32

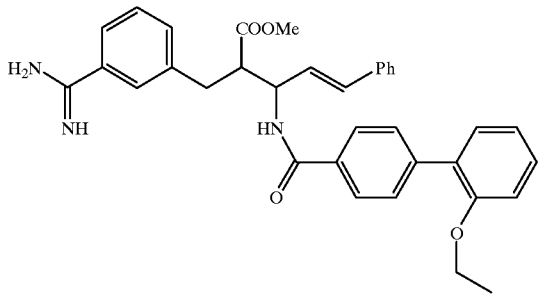

Compound 32

This compound is prepared in a manner similar to compound 10 above starting from imine 5 and thioester 4. 2'-Ethoxy4-biphenylcarbonyl chloride is substituted for 4-biphenylcarbonyl chloride in the β-lactam acylation step. The final product 32 is purified by reverse phase HPLC (CH$_3$CN:H$_2$O, 0.1% TFA) and lyophilized.

$^1$H NMR (DMSO-d$_6$, d): 9.24 (s, 1H), 9.11 (s, 1H), 8.68 (d, J=8.7 Hz, 1H), 7.85 (d, J=9 Hz, 2H), 7.6 (d, J=9 Hz, 2H), 7.59–6.95 (m, 13H), 6.65 (d, J=15.9 Hz, 1H), 6.39 (dd, J=15.9, 7.8 Hz, 1H), 4.98 (dd, J=16, 7.8 Hz, 1H), 4.03 (q, J=8.1 Hz, 2H), 3.47 (s, 3H), 3.28–3.18 (m, 1H), 3.1–2.88 (m, 2H), 1.24 (t, J=8.1 Hz, 3H).

EXAMPLE 33

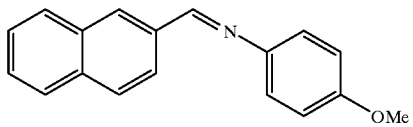

Compound 33

To a stirred solution of 2-Naphthaldehyde (20 g; 0.13 mol) in 200 mL of CH$_2$Cl$_2$ at room temp is added p-anisidine (15.8 g; 0.13 mol) followed by anhydrous magnesium sulfate (16.9 g; 0.14 mol). After 3.5 hours, the mixture is filtered and the filtrate concentrated in vacuo to give 31.5 g (92%) of the imine 33.

$^1$H NMR (CDCl$_3$, d): 8.64 (s, 1H), 8.19 (m, 2H), 7.78–7.98 (m, 3H), 7.43–7.56 (m, 2H), 7.32 (m, 2H), 6.96 (m, 2H), 3.83 (s, 3H).

EXAMPLE 34

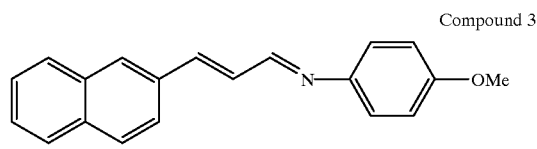

Compound 34

Prepared using trans-3-(2'-naphthyl)acrolein, p-anisidine and anhydrous magnesium sulfate as described for compound 33 above.

$^1$H NMR (CDCl$_3$, d): 8.35 (d, J=9 Hz, 1H), 7.78–7.9 (m, 4H), 7.72 (m, 1H), 7.5 (m, 2H), 7.25 (m, 4H), 6.93 (m, 2H), 3.82 (s, 3H).

EXAMPLE 35

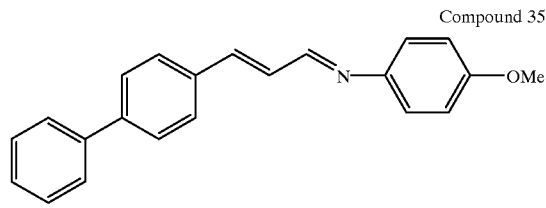

Compound 35

Prepared using trans-3-(4'-biphenyl)acrolein, p-anisidine and anhydrous magnesium sulfate as described for compound 33 above.

$^1$H NMR (CDCl$_3$, d): 8.33 (d, J=9 Hz,1H), 7.2–7.68 (m, 13H), 6.9 (m, 2H), 3.82 (s, 3H).

EXAMPLE 36

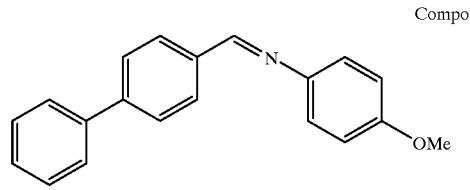

Compound 36

Prepared using 4-biphenylcarboxaldehyde, p-anisidine and anhydrous magnesium sulfate as described for compound 33 above.

¹H NMR (CDCl₃, d): 8.52 (s, 1H), 7.97 (m, 2H), 7.62–7.73 (m, 4H), 7.35–7.52 (m, 3H), 7.27 (m, 2H), 6.95 (m, 2H), 3.85 (s, 3H).

EXAMPLE 37

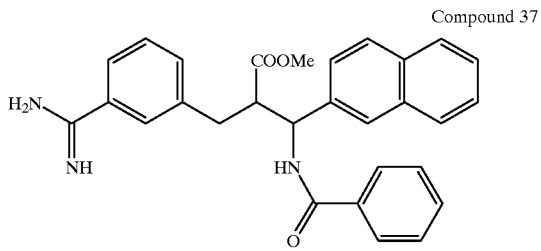

Compound 37

This compound is prepared in a manner similar to compound 10 starting from imine 33 and thioester 4. Benzoyl chloride is substituted for 4-biphenylcarbonyl chloride in the β-lactam acylation step. The final product 37 is purified by reverse phase HPLC (CH₃CN:H₂O, 0.1% TFA) and lyophilized.

¹H NMR (MeOH-d₄, d): 9.01 (d, J=9.4 Hz, 1H), 7.77–7.98 (m, 6H), 7.43–7.67 (m, 9H), 5.53 (m, 1H), 3.56 (m, 1H), 3.54 (s, 3H), 3.1 (m, 1H), 2.81 (m, 1H).

EXAMPLE 38

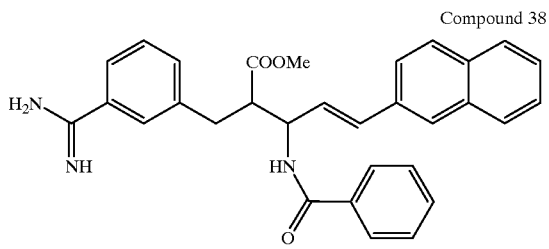

Compound 38

This compound is prepared in a manner similar to compound 10 starting from imine 34 and thioester 4. Benzoyl chloride is substituted for 4-biphenylcarbonyl chloride in the β-lactam acylation step. The final product 38 is purified by reverse phase HPLC (CH₃CN:H₂O, 0.1% TFA) and lyophilized.

¹H NMR (DMSO-d₆, d): 9.27 (s, 2H), 9.1 (s, 2H), 8.72 (d, 1H), 7.4–7.95 (m, 16H), 6.86 (d, J=18 Hz, 1H), 6.54 (dd, J=10, 6 Hz, 1H), 5.03 (m, 1H), 3.48 (s, 3H), 3.32 (m, 1H), 3.04 (m, 2H).

EXAMPLE 39

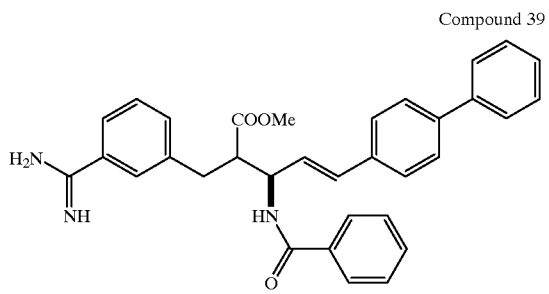

Compound 39

This compound is prepared in a manner similar to compound 10 starting from imine 35 and thioester 4. Benzoyl chloride is substituted for 4-biphenylcarbonyl chloride in the β-lactam acylation step. The final product 39 is purified by reverse phase HPLC (CH₃CN:H₂O, 0.1% TFA) and lyophilized.

¹H NMR (DMSO-d₆, d): 9.25 (s, 2H), 9.11 (s, 2H), 8, 74 (d, 1H), 7.30–8 (m, 22H), 6.23 (d, J=18 Hz, 1H), 6.47 (dd, J=18, 6 Hz, 1H), 5.04 (m, 1H), 3.49 (s, 3H), 3.3 (m, 1H), 3.03 (m, 2H).

EXAMPLE 40

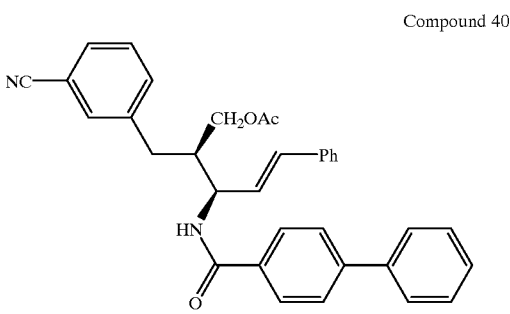

Compound 40

This compound is prepared in a manner similar to compound 10 starting from imine 36 and thioester 4. Benzoyl chloride is substituted for 4-biphenylcarbonyl chloride in the β-lactam acylation step. The final product 40 is purified by reverse phase HPLC (CH₃CN:H₂O, 0.1% TFA) and lyophilized.

¹H NMR (DMSO-d₆, d): 9.23 (s, 2H), 9.05 (s, 2H), 8.97 (s, 2H), 7.28–7.8 (m, 18H), 5.35 (t, 1H), 3.42 (s, 3H), 3.31 (m, 1H), 2.89 (dd, 1H), 2.6 (dd, 1H).

EXAMPLE 41

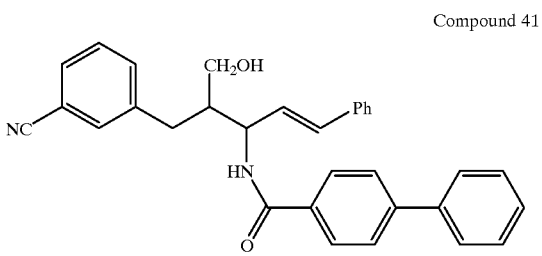

Compound 41

To a stirring solution of the carboxylic acid 9 (980 mg; 2 mmol) and triethylamine (0.44 mL; 3.2 mmol) in dry THF under N₂ at 0° C. is added i-butylchloroformate (0.39 mL; 3 mmol) dropwise. After 15 minutes, a solution of sodium borohydride (153 mg; 4 mmol in 5 mL water) is added dropwise. The mixture is allowed to warm up to room temperature. After 1 hour, most of the THF is removed in vacuo. Water is then added and the mixture extracted with ethyl acetate. The combined extracts are dried (MgSO₄), filtered and concentrated. The crude product is purified by chromatography (eluent=35% EtOAc:Hexane) to give 720 mg (76%) of the alcohol 41.

¹H NMR (CDCl₃, d): 7.92 (d, J=9 Hz, 2H), 7.2–7.72 (m, 16H), 6.67 (d, J=15.5 Hz, 1H), 6.27 (dd, J=15.5, 7.8 Hz, 1H), 4.94 (m, 1H), 3.88 (m, 1H), 3.5 (m, 1H), 3.12 (m, 1H), 2.82–3.03 (m, 2H), 1.95 (m, 1H).

EXAMPLE 42

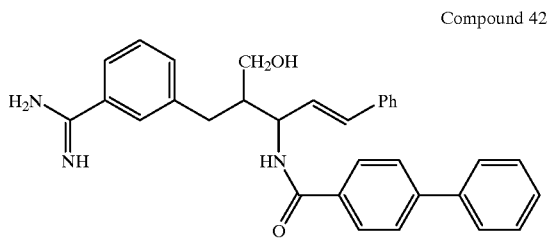

Compound 42

To a stirred solution of the alcohol 41 (106 mg; 0.22 mmol) in 3 mL of dry MeOH at r.t. is added molecular sieves (ca. 50 mg). Gaseous HCl is then bubbled in for ca. 2 minutes. The mixture is then allowed to stir over night at room temperature and then concentrated under a stream of $N_2$. A solution of $NH_3$ in MeOH (3 mL of 7 N solution) is then added to the residue and the mixture refluxed for 1.5 hour, allowed to cool and the solvent removed in vacuo. The residue is purified by RPHPLC ($CH_3CN$:water:0.1% TFA, 40–100 gradient) and the fractions containing product are lyophilized to give 29 mg (22 %) of the product 42 as the trifluoroacetate salt.

EXAMPLE 43

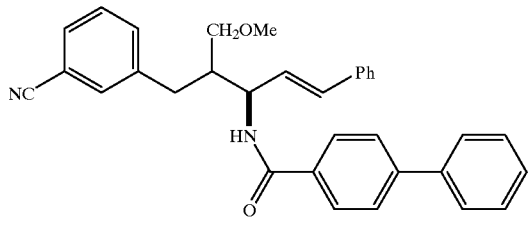

Compound 43

To a stirring solution of the alcohol compound (88 mg; 0.2 mmol) in 2 mL of 2:1 THF:DMF under $N_2$ at 0° C. is added NaH (15 mg of 60% dispersion; 0.4 mmol). After 15 minutes, methyl iodide (0.02 mL; 0.3 mmol) is added and the mixture allowed to warm to room temperature. After 2 hours, the mixture is quenched with saturated $NaHCO_3$ solution. Most of the THF is removed in vacuo and the residue diluted with water and extracted with $CH_2Cl_2$. The combined extracts are dried ($Na_2SO_4$), filtered and concentrated. The crude product is chromatographed (eluent=35% EtOAc:Hexane) to give 21 mg (23%) of the product 43 together with 34 mg of recovered alcohol 41.

$^1$H NMR ($CDCl_3$, d): 7.93 (d, J=9.3 Hz, 2H), 7.15–7.83 (m, 16H), 6.57 (d, J=15.8 Hz, 1H), 6.22 (dd, J=15.8, 6.8 Hz, 1H), 5 (m, 1H), 3.75 (m, 1H), 3.42 (s, 3H), 3.27 (m, 1H), 2.87–3.03 (m, 2H), 2.12 (m, 1H).

EXAMPLE 44

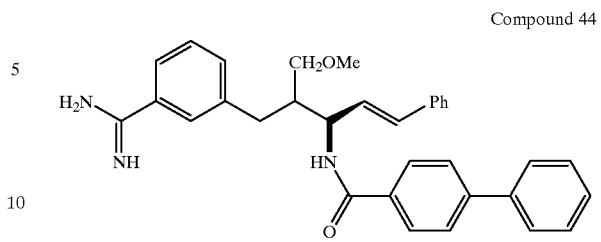

Compound 44

Into a stirring solution of compound 43 (20 mg; 0.04 mmol) in 1.5 mL of 2:1 pyridine:$Et_3N$ is bubbled $H_2S$ for about 1 minute. The mixture is allowed to stir overnight at room temperature and then concentrated under a stream of $N_2$ and then taken up into 2 mL of $CH_2Cl_2$. Methyl iodide (1 mL) is added and the mixture refluxed for 1 hour. The solvent is then removed in vacuo, the residue taken up into 2 mL of MeOH and $NH_4OAc$ (30 mg) is added. The resulting mixture is refluxed for 1 hour and then allowed to cool. The solvent is then removed in vacuo and the residue is purified by RPHPLC ($CH_3CN$:$H_2O$, 0.1% TFA, 40 to 100% $CH_3CN$ gradient ) and the fractions containing product are lyophilized to give 13 mg (51 %) of product 44 as the trifluoroacetate salt.

$^1$H NMR (MeOH-$d_4$, d): 8.47 (d, J=7.9 Hz, 1H), 7.95 (d, J=8 Hz, 2H), 7.78 (d, J=8 Hz, 2H), 7.17–7.73 (m, 14 H), 6.55 (d, J=15.8 Hz, 1H), 6.31 (dd, J=15.8, 7.9 Hz, 1H), 4.77 (m, 1H), 3.7 (dd, J=9.5, 3.1 Hz, 1H), 3.47 (dd, J=9.5, 3.1 Hz, 1H), 3 (d, J=7.9 Hz, 2H), 2.35 (m, 1H).

EXAMPLE 45

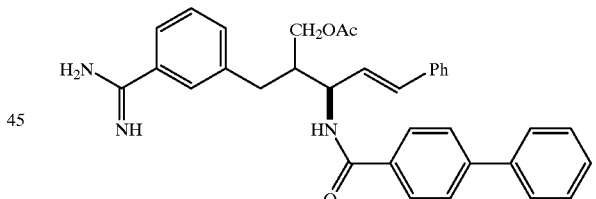

Compound 45

A mixture of alcohol 41 (480 mg; 1 mmol), pyridine (0.40 mL; 4.9 mmol) and acetic anhydride (0.12 mL; 1.2 mmol) is stirred overnight at room temperature. The next day, 3 drops of pyridine and acetic anhydride are added. The next day, the reaction is not complete and so 4 mg of DMAP is added. After 1 hour, the reaction is complete by tlc. The mixture is diluted with $CH_2Cl_2$ and washed with 0.1 N HCl solution. The organic layer is dried ($MgSO_4$), filtered and concentrated to give 520 mg of 45.

$^1$H NMR ($CDCl_3$, d): 7.98 (d, J=8 Hz, 2H), 7.73 (d, J=8 Hz, 2H), 7.67 (d, J=8 Hz, 2H), 7.17–7.58 (m, 12H), 6.94 (d, 1H), 6.55 (d, J=18 Hz, 1H), 6.21 (dd, J=18, 5 Hz, 1H ), 5.1 (m, 1H), 4.38 (m, 1H), 4.08 (m, 1H), 2.68–2.97 (m, 2H), 2.51 (m, 1H).

EXAMPLE 46

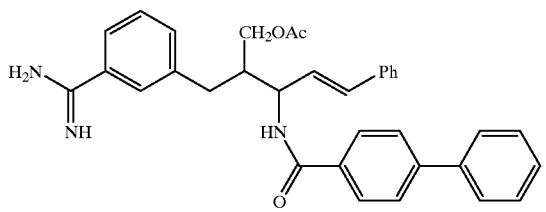

Compound 46

Compound 45 is converted to the corresponding amidine 46 using the hydrogen sulfide/methyl iodide: ammonium acetate sequence described for the conversion of 43 to 44. The product 46 is purified by RPHPLC and isolated as its trifluoroacetate salt.

$^1$H NMR (DMSO-d$_6$, d): 9.31 (s, 2H), 8.97 (s, 2H), 8.7 (d, 1H), 7.18–8 (m, 18H), 6.6 (d, J=18 Hz, 1H), 6.40 (dd, J=18, 6 Hz, 1H), 4.83 (m, 1H), 4.02 (m, 1H), 3.84 (m, 2H), 2.95 (m, 1H), 2.57 (m, 1H), 1.93 (s, 3H).

EXAMPLE 47

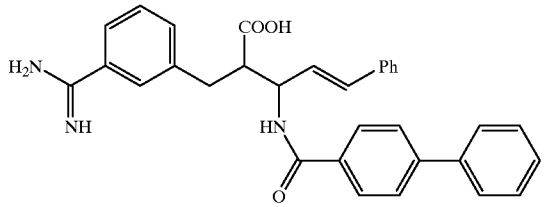

Compound 47

Carboxylic acid 9 is converted to its corresponding amidine 47 using the hydrogen sulfide: methyl iodide: ammonium acetate sequence described for the conversion of 43 to 44. The product 47 is isolated by RPHPLC as its trifluoroacetate salt.

$^1$H NMR (MeOH-d$_4$, d): 8 (d, J=9 Hz, 2H), 7.82 (d, J=9 Hz, 2H), 7.22–7.77 (m, 14H), 6.73 (d, J=15.8 Hz, 1H), 6.4 (dd, J=15.8, 7.9 Hz, 1H), 4.95 (m, 1H), 3.08–3.45 (m, 3H).

EXAMPLE 49

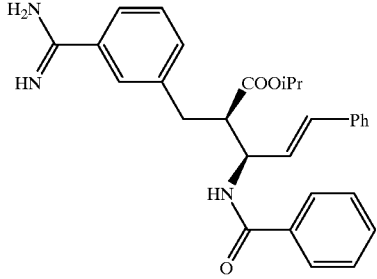

Compound 49

To a stirring solution of the carboxylic acid 48 (120 mg; 0.29 mmol) in 5 mL of dry CH$_2$Cl$_2$ under N$_2$ at room temperature is added triethylamine (0.05 mL; 0.38 mmol). iso-propyl chloroformate (0.38 mL of 1 M solution in toluene) is added dropwise. After 30 minutes, DMAP (18 mg; 0.15 mmol) is added and the mixture allowed to further stir for 1.5 hours at room temperature. The mixture is then diluted with CH$_2$Cl$_2$ and washed with 1 N HCl. The organic layer is then dried (MgSO$_4$), filtered and concentrated. The crude product is chromatographed (eluent=40% EtOAc:Hexane to give 44 mg (33 %) of the corresponding isopropyl ester. This compound is then converted to the corresponding amidine 49 via the hydrogen sulfide: methyl iodide: ammonium acetate procedure as described for the conversion of 43 to 44. The product 49 is purified by RPHPLC and isolated as its trifluoroacetate salt.

$^1$H NMR (MeOH-d$_4$, d): 8.6 (d, J=7.9 Hz, 1H), 7.85 (d, J=8 Hz, 2H), 7.16–7.7 (m, 12H), 6.69 (d, J=15.8 Hz, 1H), 6.32 (dd, J=15.8, 7.9 Hz, 1H), 4.98 (m, 1 H), 4.85 (m, 1H), 3.23 (m, 1H), 3.08 (m, 2H), 1.07 (d, J=6 Hz, 3H), 0.97 (d, J=6 Hz, 3H).

EXAMPLE 50

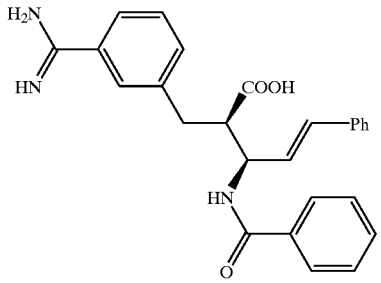

Compound 50

This compound is prepared by conversion of 48 to the corresponding amidine using the hydrogen sulfide: methyl iodide: ammonium acetate sequence described for the conversion of 43 to 44. The product 50 is purified by RPHPLC and isolated as its trifluoroacetate salt.

$^1$H NMR (MeOH-d$_4$, d): 8.6 (d, J=7.9 Hz, 1H), 7.85 (d, J=8 Hz, 2H), 7.16–7.7 (m, 12H), 6.69 (d, J=15.8 Hz, 1H), 6.32 (dd, J=15.8, 7.9 Hz, 1H), 4.98 (m, 1H), 4.85 (m, 1H), 3.23 (m, 1H), 3.08 (m, 2H), 1.07 (d, J=6 Hz, 3H), 0.97 (d, J=6 Hz, 3H).

EXAMPLE 51

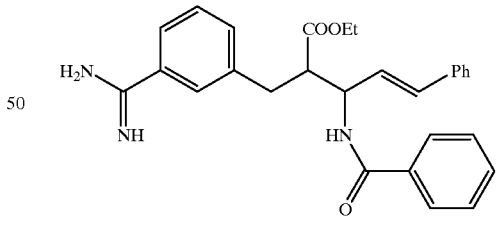

Compound 51

Into a stirred solution of the carboxylic acid 50 (96 mg; 0.18 mmol) in 3 mL of EtOH at room temperature is bubbled HCl for ca. 3 minutes. The mixture is allowed to stir for 7 hours at room temperature and then stored in the refrigerator (0° C.) over the weekend. The solvent is then removed in vacuo and the residue purified by RPHPLC. The product 51 is isolated as its trifluoroacetate salt.

$^1$H NMR (MeOH-d$_4$, d): 8.63 (d, J=7.9 Hz, 1H), 7.84 (d, J=8 Hz, 2H), 7.16–7.68 (m, 12H), 6.68 (d, J=15.8 Hz, 1H), 6.32 (dd, J=15.8, 7.9 Hz, 1H), 5 (m, 1H), 4.02 (q, 2H), 3.25 (m, 1H), 3.07 (d, J=7.9 Hz, 2H), 1.05 (t, 3H).

EXAMPLE 52

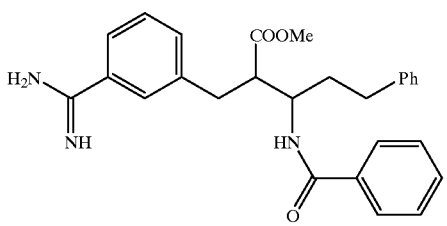
Compound 52

A mixture of compound 11 and 10% Pd/C (25 mg) in EtOAc (2 mL): EtOH (5 mL) is hydrogenated under 45 PSI $H_2$ for 19 hours at room temperature. The mixture is then filtered through a bed of celite and the filtrate concentrated. The crude product is purified by RPHPLC ($CH_3CN$:water: 0.1 % TFA, 10–100% $CH_3CN$ gradient) and the fractions containing product are lyophilized to give 21 mg of 52.

$^1$H NMR (MeOH-$d_4$, d): 8.27 (d, J=9.3 Hz, 1H), 7.83 (m, 2H), 7.43–7.65 (m, 7H), 7.09–7.27 (m, 5H), 4.35 (m, 1H), 3.58 (s, 3H), 2.95–3.15 (m, 3H), 2.54–2.75 (m, 2H), 1.93 (m, 2H).

Resolution of Compound 10

Racemic compound 10 (ca. 650 mg, single diastereomer with the presumed syn-stereochemistry shown) is resolved into its two enantiomers 53 (late eluting isomer) and 54 (early eluting isomer) using preparative HPLC (Chiralpak AD column, 50 mm ID×500 mm, 15 microns). The mobile phase is heptane (A) with 0.1% TFA and i-propanol (B) with 0.1% TFA, isocratic 20% A, 80% B (Flow=200 mL: minute). The late eluting isomer is isolated by concentration in vacuo. The yield is 180 mg. The %ee enantiomer 53 is found to be 100% by analytical HPLC (Chiralpak AD). The $^1$H NMR spectra for 53 and 54 are identical.

$^1$H NMR (DMSO-$d_6$, d): 8.7 (d, J=8.6 Hz, 1H), 7.92 (d, J=9 Hz, 2H), 7.78 (d, J=9 Hz, 2H), 7.75–7.21 (m, 14H), 6.67 (d, J=16.1 Hz, 1H), 6.4 (dd, J=16.1, 7.8Hz, 1H), 4.98 (dd, J=16.1, 7.8Hz, 1H), 3.46 (s, 3H), 3.25–3.18 (m, 1H), 3.05–2.88 (m, 2H).

EXAMPLE 55

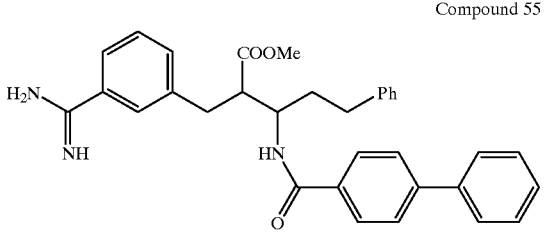
Compound 55

The hydrogenation of compound 53 (late eluting enantiomer) is carried out as for compound 52 above except ethyl acetate is omitted. The product is purified by RPHPLC ($CH_3CN$:water: 0.1% TFA, 40–100% $CH_3CN$) and the product 55 is isolated as the trifluoroacetate salt.

$^1$H NMR (MeOH-$d_4$, d): 8.3 (d, J=9.3 Hz, 1H), 7.84 (m, 2H), 7.07–7.8 (m, 16H), 4.37 (m, 1H), 3.6 (s, 3H), 2.97–3.17 (m, 3H), 2.57–2.77 (m, 2H), 1.95 (m, 2H).

EXAMPLE 56

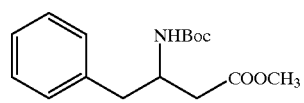
Compound 56

To a solution of N- -Boc-D-Phenylalanine (38 mmol) in 80 mL of dry tetrahydrofuran is added N-methyl morpholine (38 mmol) in a single portion, followed by isobutyl chloroformate (38 mmol) in a similar fashion, at −20° C. The reaction mixture is stirred for 10 minutes at −20° C. and filtered into a preformed ethereal solution of diazomethane (~70 mmol) at 0° C. The resulting solution is allowed to stand at 0° C. for 20 minutes. Excess diazomethane is decomposed by the dropwise addition of glacial acetic acid and solvents are removed in vacuo.

The resulting oil is dissolved in 150 mL of dry methanol. A solution of silver benzoate (8 mmol) in 17 mL of triethylamine is slowly added with stirring, at room temperature. The resulting black reaction mixture is stirred for 45 minutes at room temperature. Methanol is removed in vacuo and the residue taken up in 700 mL of ethyl acetate. The mixture is filtered through celite and washed sequentially with saturated sodium bicarbonate (3×150 mL), water (1×150 mL), 1N potassium bisulfate (3×150 mL) and brine (1×150 mL). The organic layer is dried over magnesium sulfate, filtered, concentrated in vacuo, and purified by flash chromatography (3:1 hexanes:ethyl acetate).

EXAMPLE 57

Compound 57

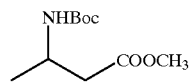

Compound 57 is prepared using the procedure described for Compound 56, substituting N- -Boc-D-alanine.

EXAMPLE 58

Compound 58

Compound 58 is prepared using the procedure described for Compound 56, subsubtituting N- -Boc-D-homophenylalanine.

EXAMPLE 59

Compound 59

Compound 59 is prepared using the procedure described for Compound 56, substituting N- -Boc-D-3-pyridylalanine.

EXAMPLE 60

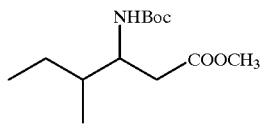

Compound 60

Compound 60 is prepared using the procedure described for 56, substituting N- -Boc-D-isoleucine.

EXAMPLE 61

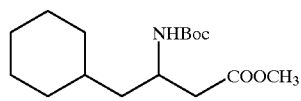

Compound 61

Compound 61 is prepared using the procedure described for Compound 56, substituting N- -Boc-D-cyclohexylalanine.

EXAMPLE 62

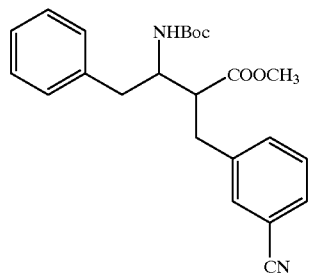

Compound 62

A solution of Compound 56 (11 mmol) in 70 mL of dry tetrahydrofuran is cooled to −78° C. and a solution of lithium hexamethyldisilazane in tetrahydrofuran (33 mmol) is added via syringe at such a rate that the temperature did not rise above −60° C. The reaction mixture is warmed to −25° C. over 40 minutes and recooled to −78° C. A solution of 3-cyanobenzyl bromide (27 mmol) in 20 mL of tetrahydrofuran is added via syringe at such a rate that the temperature did not rise above −60° C. The reaction mixture is allowed to come to room temperature and stirred at room temperature for 1 hour.

125 mL of saturated sodium bicarbonate is added and tetrahydrofuran is removed in vacuo. The remaining material is partitioned between 500 mL of ethyl acetate and 150 mL of saturated sodium bicarbonate. The organic phase is further washed with saturated sodium bicarbonate (2×100 mL) and brine. The organic layer is dried over magnesium sulfate, filtered, concentrated in vacuo. The residue is triturated with 40 mL of 4:1 hexanes:ethyl acetate. The solid material is filtered off and discarded. The filtrate, containing the desired product, is concentrated in vacuo.

EXAMPLE 63

Compound 63

Compound 63 is prepared following the method described for Compound 62, substituting the product obtained in Example 57.

EXAMPLE 64

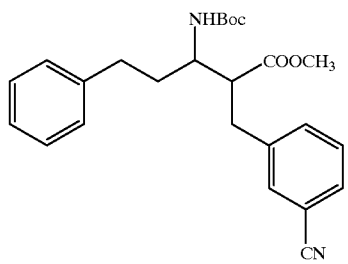

Compound 64

Compound 64 is prepared following the method described for Compound 62, substituting the product obtained in Example 58.

EXAMPLE 65

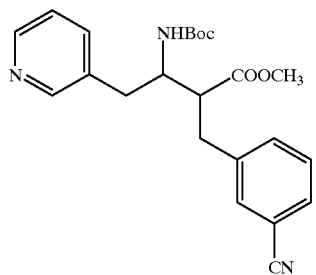

Compound 65

Compound 65 is prepared following the method described for Compound 62, substituting the product obtained in Example 59.

EXAMPLE 66

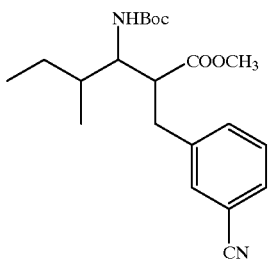
Compound 66

Compound 66 is prepared following the method described for Compound 62, substituting the product obtained in Example 60.

EXAMPLE 67

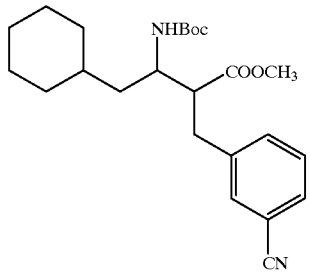
Compound 67

Compound 67 is prepared following the method described for Compound 62, substituting the product obtained in Example 61.

EXAMPLE 68

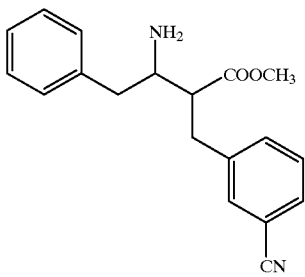
Compound 68

To a solution of Compound 62 (5 mmol) in 60 mL of methylene chloride is added 20 mL of trifluoroacetic acid, dropwise at 0° C. The resulting solution is stirred for 2 hours at 0° C. Solvents are removed in vacuo and the residue purified by reverse phase HPLC using a gradient of 30% to 70% acetonitrile in water containing 0.1% trifluoroacetic acid.

Acetonitrile is removed in vacuo and the remaining material partitioned between saturated sodium bicarbonate and ethyl acetate. The aqueous layer is extracted twice with ethyl acetate and the combined organic layers are dried over magnesium sulfate, filtered, and concentrated in vacuo.

EXAMPLE 69

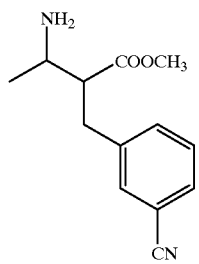
Compound 69

Compound 69 is prepared according to the method described in Example 68, substituting the product obtained in Example 63.

EXAMPLE 70

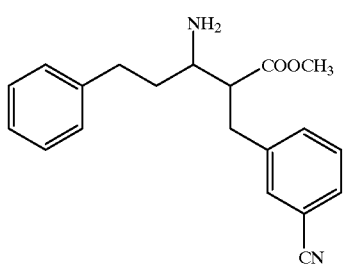
Compound 70

Compound 70 is prepared according to the method described in Example 68, substituting the product obtained in Example 64.

EXAMPLE 71

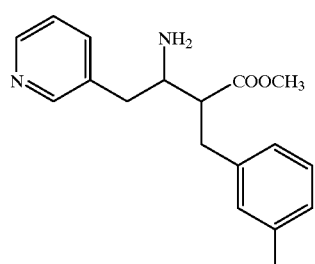
Compound 71

Compound 71 is prepared according to the method described in Example 68, substituting the product obtained in Example 65.

EXAMPLE 72

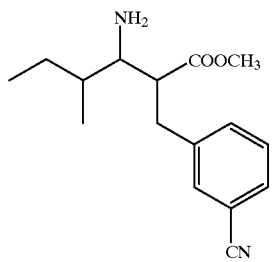

Compound 72

Compound 72 is prepared according to the method described in Example 68, substituting the product obtained in Example 66.

EXAMPLE 73

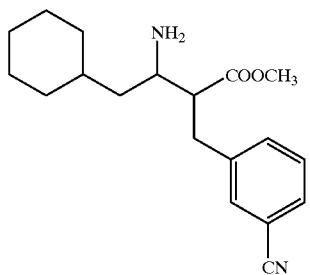

Compound 73

Compound 73 is prepared according to the method described in Example 68, substituting the product obtained in Example 67.

EXAMPLE 74

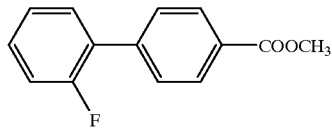

Compound 74

Solution (A): To a solution of 11.8 mL of n-butyl lithium in hexanes (19 mmol) in 13 mL of tetrahydrofuran is added a solution of 1-bromo-2-fluorobenzene (19 mmol) in 2 mL of tetrahydrofuran, dropwise via syringe at −78° C. Stirring at −78° C. is continued for 1 hour. A solution of zinc chloride (19 mmol) in 38 mL of tetrahydrofuran is added over 2 minutes at −78° C. The resulting solution is allowed to come to room temperature over 40 minutes.

Solution (B): To a solution of bis(triphenylphosphine) palladium dichloride (1 mmol) in 11 mL of tetrahydrofuran is added diisobutyl aluminum hydride (1 mmol) as a solution in hexanes, at room temperature, followed by methyl iodobenzoate(16 mmol) in a single portion at room temperature.

Solution (A) is added to solution (B) and the reaction mixture allowed to stir at room temperature overnight. The reaction mixture is diluted with 300 mL of diethyl ether and washed with 1N hydrochloric acid (3×75 mL) and brine. The organic layer is dried over magnesium sulfate, filtered, and concentrated in vacuo.

EXAMPLE 75

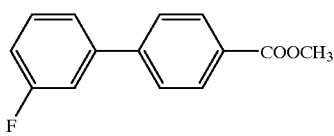

Compound 75

Compound 75 is prepared according to the method described for Compound 74, substituting 1-bromo-3-fluorobenzene in the preparation of Solution (A).

EXAMPLE 76

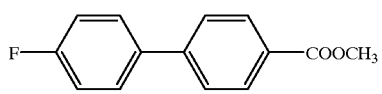

Compound 76

Compound 76 is prepared according to the method described for Compound 74, substituting 1-bromo-4-fluorobenzene in the preparation of Solution (A).

EXAMPLE 77

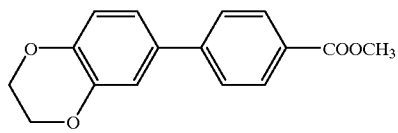

Compound 77

Compound 77 is prepared according to the method described in EXAMPLE 74, substituting 3,4-ethylenedioxy bromobenzene in the preparation of Solution (A).

EXAMPLE 78

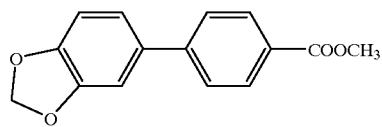

Compound 78

Compound 78 is prepared according to the method described in EXAMPLE 74, substituting 3,4-methylenedioxy bromobenzene in the preparation of Solution (A).

EXAMPLE 79

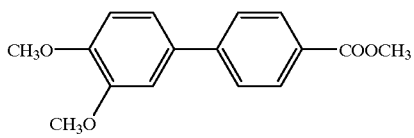

Compound 79

Compound 79 is prepared according to the method described in Example 74, substituting 3,4-dimethoxy bromobenzene in the preparation of Solution (A).

EXAMPLE 80

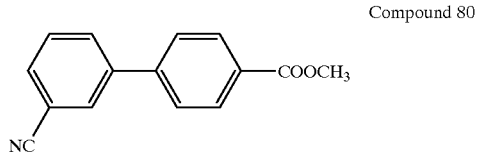
Compound 80

Compound 80 is prepared according to the method described in Example 74, substituting 3-cyano bromobenzene in the preparation of Solution (A).

EXAMPLE 81

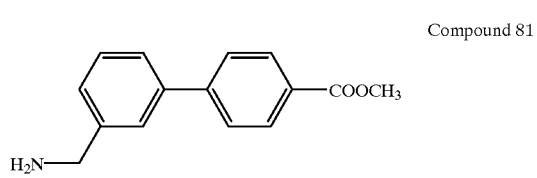
Compound 81

Ammonia gas is bubbled into a suspension of Compound 80 (24 mmol) in 200 mL of methanol for five minutes. To the resulting solution is added rhodium on alumina (5 g) and the suspension is shaken under a positive pressure of hydrogen for 36 hours. Catalyst is filtered off and methanol is removed in vacuo to give an oil which is triturated with ether and filtered.

EXAMPLE 82

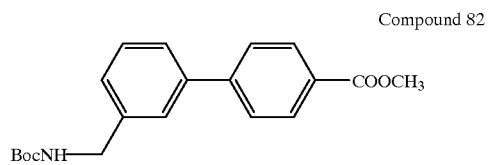
Compound 82

A solution of Compound 81 (15.4 mmol), triethylamine (17 mmol), di-tert-butyl dicarbonate (15.4 mmol), and 4-dimethylaminopyridine (1.5 mmol) in 60 mL of dimethylformamide is stirred at room temperature overnight. The solution is diluted with 800 mL of ethyl acetate and washed with 1N hydrochloric acid (3×150 mL) and brine. The organic layer is dried over magnesium sulfate, filtered, concentrated in vacuo, and purified by flash chromatography (3:2 hexanes:ethyl acetate).

EXAMPLE 83

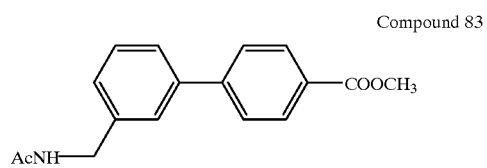
Compound 83

A solution of Compound 81 (2 mmol), acetic anhydride (8 mmol), and dimethylamino pyridine (0.2 mmol) in 20 mL of pyridine is stirred at room temperature overnight. The reaction mixture is poured into 200 mL of 5% hydrochloric acid and extracted with ethyl acetate (3×200 mL). The combined organic extracts are dried over magnesium sulfate, filtered, concentrated in vacuo, and purified by flash chromatography (3:1 hexanes:ethyl acetate).

EXAMPLE 84

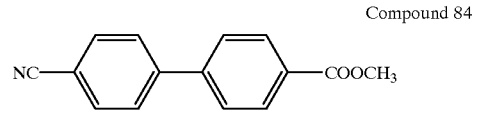
Compound 84

Compound 84 is prepared according to the method described for Compound 74, substituting 4-cyano bromobenzene in the preparation of Solution (A).

EXAMPLE 85

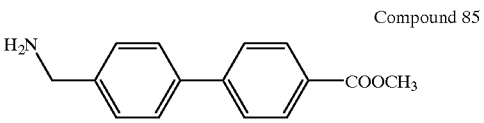
Compound 85

Compound 85 is prepared according to the method described for Compound 81, substituting the product obtained in Example 84.

EXAMPLE 86

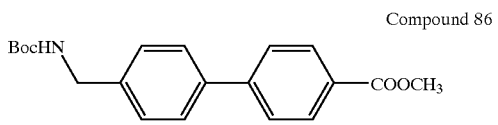
Compound 86

Compound 86 is prepared according to the method described for Compound 82, substituting the product obtained in Example 85.

EXAMPLE 87

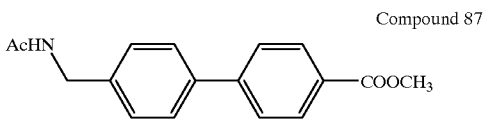
Compound 87

Compound 87 is prepared according to the method described for Compound 83, substituting the product obtained in Example 85.

EXAMPLE 88

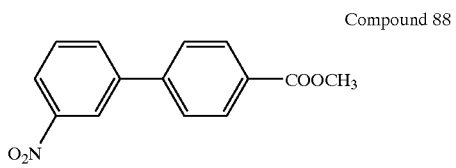
Compound 88

To a solution of methyl coumalate (6.5 mmol) and 3-nitrostyrene (32.5 mmol) in 30 mL of m-xylene is added 10% palladium on carbon (2.5 g) in a single portion. The reaction mixture is heated at 140° C. overnight. After cooling, the reaction mixture is filtered through celite and the filtrate concentrated in vacuo. The resulting slurry is triturated with 3:1 hexanes:ethyl acetate. The solid, which is the desired product, is removed by filtration.

EXAMPLE 89

Compound 89

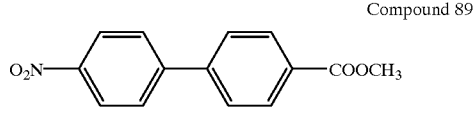

Compound 89 is prepared using a method identical to the one used for Compound 88, substituting 4-nitrostyrene.

EXAMPLE 90

Compound 90

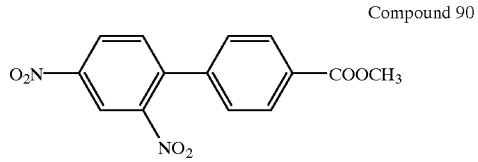

To a flask containing 100 mL of fuming nitric acid is added 4-biphenyl carboxylic acid (20 mmol), portionwise at 0° C. Stirring is continued 15 minutes at 0° C. Water (100 mL) is slowly added and the filtrate collected and recrystallized from ethanol.

EXAMPLE 91

Compound 91

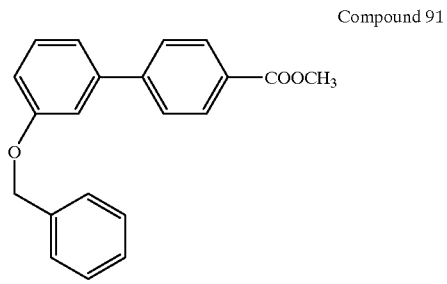

Compound 91 is prepared according to the method described for Compound 74, substituting 3-benzyloxy bromobenzene in the preparation of Solution (A).

EXAMPLE 92

Compound 92

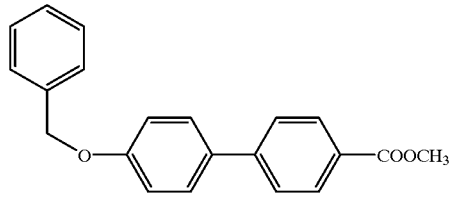

Compound 92 is prepared according to the method described for Compound 74, substituting 4-benzyloxy bromobenzene in the preparation of Solution (A).

EXAMPLE 93

Compound 93

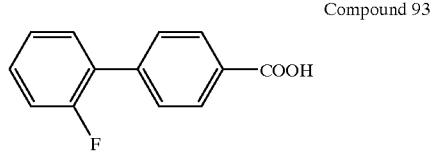

To a suspension of Compound 74 (1.6 mmol) in 10 mL of methanol and 20 mL of tetrahydrofuran is added 10 mL of 2N sodium hydroxide, dropwise at room temperature. The resulting solution is allowed to stir at room temperature for 2 hours. Organic solvents are removed in vacuo and the residue diluted with 20 mL of water and brought to pH 2 with 1N hydrochloric acid. Solid material is filtered off and dried under vacuum.

EXAMPLE 94

Compound 94

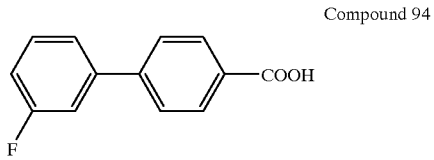

Compound 94 is prepared according to the method described for 93, substituting the product obtained in Example 75.

EXAMPLE 95

Compound 95

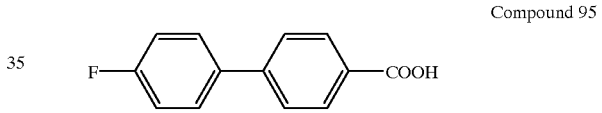

Compound 95 is prepared according to the method described for Compound 93, substituting the product obtained in Example 76.

EXAMPLE 96

Compound 96

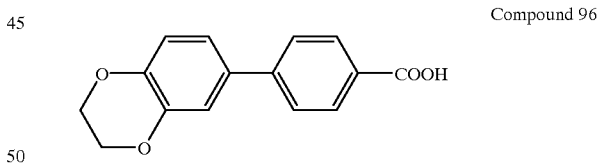

Compound 96 is prepared according to the method described for Compound 93, substituting the product obtained in Example 77.

EXAMPLE 97

Compound 97

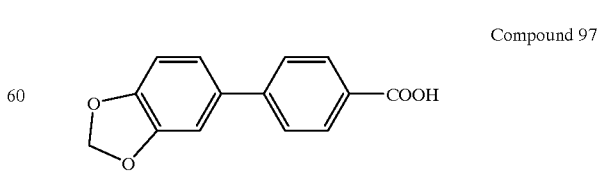

Compound 97 is prepared according to the method described for Compound 93, substituting the product obtained in Example 78.

EXAMPLE 98

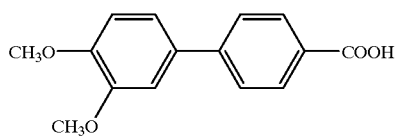
Compound 98

Compound 98 is prepared according to the method described for Compound 93, substituting the product obtained in Example 79.

EXAMPLE 99

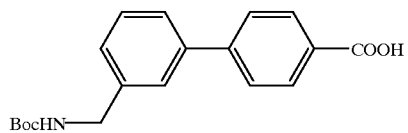
Compound 99

Compound 99 is prepared according to the method described for Compound 93, substituting the product obtained in Example 82.

EXAMPLE 100

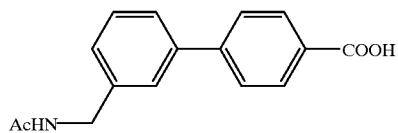
Compound 100

Compound 100 is prepared according to the method described for Compound 93, substituting the product obtained in Example 83.

EXAMPLE 101

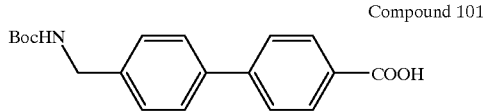
Compound 101

Compound 101 is prepared according to the method described for Compound 93, substituting the product obtained in Example 86.

EXAMPLE 102

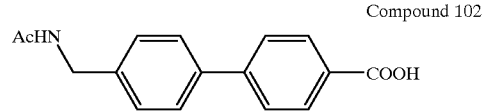
Compound 102

Compound 102 is prepared according to the method described for Compound 93, substituting the product obtained in Example 87.

EXAMPLE 103

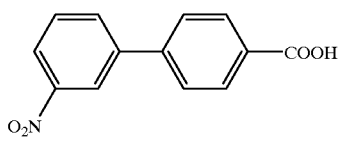
Compound 103

Compound 103 is prepared according to the method described for Compound 93, substituting the product obtained in Example 88.

EXAMPLE 104

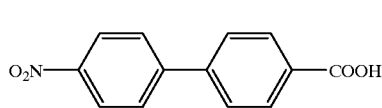
Compound 104

Compound 104 is prepared according to the method described for Compound 93, substituting the product obtained in Example 89.

EXAMPLE 105

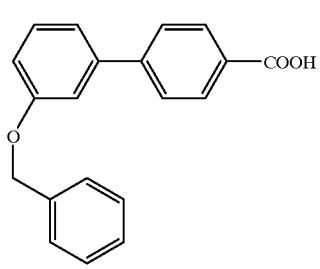
Compound 105

Compound 105 is prepared according to the method described for Compound 93, substituting the product obtained in Example 91.

EXAMPLE 106

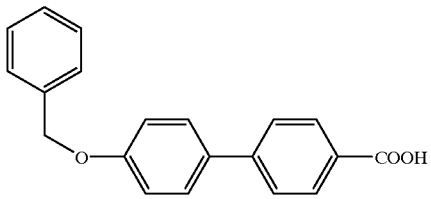
Compound 106

Compound 106 is prepared according to the method described for Compound 93, substituting the product obtained in Example 90.

EXAMPLE 107

Compound 107

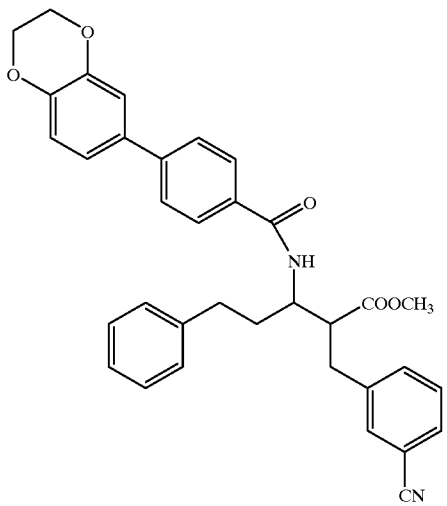

To a solution of Compound 96 (2 mmol) in 10 mL of DMF is added diisopropyl ethylamine (2 mmol) in a single portion at room temperature, followed by 2-(1H-benzotriazol -1-yl)-1,1,3,3-tetramethyluronium tetrafluoroborate (2 mmol) in a similar fashion. The reaction mixture is stirred for 2 minutes at room temperature and a solution of Compound 70 (2 mmol) in 15 mL of dimethylformamide is added in a single portion. Stirring is continued overnight at room temperature.

The reaction mixture is diluted with 300 mL of ethyl acetate and washed sequentially with 1N hydrochloric acid (3×75 mL), water, saturated sodium bicarbonate (3×75 mL) and brine. The organic phase is dried over magnesium sulfate, filtered and concentrated in vacuo.

EXAMPLE 108

Compound 108

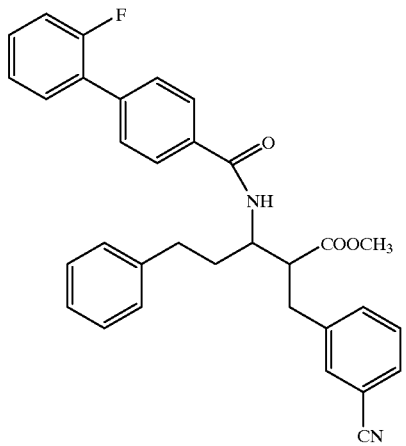

Compound 108 is prepared using the same procedure described for Compound 107, substituting Compound 93 for Compound 96.

EXAMPLE 109

Compound 109

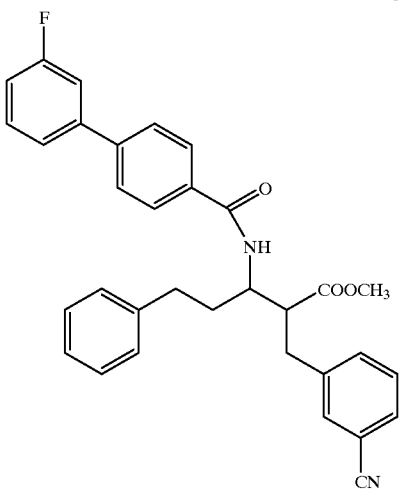

Compound 109 is prepared using the same procedure described for Compound 107, substituting Compound 94 for Compound 96.

EXAMPLE 110

Compound 110

Compound 110 is prepared using the same procedure described for Compound 107, substituting Compound 95 for Compound 96.

EXAMPLE 111

Compound 111

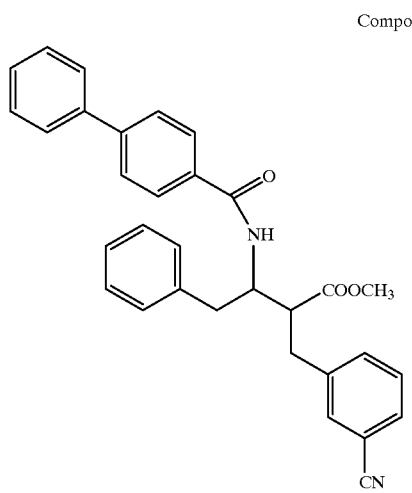

Compound 111 is prepared using the same procedure described for Compound 107, substituting 4-biphenyl carboxylic acid for Compound 96 and substituting Compound 68 for Compound 70.

EXAMPLE 112

Compound 112

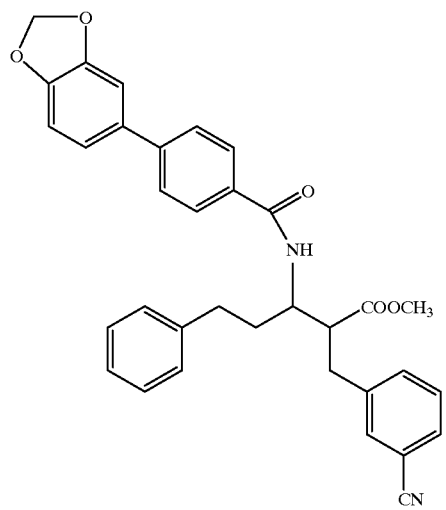

Compound 112 is prepared using the same procedure described for Compound 107, substituting Compound 97 for Compound 96.

EXAMPLE 113

Compound 113

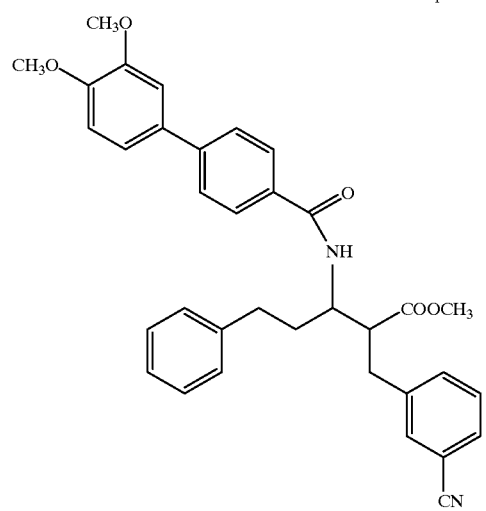

Compound 113 is prepared using the same procedure described for Compound 107, substituting Compound 98 for Compound 96.

EXAMPLE 114

Compound 114

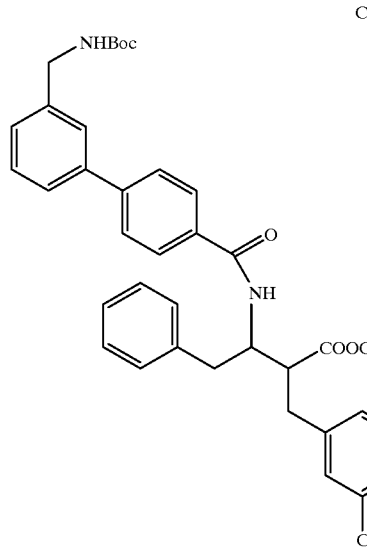

Compound 114 is prepared using the same procedure described for Compound 107, substituting Compound 99 for Compound 96 and substituting Compound 68 for Compound 70.

EXAMPLE 115

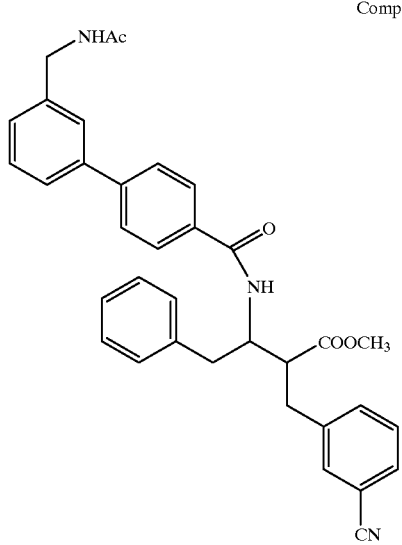

Compound 115

Compound 115 is prepared using the same procedure described for Compound 107, substituting Compound 100 for Compound 96 and substituting Compound 68 for Compound 70.

EXAMPLE 116

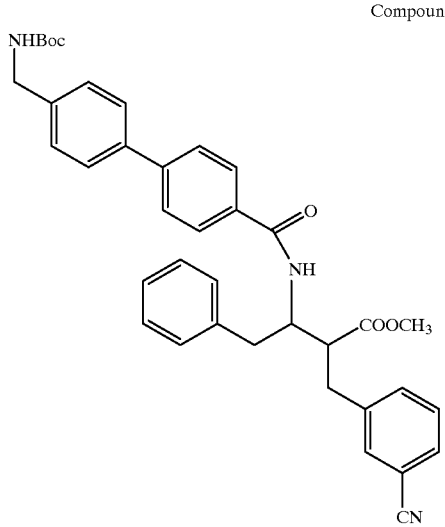

Compound 116

Compound 116 is prepared using the same procedure described for Compound 107, substituting Compound 101 for Compound 96 and substituting Compound 68 for Compound 70.

EXAMPLE 117

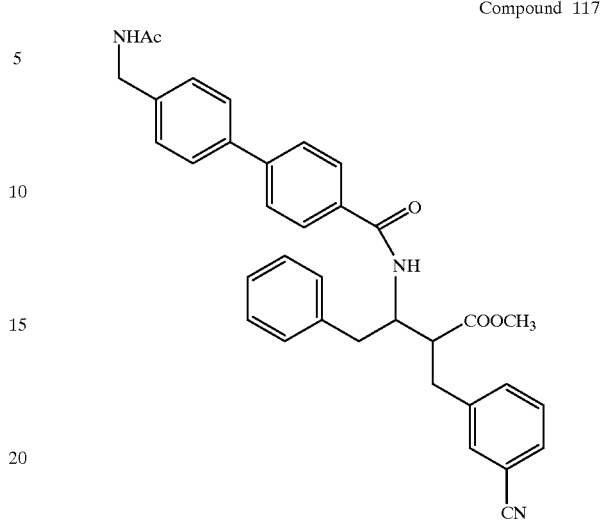

Compound 117

Compound 117 is prepared using the same procedure described for Compound 107, substituting Compound 102 for Compound 96 and substituting Compound 68 for Compound 70.

EXAMPLE 118

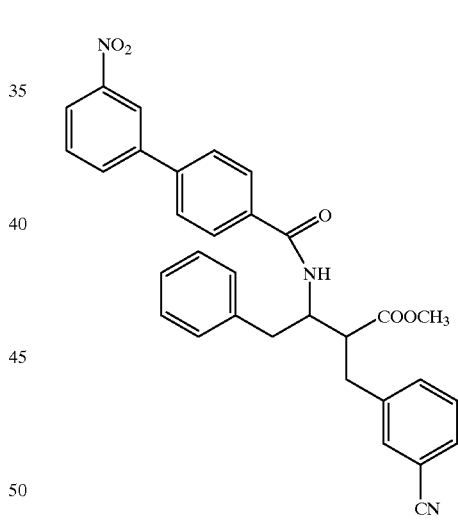

Compound 118

Compound 118 is prepared using the same procedure described for Compound 107, substituting Compound 103 for Compound 96 and substituting Compound 68 for Compound 70.

EXAMPLE 119

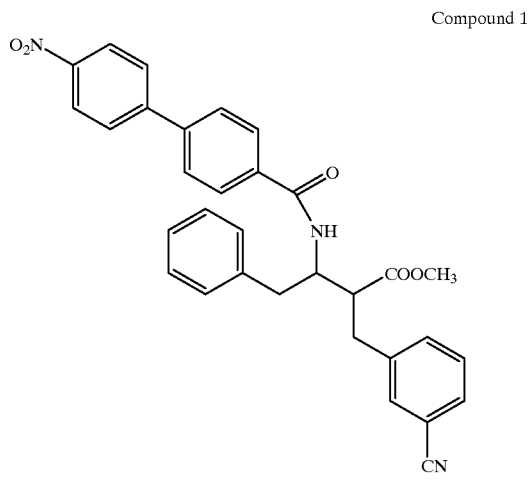

Compound 119

Compound 119 is prepared using the same procedure described for Compound 107, substituting Compound 104 for Compound 96 and substituting Compound 68 for Compound 70.

EXAMPLE 120

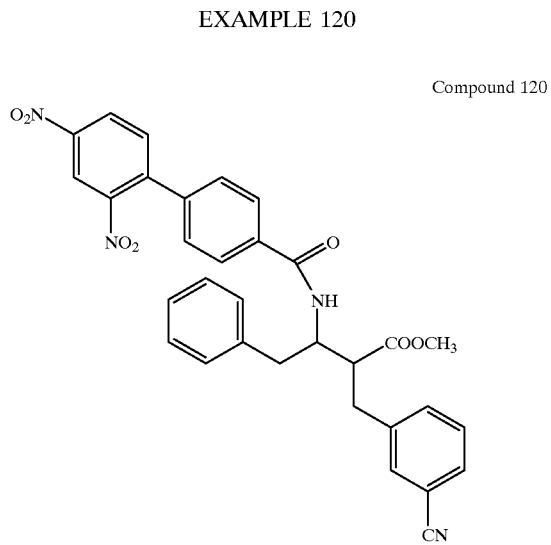

Compound 120

Compound 120 is prepared using the same procedure described for Compound 107, substituting Compound 90 for Compound 96 and substituting Compound 68 for Compound 70.

EXAMPLE 121

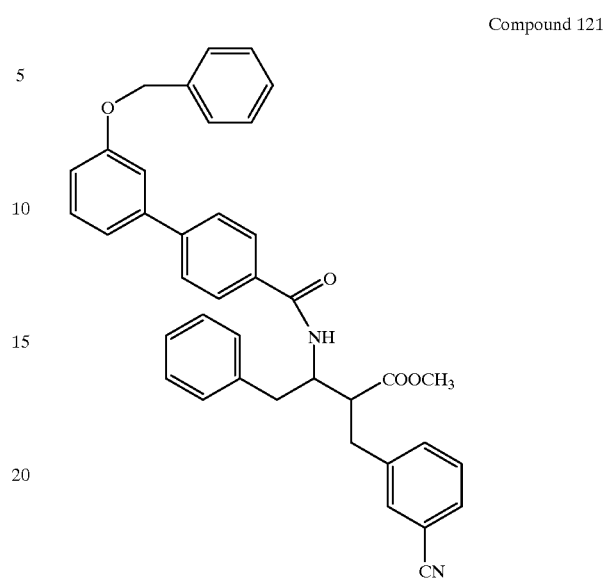

Compound 121

Compound 121 is prepared using the same procedure described for Compound 107, substituting Compound 105 for Compound 96 and substituting Compound 68 for Compound 70.

EXAMPLE 122

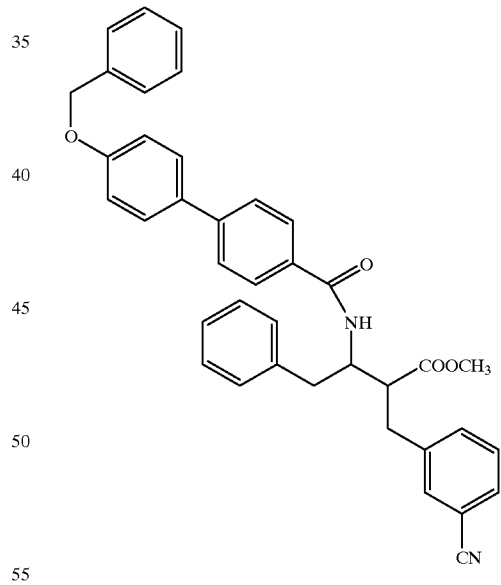

Compound 122

Compound 122 is prepared using the same procedure described for Compound 107, substituting Compound 106 for Compound 96 and substituting Compound 68 for Compound 70.

EXAMPLE 123

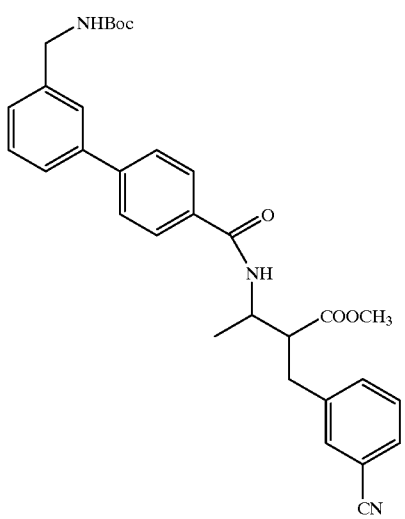

Compound 123

Compound 123 is prepared using the same procedure described for Compound 107, substituting Compound 99 for 96 and substituting Compound 69 for Compound 70.

EXAMPLE 124

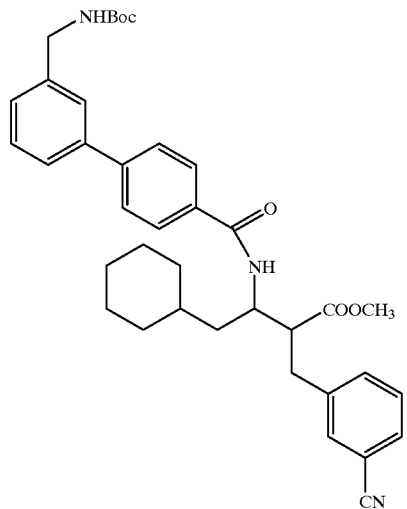

Compound 124

Compound 124 is prepared using the same procedure described for Compound 107, substituting Compound 99 for Compound 96 and substituting Compound 73 for Compound 70.

EXAMPLE 125

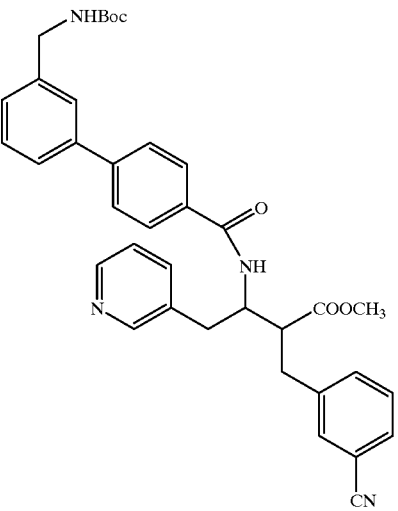

Compound 125

Compound 125 is prepared using the same procedure described for Compound 107, substituting Compound 99 for Compound 96 and substituting Compound 71 for Compound 70.

EXAMPLE 126

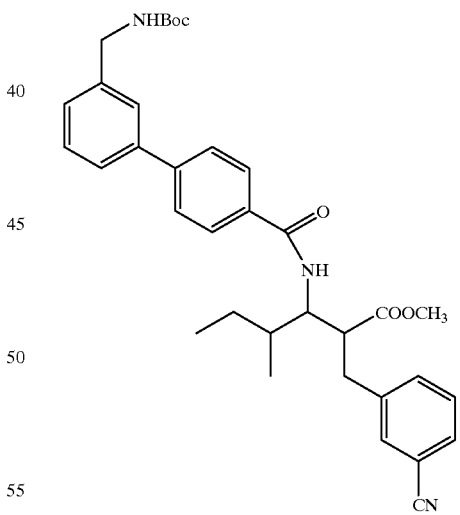

Compound 126

Compound 126 is prepared using the same procedure described for Compound 107, substituting Compound 99 for Compound 96 and substituting Compound 72 for Compound 70.

EXAMPLE 127

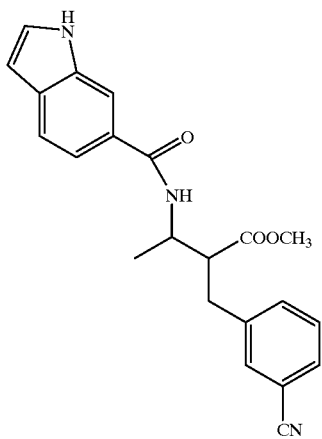

Compound 127

Compound 127 is prepared using the same procedure described for Compound 107, substituting indole-6-carboxylic acid for Compound 96 and substituting Compound 69 for Compound 70.

EXAMPLE 128

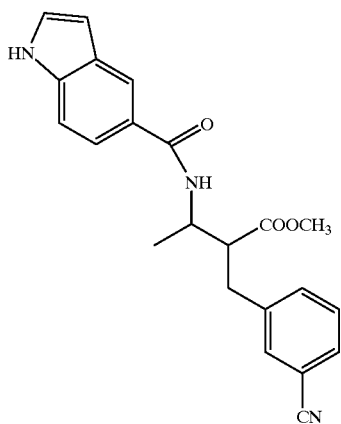

Compound 128

Compound 128 is prepared using the same procedure described for Compound 107, substituting indole-5-carboxylic acid for Compound 96 and substituting Compound 69 for Compound 70.

EXAMPLE 129

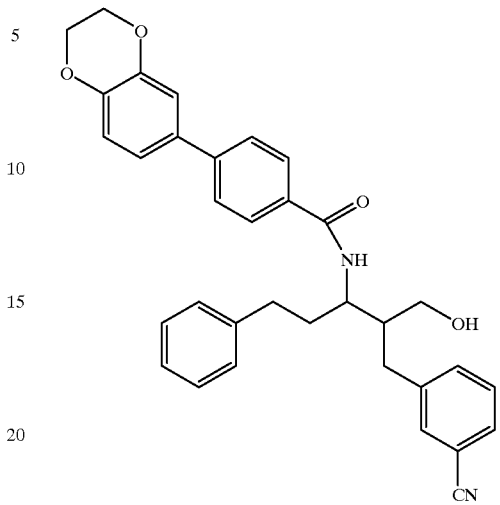

Compound 129

To a solution of Compound 107 (1.2 mmol) in 10 mL of methanol and 10 mL of tetrahydrofuran is added 10 mL of 2N sodium hydroxide, dropwise at 0° C. The solution is allowed to come to room temperature and stirred at room temperature for 2.5 hours. The solution is cooled to 0° C. and 1N hydrochloric acid is added until the pH is 7. Organic solvents are removed in vacuo and the residue diluted with 25 mL of water. 1N hydrochloric acid is added to bring the pH down to 2 and the mixture is extracted with ethyl acetate (3×75 mL). The combined organic extracts are dried over magnesium sulfate, filtered, concentrated, and dried under vacuum.

The acid (1.1 mmol) is dissolved in 15 mL of tetrahydrofuran and cooled to −20° C. N-methyl morpholine (1.45 mmol) is added in a single portion, followed by isobutyl chloroformate (1.45 mmol) dropwise via syringe. The reaction mixture is allowed to stir at −20° C. for 20 minutes. The reaction mixture is filtered into a solution of sodium borohydride (11 mmol) in 20 mL of water at 0° C. Stirring is continued 1.5 hours at 0° C. The reaction mixture is diluted with 300 mL of ethyl acetate and washed with water (3×100 mL) and brine. The organic phase is dried over magnesium sulfate, filtered, and concentrated. The resulting alcohol is purified by flash chromatography (2:3 ethyl acetate:hexanes).

EXAMPLE 130

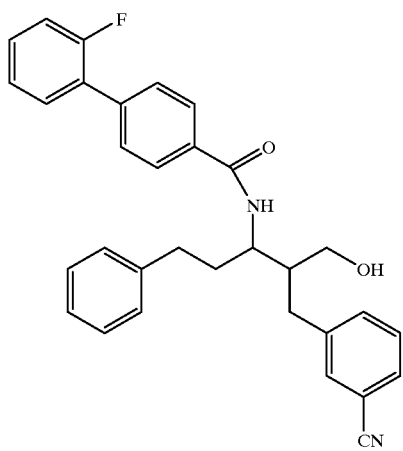
Compound 130

Compound 130 is prepared following the procedure described for Compound 129, substituting Compound 108 for Compound 107.

EXAMPLE 131

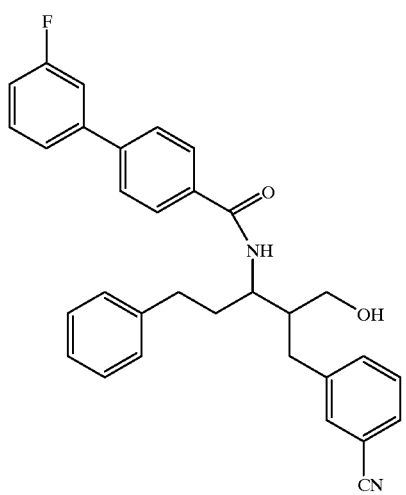
Compound 131

Compound 131 is prepared following the procedure described for Compound 129, substituting Compound 109 for Compound 107.

EXAMPLE 132

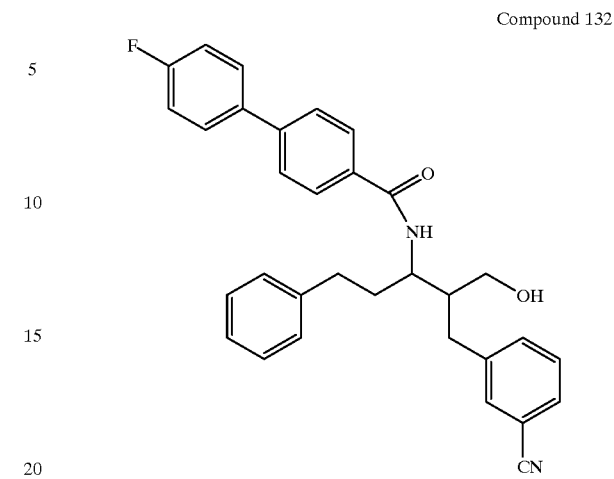
Compound 132

Compound 132 is prepared following the procedure described for Compound 129, substituting Compound 110 for Compound 107.

EXAMPLE 133

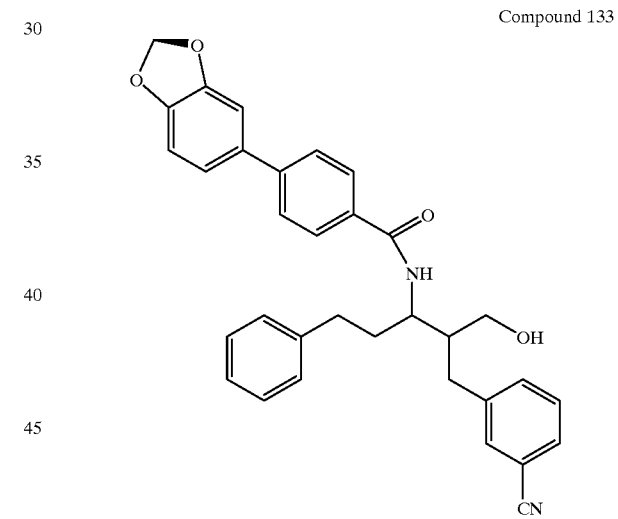
Compound 133

Compound 133 is prepared following the procedure described for Compound 129, substituting Compound 112 for Compound 107.

EXAMPLE 134

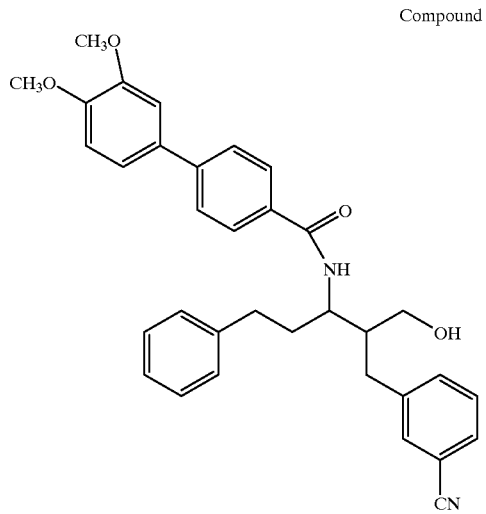
Compound 134

Compound 134 is prepared following the procedure described for Compound 129, substituting Compound 113 for Compound 107.

EXAMPLE 135

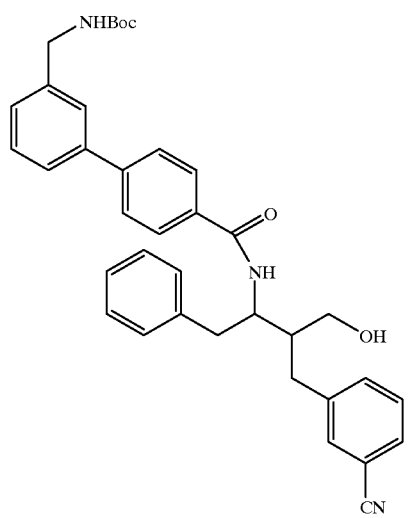
Compound 135

Compound 135 is prepared following the procedure described for Compound 129, substituting Compound 114 for Compound 107.

EXAMPLE 136

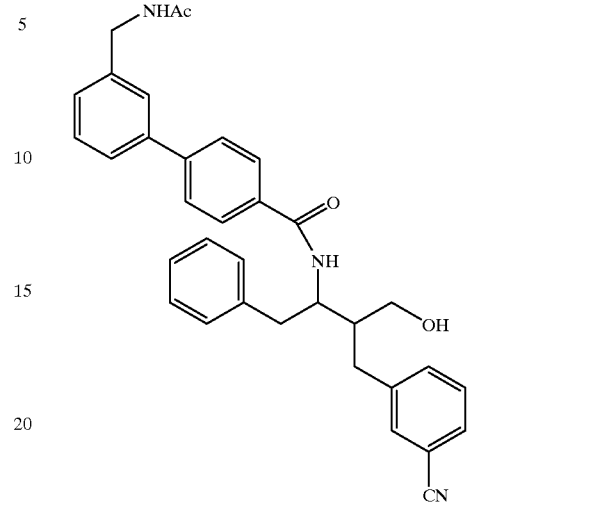
Compound 136

Compound 136 is prepared following the procedure described for Compound 129, substituting Compound 115 for Compound 107.

EXAMPLE 137

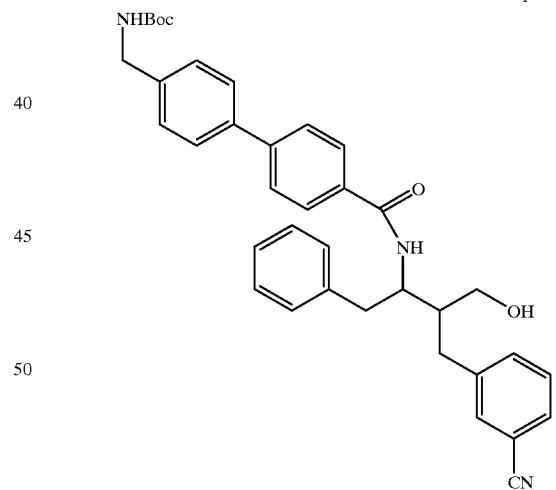
Compound 137

Compound 137 is prepared following the procedure described for Compound 129, substituting Compound 116 for Compound 107.

EXAMPLE 138

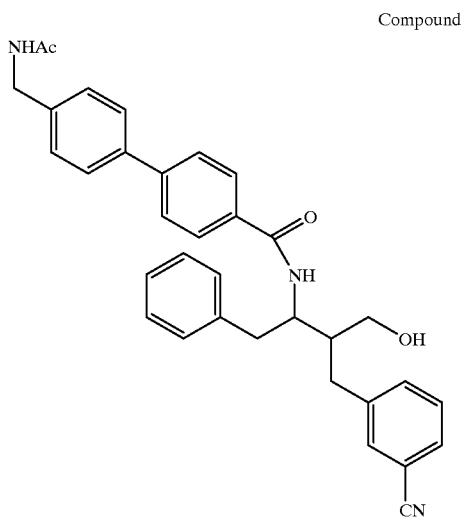
Compound 138

Compound 138 is prepared following the procedure described for Compound 129, substituting Compound 117 for Compound 107.

EXAMPLE 139

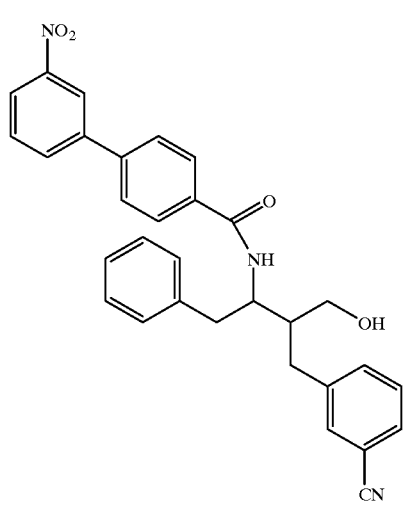
Compound 139

Compound 139 is prepared following the procedure described for Compound 129, substituting Compound 118 for Compound 107.

EXAMPLE 140

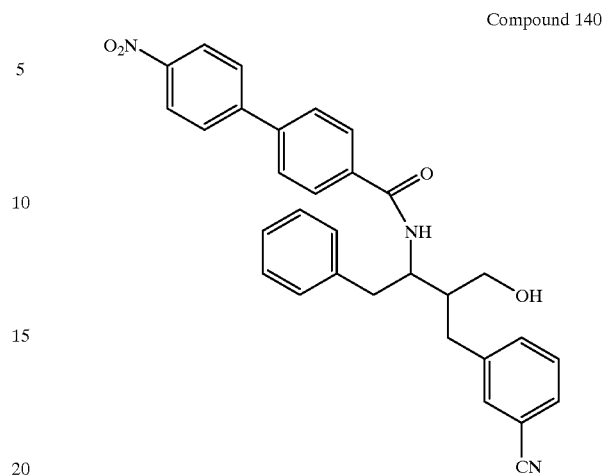
Compound 140

Compound 140 is prepared following the procedure described for Compound 129, substituting Compound 119 for Compound 107.

EXAMPLE 141

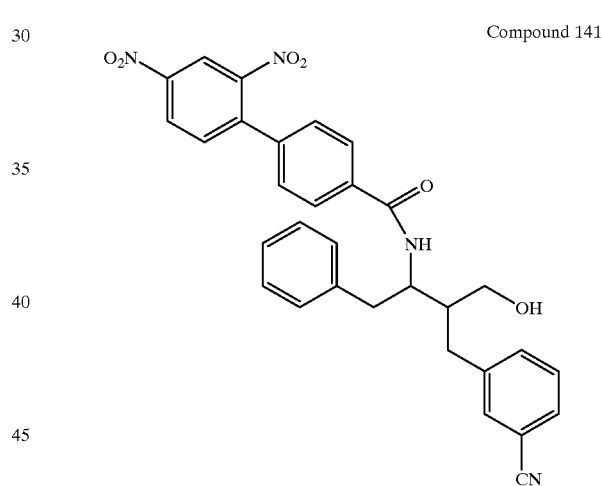
Compound 141

Compound 141 is prepared following the procedure described for Compound 129, substituting Compound 120 for Compound 107.

EXAMPLE 142

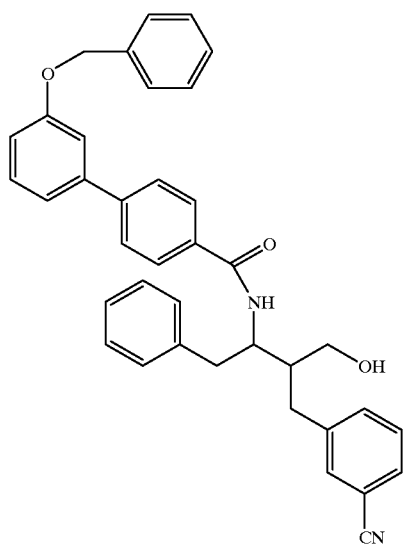

Compound 142

Compound 142 is prepared following the procedure described for Compound 129, substituting Compound 121 for Compound 107.

EXAMPLE 143

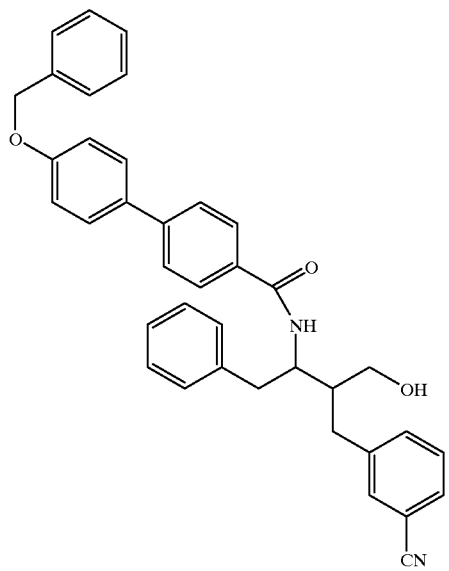

Compound 143

Compound 143 is prepared following the procedure described for Compound 129, substituting Compound 122 for Compound 107.

EXAMPLE 144

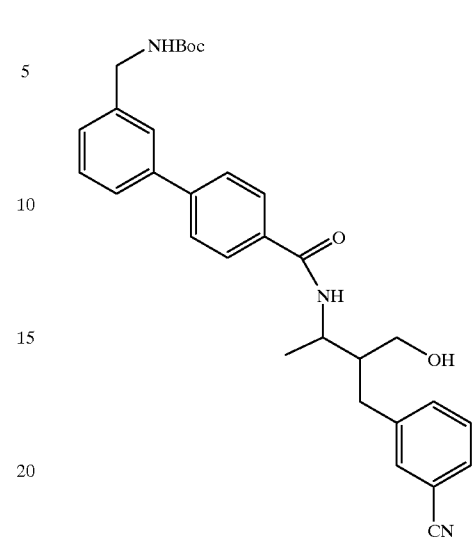

Compound 144

Compound 144 is prepared following the procedure described for Compound 129, substituting Compound 123 for Compound 107.

EXAMPLE 145

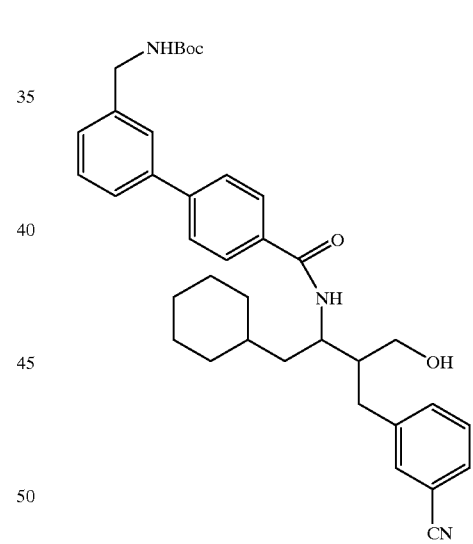

Compound 145

Compound 145 is prepared following the procedure described for Compound 129, substituting Compound 124 for Compound 107.

EXAMPLE 146

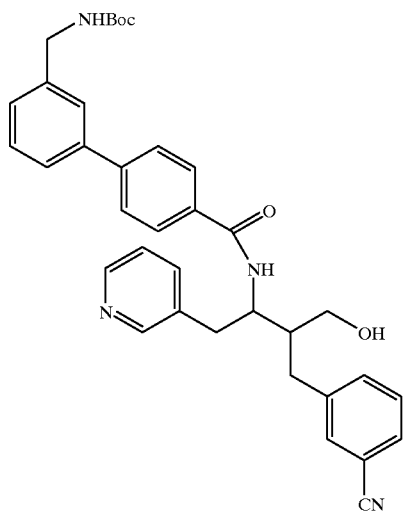

Compound 146

Compound 146 is prepared following the procedure described for Compound 129, substituting Compound 125 for Compound 107.

EXAMPLE 147

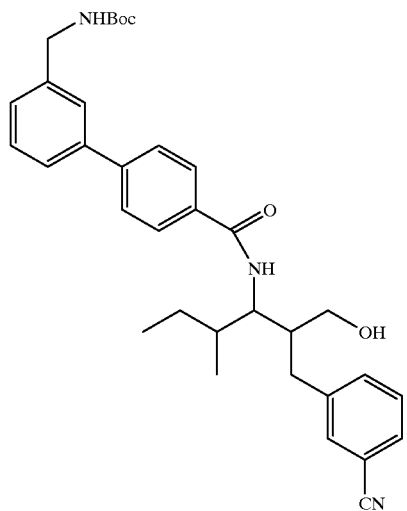

Compound 147

Compound 147 is prepared following the procedure described for Compound 129, substituting Compound 126 for Compound 107.

EXAMPLE 148

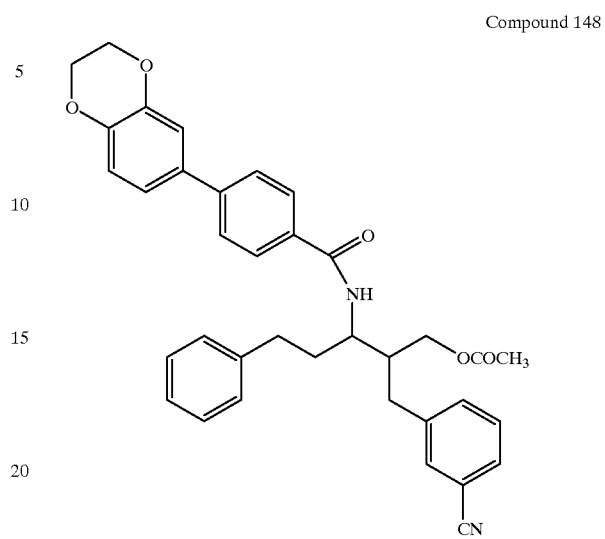

Compound 148

To a solution of Compound 129 (0.5 mmol) in 8 mL of methylene chloride is added pyridine (0.6 mmol) in a single portion at 0° C. Acetic anhydride (0.6 mmol) is added in a single portion, followed by dimethylaminopyridine in a similar fashion. The reaction mixture is allowed to come to room temperature and stirring is continued overnight. The reaction mixture is partitioned between 10 mL of 0.1N hydrochloric acid and 30 mL of methylene chloride. The organic layer is dried over sodium sulfate, filtered and concentrated in vacuo.

EXAMPLE 149

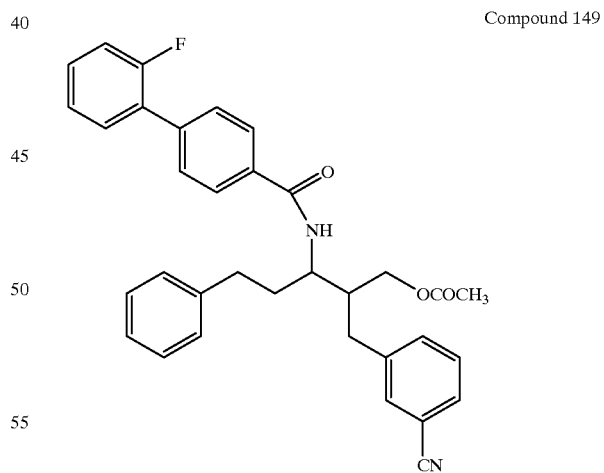

Compound 149

Compound 149 is prepared following the method described for Compound 148, substituting Compound 130 for Compound 129.

EXAMPLE 150

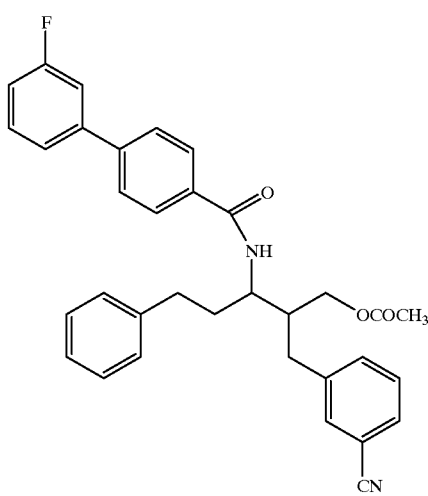

Compound 150

Compound 150 is prepared following the method described for Compound 148, substituting Compound 131 for Compound 129.

EXAMPLE 151

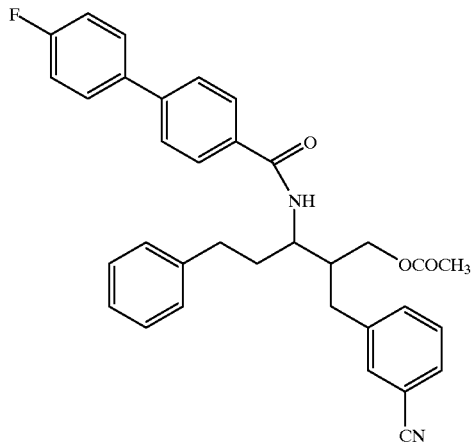

Compound 151

Compound 151 is prepared following the method described for Compound 148, substituting Compound 132 for Compound 129.

EXAMPLE 152

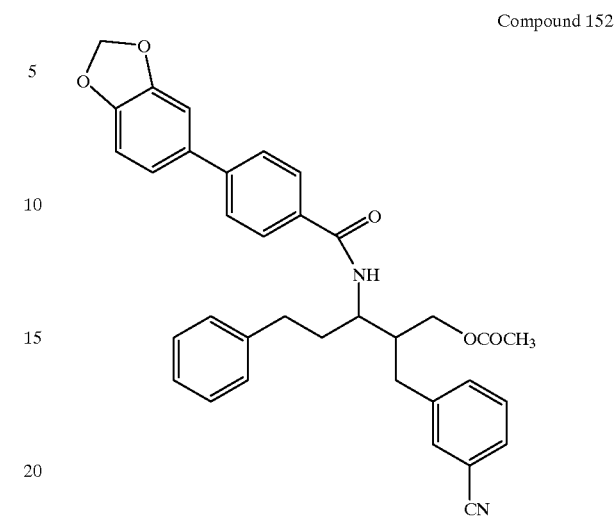

Compound 152

Compound 152 is prepared following the method described for Compound 148, substituting Compound 133 for Compound 129.

EXAMPLE 153

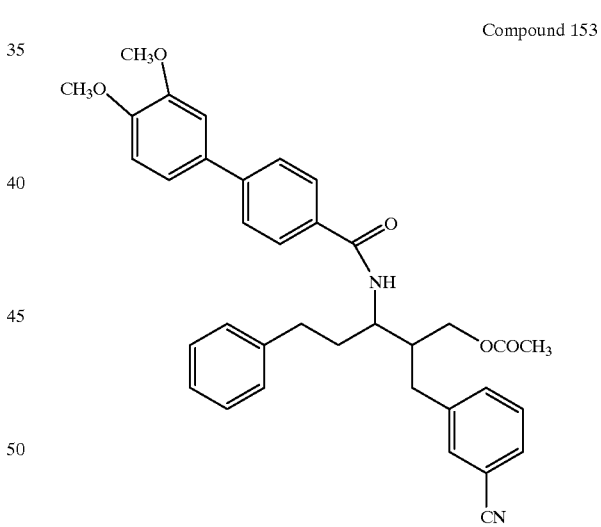

Compound 153

Compound 153 is prepared following the method described for Compound 148, substituting Compound 134 for Compound 129.

EXAMPLE 154

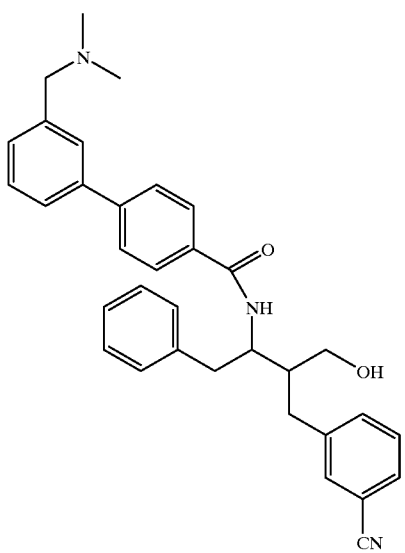
Compound 154

To a solution of Compound 135 (1.1 mmol) in 30 mL of methylene chloride is added 10 mL of trifluoroacetic acid in a single portion at 0° C. The resulting solution is stirred for 3 hours at 0° C. Solvents are removed in vacuo and the residue partitioned between 10% aqueous sodium bicarbonate and ethyl acetate. The organic phase is dried over magnesium sulfate, filtered, and concentrated in vacuo. The free amine (1.1 mmol) is dissolved in 10 mL of glacial acetic acid and paraformaldehyde (11 mmol) is added in a single portion at room temperature. Stirring is continued overnight at room temperature.

The reaction mixture is poured into 50 mL of ice cold 2N sodium hydroxide and extracted with ethyl acetate (3×100 mL). The combined organic extracts are backwashed with water, dried over magnesium sulfate, filtered, and concentrated in vacuo. The desired product is purified by reverse phase HPLC using a gradient of 20% to 100% acetonitrile in water, buffered with 0.1% trifluoroacetic acid.

EXAMPLE 155

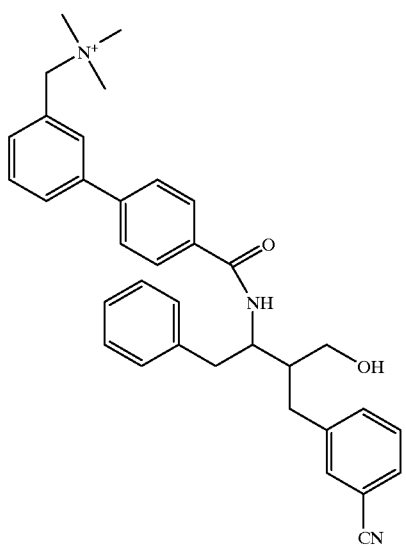
Compound 155

To a solution of Compound 154 (0.5 mmol) in 10 mL of dry acetone is added methyl iodide (large excess, 2 mL) in a single portion at room temperature. The resulting solution is allowed to stir at room temperature overnight. Solvents are removed in vacuo to provide the desired tetramethylammonium salt.

EXAMPLE 156

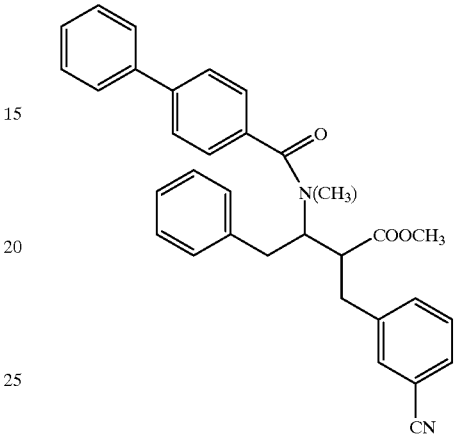
Compound 156

To a solution of Compound 111 (0.8 mmol) in 2 mL of dimethylformamide and 8 mL of tetrahydrofuran is added sodium hydride (1 mmol) in a single portion at 0° C. The solution is stirred for 1 hour at 0° C. and methyl iodide (large excess) is added in a single portion. The solution is allowed to come to room temperature and stirred overnight. The reaction mixture is poured into 100 mL of ice water and extracted with ethyl acetate (3×75 mL). The combined organic extracts are backwashed with water, dried over magnesium sulfate, filtered, concentrated in vacuo, and purified by flash chromatography (1:2 ethyl acetate:hexanes).

EXAMPLE 157

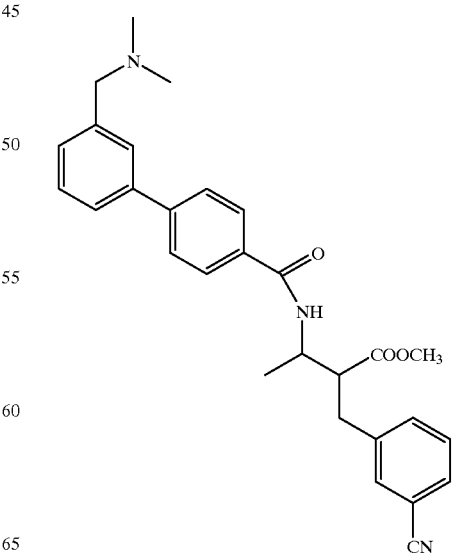
Compound 157

Compound 157 is prepared following the procedure described for Compound 154, substituting Compound 123 for 135.

EXAMPLE 158

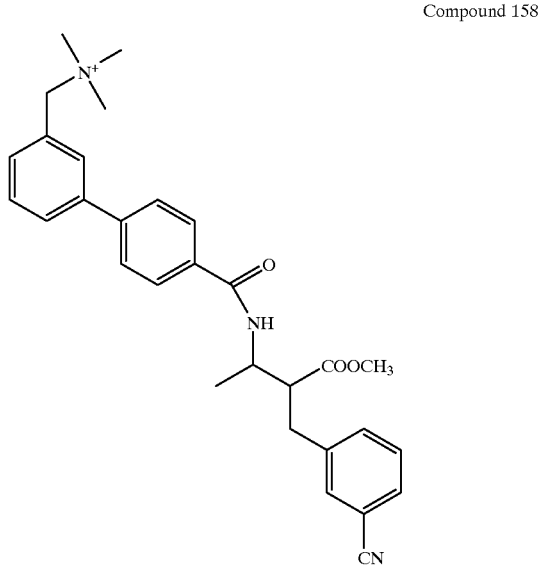

Compound 158

Compound 158 is prepared according to the method described for Compound 155, starting from Compound 157.

EXAMPLE 159a

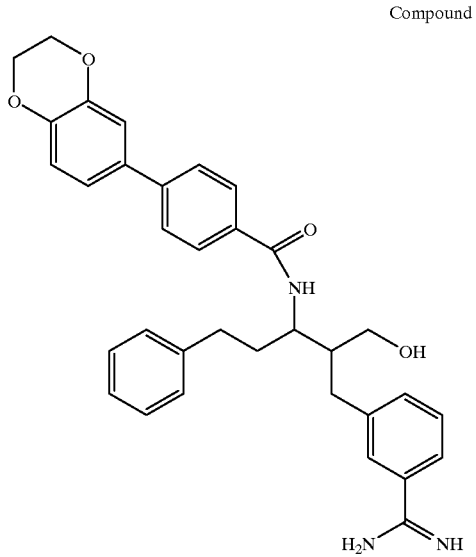

Compound 159

To a solution of Compound 129 (1 mmol) in 50 mL of dry methanol is added crushed 3 Å molecular sieves (approximately 1 g). The mixture is stirred for 10 minutes at 0° C. and hydrogen chloride gas is bubbled through the reaction mixture for 10 minutes at 0° C. The reaction mixture is allowed to come to room temperature and stirred overnight. Nitrogen gas is bubbled through the reaction mixture for 5 minutes and methanol is removed in vacuo. The residue is dried under vacuum to remove all traces of hydrogen chloride, then remixed with 75 mL of dry methanol. The mixture is then cooled to 0° C. and ammonia gas is bubbled through the reaction mixture for 10 minutes. The reaction mixture is allowed to come to room temperature, then heated at 60° C. for 3 hours. After cooling to room temperature, nitrogen gas is bubbled through the reaction for 5 minutes and the mixture is filtered through celite, concentrated in vacuo, and purified by reverse phase HPLC using a gradient of 20% to 80% acetonitrile in water buffered with 0.1% trifluoroacetic acid. Acetonitrile is removed in vacuo and the aqueous phase lyophilized to provide the desired product as its trifluoroacetate salt.

EXAMPLE 159b

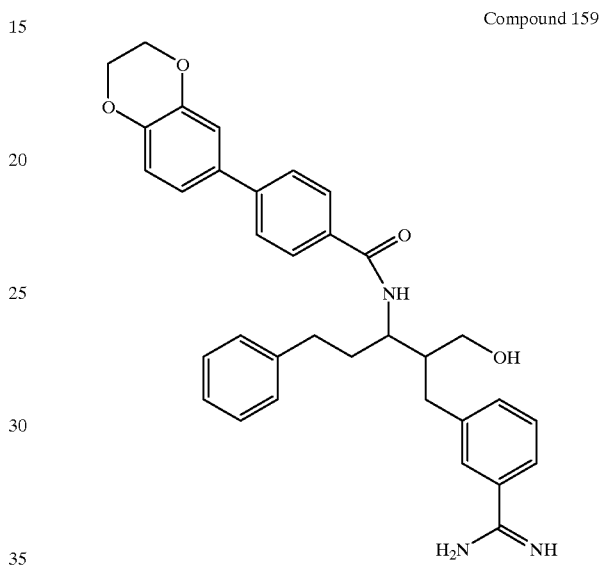

Compound 159

1H NMR (300 Mhz, d6 DMSO) d 9.21 (s, 2H), 9.01 (s, 2H), 8.22 (d, 1H, J=9.6 Hz), 7.85 (d, 2H, J=7.2 Hz), 7.70 (d, 2H, J=7.2 Hz), 7.62–7.38 (m, 4H), 7.25–7.05 (m, 7H), 6.93 (d, 1H, J=8.4 Hz), 4.90–4.65 (m, 1H), 4.24 (s, 4H), 4.18–4.05 (m, 2H), 2.78–2.63 (m, 2H), 2.65–2.45 (m, 2H), 2.08–1.75 (m, 3H).

MS, LRFAB, calc. 591, found 592 (M+H)+.

Into a solution of Compound 129 (1 mmol) in 20 mL of pyridine and 4 mL of triethylamine is bubbled hydrogen sulfide for 10 minutes at room temperature. The solution is allowed to stir at room temperature overnight. Nitrogen gas is bubbled through the reaction for 5 minutes and solvents are removed in vacuo. The residue is dried under vacuum, then dissolved in 15 mL of dry acetone. To this solution is added 5 mL of methyl iodide and this solution is heated at 50° C. for 1 hour, then concentrated in vacuo. The residue is dissolved in 20 mL of methanol and ammonium acetate (2 mmol) is added in a single portion at room temperature. The reaction mixture is heated at 65° C. for 2 hours. After cooling, methanol is removed in vacuo and the residue purified by reverse phase HPLC using a gradient of 20% to 80% acetonitrile in water buffered with 0.1% trifluoroacetic acid. Acetonitrile is removed in vacuo and the aqueous phase lyophilized to provide the desired product as its trifluoroacetate salt.

The following compounds are prepared from the appropriate starting materials by procedures substantially similar to the procedures described above.

EXAMPLE 161

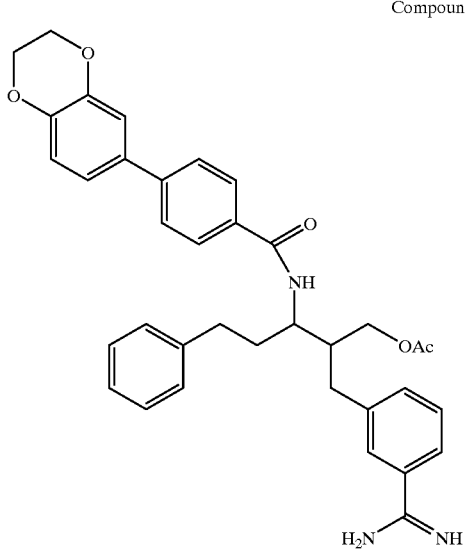
Compound 161

1H NMR (300 MHz, d6 DMSO) d 9.23 (s, 2H), 9.01 (s, 2H), 8.27 (d, 1H, J=9.6 Hz), 7.93 (d, 2H, J=7.2 Hz), 7.72 (d, 2H, J=7.2 Hz), 7.65–7.55 (m, 2H), 7.54– 7.42 (m, 2H), 7.28–7.08 (m, 7H), 6.94 (d, 1H, J=8.4 Hz), 4.25 (s, 4H), 4.24–4.11 (m,1H), 4.05–3.83 (m,2H), 2.86 (dd, 1H, J=6.0, 15.6 Hz), 2.70–2.55 (m, 2H), 2.53–2.43 (m, 1H), 2.35–2.20 (m, 1H), 1.98–1.90 (m, 2H), 1.87 (s, 3H).

MS, LRFAB, calc. 591, found 592 (M+H)+.

EXAMPLE 162

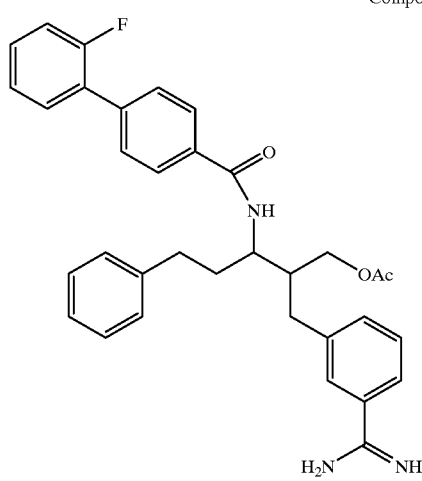
Compound 162

1H NMR (300 Mhz, d6 DMSO) d 9.21 (s, 2H), 9.01 (s, 2H), 8.22 (d, 1H, J=9.6 Hz), 7.85 (d, 2H, J=7.2 Hz), 7.70 (d, 2H, J=7.2 Hz), 7.62–7.38 (m, 4H), 7.25–7.05 (m, 7H), 6.93 (d, 1H, J=8.4 Hz), 4.90–4.65 (m, 1H), 4.24 (s, 4H), 4.18–4.05 (m, 2H), 2.78–2.63 (m, 2H), 2.65–2.45 (m, 2H), 2.08–1.75 (m, 3H).

MS, LRFAB, calc. 591, found 592 (M+H)+.

EXAMPLE 163

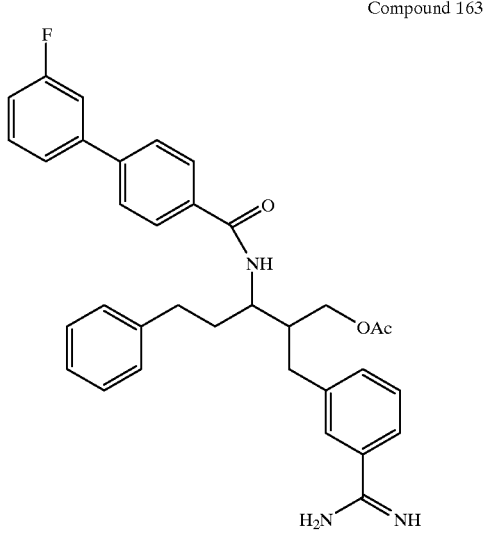
Compound 163

NMR 300 MHz, d6 DMSO, d 9.23 (s, 2H), 9.09 (s, 2H), 8.83 (d, 1H, J=9.6 Hz), 7.97 (d, 2H, J=7.2 Hz), 7.83 (d, 1H, J=7.2 Hz), 7.65–7.35 (m, 7H), 7.28–7.05 (m, 6H), 4.26–4.10 (m, 1H), 4.05–3.83 (m, 2H), 2.87 (dd, 1H, J=6.0 Hz, 15.6 Hz), 2.70–2.55 (m, 2H), 2.32–2.18 (m, 1H), 2.03–1.90 (m, 2H), 1.87(s, 3H).

MS ion spray: calc. 551, found 552 (M+H)+.

EXAMPLE 164

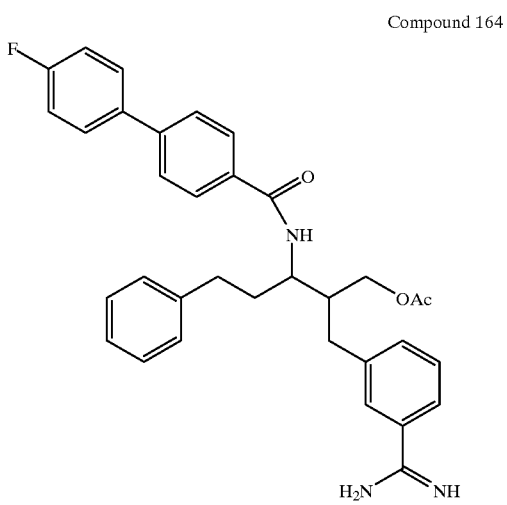
Compound 164

NMR 300 MHz, d6 DMSO, d 9.22 (s, 2H), 9.02 (s, 2H), 8.32 (d, 1H, J=9.6 Hz), 7.96 (d, 2H, J=7.2 Hz), 7.81–7.65 (m, 4H), 7.65–7.40 (m, 4H), 7.38–7.05 (m, 7H), 4.25–4.10 (m, 1H), 4.05–3.85 (m, 2H), 2.87 (dd, 1H, J=6.0, 15.6Hz), 2.70–2.55 (m, 2H), 2.54–2.43 (m, 1H), 2.35–2.20 (m, 1H), 1.98–1.90 (m, 2H), 1.89 (s, 3H).

MS ion spray: calc. 551, found 552 (M+H)+.

EXAMPLE 165

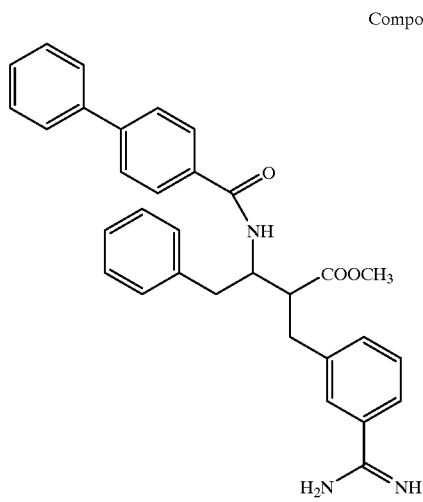

Compound 165

H1 NMR, 300 MHz, d6 DMSO, d 9.25 (s, 2H), 9.18 (s, 2H), 8.35 (d, 1H, J=9.6 Hz), 7.80 (d, 2H, 7.2 Hz), 7.73 (d, 2H, J=7.2 Hz), 7.68 (d, 2H, J=6.0 Hz), 7.62 (br.s, 2H), 7.55–7.31 (m, 5H), 7.25–7.03 (m, 5H), 4.65–4.45 (m, 1H), 3.53 (s, 3H), 3.20–2.82 (m, 5H).

MS LRFAB: cal'd 505, found 506 (M+H)+.

EXAMPLE 166

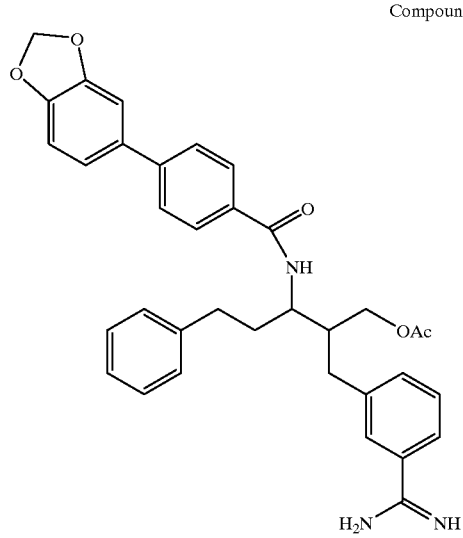

Compound 166

1H NMR (300 MHz, d6 DMSO) d 9.23 (s, 2H), 8.99 (s, 2H), 8.26 (d, 1H, J=9.6 Hz), 7.93 (d, 2H, J=7.2 Hz), 7.72 (d, 2H, J=7.2 Hz), 7.65–7.56 (m, 2H), 7.54–7.42 (m, 2H), 7.32 (d, 1H, J=2.4 Hz), 7.28–7.08 (m, 6H), 7.02 (d, 1H, J=8.4 Hz), 6.07 (s, 2H), 4.25–4.12 (m, 1H), 4.06–3.85 (m, 2H), 2.85 (dd, 1H, J=6.0, 15.6 Hz), 2.68–2.55 (m, 2H), 2.53–2.43 (m, 1H), 2.32–2.20 (m, 1H), 2.01–1.90 (m, 2H), 1.87 (s, 3H).

MS, LRFAB, calc. 557, found 558 (M+H)+.

EXAMPLE 167

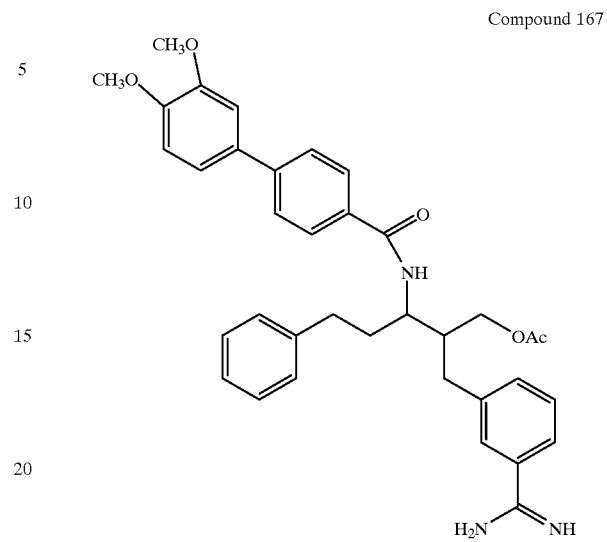

Compound 167

NMR: 9.5 (s, 1H), 9.4 (s, 1H), 8.4 (d, 1H J=9.0 Hz), 8.1 (d, 2H, J=8.0 Hz), 7.9 (d, 2H, J=8.0 Hz), 7.5–7.8 (m, 5H), 7.1–7.4 (m, 7H), 5.0 (m, 1H), 4.0–4.1 (m, 1H), 4.0 (s, 3H), 3.9 (s, 3H), 3.6 (m, 1H), 2.9–3.1 (m, 4H), 2.1–2.3 (m, 2H), 2.0 (s, 3H)

M.S. Cal'd 594.3, Found 594.

EXAMPLE 168

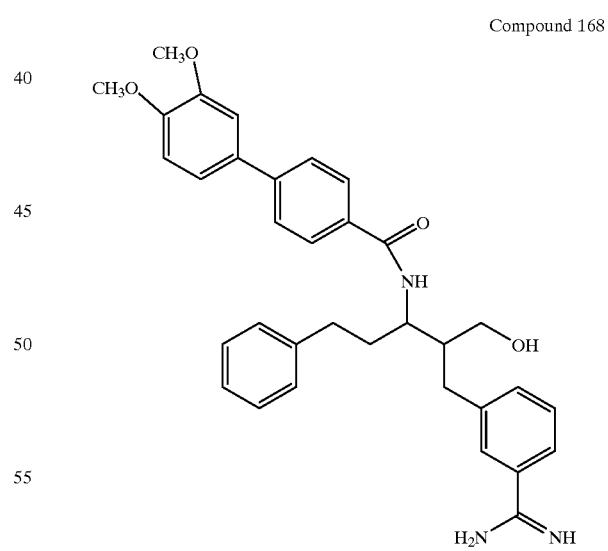

Compound 168

NMR: 9.4 (s, 1H), 9.0 (s, 1H), 8.4 (d, 1H, J=9.0 Hz), 8.1 (d, 2H, J=7.0 Hz), 7.9 (d, 2H, J=7.0 Hz), 7.5–7.8 (m, 5H), 7.1–7.4 (m, 7H), 5.0 (m, 1H), 4.04–4.1 (m, 1H), 4.0 (s, 3H), 3.9 (s, 3H), 3.6 (m, H), 2.9–3.1 (m, 4H), 2.1–2.3 (m, 2H).

M.S. Cal'd 552.1, Found 552

EXAMPLE 169

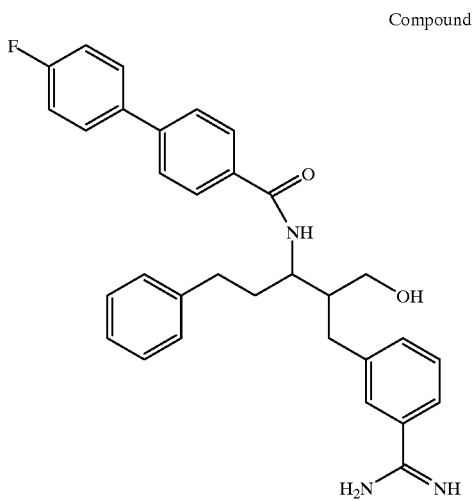

Compound 169

H1 NMR, 300 MHz, d6 DMSO, d 9.22 (s, 2H), 9.11 (s, 2H), 7.92 (d, 2H, J=7.2 Hz), 7.80–7.65 (m, 4H), 7.62–7.40 (m, 4H), 7.37–7.01 (m, 7H), 4.85–4.65 (m, 1H), 4.22–4.02 (m, 1H), 3.55–3.36 (m, 2H), 2.82–2.62 (m, 2H), 2.60–2.45 (m, 1H), 2.05–1.73 (m, 3H).

MS LRFAB: calc. 509, found 510 (M+H).

EXAMPLE 170

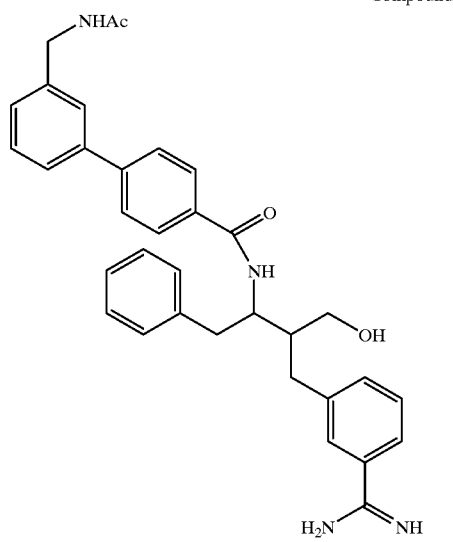

Compound 170

NMR: 8.5 (d, 1H, J=9.0 Hz), 7.8 (d, 2H, J=9.0 Hz), 7.7 (d, 2H, J=9.0 Hz), 7.1–7.6 (m, 11H), 4.5 (m, 1H), 4.4 (s, 2H), 4.0 (dd, 1H, J=6.0 Hz, 10.0 Hz), 3.7 (dd, 1H, (J=6.0 Hz, 10.0 Hz), 3.0 (d, 2H, J=9.0 Hz), 2.9 (d, 2H, J=9.0 Hz), 2.0 (d, 1H, J=7.0 Hz).

Mass spec M+H calc 549.2, found 549.

EXAMPLE 171

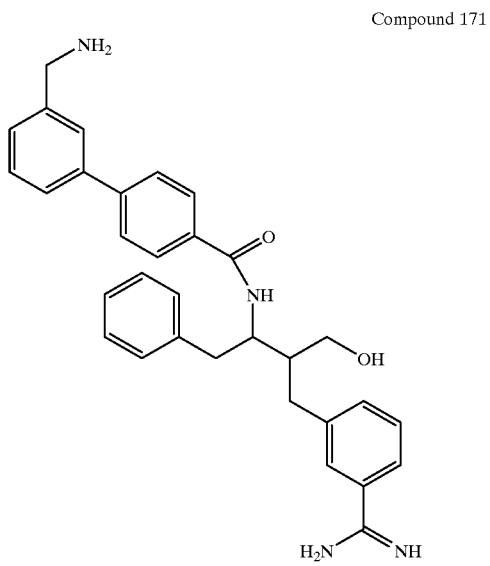

Compound 171

NMR: 8.5 (d, 1H, J=9.0 Hz), 7.75–7.9 (m, 6H), 7.4–7.7 (m, 6H), 7.0–7.2 (m, 1H), 4.2 (s, 2H), 4.0 (dd, 1H, (J=6.0 Hz, 10.0 Hz), 3.7 (dd, 1H, J=6.0 Hz, 10.0 Hz), 3.0 (d, 2H, J=9.0 Hz), 2.9 (d, 1H, (J=9.0 Hz), 2.0 (m, 1H).

Mass spec M+H calc 507.3, found 507.

EXAMPLE 172

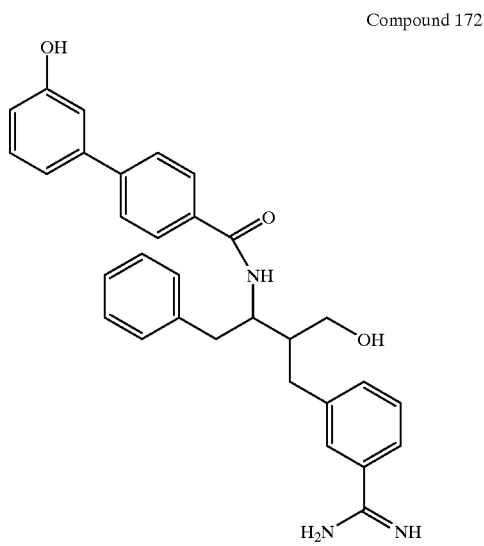

Compound 172

NMR: 8.5 (d, 1H, J=9.0 Hz), 7.8 (d, 2H, J=10.0 Hz), 7.7 (d, 2H, J=10.0 Hz), 7.6 (d, 1H, J=10.0 Hz), 7.5 (m, 3H), 7.0–7.3 (m, 8H), 6.8 (d, 1H, J=9.0 Hz), 4.5 (m, 3H), 4.1 (dd, 1H, J=6.0 Hz, 10.0 Hz), 3.9 (dd, H J=6.0 Hz, 10.0 Hz), 3.1 (d, 2H, J=9.0 Hz) 2.9 (d, 2H, J=9.0 Hz), 2.0 (m, 1H).

Mass Spec M+H calc 494.2, found 494.

EXAMPLE 173

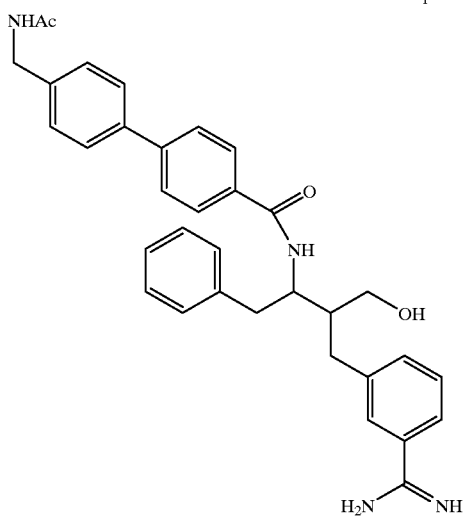

Compound 173

NMR: 8.5 (d, 1H, J=9.0 Hz), 7.9 (d, 2H, J=10.0 Hz), 7.8 (d, 2H, J=10.0 Hz), 7.7 (d, 2H, J=10.0 Hz), 7.6 (d, 2H, J=10.0 Hz), 7.4 (s, 1H), 7.0–7.2 (m, 3H), 4.5 (m, 3H), 4.1 (dd, H, J=6.0 Hz, 10.0 Hz), 3.9 (dd, 1H J=6.0 Hz, 10.0 Hz), 3.1 (d, 2H, J=9.0 Hz) 2.9 (d, 2H, J=9.0 Hz), 2.1 (d, 3H, J=10.0 Hz).

Mass Spec M+H calc 549.3, found 549.

EXAMPLE 174

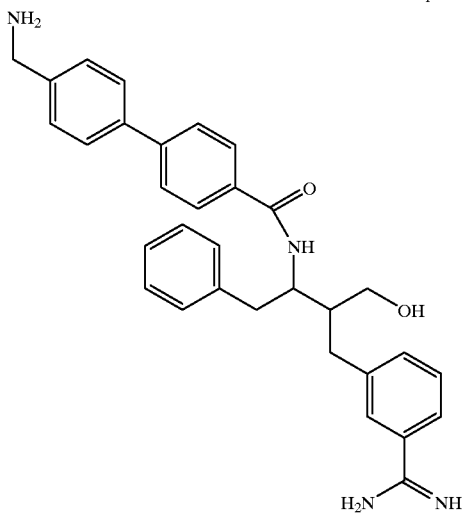

Compound 174

NMR: 8.5 (d, 1H, J=9.0 Hz), 7.8 (d, 2H, J=8.0 Hz), 7.6–7.8 (m,4H), 7.4–7.6 (m, 4H), 7.1–7.3 (m, 4H), 6.8 (d, 2H, J=9.0 Hz), 4.3 (m, 1H), 4.0 (dd, 1H, J=6.0 Hz, 10.0 Hz), 3.7 (dd, 1H, J=6.0 Hz, 10.0 Hz), 3.0 (d, 2H, J=4.0 Hz), 2.9 (d, 1H, J=9.0 Hz), 2.0 (m, 1H)

Mass spec. M+H calc 507.3, found 507

EXAMPLE 175

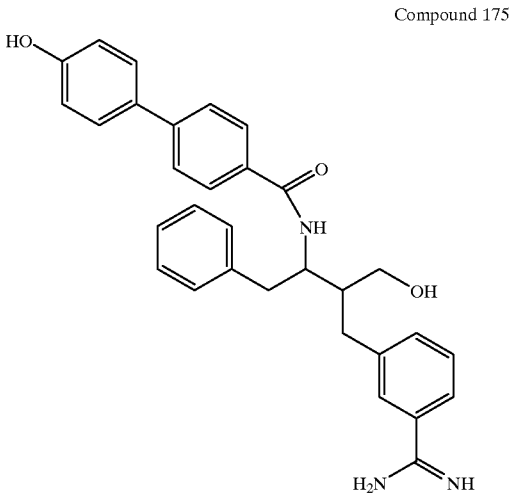

Compound 175

M.S. Cal'd 494.2, Found 494

EXAMPLE 176

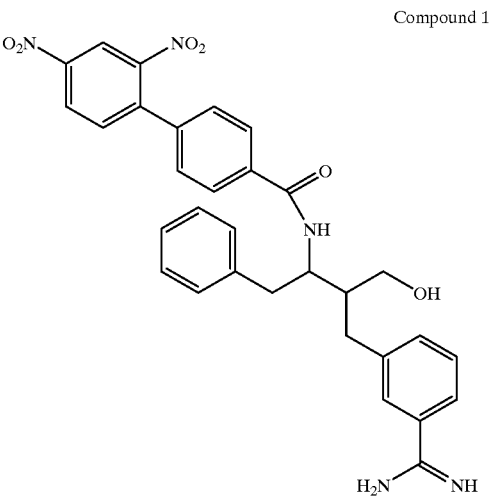

Compound 176

NMR 300 MHz, d6 DMSO d 9.23 (s, 2H), 9.04 (s, 2H), 8.57 (d, 1H, 9.6 Hz), 8.42 (s, 1H), 8.32 (d, 2H, 7.2 Hz), 8.13 (dd, 1H, J=1.2, 7.2 Hz), 7.75–7.40 (m, 7H), 7.25–7.13 (m, 4H), 7.12–7.05 (m, 2H), 4.48–4.35 (m, 1H), 3.58–3.42 (m, 2H) 3.10–2.62 (m, 4H), 2.15–1.95 (m, 1H).

MS (LRFAB): calc. 567, found 568 (M+H)+.

EXAMPLE 177

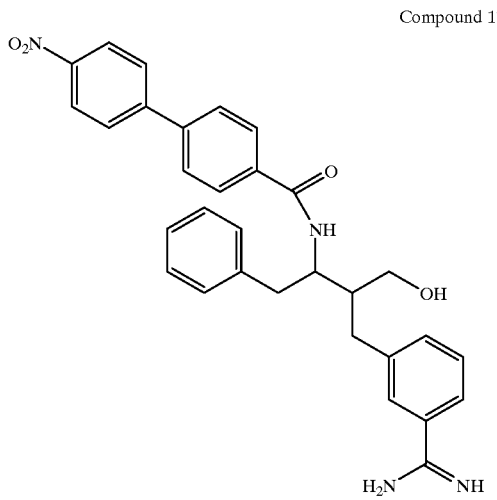

Compound 177

NMR 300 MHz, d6 DMSO d 9.23 (s, 2H), 8.98 (s, 2H), 8.37–8.22 (m, 3H), 7.97 (d, 2H, J=7.2 Hz), 7.86 (s, 4H), 7.65–7.40 (m, 4H), 7.25–7.15 (m, 3H), 7.13–7.05 (m, 2H), 4.45–4.25 (m, 1H), 3.62–3.48 (m, 2H), 3.00–2.86 (m, 2H), 2.85–2.65 (m, 2H), 2.06–1.92 (m, 1H).

MS (LRFAB): calc. 522, found 523 (M+H)+.

EXAMPLE 178

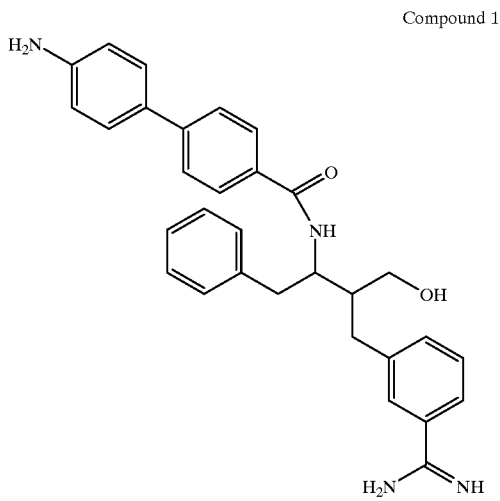

Compound 178

NMR 300 MHz, d6 DMSO, 9.23(d, 4H, J=6 Hz), 8.28(d, 1H, J=10 Hz), 7.77(d, 2H, J=10 Hz), 7.71–7.42(m, 8H), 7.22–7.12 (m, 4H), 7.10–7.01(m, 3H), 4.45–4.25(m, 1H), 3.65–3.45(m, 2H), 3.05–2.87(m, 2H), 2.85–2.65(m, 2H), 2.05–1.95(m, 1H).

MS (LRFAB): calc'd 492, found 493 (M+H)+.

EXAMPLE 179

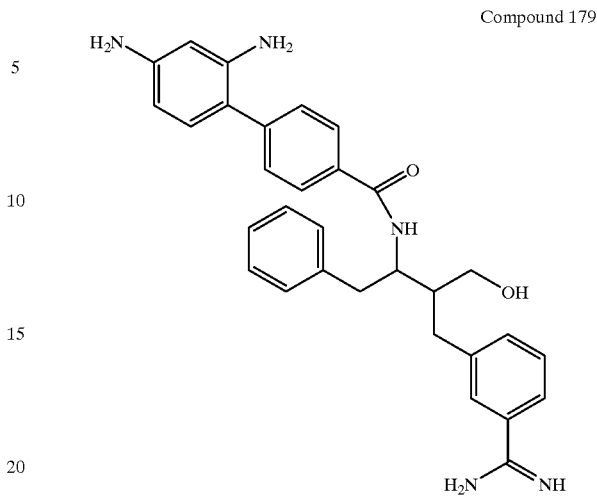

Compound 179

Nmr 300 MHz, d6 DMSO, 9.38–9.21(m, 4H), 8.28(d, 1H, J=10 Hz), 8.16(d, 1H, J=10 Hz), 7.70–7.45(m, 5H), 7.42(d, 2H,J=7 Hz), 7.23(s, 1H), 7.21–7.03(m, 8H), 4.48–4.23(m, 1H), 3.64–3.40(m, 2H), 3.10–2.85(m, 2H), 2.84–2.62(m, 2H), 2.03–1.87(m, 1H).

MS (LRFAB): calc'd 507, found 508 (M+H)+.

EXAMPLE 180

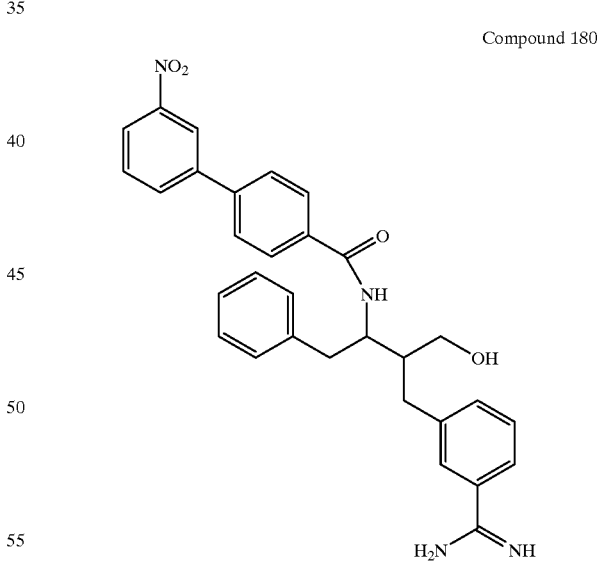

Compound 180

NMR 300 MHz, d6 DMSO, 9.23 (s, 2H), 8.95 (s, 2H), 8.45 (s, 1H), 8.32 (d, 1H, J=8.4 Hz), 8.24 (d, 1H, J=8.4 Hz), 8.18 (d, 1H, J=7.2 Hz), 7.86 (br.s, 4H), 7.83–7.73 (m, 1H), 7.63–7.43 (m, 4H), 7.25–7.16 (m, 4H), 7.14–7.05 (m, 1H), 4.45–4.30 (m, 1H), 3.63–3.48 (m, 2H), 3.02–2.88 (m, 2H), 2.87–2.65 (m, 2H), 2.08–1.93 (m, 1H).

MS(LRFAB): calc'd 522, found 523 (M+H)+.

EXAMPLE 181

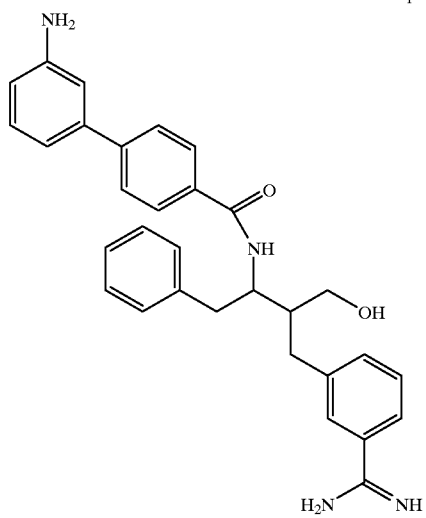

Compound 181

NMR 300 MHz, d6 DMSO, 9.25 (s, 2H), 9.19 (s, 2H), 8.30 (d, 1H, J=9.6 Hz), 7.82 (s, 1H), 7.82 (d, 2H,J=7.2 Hz), 7.66 (d, 2H, J=7.2 Hz), 7.63–7.45 (m, 4H), 7.38–7.27 (m, 1H), 7.25–7.13 (m, 6H), 7.13–7.05 (m, 1H), 6.93 (d, 1H, J=8.4 Hz), 4.43–4.28 (m, 1H), 3.65–3.45 (m, 2H), 3.05–2.86 (m, 2H), 2.83–2.68 (m, 2H), 2.08–1.92 (m, 1H).

MS(LRFAB): calc'd 492, found 493 (M+H)+.

EXAMPLE 182

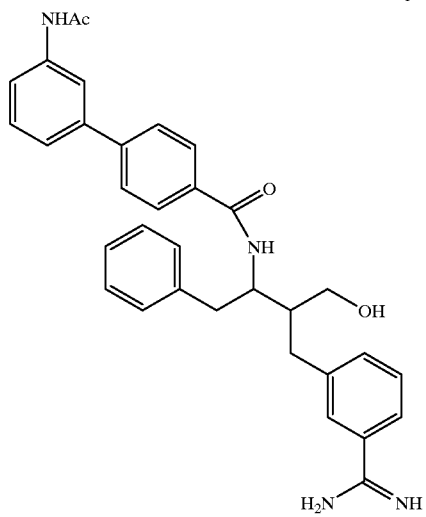

Compound 182

Nmr 300 MHz, d6 DMSO, 9.22(s,2H), 9.07(s,2H), 8.38 (d, 1H,J=10 Hz), 7.93(s, 1H), 7.83(d,2H,J=7 Hz), 7.65(d, 2H,J=7 Hz), 7.62–7.45(m,5H), 7.42–7.28(m,2H), 7.25–7.16 (m,4H), 7.13–7.07(m,1H), 4.45–4.28(m,1H), 3.63–3.53(m, 2H), 3.05–2.87(m,2H), 2.85–2.68(m,2H), 2.03(s,3H), 2.02–1.93(m,1H).

MS(LRFAB): calc'd 534, found 535 (M+H)+.

EXAMPLE 183

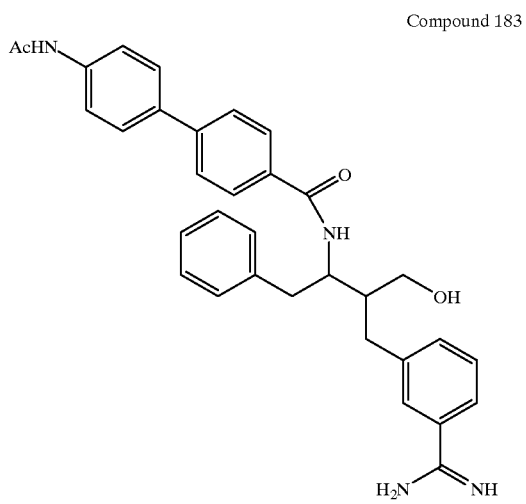

Compound 183

Nmr 300 MHz, d6 DMSO, 10.05(s, 1H),9.23(s,2H), 9.10 (s,2H), 8.25 (d, 1H,J=10 Hz), 7.78(d,2H,J=7 Hz),7.73–7.40 (m, 10H), 7.21–7.13(m,4H), 7.13–7.05(m,1H), 4.43–4.25 (m, 1H), 3.63–3.45(m,2H), 3.03–2.85(m,2H), 2.83–2.68(m, 2H), 2.04(s,3H), 2.01–1.93(m, 1H).

MS(LRFAB): calc'd 534, found 535 (M+H)+.

EXAMPLE 184

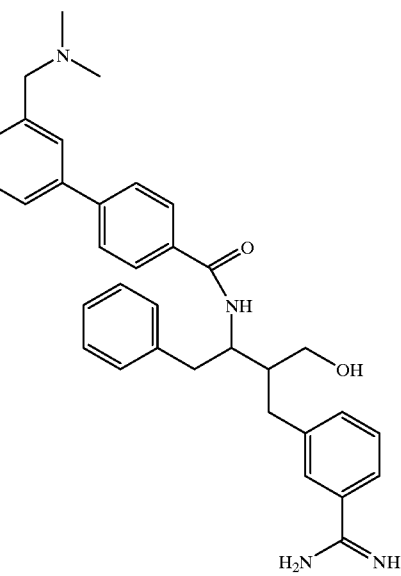

Compound 184

NMR: 8.5 (d, 1H, J=7.0 Hz), 7.8–8.0 (m, 6H), 7.4–7.7 (M, 6H), 7.1–7.3 (m, 5H) 4.6 (m, 3H),4.1 (dd, 1H, J=6.0 Hz, 10.0 Hz), 3.7 (dd, 1H, J=6.0 Hz, 10.0 Hz), 3.0 (d, 2H, J=9.0 Hz), 2.9 (d, 2H, J=9.0 Hz), 2.9 (s, 6H), 2.0 (m, 1H).

Mass Spec M+H calc 535.3, found 535.

EXAMPLE 185

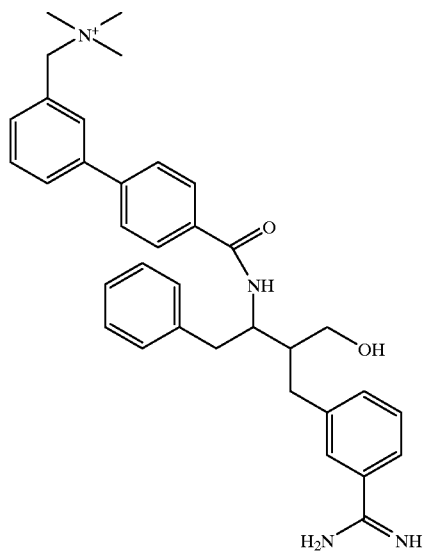

Compound 185

NMR: 8.5 (d, 1H, J=7.0 Hz), 7.8–8.0 (m, 6H), 7.4–7.7 (M, 6H), 7.1–7.3 (m, 5H) 4.6 (m,3H), 4.0 (dd, 1H, J=6.0 Hz, 10.0 Hz), 3.6 (dd, 1H, J=6.0 Hz, 10.0 Hz), 3.2 (s, 9H), 3.0 (d, 2H, J=9.0 Hz), 2.9 (d, 2H, J=9.0 Hz), 2.0 (m, 1H).

Mass Spec M+H calc 549.3, found 549.

EXAMPLE 186

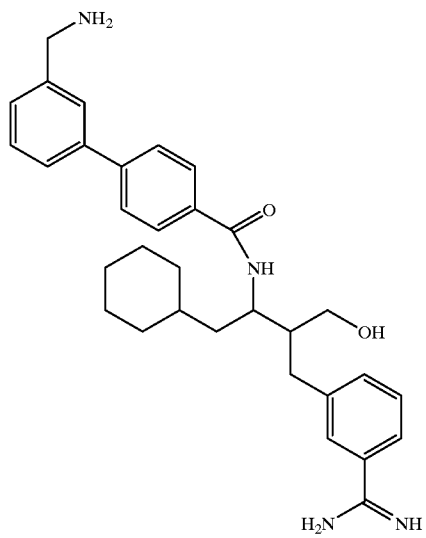

Compound 186

1H NMR (300 MHz, d6 DMSO), d 9.30–9.11 (m, 3H), 8.31 (br.s, 2H), 8.15 (d, 1H, J=8.4 Hz), 7.93 (d, 2H, J=7.2 Hz), 7.86–7.68 (m, 2H), 7.64–7.48 (m, 6H), 4.30–4.15 (m, 1H), 4.14–4.04 (m, 2H), 2.75 (d, 2H, J=6.0 Hz), 1.95–1.82 (m, 1H), 1.80–1.68 (m, 2H), 1.65–1.46 (m, 5H), 1.42–1.32 (m, 1H), 1.31–1.15(m, 1H), 1.13–0.93 (m, 2H), 0.92–0.65 (m, 4H).

MS, LRFAB, calc'd. 512, found 513 (M+H)+.

EXAMPLE 187

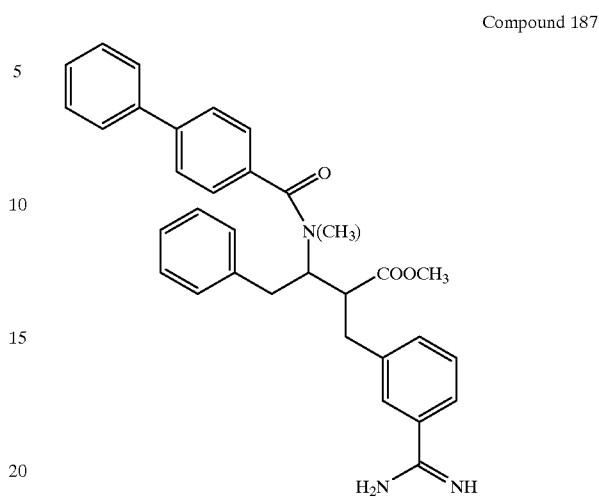

Compound 187

NMR: 9.0 (s, 1H), 8.5 (d, 1H, J=9.0 Hz), 7.9 (d, 2H, J=9.0 Hz), 7.6–7.8 (m, 4H), 7.3–7.5 (m, 6H), 7.2–7.1 (m, 6H), 3.5 (s, 3H), 3.1 (s, 3H), 3.0 (d, 2H, J=8.0 Hz), 2.9 (d, 2H, J=8.0 Hz).

M.S. Cal'd 520.1, Found 520.

EXAMPLE 188

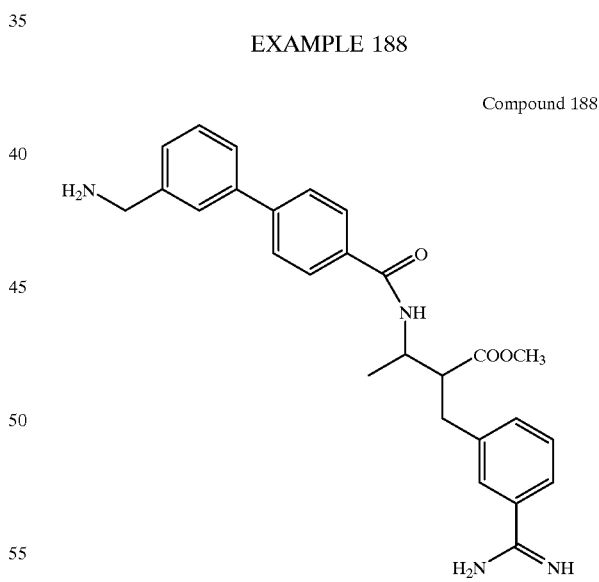

Compound 188

NMR: 9.4 (d, 1H, J=12.0 Hz), 8.6 (d, 1H, J=10.0 Hz), 8.1 (d, 2H, J=10.0 Hz), 7.9–8.1 (m, 4H), 7.6–7.8 (m, 6H), 4.7 (m, 1H) 4,4 (d, 2H, J=9.0 Hz), 3.7 (s, 3H), 3.1–3.4 (m, 4H), 1.6 (d, 3H, J=9.0 Hz).

Mass Spec M+H calc 459.2 found 459.

EXAMPLE 189
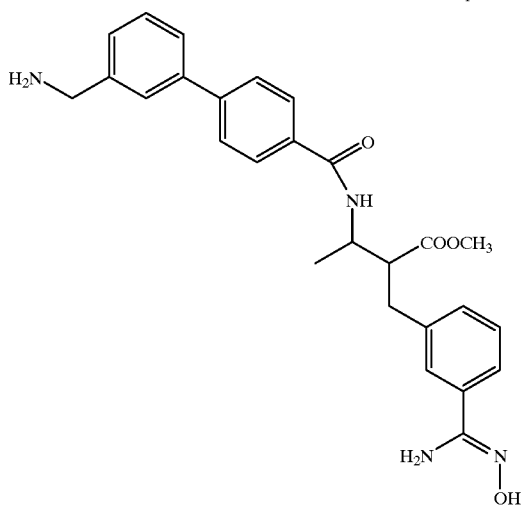
Compound 189
NMR: 9.4 (d, 1H, J=12.0 Hz), 8.0 (d, 1H, J=10.0 Hz), 8.1 (d, 2H, J=10.0 Hz), 7.7–7.9 (m,4H), 7.4–7.6 (m, 6H), 4.5 (m, 1H), 4.2 (d,2H, J=9.0 Hz), 3.6 (s, 3H), 1.6 (d, 3H,J=9.0 Hz). Mass Spec M+H calc 475.1, found 475.
EXAMPLE 190
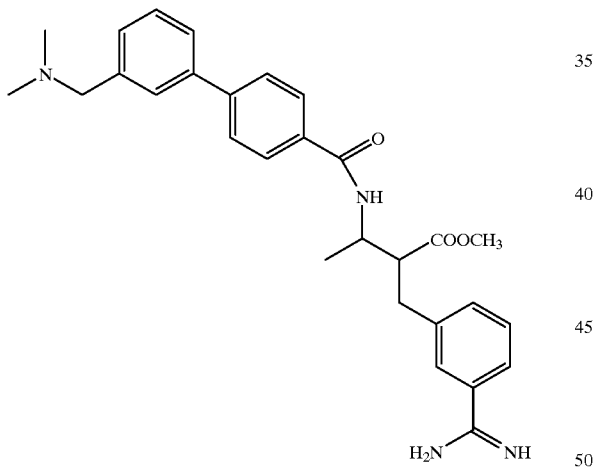
Compound 190
NMR: 8.4 (d, 1H, J=9.0 Hz), 7.9 (d, 2H, J=10.0 Hz), 7.7–7.9 (m,4H), 7.4–7.6 (m, 6H), 4.6 (m,H), 4.5 (s,2H), 3.6 (s, 3H), 3.1–3.2 (m, 3H), 2.9 (s,6H), 1.3 (d, 3H,J=9.0 Hz). Mass Spec M+H calc 459.2 found 459.
EXAMPLE 191
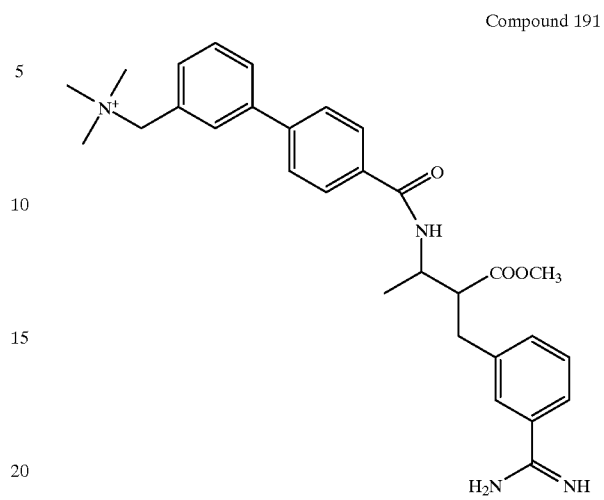
Compound 191
NMR: 9.3 (d, 1H, J=9.0 Hz), 9.1 (d, 1H, J=9.0 Hz), 8.4 (d, 1H, J=10.0 Hz), 7.7–8.0 (m,4H), 7.3–7.6 (m, 5H), 4.6 (s, 2H), 4,4 (m, 1H), 3.5 (s, 3H), 3.1 (s,9H), 2.9–3.1 (m, 3H), 1.6 (d, 3H,J=9.0 Hz).
Mass Spec M+H calc 501.1 found 501.
EXAMPLE 192
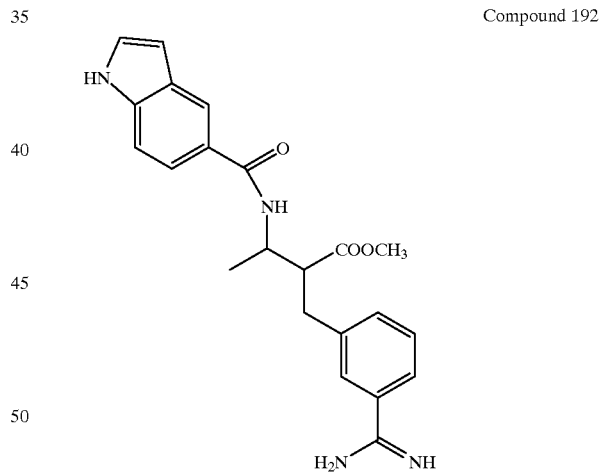
Compound 192
M.S., APCI Cal'd 392, Found 393 (M+H)$^+$.

EXAMPLE 193

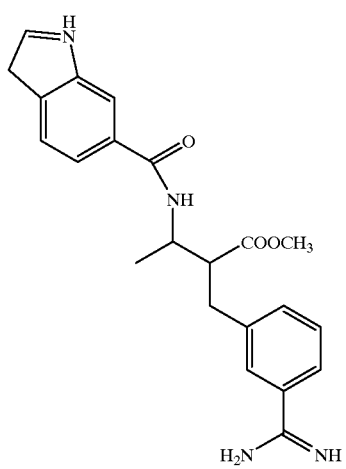

Compound 193

M.S., APCI Cal'd 392, Found 393 (M+H)+.

EXAMPLE 194

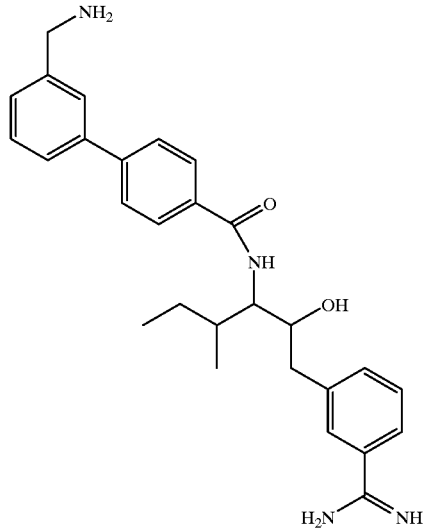

Compound 194

NMR: 9.4 (d, 1H, J=12.0 Hz), 8.6 (d, 1H, J=10.0 Hz), 8.0 (d, 2H, J=9.0 Hz), 7.7 (d, 2H, J=9.0 Hz), 7.3–7.6 (m, 6H), 7.0–7.2 (m,2H), 4.2 (m,3H), 4.0 (dd, 1H, (J=6.0 Hz, 10.0 Hz), 3.6 (dd, 1H, (J=6.0 Hz, 10.0 Hz), 3.0 (d, 2H, J=8.0 Hz), 2.0 (m, 1H), 1.6 (m,H) 1.1–1.3 (m, 8H).

Mass Spec M+H calc 473.1, found 473.

EXAMPLE 195

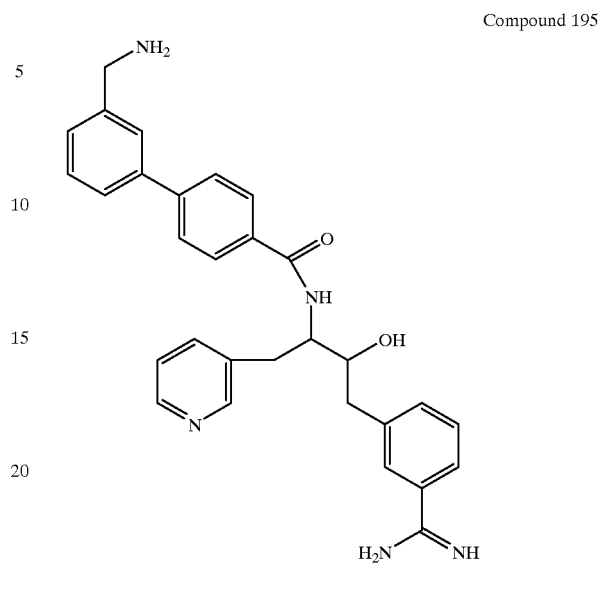

Compound 195

EXAMPLE 196

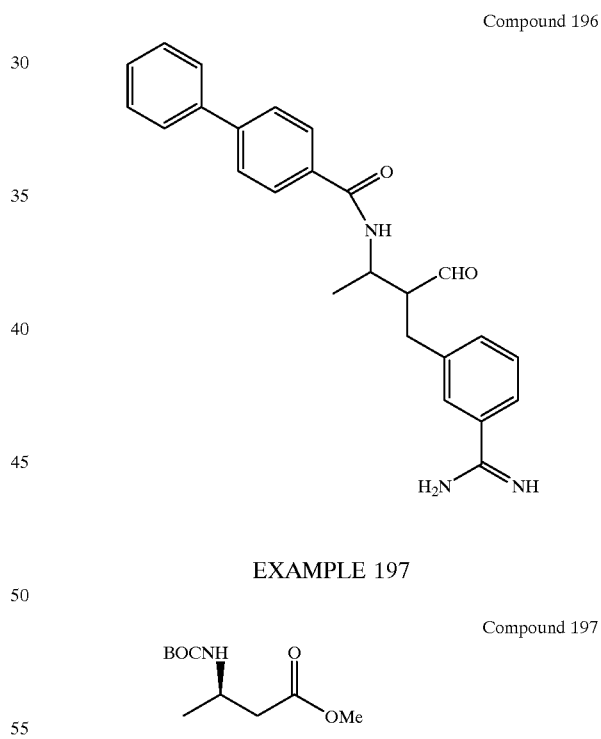

Compound 196

EXAMPLE 197

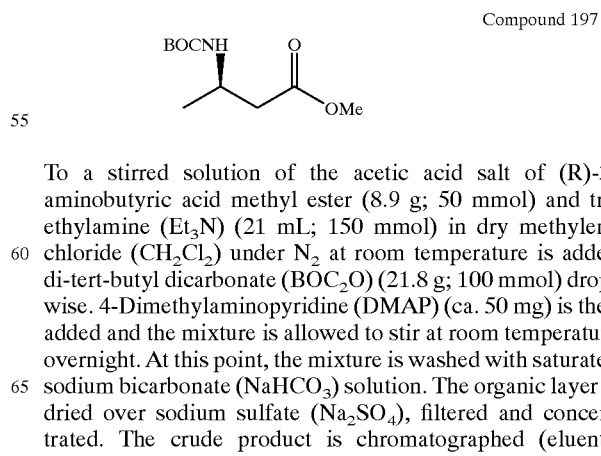

Compound 197

To a stirred solution of the acetic acid salt of (R)-3-aminobutyric acid methyl ester (8.9 g; 50 mmol) and triethylamine (Et₃N) (21 mL; 150 mmol) in dry methylene chloride (CH₂Cl₂) under N₂ at room temperature is added di-tert-butyl dicarbonate (BOC₂O) (21.8 g; 100 mmol) dropwise. 4-Dimethylaminopyridine (DMAP) (ca. 50 mg) is then added and the mixture is allowed to stir at room temperature overnight. At this point, the mixture is washed with saturated sodium bicarbonate (NaHCO₃) solution. The organic layer is dried over sodium sulfate (Na₂SO₄), filtered and concentrated. The crude product is chromatographed (eluent=

20%–40% ethyl acetate (EtOAc, or EtOAc) in hexanes) to give Compound 197.

¹H NMR (CDCl₃, d): 4.92 (bs, 1H), 3.96 (bm, 1H), 3.65 (s, 3H), 2.45–2.37 (m, 2H), 1.39 (s, 9H), 1.16 (d, J=7.9 Hz, 3H).

EXAMPLE 198

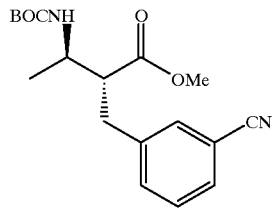

Compound 198

To a stirred solution of Compound 197 (2.00 g; 9.21 mmol) in 50 mL of dry tetrahydrofuran (THF) under nitrogen at −78° C. is added lithium hexamethyidisilazane (LHMDS) solution (25.8 mL of 1.0 M solution in THF) dropwise. The mixture is then warmed up to −20 to −25° C. for 30 min and then cooled back to −78° C. A solution of 3-cyanobenzyl bromide (4.51 g; 23.0 mmol) in dry THF is then added dropwise and the resulting solution allowed to warm to room temperature. After 1 hour at room temperature, the mixture is quenched with saturated NaHCO₃ solution and most of the THF is removed in vacuo. The residue is taken up into CH₂Cl₂ and washed with water. The organic layer is dried (Na₂SO₄), filtered and concentrated. The crude product is purified by flash chromatography (eluent=25% ethyl acetate/Hexanes). The semi-solid residue is then triturated with 20% EtOAc/Hexanes and the white solid filtered off. The filtrate is then concentrated in vacuo to give Compound 198.

¹H NMR (CDCl₃, d): 7.25–7.50 (m, 4H), 5.21 (bd, 1H), 3.88 (m, 1H), 3.60 (s, 3H), 3.07–2.73 (m, 3H), 1.48 (s, 9H), 1.14 (d, J =7.9 Hz, 3H).

EXAMPLE 199

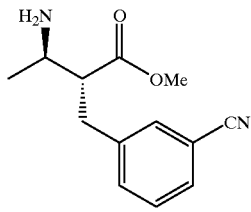

Compound 199

To a stirred solution of Compound 198 (4.20 g; 12.7 mmol) in 10 mL of CH₂Cl₂ under N₂ at room temperature is added 20 mL of trifluoroacetic acid. The mixture is allowed to stir overnight at room temperature and then concentrated in vacuo to give 4.20 g of Compound 199 as the trifluoroacetic acid (TFA) salt.

¹H NMR (DMSO-d₆, d): 8.07 (bs, 1H), 7.73–7.43 (M, 4H), 3.50 (S, 3H), 3.51 (M, 1H), 3.05–2.82 (M, 3H), 1.23 (D, J=7.9 HZ, 3H).

Alternatively, compound 4 may be prepared as outlined below:

EXAMPLE 200

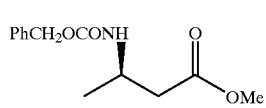

Compound 200

To a stirred solution of D-3-aminobutyric acid methyl ester (6.98 g; 39.4 mmol) acetic acid salt in 40 mL of CH₂Cl₂ is added sat. NaHCO₃ solution (40 mL). Benzyl chloroformate (9.0 mL; 63 mmol) is then added dropwise and the mixture allowed to stir vigorously at room temperature. After 3 hours, the organic layer is separated and washed with water. The organic layer is dried (Na₂SO₄), filtered and concentrated. The crude product is chromatographed (eluent=10% EtOAc/CHCl₃) to give Compound 200.

¹H NMR (CDCl₃, d): 7.40–7.22 (m, 5H), 5.25 (m, 1H), 5.08 (s, 2H), 4.11 (m, 1H), 3.65 (s, 3H), 2.53 (d, J=7.0 Hz, 2H), 1.23 (d, J=7.9 Hz, 3H).

EXAMPLE 201

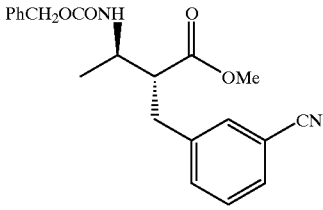

Compound 201

To a stirred solution of Compound 200 (3.45 g; 13.71 mmol) in 20 mL of dry THF under N₂ at −78° C. is added LHMDS solution (41.2 mL of 1.0 M solution) dropwise. The mixture is then warmed up to −20° C. for 30 minutes and then cooled back to −78° C. A solution of 3-cyanobenzyl bromide (4.51 g; 23.0 mmol) in dry THF is then added dropwise and the resulting solution allowed to warm to room temperature. After 1 hour at room temperature, the mixture is quenched with saturated NaHCO₃ solution and most of the THF is removed in vacuo. The residue is taken up into CH₂Cl₂ and washed with water. The organic layer is dried (Na₂SO₄), filtered and concentrated. The crude product is purified by flash chromatography (eluent=30% EtOAc/Hexanes). The semi-solid residue is then triturated with 20% EtOAc/Hexanes and the white solid filtered off. The filtrate is then concentrated in vacuo to Compound 201.

¹H NMR (CDCl₃, d) 7.20–7.65 (m, 9H), 5.57 (bd, 1H), 5.12 (s, 2H), 3.97 (m, 1H), 3.60 (s, 3H), 3.07–2.75 (m, 3H), 1.16 (d, J=7.9 Hz, 3H).

EXAMPLE 202

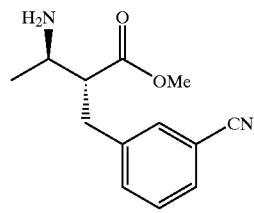

Compound 202

To a stirred solution of Compound 201 (2.6 g; 7.1 mmol) in 25 mL of ethanol (EtOH) is added 520 mg of 10% Pd/C. The mixture is stirred under 1 atm of hydrogen for 3 hours at room temperature. The mixture is then filtered through a bed of celite to remove the catalyst. The filtrate is then concentrated in vacuo to give 1.45 g of Compound 202.

EXAMPLE 203

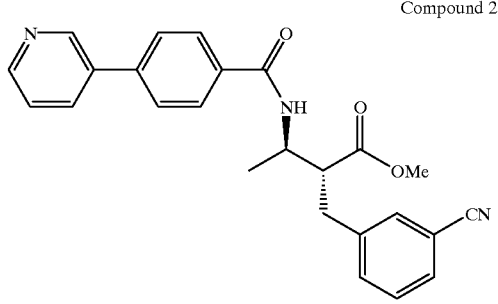

Compound 203

3'-pyridyl-4-phenyl carbonyl chloride (Compound 228, prepared as in Example 228) (384 mg; 1.8 mmol) is added in one portion to a solution of Compound 199 TFA salt (373 mg; 1.6 mmol) and $Et_3N$ (0.67 mL; 4.8 mmol) in 5.0 mL of absolute EtOH under $N_2$ at room temperature. The mixture is allowed to stir overnight at room temperature. The solvent is then removed in vacuo and the crude product is purified by chromatography on silica gel (eluent=70% EtOAc/Hexanes) to provide Compound 203.

$^1$H NMR ($CDCl_3$, d): 8.88 (m, 1H), 8.63 (m, 1H), 7.85–8.00 (m, 7.70 (m, 2H), 7.57–7.33 (m, 6H), 4.51 (m, 1H), 3.65 (s, 3H), 3.10–2.82 (m, 3H), 1.28 (d, J=7.9 Hz, 3H).

EXAMPLE 204

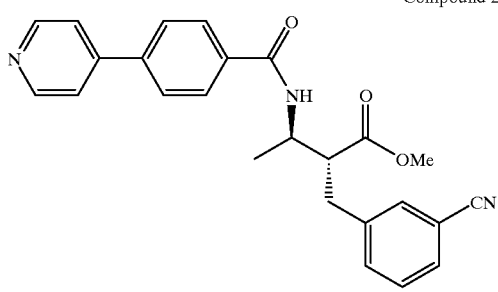

Compound 204

Acylation of Compound 199 according to the procedure of Example 203, substituting Compound 228 with 4'-pyridyl-4-phenylcarbonyl chloride (Compound 231, prepared as in Example 231) provides, after workup and chromatography, Compound 204.

hu 1H NMR ($CDCl_3$, d): 8.70 (m, 2H), 8.02–7.65 (m, 4H), 7.57–7.32 (m, 7H), 4.50 (m, 1H), 3.68 (s, 3H), 3.10–2.83 (M, 3H), 1.30 (d, J=7.9 Hz, 3H).

EXAMPLE 205

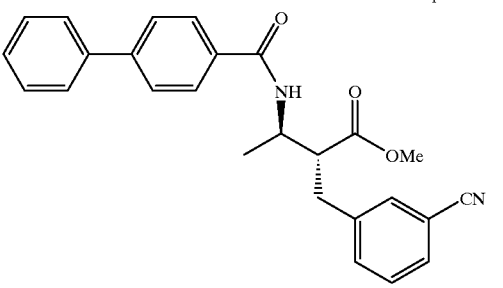

Compound 205

Acylation of Compound 199 according to Example 203, in $CH_2Cl_2$ rather than absolute EtOH, and substituting 3'-pyridyl-4-phenylcarbonyl chloride with 4-biphenylcarbonyl chloride provides, after workup and chromatography, Compound 205.

$^1$H NMR ($CDCl_3$, d): 7.93 (m, 2H), 7.73–7.30 (m, 12H), 4.50 (m, 1H), 3.66 (s, 3H), 3.10–2.83 (m, 3H), 1.26 (d, J=7.9 Hz, 3H).

EXAMPLE 206

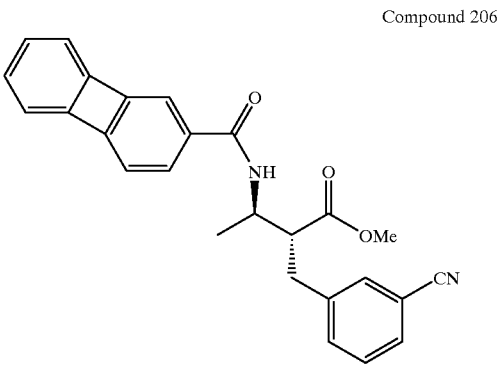

Compound 206

Acylation of Compound 199 according to Example 203 substituting 3'-pyridyl-4-phenylcarbonyl chloride with 2-biphenylenecarbonyl chloride provides, after workup and chromatography, Compound 206.

$^1$H NMR ($CDCl_3$, d): 7.55–7.27 (m, 5H), 7.07 (m, 2H), 6.85–6.66 (m, 5H), 4.44 (m, 1H), 3.65 (s, 3H), 3.05–2.80 (m, 3H), 1.23 (d, J=7.9 Hz, 3H).

EXAMPLE 207

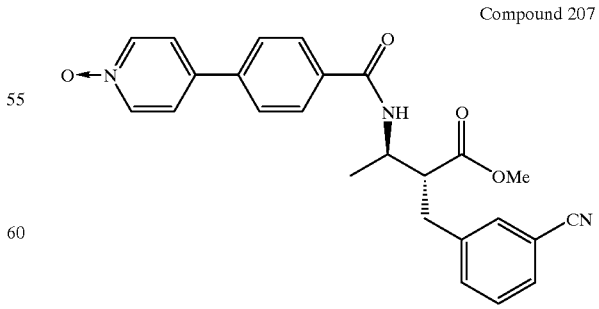

Compound 207

Add m-chloroperbenzoic acid (mCPBA) (381 mg; 2.21 mmol) to a solution of Compound 204 (608 mg; 1.47 mmol) in 10 mL of $CH_2Cl_2$ under $N_2$ at room temperature. The resulting mixture is allowed to stir overnight at room temperature. At this point, the mixture is diluted with CH$_2$Cl$_2$ and washed with 5% Na$_2$CO$_3$ solution. The organic layer is dried (Na$_2$SO$_4$), filtered and concentrated to give Compound 207.

MS: M$^+$·+H$^+$(Calc.)=430; Found (FAB)=430.

EXAMPLE 208

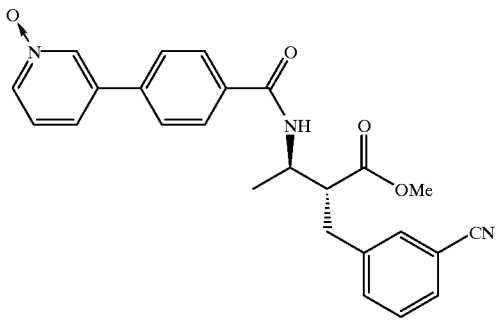

Compound 208

Add mCPBA (124 mg; 0.72 mmol) to a solution of Compound 203(150 mg; 0.36 mmol) in 10 mL of CH$_2$Cl$_2$ under N$_2$ at room temperature. The resulting mixture is allowed to stir overnight at room temperature. At this point, the mixture is diluted with CH$_2$Cl$_2$ and washed with 5% Na$_2$CO$_3$ solution. The organic layer is dried (Na$_2$SO$_4$), filtered and concentrated to give Compound 208.

$^1$H NMR (CDCl$_3$, d): 8.57 (m, 1H), 8.30 (m, 1H), 7.95 (m, 2H), 7.73–7.35 (m, 9H), 4.50 (m, 1H), 3.68 (s, 3H), 3.07–2.85 (m, 3H), 1.20 (d, J=7.9 Hz, 3H).

EXAMPLE 209

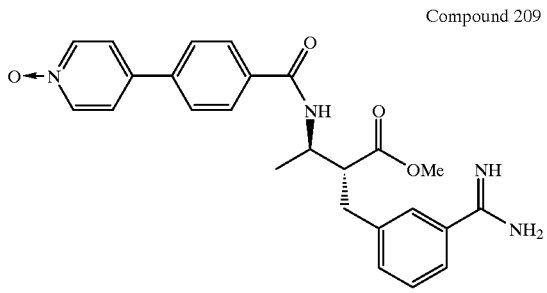

Compound 209

Bubble hydrogen chloride gas (HCl(g)) into a solution of Compound 207 (480 mg) in 5.0 mL of dry methanol (MeOH) containing 3 Å molecular sieves (pellets, ca. 50 mg) for about 2 minutes at room temperature. The mixture is allowed to stir overnight at room temperature and then concentrated in vacuo. A solution of ammonia (NH$_3$) in MeOH (5.0 mL of 7N solution) is added and the mixture refluxed for 1 hour. The solvent is then removed in vacuo and the crude product purified by RPHPLC (CH$_3$CN/H$_2$O, 0.1% TFA, gradient: 10% to 100% CH$_3$CN and the fractions containing product are lyophilized to give Compound 209.

$^1$H NMR (MeOH-d$_4$, d): 8.42 (m, 2H), 8.00–7.85 (m, 6H), 7.68–7.47 (m, 4H), 4.47 (m, 1H), 3.60 (s, 3H), 3.18–3.00 (m, 3H), 1.33 (d, J=7.9 Hz, 3H). MS: M$^+$·+H$^+$(Calc.)=447; Found (FAB)=447.

EXAMPLE 210

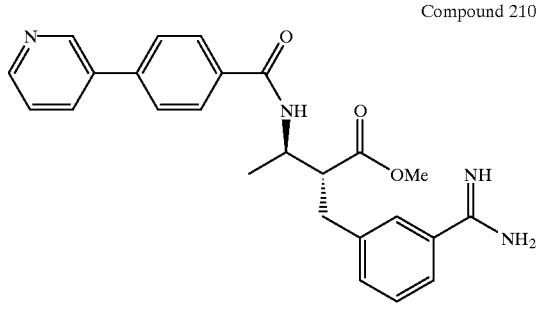

Compound 210

Treatment of Compound 203 in a similar manner as in Example 209 provides, after purification by RPHPLC, Compound 210.

$^1$H NMR (DMSO-d6, d): 9.36 (m, 3H), 8.50–8.27 (m, 2H), 8.00–7.80 (m, 3H), 7.80–7.40 (m, 4H), 4.40 (m, 1H), 3.49 (s, 3H), 3.13–2.81 (m, 3H), 1.25 (d, J=7.9 Hz, 3H).

MS: M$^+$·+H$^+$(Calc.)=431; Found (FAB)=431

EXAMPLE 211

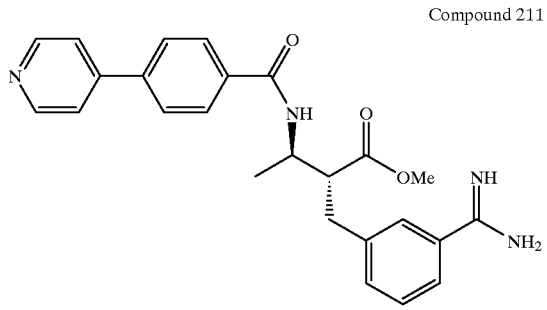

Compound 211

Treatment of Compound 204 in a similar manner as in Example 209 provides, after purification by RPHPLC, Compound 211.

EXAMPLE 212

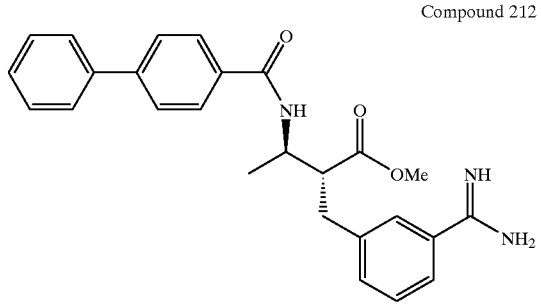

Compound 212

Treatment of Compound 205 in a similar manner as in Example 209 above provides, after purification by RPHPLC, compound 212.

$^1$H NMR (DMSO-d$_6$, d): 9.30 (s, 1H), 9.00 (s, 1H), 8.40 (m, 2H), 8.05–7.40 (m, 12H), 4.46 (m, 1H), 3.56 (s, 3H), 3.20–2.97 (m, 3H), 1.28 (d, J=7.9 Hz, 3H).

MS: M$^+$·+H$^+$(Calc.)=430; Found (FAB)=430.

EXAMPLE 213

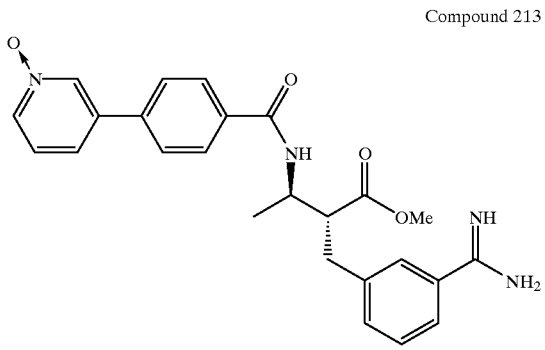

Compound 213

Treatment of Compound 208 in a similar manner as in Example 209 above provides, after purification by RPHPLC, Compound 213.

$^1$H NMR (MeOH-d$_4$, d): 8.67 (m, 1H), 8.50–8.35 (m, 2H), 8.00–7.78 (m, 5H), 7.72–7.48 (m, 5H), 4.47 (m, 1H), 3.60 (s, 3H), 3.16–3.05 (m, 3H), 1.32 (d, J=7.9Hz, 3H).

MS: M$^+$·+H$^+$(Calc.)=447; Found (FAB)=447.

EXAMPLE 214

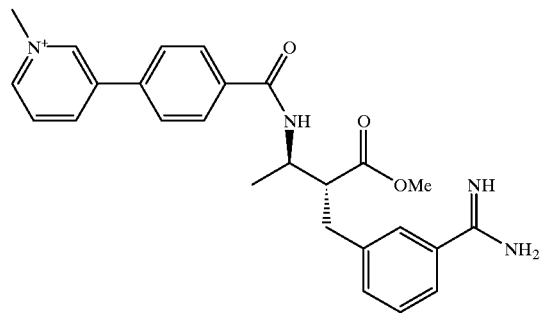

Compound 214

Hydrogen sulfide gas (H$_2$S) is bubbled into a solution of Compound 203 (498 mg; 1.21 mmol) in 5.0 mL of pyridine and 1.0 mL of Et$_3$N for ca. 2 minutes. The resulting mixture is allowed to stir overnight at room temperature and then concentrated to dryness under a stream of N$_2$. The residue is taken up into 5 mL of CH$_2$Cl$_2$ and 5 mL of methyl iodide is added. The mixture is refluxed for 3 hours, allowed to cool to room temperature and concentrated in vacuo. The residue is then taken up into 5 mL dry MeOH and NH$_4$OAc (300 mg) is added. The resulting mixture is refluxed for 3 h and then concentrated in vacuo. The crude product is purified by RPHPLC (CH$_3$CN/H$_2$O, 0.1% TFA, gradient:10% to 100% CH$_3$CN and the fractions containing product are lyophilized to give Compound 214.

$^1$H NMR (MeOH-d$_4$, d): 9.35 (s, 1H), 8.92 (m, 2H), 8.50 (d, 1H), 8.17 (m, 1H), 8.08–7.92 (m, 4H), 7.66–7.50 (m, 4H), 4.50 (s, 3H), 4.50 (m, 1H), 3.58 (s, 3H), 3.15–3.02 (m, 3H), 1.34 (d, J=7.9 Hz, 3H).

MS: M$^+$·(Calc.)=445; Found (FAB)=445.

EXAMPLE 215

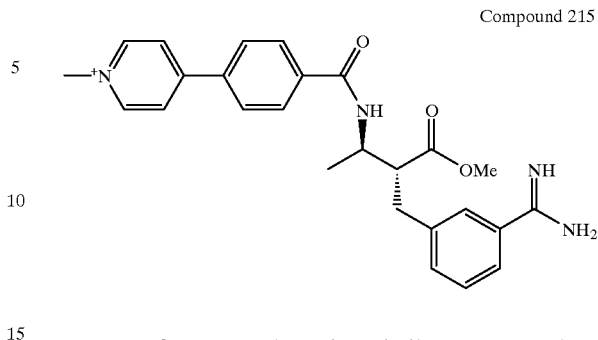

Compound 215

Treatment of Compound 204 in a similar manner to that of Compound 203 in EXAMPLE 214 above provides, after purification by RPHPLC, Compound 215.

$^1$H NMR (DMSO-d$_6$, d): 9.05 (m, 1H), 8.55 (m, 3H), 8.20–7.97 (m, 5H), 7.65–7.47 (m, 4H), 4.33 (s, 3H), 4.10 (m, 1H), 3.13 (s, 3H), 3.13–2.90 (m, 3H), 1.27 (d, J=7.9 Hz, 3H).

MS: M$^+$·(Calc.)=445; Found (FAB)=445.

EXAMPLE 216

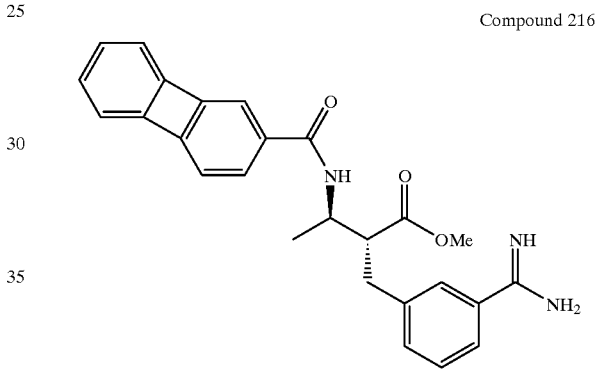

Compound 216

Treatment of Compound 206 in a similar manner to that of Compound 203 in EXAMPLE 214 above provides, after purification by RPHPLC, compound 216.

EXAMPLE 217

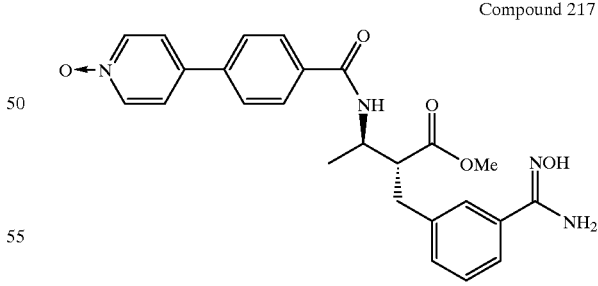

Compound 217

To a stirred solution of sodium methoxide in MeOH (12.4 mL of 0.5 M solution) is added hydroxylamine hydrochloride. Once all the solid dissolves, the solution is added to a solution of Compound 207 (530 mg; 1.24 mmol) in 5 mL of MeOH at room temperature. The resulting mixture is allowed to stir at room temperature under N$_2$ overnight. At this point, the solvent is removed in vacuo and the product purified by flash chromatography (eluent=10% MeOH/CH$_2$Cl$_2$). The fractions containing product are concentrated in vacuo and the residue is then lyophilized from water to give Compound 217.

$^1$H NMR (CDCl$_3$, d): 9.60 (s, 1H), 8.60–7.10 (m, 12H), 5.80 (bs, 1H), 4.40 (m, 1H), 4.45 (s, 3H), 3.15–2.80 (m, 3H), 1.15 (d, J=7.9 Hz, 3H).

MS: M$^+$·+H$^+$(Calc.)=463; Found (FAB)=463.

EXAMPLE 218

Compound 218

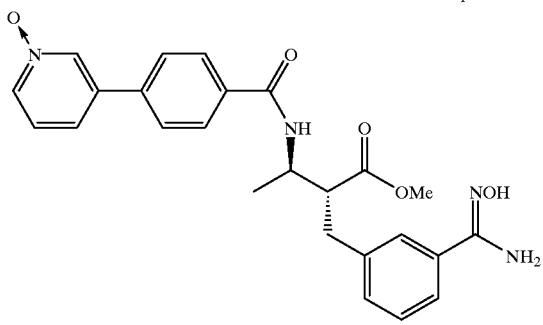

Treatment of Compound 208 in a similar manner to that of Compound 207 in Example 217 above provides, after purification by flash chromatography, compound 218.

$^1$H NMR (MeOH-d$_4$, d): 8.69 (m, 1H), 8.35 (m, 1H), 8.00–7.75 (m, 5H), 7.72–7.25 (m, 5H), 4.47 (m, 1H), 3.57 9s, 3H), 3.15–2.95 (m, 3H), 1.33 (d, J=7.9 Hz, 3H).

MS: M$^+$·+H$^+$(Calc.)=463; Found (ion spray)=463.

EXAMPLE 219

Compound 219

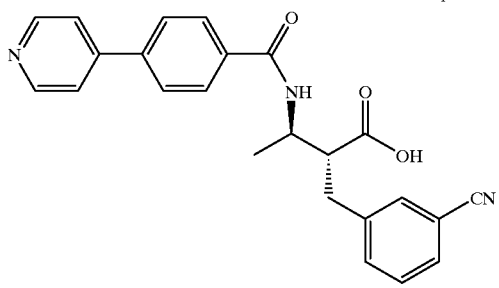

To a stirred solution of Compound 204 (319 mg; 0.77 mmol) in 4 mL of MeOH/THF (1/1) is added 1 N NaOH solution (10 mL). The resulting mixture is allowed to stir for 2 hours at room temperature and then acidified with 12 mL of 1 N HCl solution. The solid product Compound 219 is filtered off and dried in vacuo.

1H NMR (CDCl$_3$, d): 9.30 (bs, 1H), 8.50 (bs, 1H), 8.30–7.80 (m, 6H), 7.65–7.28 (m, 5H), 4.40 (m, 1H), 3.20–2.85 (m, 3H), a.33 (d, J=7.9 Hz, 3H).

EXAMPLE 220

Compound 220

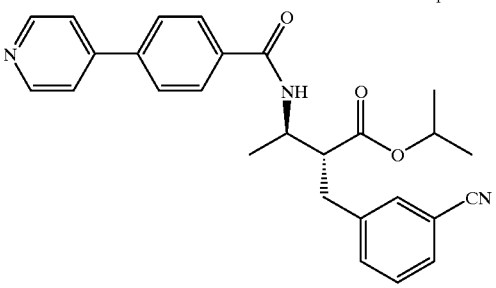

Triethylamine (0.11 mL; 0.77 mmol) is added dropwise to a suspension of Compound 219 in dry CH$_2$Cl$_2$ (10 mL) under N$_2$ at room temperature. After 10 minutes, isopropyl chloroformate (0.77 mL; 0.77 mmol) is added dropwise. After 30 minutes, DMAP (31 mg) is added and the mixture allowed to stir overnight at room temperature. At this point, the mixture is diluted with CH$_2$Cl$_2$ and washed with 1 N HCl. The organic layer is dried (Na$_2$SO$_4$), filtered and concentrated. The crude product is chromatographed with 40% EtOAc/hexanes followed by 70% EtOAc/hexanes to give Compound 220.

MS: M$^+$·+H$^+$(Calc.)=442; Found (Ion spray)=442.

EXAMPLE 221

Compound 221

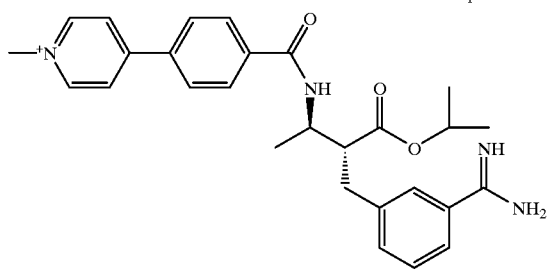

Treatment of Compound 220 in a similar manner to that of Compound 203 in Example 214 above provides, after purification by RPHPLC, Compound 221.

$^1$H NMR (DMSO-d$_6$, d): 9.28 (m, 1H), 9.00 (m, 3H), 8.53 (m, 1H), 8.23–7.92 (m, 4H), 7.32 (s, 1H), 7.15 (s, 1H), 7.00 (s, 1H), 4.38 (m, 1H), 4.32 (s, 3H), 3.14–2.93 (m, 3H), 1.25 (m, 3H), 0.99 (m, 3H), 0.87 (m, 3H).

MS: M$^+$·(Calc.)=473; Found (FAB)=473.

EXAMPLE 222

Compound 222

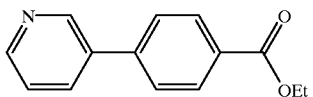

Ethyl-4-bromobenzoate (7.0 g; 31 mmol) is dissolved in 100 mL of THF. To this solution is added Pd(Ph$_3$P)$_4$ (1.0 g; 1.0 mmol), tetrabutylammonium bromide (592 mg; 1.8 mmol), powdered potassium hydroxide (KOH) (3.4 g; 61 mmol) and diethyl-(3-pyridyl)borane (3.0 g). The resulting mixture is refluxed for 2.5 hours, allowed to cool to room temperature and concentrated in vacuo. The crude product is taken up into MeOH and chromatographed (eluent=gradient, 50% EtOAc/Hexanes to 70% EtOAc/Hexanes) to give, after solvent evaporation, Compound 222.

$^1$H NMR (CDCl$_3$, d): 8.83 (s, 1H), 8.60 (m, 1H), 8.10 (m, 2H), 7.90–7.30 (m, 3H), 4.34 (m, 2H), 1.37 (m, 3H).

EXAMPLE 223

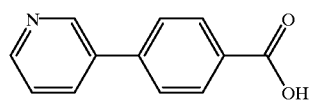

Compound 223

Sodium hydroxide solution (25.5 mL of 1.0N solution) is added dropwise to a stirred solution of Compound 222 (2.7 g; 12 mmol) in 21 mL of 1/1 THF/MeOH at room temperature. After 3 hours, 25 mL of 1N HCl is added and the white precipitate is filtered off. The solid is dried in vacuo. to give Compound 223.

$^1$H NMR (DMSO-d$_6$, d): 8.90 (s, 1H), 8.60 (s, 1H), 8.13 (m, 1H), 8.05–7.80 (m, 4H), 7.50 (m, 1H).

EXAMPLE 224

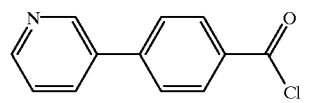

Compound 224

Thionyl chloride (5 mL) is added to 1.3 g of Compound 223. The resulting mixture is refluxed for 2 hours and then concentrated in vacuo to give Compound 224.

MS: M$^+$·(Calc.)=217; Found (EI)=217.

EXAMPLE 225

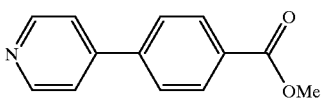

Compound 225

A mixture of methyl coumalate (10 g; 65 mmol), 4-vinylpyridine (35 mL; 325 mmol) and 10% Pd/C (25 g) in mesitylene (300 mL) is heated at 200° C. for 30 hours. At this point, the mixture is allowed to cool and filtered through celite washing with CHCl$_3$. Most of the solvent is then removed in vacuo and the remaining liquid is chromatographed (eluent: Gradient, 50% EtOAc/Hex. to 70% EtOAc/Hex.) to give Compound 225.

MS: M$^+$·(Calc.)=217; Found (EI)=217.

EXAMPLE 226

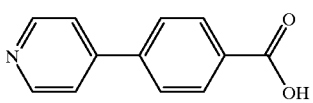

Compound 226

Treatment of Compound 225 with sodium hydroxide in THF/MeOH as in Example 223 provides Compound 226.

MS: M$^+$·(Calc.)=199; Found (EI)=199.

EXAMPLE 227

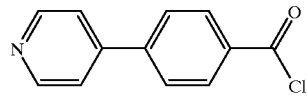

Compound 227

Treatment of Compound 226 with refluxing thionyl chloride as in Example 224 provides Compound 227.

MS: M$^+$·(Calc.)=213; Found (EI)=213.

EXAMPLE 228

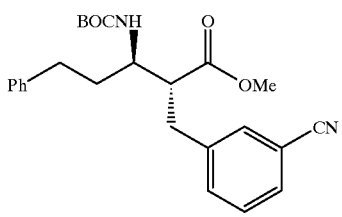

Compound 228

To N-BOC homophenylalanine methylester (5.57 g; 18.1 mmol) in 30 mL of THF under N$_2$ at −78° C. is added LHMDS solution dropwise (54.3 mL of 1N solution in THF). The mixture is then allowed to warm up to 0° C. for 30 min and then cooled back to −78° C. A solution of 3-cyanobenzyl bromide (7.46 g; 38.0 mmol) in dry THF is then added dropwise and the resulting solution allowed to warm to room temperature. After 1 hour at room temperature, the mixture is quenched with saturated NaHCO$_3$ solution and most of the THF is removed in vacuo. The residue is taken up into CH$_2$Cl$_2$ and washed with water. The organic layer is dried (Na$_2$SO$_4$), filtered and concentrated. The crude product is purified by flash chromatography (eluent=25% EtOAc/Hexanes. The semi-solid residue is then triturated with 20% EtOAc/Hexanes and the white solid filtered off. The filtrate is then concentrated in vacuo to Compound 228.

$^1$H NMR (CDCl$_3$, d): 7.82–7.08 ((m, 9H), 5.32 (bd, 1H), 3.84 (m, 1H), 3.60 (s, 3H), 3.06–2.57 (m, 5H), 1.70 (m, 2H), 1.47 (s, 9H).

EXAMPLE 229

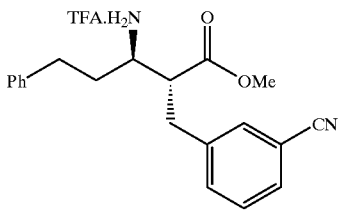

Compound 229

To a stirred solution of Compound 228 (1.42 g; 3.35 mmol) in 5.0 mL of CH$_2$Cl$_2$ under N$_2$ at 0° C. is added 3.5 mL of trifluoroacetic acid. The mixture is allowed to stir for 2 hours at room temperature and then concentrated in vacuo to give Compound 229 as the TFA salt.

MS: M$^+$·(Calc.)=322; Found (EI)=322.

EXAMPLE 230

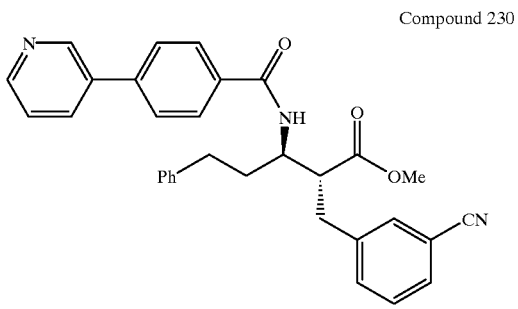
Compound 230

Acylation of Compound 229 according to Example 203 with Compound 224 provides, after workup and chromatography, Compound 230.

MS: M$^+$·(Calc.)=503; Found (EI)=503.

EXAMPLE 231

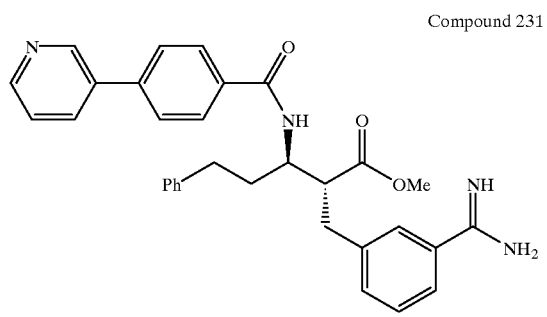
Compound 231

Treatment of Compound 230 with HCl/MeOH, then NH$_4$OAc in a similar manner to Compound 207 in Example 209 above provides, after purification by RPHPLC, Compound 231.

MS: M$^+$·+ H$^+$ (Calc.)=521; Found (FAB)=521.

EXAMPLE 232

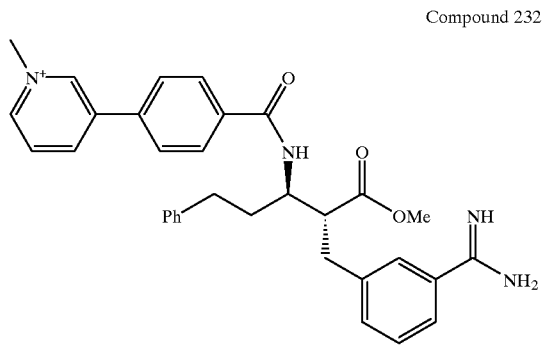
Compound 232

Treatment of Compound 230 in a similar manner to that of Compound 203 in EXAMPLE 214 above provides, after purification by RPHPLC, Compound 232.

$^1$H NMR (MeOH-d$_4$): 9.35 (s, 1H), 8.90 (m, 2H), 8.45 (m, 1H), 8.17 (m, 1H), 8.11–7.92 (m, 4H), 7.68–7.46 (m, 5H), 7.27–7.10 (m, 6H), 4.50 (s, 3H), 4.40 (m, 1H), 3.57 (s, 3H), 3.05 (m, 3H), 2.67 (m, 2H), 2.00 (m, 2H).

EXAMPLE 233

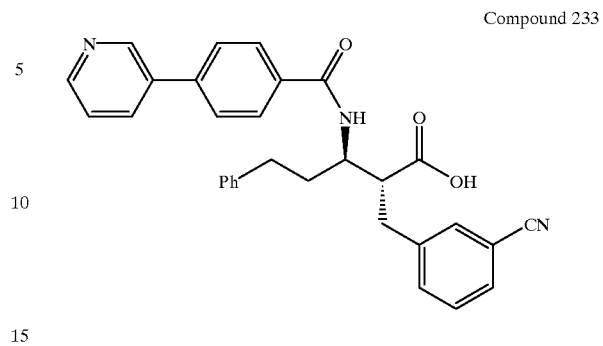
Compound 233

Hydrolysis of Compound 230 with sodium hydroxide in THF/MeOH using the procedure of Example 223 provides after workup, Compound 233.

MS: M$^+$·+ H$^+$ (Calc.) 490; Found (FAB)=490.

EXAMPLE 234

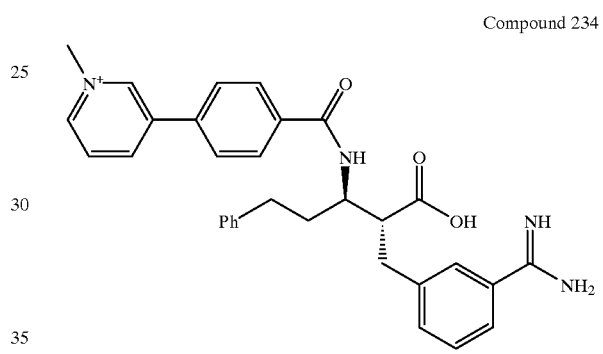
Compound 234

Treatment of Compound 233 in a similar manner to Compound 203 in Example 214 above provides, after purification by RPHPLC, Compound 234.

$^1$H NMR (MeOH-d$_4$): 9.38 (s, 1H), 8.90 (m, 2H), 8.47 (m, 1H), 8.17 (m, 1H), 8.11–7.92 (m, 4H), 7.68–7.46 (m, 5H), 7.26–7.10 (m, 6H), 4.50 (s, 3H), 4.38 (m, 1H), 3.12–2.97 (m,. 3H), 2.68 (m, 2H), 2.03 (m, 2H).

EXAMPLE 235

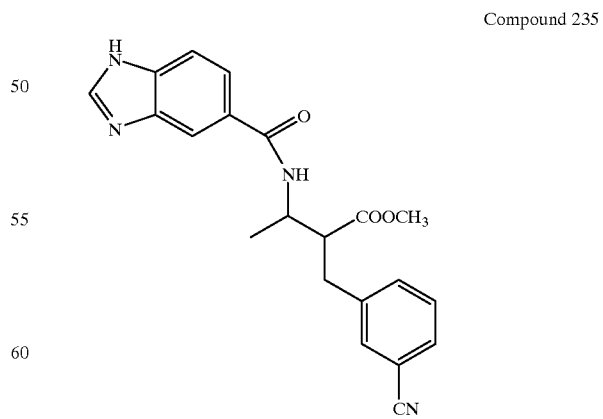
Compound 235

This material is prepared following the procedure described for compound 123 and substituting benzimidazole-5-carboxyic acid for 99.

EXAMPLE 236

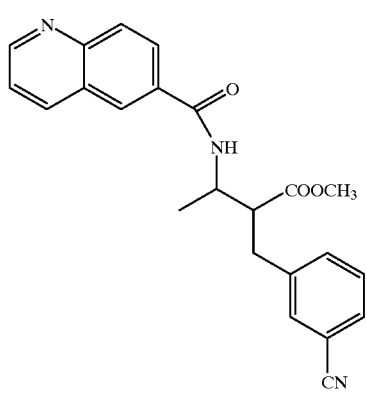

Compound 236

This material is prepared following the procedure described for compound 123 and substituting quinoline-7-carboxylic acid for 99.

EXAMPLE 237

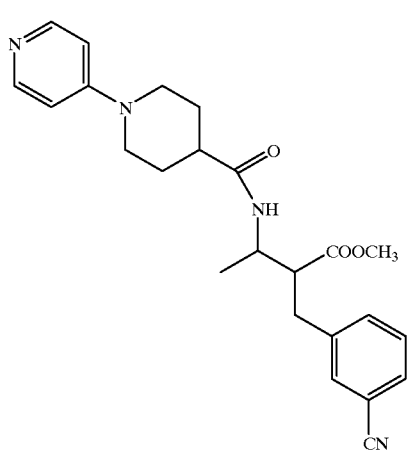

Compound 237

This material is prepared following the procedure described for compound 123 and substituting N-(4-pyridyl)-piperidine4-carboxylic acid for 99.

EXAMPLE 238

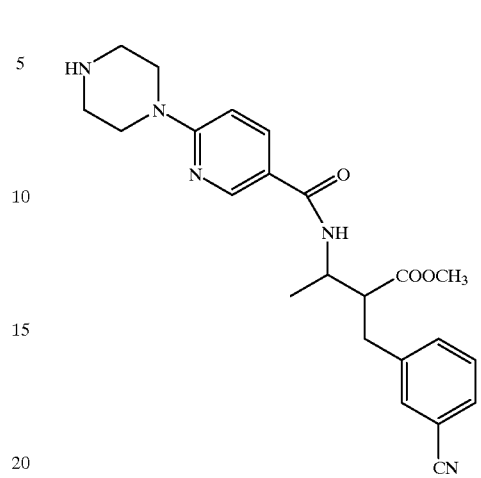

Compound 238

This material is prepared following the procedure described for compound 123 and substituting 2-(1-piperazinyl)-pyridine-5-carboxylic acid for 99.

EXAMPLE 239

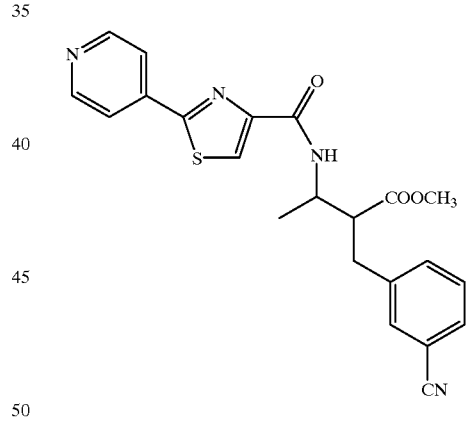

Compound 239

This material is prepared following the procedure described for compound 123 and substituting 2-(4-pyridinyl)-1,3-thiazole-4-carboxylic acid for 99.

EXAMPLE 240

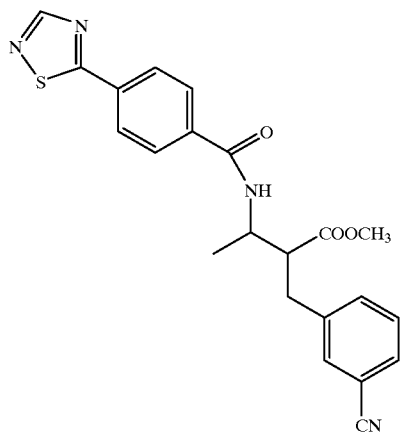

Compound 240

This material is prepared following the procedure described for compound 123 and substituting 4-(5-(1,2,4-thiadiazolyl))benzoic acid for 99.

EXAMPLE 241

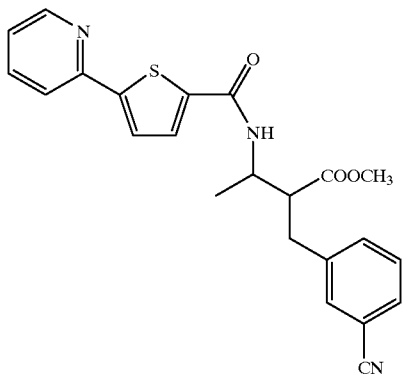

Compound 241

This material is prepared following the procedure described for compound 123 and substituting 2-(2-pyridyl)thiazole-5-carboxylic acid for 99.

EXAMPLE 242

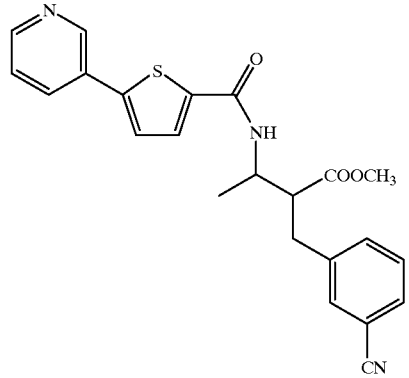

Compound 242

This material is prepared following the procedure described for compound 123 and substituting 2-(3-pyridyl)thiazole-5-carboxylic acid for 99.

EXAMPLE 243

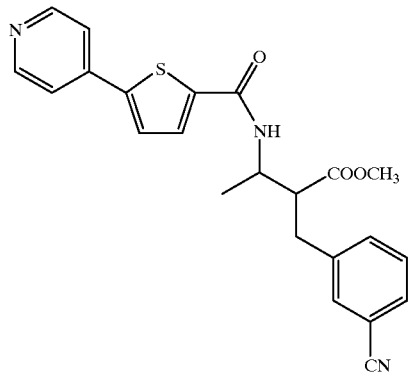

Compound 243

This material is prepared following the procedure described for compound 123 and substituting 2-(4-pyridyl)thiazole-5-carboxylic acid for 99.

EXAMPLE 244

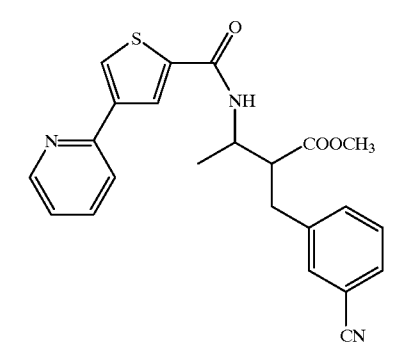

Compound 244

This material is prepared following the procedure described for compound 123 and substituting 3-(2-pyridyl)thiazole-5-carboxylic acid for 99.

EXAMPLE 245

Compound 245

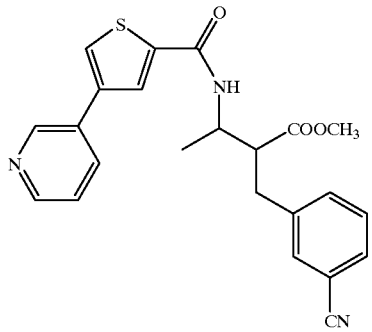

This material is prepared following the procedure described for compound 123 and substituting 3-(3-pyridyl)thiazole-5-carboxylic acid for 99.

EXAMPLE 246

Compound 246

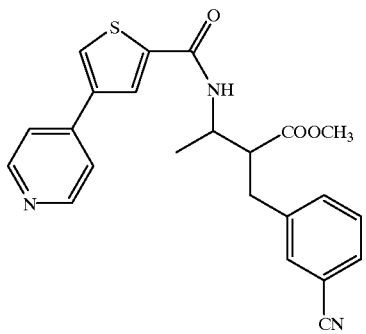

This material is prepared following the procedure described for compound 123 and substituting 3-(4-pyridyl)thiazole-5-carboxylic acid for 99.

EXAMPLE 247

Compound 247

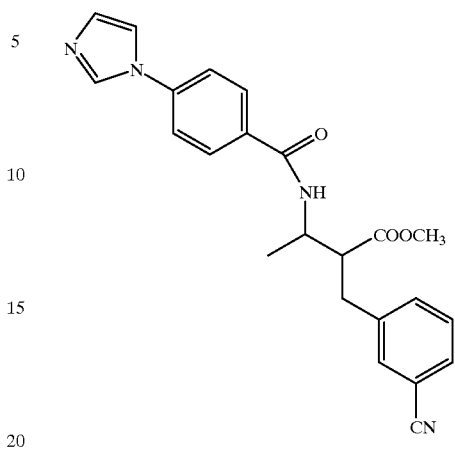

This material is prepared following the procedure described for compound 123 and substituting 4-(1-imidazolyl)benzoic acid for 99.

EXAMPLE 248

Compound 248

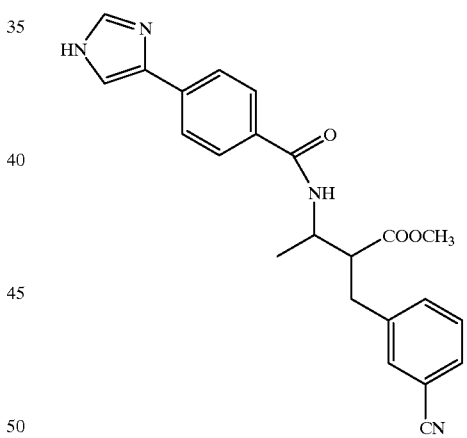

This material is prepared following the procedure described for compound 123 and substituting 4-(4-imidazolyl)benzoic acid for 99.

EXAMPLE 249

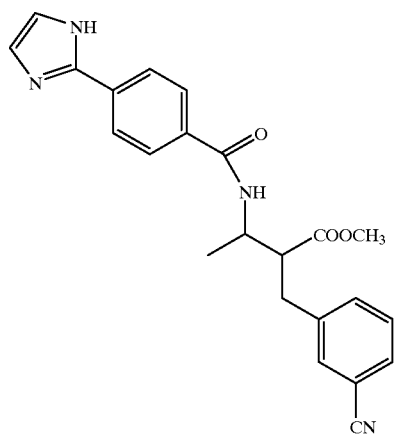

Compound 249

This material is prepared following the procedure described for compound 123 and substituting 4-(2-imidazolyl)benzoic acid for 99.

EXAMPLE 250

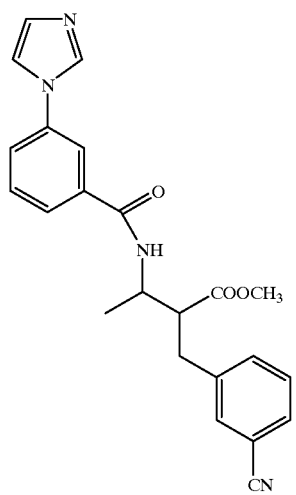

Compound 250

This material is prepared following the procedure described for compound 123 and substituting 3-(1-imidazolyl)benzoic acid for 99.

EXAMPLE 251

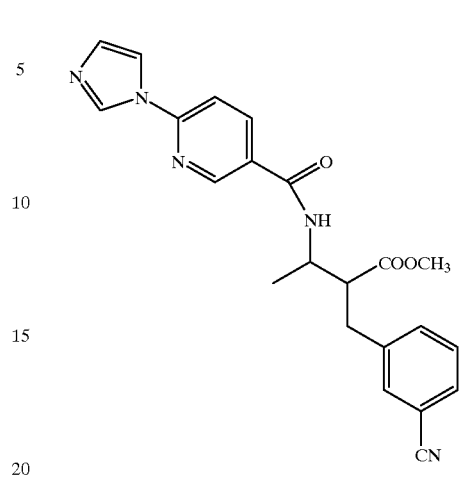

Compound 251

This material is prepared following the procedure described for compound 123 and substituting 2-(1-imidazolyl)-pyridine-5-carboxylic acid for 99.

EXAMPLE 252

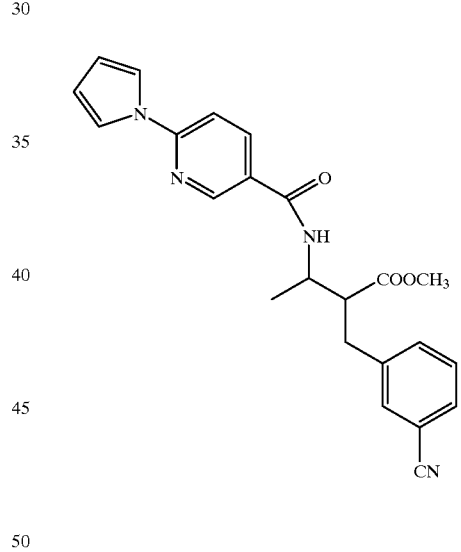

Compound 252

This material is prepared following the procedure described for compound 123 and substituting 2-(1-pyrrolyl)-pyridine-5-carboxylic acid for 99.

EXAMPLE 253

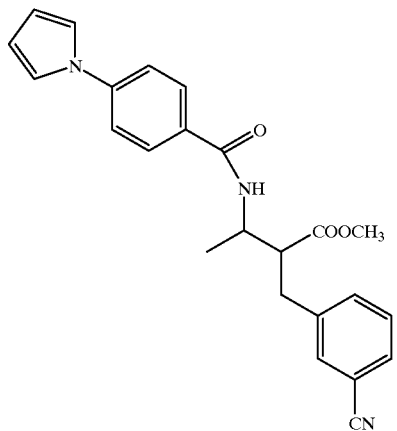

Compound 253

This material is prepared following the procedure described for compound 123 and substituting 4-(1-pyrrolyl) benzoic acid for 99.

EXAMPLE 254

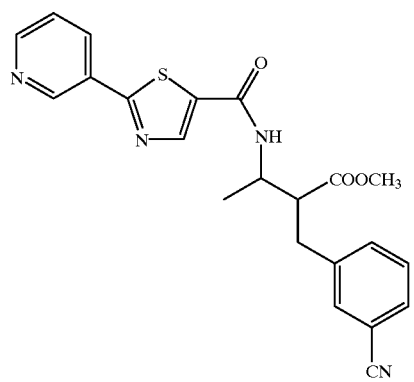

Compound 254

This material is prepared following the procedure described for compound 123 and substituting 5-(3-pyridyl)-1,3-thiazole-2-carboxylic acid for 99.

EXAMPLE 255

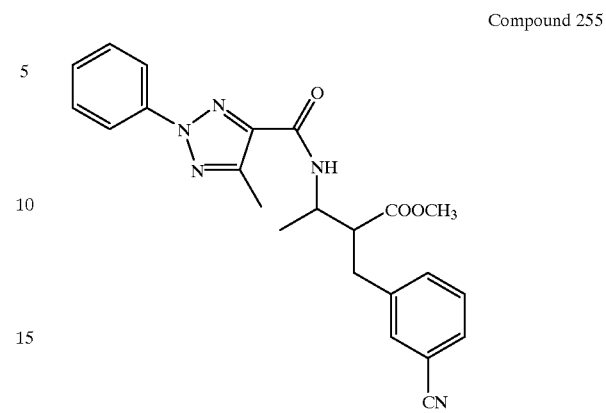

Compound 255

This material is prepared following the procedure described for compound 123 and substituting 2-phenyl-5-methyl-1,2,3-triazole-4-carboxylic acid for 99.

EXAMPLE 256

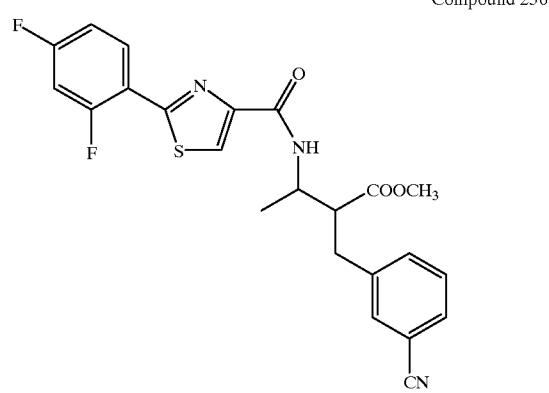

Compound 256

This material is prepared following the procedure described for compound 123 and substituting 2-(2,4-difluorophenyl)-1,3-thiazole-4-carboxylic acid for 99.

EXAMPLE 257

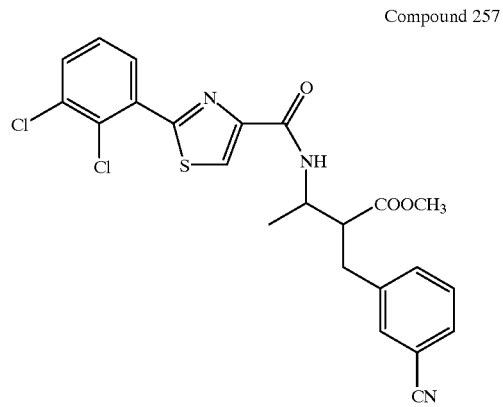

Compound 257

This material is prepared following the procedure described for compound 123 and substituting 2-(2,3-dichlorophenyl)-1,3-thiazole-4-carboxylic acid for 99.

EXAMPLE 258

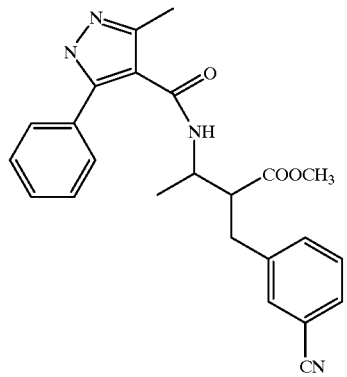

Compound 258

This material is prepared following the procedure described for compound 123 and substituting 3-phenyl-5-methyl-1,2-diazole-4-carboxylic acid for 99.

EXAMPLE 259

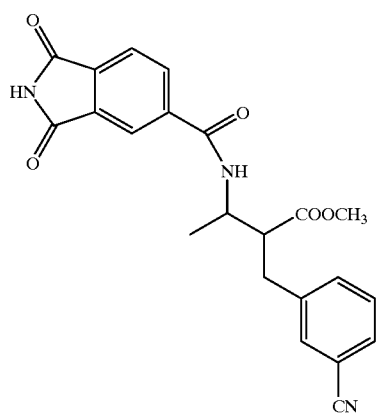

Compound 259

This material is prepared following the procedure described for compound 123 and substituting 1,2-phthalimide-4-carboxylic acid for 99.

EXAMPLE 260

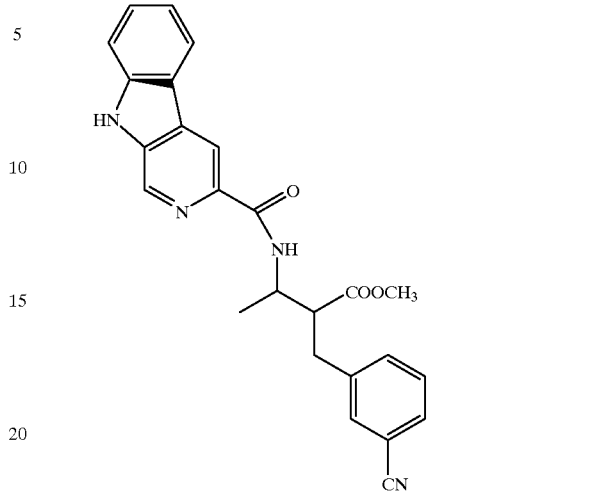

Compound 260

This material is prepared following the procedure described for compound 123 and substituting 3-aza-b-carboline-4-carboxylic acid for 99.

EXAMPLE 261

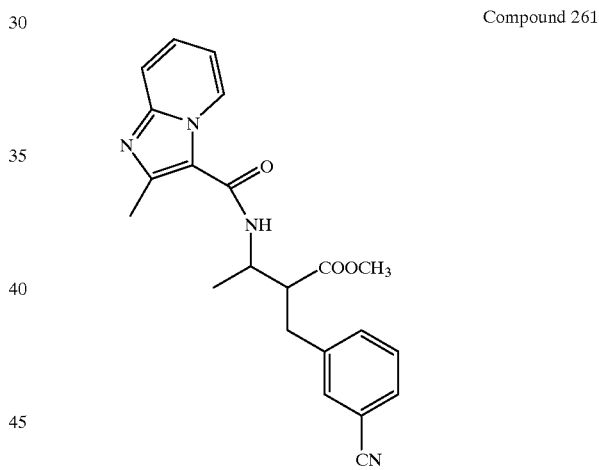

Compound 261

This material is prepared following the procedure described for compound 123 and substituting 2-methyl-1-azaindolizine-3-carboxylic acid for 99.

EXAMPLE 262

Compound 262

BnO\~\~\~\~NHBoc\~\~\~COOCH₃

This material is prepared following the procedure described for compound 56 and substituting N- -Boc-O-benzyl-D-serine.

EXAMPLE 263

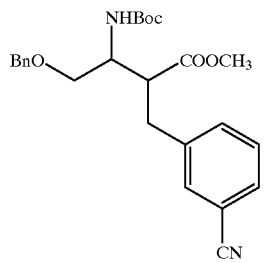

Compound 263

This material is prepared following the procedure described for compound 62 and substituting Compound 262.

EXAMPLE 264

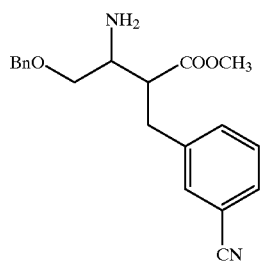

Compound 264

This material is prepared following the procedure described for compound 68 and substituting Compound 263.

EXAMPLE 265

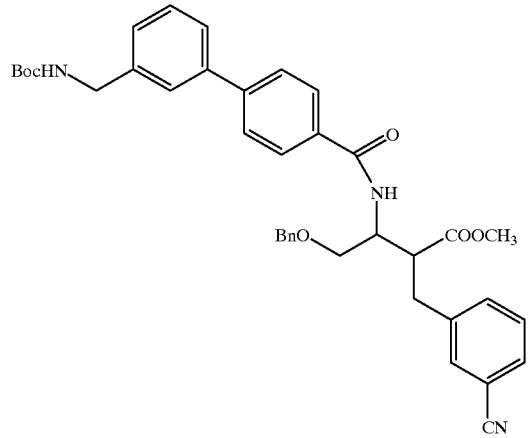

Compound 265

This material is prepared following the procedure described for compound 114 and substituting Compound 264.

EXAMPLE 266

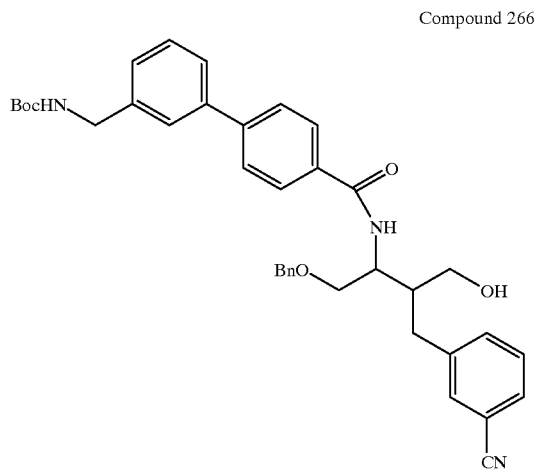

Compound 266

This material is prepared following the procedure described for compound 129 and substituting Compound 265.

EXAMPLE 267

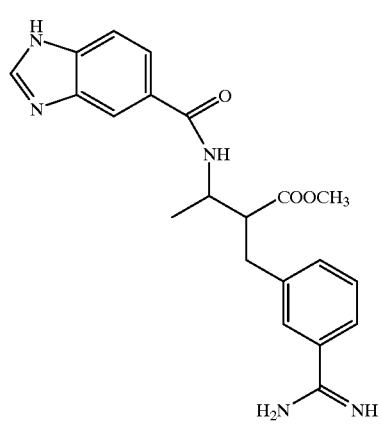

Compound 267

This material is prepared following the procedure described for compound 159a and substituting Compound 235. MS: $(M+H)^+$ 395.

EXAMPLE 268

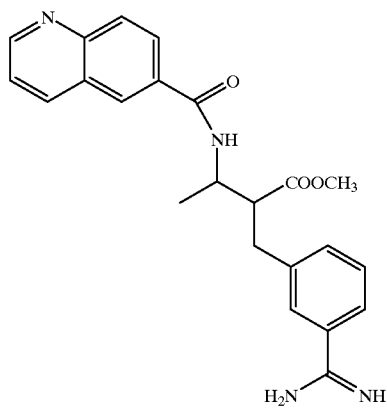

Compound 268

This material is prepared following the procedure described for compound 159a and substituting Compound 236. MS: $(M+H)^+$ 406.

EXAMPLE 269

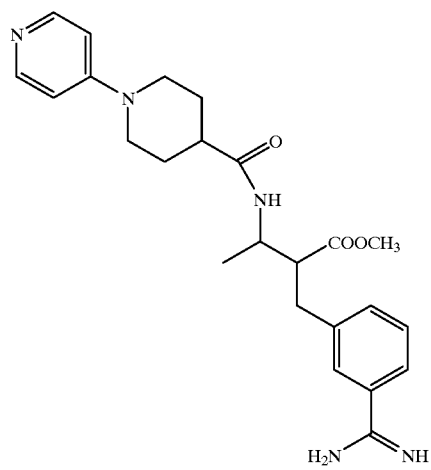

Compound 269

This material is prepared following the procedure described for compound 159a and substituting Compound 237. MS: $(M+H)^+$ 439.

EXAMPLE 270

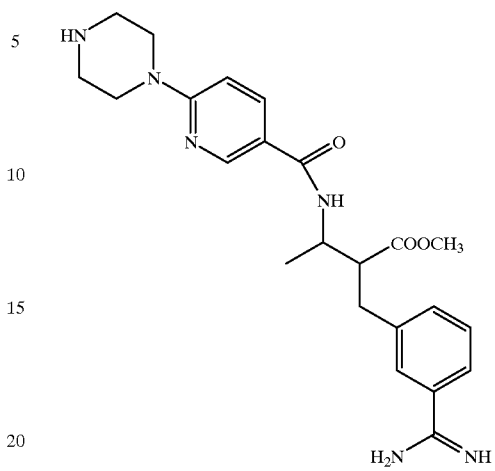

Compound 270

This material is prepared following the procedure described for compound 159a and substituting Compound 238. MS: $(M+H)^+$ 440.

EXAMPLE 271

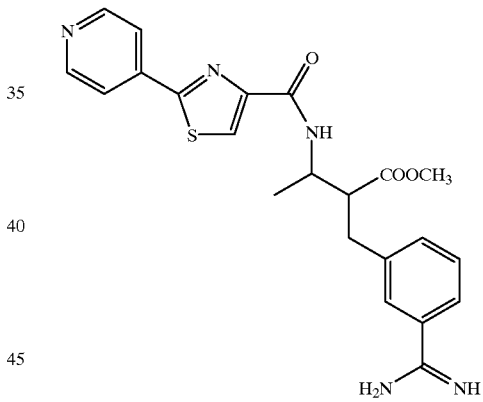

Compound 271

This material is prepared following the procedure described for compound 159a and substituting Compound 239. MS: $(M+H)^+$ 439.

EXAMPLE 272

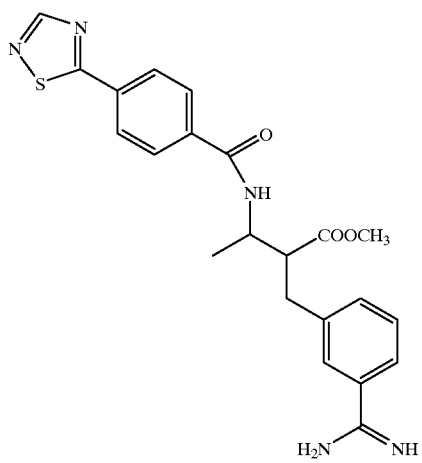
Compound 272

This material is prepared following the procedure described for compound 159a and substituting Compound 240. MS: (M+H)$^+$ 439.

EXAMPLE 273

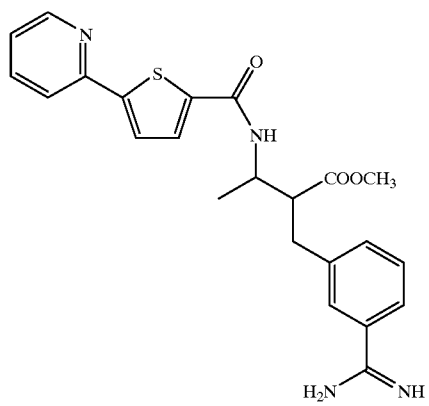
Compound 273

This material is prepared following the procedure described for compound 159a and substituting Compound 241. $^1$H NMR (DMSO-d$_6$) d 8.56–8.50 (m, 1H), 7.94–7.82 (m, 2H), 7.70 (s, 2H), 7.66–7.46 (m, 4H), 7.38–7.3 (m, 1H), 4.46–4.32 (m, 1H), 3.60 (s, 3H), 3.13–2.95 (m, 3H), 1.32 (d, J=7.2 Hz, 3H).

MS: (M+H)$^+$ 438.

EXAMPLE 274

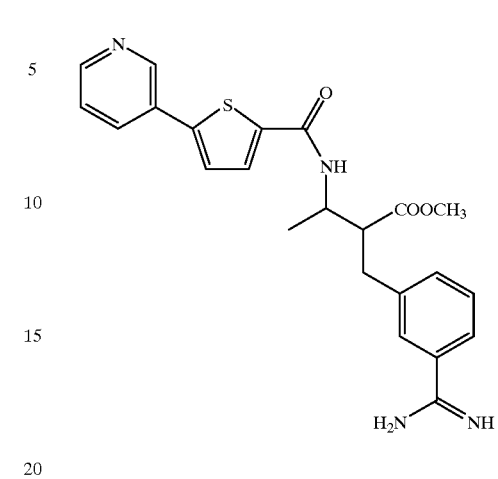
Compound 274

This material is prepared following the procedure described for compound 159a and substituting Compound 242. $^1$H NMR (DMSO-d$_6$) d 9.06 (s, 1H), 8.68–8.62 (m, 1H), 8.53 (d, J=8.4 Hz, 1H), 7.85–7.78 (m, 1H), 7.75 (d, J=3.6 Hz, 1H), 7.68 (d, J=3.6 Hz, 1H), 7.65–7.45 (m, 4H), 4.48–4.33 (m, 1H), 3.57 (s, 3H), 3.13–3.00 (m, 3H), 1.32 (d, J=7.2 Hz, 3H). MS: (M+H)$^+$ 438.

EXAMPLE 275

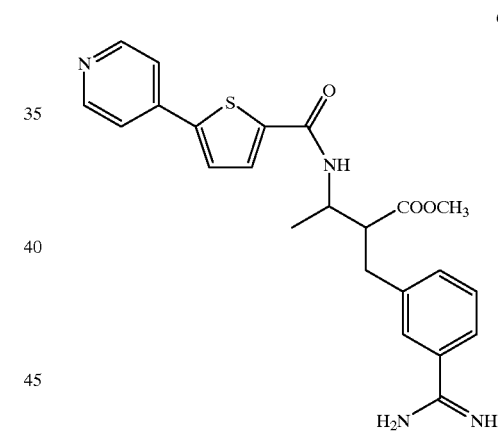
Compound 275

This material is prepared following the procedure described for compound 159a and substituting Compound 243. $^1$H NMR (DMSO-d$_6$) d 8.70 (s, 1H), 8.52 (d, J=9.6 Hz, 1H), 8.18–8.08 (m, 1H), 7.96 (d, J=3.6 Hz, 1H), 7.82 (d, J=3.6 Hz, 1H), 7.65–7.45 (m, 4H), 4.50–4.35 (m, 1H), 3.57 (s, 3H), 3.13–3.02 (m, 3H), 1.34 (d, J=7.2 Hz, 3H). MS: (M+H)$^+$ 438.

EXAMPLE 276

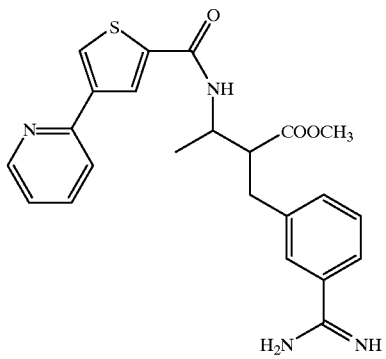

Compound 276

This material is prepared following the procedure described for compound 159a and substituting Compound 244. $^1$H NMR (DMSO-d$_6$) d 8.66 (d, J=6.0 Hz, 1H), 8.37 (s, 1H), 8.32 (s, 1H), 8.20–8.11 (m, 1H), 8.04 (d, J=7.2 Hz, 1H), 7.65–7.44 (m, 5H), 4.50–4.35 (m, 1H), 3.60 (s, 3H), 3.17–3.02 (m, 3H), 1.33 (d, J=7.2 Hz, 3H). MS: (M+H)$^+$ 438.

EXAMPLE 277

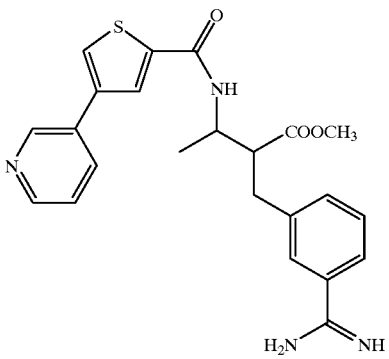

Compound 277

This material is prepared following the procedure described for compound 159a and substituting Compound 245. $^1$H NMR (DMSO-d$_6$) d 9.15– 9.02 (m, 1H), 8.75–8.61 (m, 1H), 8.54 (d, J=8.4 Hz, 1H), 8.22 (d, J=8.4 Hz, 1H), 7.88–7.78 (m, 1H), 7.65–7.45 (m, 4H), 4.50–4.35 (m, 1H), 3.57 (s, 3H), 3.17–3.02 (m, 3H), 1.35 (d, J=7.2 Hz, 3H). MS: (M+H)$^+$ 438.

EXAMPLE 278

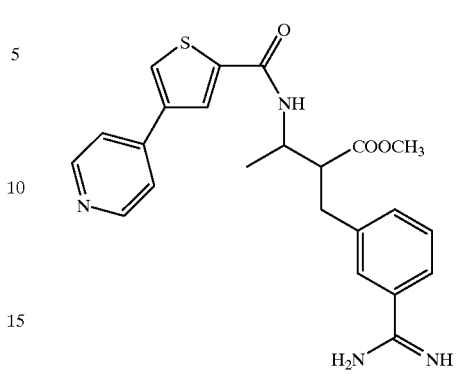

Compound 278

This material is prepared following the procedure described for compound 159a and substituting Compound 246. $^1$H NMR (DMSO-d$_6$) d 8.78 (s, 2H), 8.67 (s, 1H), 8.35 (s, 1H), 8.25 (d, J=8.4 Hz, 2H), 7.65–7.45 (m, 4H), 4.50–4.38 (m, 1H), 3.57(s, 3H), 3.17–3.02 (m, 3H), 1.35 (d, J=7.2 Hz, 3H). MS: (M+H)$^+$ 438.

EXAMPLE 279

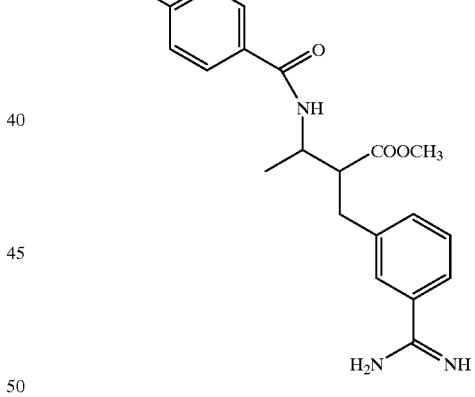

Compound 279

This material is prepared following the procedure described for compound 159a and substituting Compound 247. $^1$H NMR (DMSO-d$_6$) d 9.5 (s, 1H), 8.2 (s, 1H), 8.1 (d, J=5.0 Hz, 2H), 7.9 (d, J=5.0 Hz, 2H), 7.8 (s, 1H), 7.5–7.7 (m, 4H), 4.4–4.6 (m, 1H), 3.6 (s, 3H), 3.0–3.2 (m, 3H), 1.4 (d, J=5.0 Hz, 3H).

MS: (M+H)$^+$ 421.

EXAMPLE 280

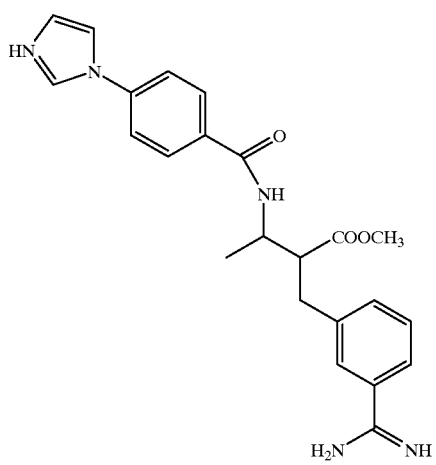

Compound 280

This material is prepared following the procedure described for compound 159a and substituting Compound 248. $^1$H NMR (DMSO-$d_6$) d 9.0 (s, 1H), 8.5 (d, J=5.0 Hz, 1H), 8.1 (s, 1H), 8.0 (d, J=5.0 Hz, 2H), 7.9 (d, J=5.0 Hz, 2H), 7.5–7.7 (m, 4H), 4.4–4.6 (m, 1H), 3.6 (s, 3H), 3.0–3.2 (m, 3H), 1.4 (d, J=5.0 Hz, 3H). MS: (M+H)$^+$ 421.

EXAMPLE 281

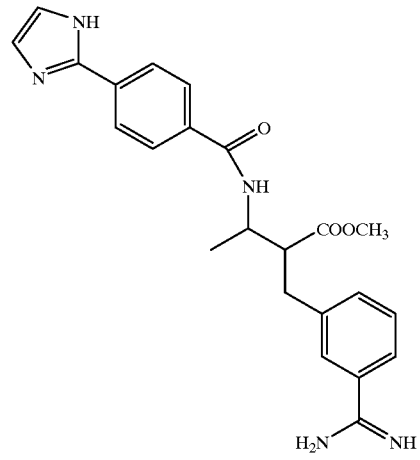

Compound 281

This material is prepared following the procedure described for compound 159a and substituting Compound 249. $^1$H NMR (DMSO-$d_6$) d 8.5 (d, J=5.0 Hz, 1H), 7.80–8.10 (m, 4H), 7.8 (d, J=5.0 Hz, 2H), 7.5–7.7 (m, 4H), 4.4–4.6 (m, 1H), 3.6 (s, 3H), 3.0–3.1 (m, 3H), 1.4 (d, J=5.0 Hz, 3H). MS: (M+H)$^+$421.

EXAMPLE 282

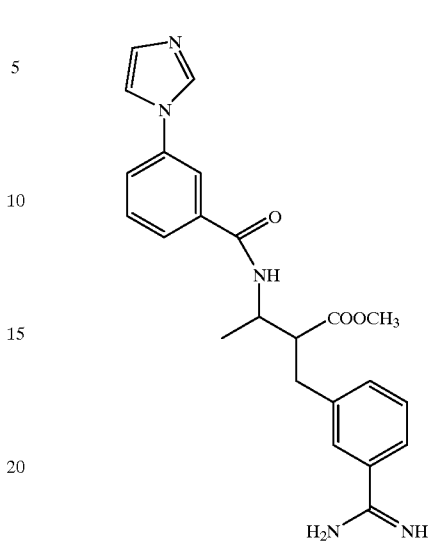

Compound 282

This material is prepared following the procedure described for compound 159a and substituting Compound 250. MS: (M+H)$^+$ 421.

EXAMPLE 283

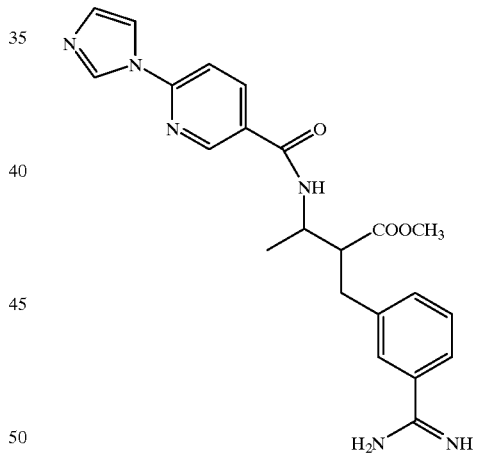

Compound 283

This material is prepared following the procedure described for compound 159a and substituting Compound 251. MS: (M+H)$^+$ 422.

EXAMPLE 284

Compound 284

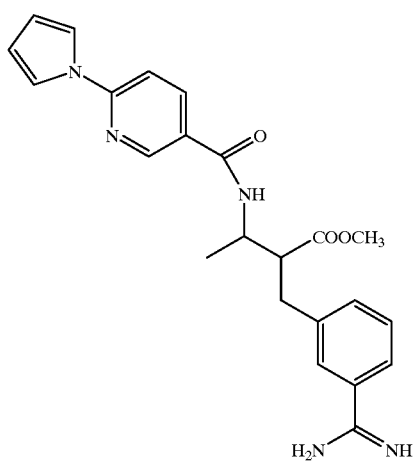

This material is prepared following the procedure described for compound 159a and substituting Compound 252. MS: (M+H)$^+$ 421.

EXAMPLE 285

Compound 285

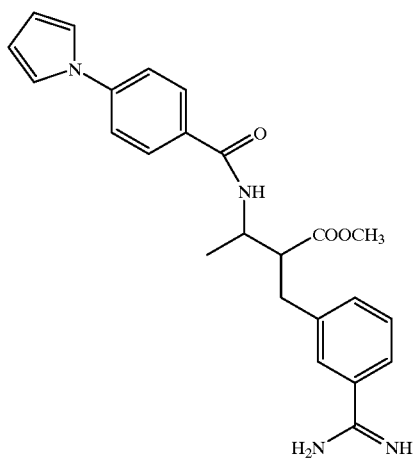

This material is prepared following the procedure described for compound 159a and substituting Compound 253. MS: (M+H)$^+$ 420.

EXAMPLE 286

Compound 286

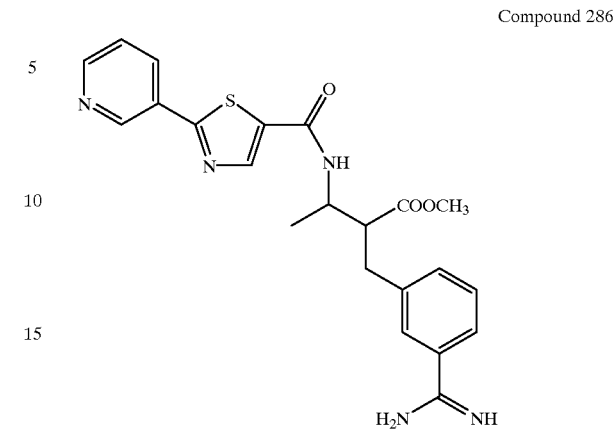

This material is prepared following the procedure described for compound 159a and substituting Compound 254. MS: (M+H)$^+$ 439.

EXAMPLE 287

Compound 287

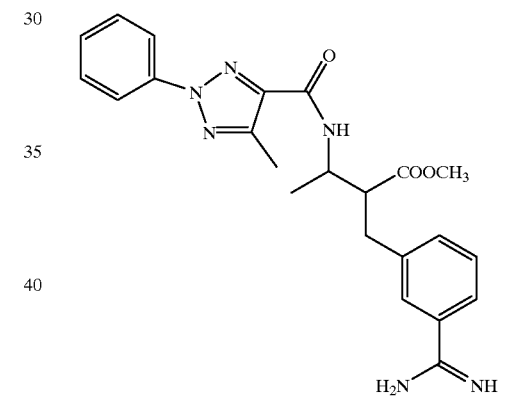

This material is prepared following the procedure described for compound 159a and substituting Compound 255. MS: (M+H)$^+$ 436.

EXAMPLE 288

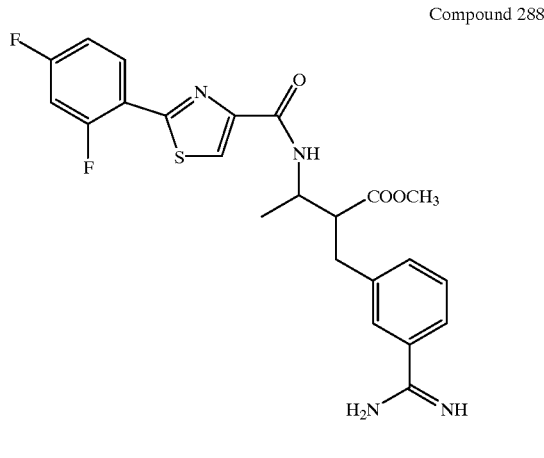

Compound 288

This material is prepared following the procedure described for compound 159a and substituting Compound 256. MS: $(M+H)^+$ 473.

EXAMPLE 289

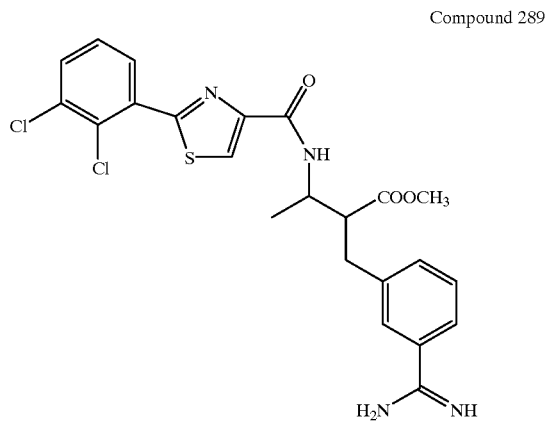

Compound 289

This material is prepared following the procedure described for compound 159a and substituting Compound 257. MS: $(M+H)^+$ 507.

EXAMPLE 290

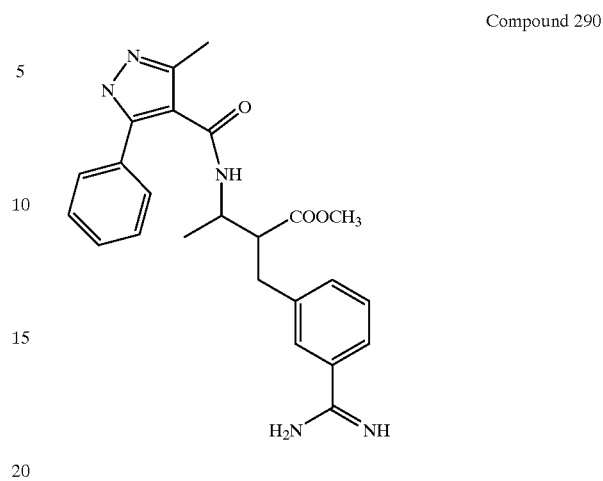

Compound 290

This material is prepared following the procedure described for compound 159a and substituting Compound 258. MS: $(M+H)^+$ 434.

EXAMPLE 291

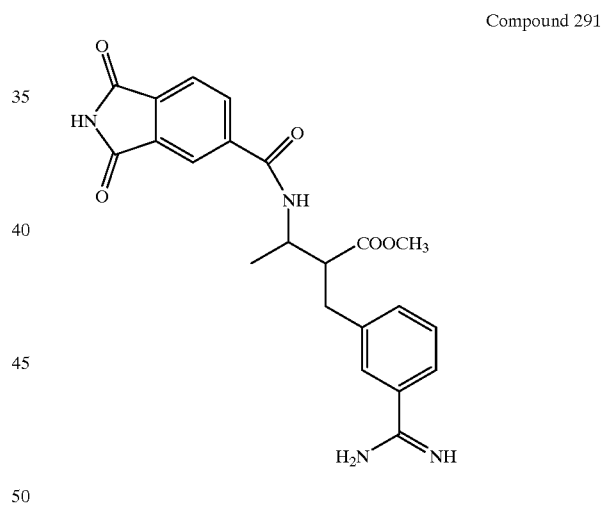

Compound 291

This material is prepared following the procedure described for compound 159a and substituting Compound 259. MS: $(M+H)^+$ 421.

EXAMPLE 292

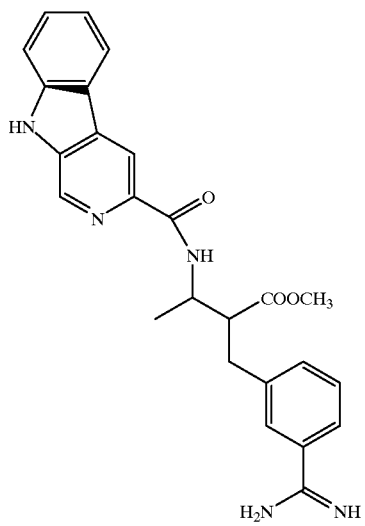

Compound 292

This material is prepared following the procedure described for compound 159a and substituting Compound 260. MS: (M+H)+ 444.

EXAMPLE 293

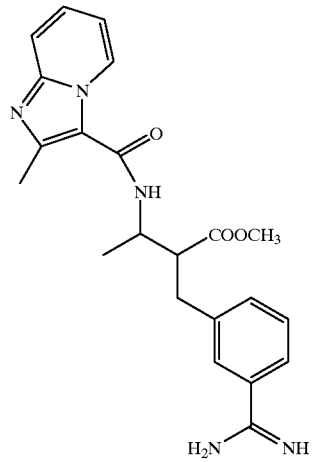

Compound 293

This material is prepared following the procedure described for compound 159a and substituting Compound 261. MS: (M+H)+ 408.

EXAMPLE 294

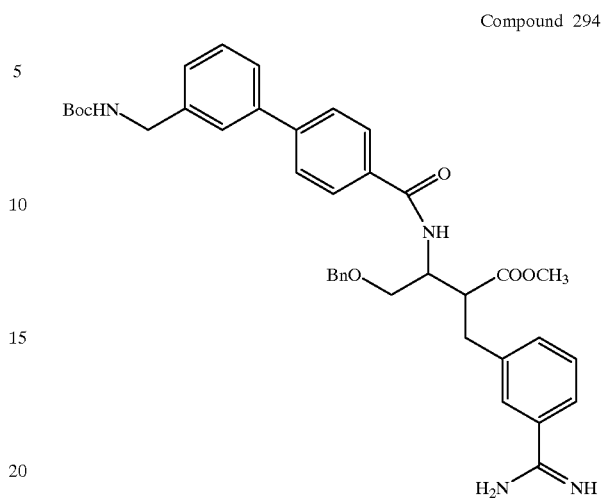

Compound 294

This material is prepared following the procedure described for compound 159b and substituting Compound 265.

EXAMPLE 295

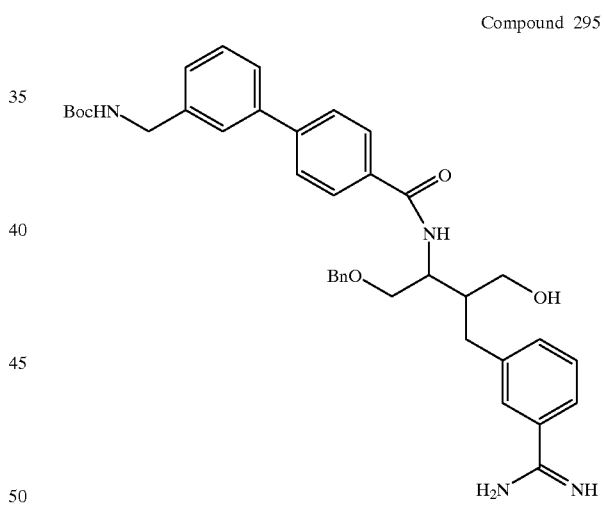

Compound 295

This material is prepared following the procedure described for compound 159b and substituting Compound 266.

EXAMPLE 296

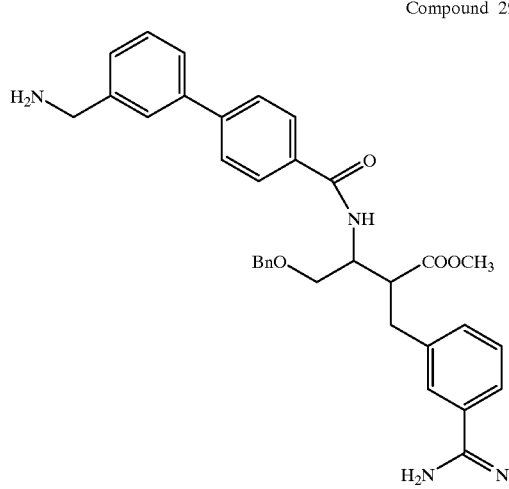

Compound 296

To a solution of compound 294 (1 mmol) in 20 mL of CH$_2$Cl$_2$ is added 5 mL of TFA at 0° C. with stirring. Stirring is continued for 1 hour at 0° C. and all solvents are removed in vacuo.

EXAMPLE 297

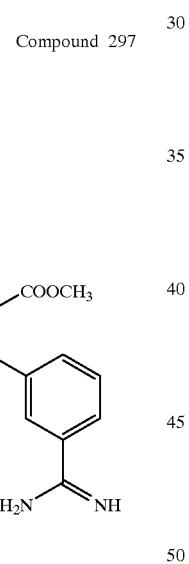

Compound 297

To a solution of compound 296 (1 mmol) in 25 mL of methanol is added approximately 50 mg of 10% palladium on charcoal. The mixture is shaken under a positive pressure of hydrogen (55 psi) for 24 hours and filtered. The filtrate is concentrated in vacuo and purified by reverse phase HPLC. $^1$H NMR (DMSO-d$_6$) d 8.3 (d, J=6.0 Hz, 1H), 8.0 (d, J=5.0 Hz, 2H), 7.8 (d, J=5.0 Hz, 2H), 7.7 (d, J=6.0 Hz, 2H), 7.4–7.7 (m, 6H), 4.3–4.5 (m, 1H), 4.2 (s, 2H), 3.8 (d, J=4.0 Hz, 2H), 3.7 (s, 3H), 3.2–3.4 (m, 3H), 3.1–3.2 (m, 2H). MS: (M+H)$^+$ 475.

EXAMPLE 298

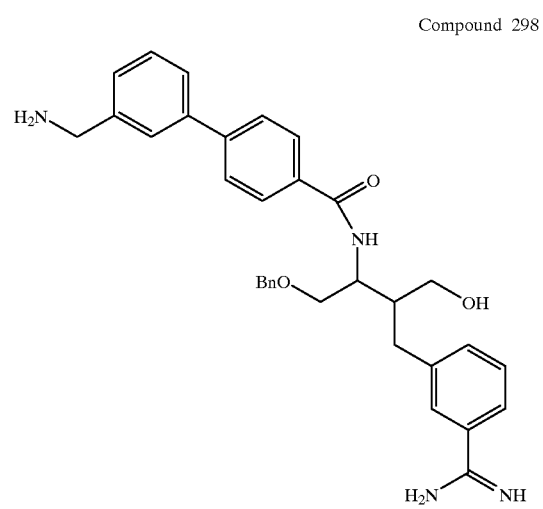

Compound 298

Compound 298 is prepared in a manner identical to compound 296, starting from compound 295.

EXAMPLE 299

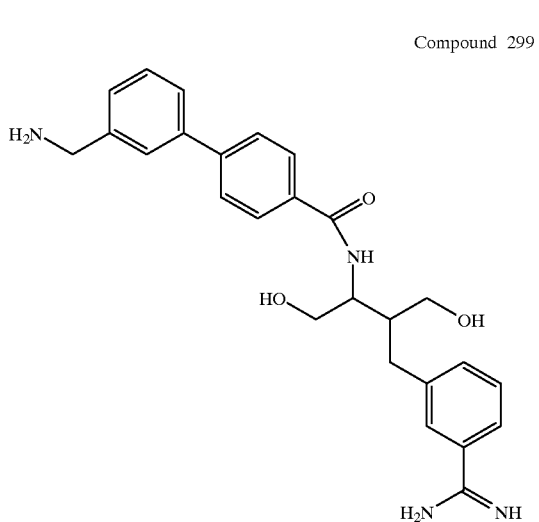

Compound 299

Compound 299 is prepared in a manner identical to compound 297, starting from compound 298. $^1$H NMR (DMSO-d$_6$) d 8.4 (d, J=5.0 Hz,1H), 8.0 (d, J=5.0 Hz, 2H), 7.8 (d, J=5.0 Hz, 2H), 7.7 (d, J=4.0 Hz, 2H), 7.5–7.7 (m, 6H), 4.2 (s, 2H), 4.1–4.2 (m, 1H), 4.0 (dd, J=8.0, 2.0 Hz, 1H), 3.8 (s, 2H), 3.7 (dd, J=8.0, 2.0 Hz, 1H), 3.0 (d, J=5.0 Hz, 2H), 2.2–2.4 (m, H). MS: (M+H)$^+$ 448.

EXAMPLE 300

Compound 300

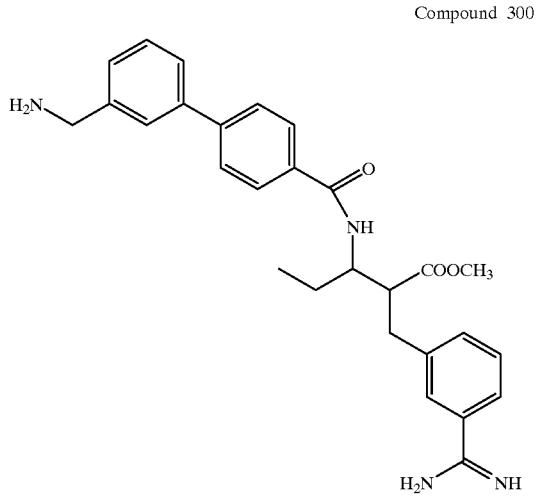

Compound 300 is prepared by procedures substantially similar to those used to prepare compound 297, starting from the appropriate materials. $^1$H NMR (CD$_{30}$D) d 7.94 (d, J=10.8 Hz, 2H), 7.85–7.72 (m, 4H), 7.70–7.45 (m, 6H), 4.32–4.23 (m, 1H), 4.22 (s, 2H), 3.62 (s, 3H), 3.83–3.55 (m, 2H), 3.18–3.02 (m, 3H), 0.94 (t, J=8.4 Hz, 3H). MS: (M+H)$^+$ 474.

EXAMPLE 301

Compound 301

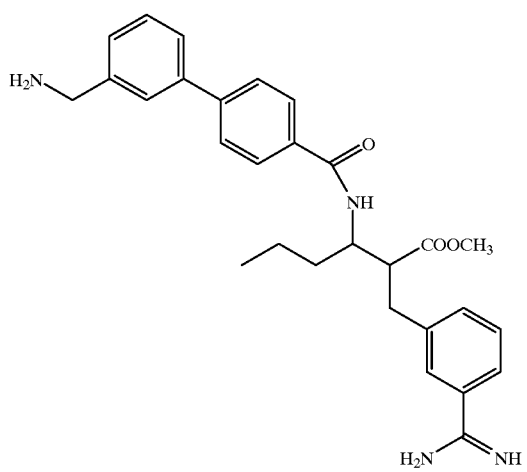

Compound 301 is prepared by procedures substantially similar to those used to prepare compound 297, starting from the appropriate materials. $^1$H NMR (CD$_3$OD) d 7.94 (d, J=10.8 Hz, 2H), 7.85–7.72 (m, 4H), 7.68–7.45 (m, 6H), 4.42–4.30 (m, 1H), 4.22 (s, 2H), 3.61 (s, 3H), 3.15–3.02 (m, 3H), 1.72–1.58 (m, 2H), 1.51–1.32 (m, 2H), 0.93 (t, J=8.4 Hz, 3H). MS: (M+H)$^+$ 488.

EXAMPLE 302

Compound 302

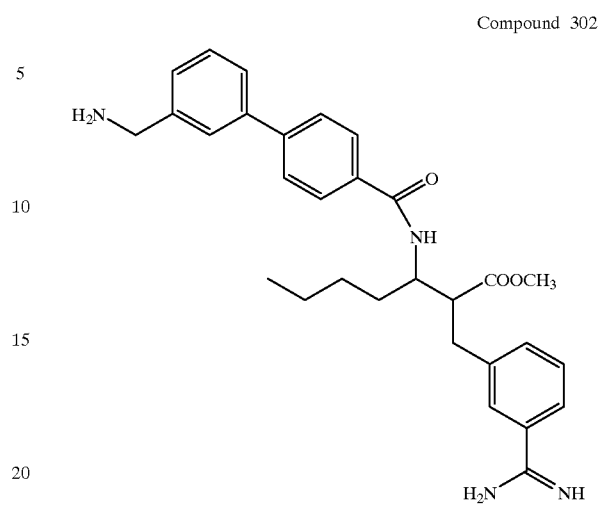

Compound 302 is prepared by procedures substantially similar to those used to prepare compound 297, starting from the appropriate materials. $^1$H NMR (CD$_3$OD) d 7.93 (d, J=10.8 Hz, 2H), 7.85–7.72 (m, 4H), 7.70–7.45 (m, 6H), 4.42–4.30 (m, 1H), 4.22 (s, 2H), 3.62 (s, 3H), 3.14–3.02 (m, 3H), 1.78–1.60 (m, 2H), 1.45–1.25 (m, 4H), 0.90 (t, J=8.4 Hz, 3H). MS: (M+H)$^+$ 502.

The molecules described herein inhibit blood coagulation by virtue of their ability to inhibit the penultimate enzyme in the coagulation cascade, factor Xa, rather than thrombin. Both free factor Xa and factor Xa assembled in the prothrombinase complex (Factor Xa, Factor Va, calcium and phospholipid) are inhibited. Factor Xa inhibition is obtained by direct complex formation between the inhibitor and the enzyme and is therefore independent of the plasma co-factor antithrombin III. Effective factor Xa inhibition is achieved by administering the compounds either by oral administration, continuous intravenous infusion, bolus intravenous administration or any other parenteral route such that it achieves the desired effect of preventing the factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening thrombin throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

These compounds may be used alone or in combination with other diagnostic, anticoagulant, antiplatelet or fibrinolytic agents. For example adjunctive administration of factor Xa inhibitors with standard heparin, low molecular weight heparin, direct thrombin inhibitors (i.e. hirudin), aspirin, fibrinogen receptor antagonists, streptokinase, urokinase and/or tissue plasminogen activator may result in greater antithrombotic or thrombolytic efficacy or efficiency. The compounds described herein may be administered to treat thrombotic complications in a variety of animals such as primates including humans, sheep, horses, cattle, pigs, dogs, rats and mice. Inhibition of factor Xa is useful not only in the anticoagulant therapy of individuals having thrombotic conditions but is useful whenever inhibition of blood coagulation is required such as to prevent coagulation of stored whole blood and to prevent coagulation in other biological samples for testing or storage. Thus, any factor Xa inhibitor can be added to or contacted with any medium containing or suspected of containing factor Xa and in which it is desired that blood coagulation be inhibited.

In addition to their use in anticoagulant therapy, factor Xa inhibitors may find utility in the treatment or prevention of other diseases in which the generation of thrombin has been implicated as playing a pathologic role. For example, thrombin has been proposed to contribute to the morbidity and mortality of such chronic and degenerative diseases as arthritis, cancer, atherosclerosis and Alzheimer's disease by virtue of its ability to regulate many different cell types through specific cleavage and activation of a cell surface thrombin receptor. Inhibition of factor Xa will effectively block thrombin generation and therefore neutralize any pathologic effects of thrombin on various cell types.

According to a further feature of the invention there is provided a method for the treatment of a human or animal patient suffering from, or subject to, conditions which can be ameliorated by the administration of an inhibitor of Factor Xa, for example conditions as hereinbefore described, which comprises the administration to the patient of an effective amount of compound of formula I or a composition containing a compound of formula I. "Effective amount" is meant to describe an amount of compound of the present invention effective in inhibiting Factor Xa and thus producing the desired therapeutic effect.

The present invention also includes within its scope pharmaceutical formulations which comprise at least one of the compounds of Formula I in association with a pharmaceutically acceptable carrier or coating.

In practice compounds of the present invention may generally be administered parenterally, intravenously, subcutaneously intramuscularly, colonically, nasally, intraperitoneally, rectally or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The compounds of the present invention may also be formulated for use in conjunction with other therapeutic agents such as agents or in connection with the application of therapeutic techniques to address pharmacological conditions which may be ameliorated through the application of a compound of formula I, as deescribed herein.

The compounds of the present invention may be used in combination with any anticoagulant, antiplatelet, antithrombotic or profibrinolytic agent. Often patients are concurrently treated prior, during and after interventional procedures with agents of these classes either in order to safely perform the interventional procedure or to prevent deleterious effects of thrombus formation. Some examples of classes of agents known to be anticoagulant, antiplatelet, antithrombotic or profibrinolytic agents include any formulation of heparin, low molecular weight heparins, pentasaccharides, fibrinogen receptor antagonists, thrombin inhibitors, Factor Xa inhibitors, or Factor VIIa inhibitors.

The compounds of the present invention may be used in combination with any antihypertensive agent or cholesterol or lipid regulating agent, or concurrently in the treatment of restenosis, atherosclerosis or high blood pressure. Some examples of agents that are useful in combination with a compound according to the invention in the treatment of high blood pressure include compounds of the following classes; beta-blockers, ACE inhibitors, calcium channel antagonists and alpha-receptor antagonists. Some examples of agents that are useful in combination with a compound according to the invention in the treatment of elevated cholesterol levels or disregulated lipid levels include compounds known to be HMGCOA reductase inhibitors, compounds of the fibrate class.

It is understood that the present invention includes combinations of compounds of the present invention with one or more of the aforementioned therapeutic class agents.

Compounds within the scope of the present invention exhibit marked pharmacological activities according to tests described in the literature and below which tests results are believed to correlate to pharmacological activity in humans and other mammals.

Enzyme Assays

The ability of the compounds in the present invention to act as inhibitors of factor Xa, thromb in, trypsin, tissue-plasm inogen ac tivator (t-PA), urokinase-plasminogen acti-vator (u-PA), plasmin and activated protein C is evaluated by determining the concentration of inhibitor which resulted in a 50% loss in enzyme activity (IC50) using purified enzymes.

All enzyme as says are carried out at room temperature in 96-well microtiter plates using a final enzyme concentration of 1 nM. The concentrations of factor Xa and thrombin are determined by active site titration and the concentrations of all other enzymes are based on the protein concentration supplied by the manufacturer. Compounds according to the invention are dissolved in DMSO, diluted with their respective buffers and assayed at a maximal final DMSO concentration of 1.25%. Compound dilutions are added to wells containing buffer and enzyme and pre-equilibrated for between 5 and 30 minutes. The enzyme reactions are initiated by the addition of substrate and the color developed from the hydrolysis of the peptide-p-nitroanilide substrates is monitored continuously for 5 minutes at 405 nm on a Vmax microplate reader (Molecular Devices). Under these conditions, less than 10% of the substrate is utilized in all assays. The initial velocities measured are used to calculate the amount of inhibitor which resulted in a 50% reduction of the control velocity (IC50). The apparent Ki values are then determined according to the Cheng-Prusoff equation (IC50= Ki[1+[S]/Km]) assuming competitive inhibition kinetics.

An additional in vitro assay may be used to evaluate the potency of compounds according to the invention in normal human plasma. The activated partial thromboplastin time is a plasma-based clotting assay that relies on the in situ generation of factor Xa, its assembly into the prothrombinase complex and the subsequent generation of thrombin and fibrin which ultimately yields the formation of a clot as the assay endpoint. This assay is currently used clinically to monitor the ex vivo effects of the commonly used anticoagulant drug heparin as well as direct acting antithrombin agents undergoing clinical evaluation. Therefore, activity in this in vitro assay is considered as a surrogate marker for in vivo anticoagulant activity.

Human Plasma Based Clotting Assay

Activated partial thromboplastin clotting times are determined in duplicate on a MLA Electra 800 instrument. A volume of 100 µl of citrated normal human pooled plasma (George King Biomedical) is added to a cuvette containing 100 µl of a compound according to the invention in Tris/NaCl buffer (pH 7.5) and placed in the instrument. Following a 3 minute warming period the instrument automatically adds 100 µl of activated cephaloplastin reagent (Actin, Dade) followed by 100 µl of 0.035 M $CaCl_2$ to initiate the clotting reaction. Clot formation is determined spectrophotometrically and measured in seconds. Compound potency is quantitated as the concentration required to double a control clotting time measured with human plasma in the absence of the compound according to the invention.

Compounds according to the invention may also be evaluated for their in vivo antithrombotic efficacy in two well established animal experimental models of acute vascular thrombosis. A rabbit model of jugular vein thrombosis and a rat model of carotid artery thrombosis are used to demonstrate the antithrombotic activity of these compounds in distinct animal model paradigms of human venous thrombosis and arterial thrombosis, respectively.

Experimental In Vivo Rabbit Venous Thrombosis Model

This is a well characterized model of fibrin rich venous thrombosis that is validated in the literature and shown to be sensitive to several anticoagulant drugs including heparin (Antithrombotic Effect of Recombinant Truncated Tissue Factor Pathway Inhibitor (TFPI 1-161) in Experimental Venous Thrombosis-a Comparison with Low Molecular Weight Heparin, J. Hoist, B. Lindblad, D. Bergqvist, O. Nordfang, P. B. Ostergaard, J. G. L. Petersen, G. Nielsen and U. Hedner. *Thrombosis and Haemostasis,* 71, 214–219 (1994). The purpose of utilizing this model is to evaluate the ability of compounds to prevent the formation of venous thrombi (clots) in vivo generated at a site of injury and partial stasis in the jugular vein.

Male and female New Zealand white rabbits weighing 1.5–2 kg are anesthetized with 35 mg/kg of ketamine and 5 mg/kg xylazine in a volume of 1 mL/kg (i.m.). The right jugular vein is cannulated for infusion of anesthetic (ketamine/xylazine 17/2.5 mg/kg/hr at a rate of approximately 0.5 mL/hr) and administration of test substances. The right carotid artery is cannulated for recording arterial blood pressure and collecting blood samples. Body temperature is maintained at 39° C. with a GAYMAR T-PUMP. The left external jugular vein is isolated and all side branches along an exposed 2–3 cm of vessel are tied off. The internal jugular vein is cannulated, just above the bifurcation of the common jugular, and the tip of the cannula is advanced just proximal to the common jugular vein. A 1 cm segment of the vein is isolated with non-traumatic vascular clamps and a relative stenosis is formed by tying a ligature around the vein with an 18 G needle just below the distal most clamp. This creates a region of reduced flow and partial stasis at the injury site. The isolated segment is gently rinsed with saline 2–3 times via the cannula in the internal jugular. Thereafter the isolated segment is filled with 0.5 mL of 0.5% polyoxyethylene ether (W-1) for 5 minutes. W-1 is a detergent which disrupts the endothelial cell lining of the segment, thus providing a thrombogenic surface for initiating clot formation. After 5 minutes the W-1 is withdrawn from the segment, and the segment is again gently rinsed with saline 2–3 times. The vascular clamps are then removed, restoring blood flow through this portion of the vessel. Clot formation is allowed to form and grow for 30 minutes after which the vein is cut just below the stenotic ligature and inspected for blood flow (the absence of blood flow is recorded as complete occlusion). The entire isolated segment of vein is then ligated and the formed clot is removed and weighed (wet weight). The effect of test agents on final clot weights is used as the primary end point. Animals are maintained for an additional thirty minutes to obtain a final pharmacodynamic measure of anticoagulation. Drug administration is initiated 15 minutes prior to vascular injury with W-1 and continued through the period of clot formation and maturation. Three blood samples (3 mL ea.) are obtained for evaluation of hemostatic parameters: one just prior to administration of W-1; a second 30 minutes after removal of the vascular clamps and a third at the termination of the experiment. Antithrombotic efficacy is expressed as a reduction in the final clot weight in preparations treated with a compound according to the invention relative to vehicle treated control animals.

Experimental In Vivo Rat Arterial Thrombosis Model

The antithrombotic efficacy of factor Xa inhibitors against platelet-rich arterial thrombosis may be evaluated using a well characterized rat carotid artery FeCl$_2$-induced thrombosis model (Schumacher et al., *J. Cardio. Pharm.*, 22, 526–533 (1993); Kurtz, et al., *Thrombosis Research*, 60, 269–280 (1990); Broersma, et al., *Thrombosis Research* 64, 405–412 (1991). This model is widely used to evaluate the antithrombotic potential of a variety of agents including heparin and the direct acting thrombin inhibitors.

Sprague Dawley rats weighing 375–450 g are anesthetized with sodium pentobarbital (50 mg/kg i.p.). Upon reaching an acceptable level of anesthesia, the ventral surface of the neck is shaved and prepared for aseptic surgery. Electrocardiogram electrodes are connected and lead II is monitored throughout the experiment. The right femoral vein and artery are cannulated with PE-50 tubing for administration of a compound according to the invention and for obtaining blood samples and monitoring blood pressure, respectively. A midline incision is made in the ventral surface of the neck. The trachea is exposed and intubated with PE-240 tubing to ensure airway patency. The right carotid artery is isolated and two 4-0 silk sutures are placed around the vessel to facilitate instrumentation. An electromagnetic flow probe (0.95–1.0 mm lumen) is placed around the vessel to measure blood flow. Distal to the probe a 4×4 mm strip of parafilm is placed under the vessel to isolate it from the surrounding muscle bed. After baseline flow measurements are made, a 2×5 mm strip of filter paper previously saturated in 35% FeCl$_2$ is placed on top of the vessel downstream from the probe for ten minutes and then removed. The FeCl$_2$ is thought to diffuse into the underlying segment of artery and cause deendothelialization resulting in acute thrombus formation. Following application of the FeCl$_2$-soaked filter paper, blood pressure, carotid artery blood flow and heart rate are monitored for an observation period of 60 minutes. Following occlusion of the vessel (defined as the attainment of zero blood flow), or 60 minutes after filter paper application if patency is maintained, the artery is ligated proximal and distal to the area of injury and the vessel is excised. The thrombus is removed and weighed immediately and recorded as the primary end point of the study.

Following surgical instrumentation a control blood sample (B1) is drawn. All blood samples are collected from the arterial catheter and mixed with sodium citrate to prevent clotting. After each blood sample, the catheter is flushed with 0.5 mL of 0.9% saline. A compound according to the invention is administered intravenously (i.v.) starting 5 minutes prior to FeCl$_2$ application. The time between FeCl$_2$ application and the time at which carotid blood flow reached zero is recorded as time to occlusion (TTO). For vessels that did not occlude within 60 minutes, TTO is assigned a value of 60 minutes. Five minutes after application of FeCl$_2$, a second blood sample is drawn (B2). After 10 minutes of FeCl$_2$ exposure, the filter paper is removed from the vessel and the animal is monitored for the remainder of the experiment. Upon reaching zero blood flow blood a third blood sample is drawn (B3) and the clot is removed and weighed. Template bleeding time measurements are performed on the forelimb toe pads at the same time that blood samples are obtained. Activated partial thromboplastin time (APTT) and prothrombin time (PT) coagulation profiles are performed on all blood samples. In some instances a compound according to the invention may be administered orally. Rats are restrained manually using standard techniques and compounds are administered by intragastric gavage using a 18 gauge curved dosing needle (volume of 5 mL/kg). Fifteen minutes after dosing, the animal is anesthetized and instrumented as described previously. Experiments are then performed according to the protocol described above.

By way of example, Compound 184 shows K$_i$ values of 27.0 nM, 1.72 pM, and 2.71 µM, and Compound 45 shows $K_i$ values of 94.0 nM, 129 nM, and 477 nM, in the Factor Xa, trypsin, and thrombin assays, respectively. Compound 167 shows $K_i$ values of 19.0 nM, 46 nM, and 1.228 µM, in the Factor Xa, trypsin, and thrombin assays, respectively.

The present invention may be embodied in other specific forms without departing from the spirit or essential attributes thereof.

What is claimed is:

1. A compound having a formula selected from the group consisting of:

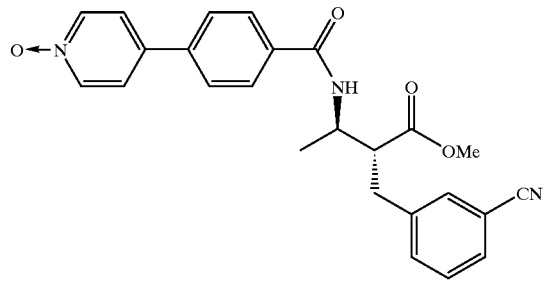

and

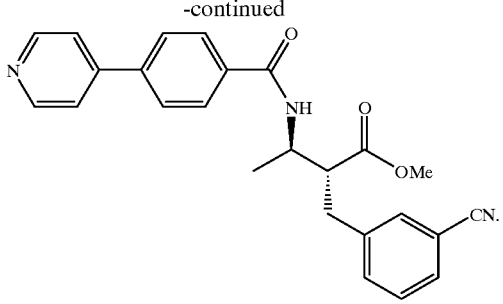

2. A compound of the formula:

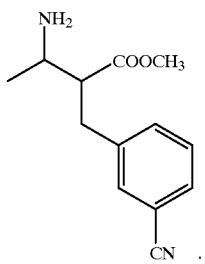

* * * * *